(12) United States Patent
Conte et al.

(10) Patent No.: US 7,989,438 B2
(45) Date of Patent: Aug. 2, 2011

(54) THERAPEUTIC COMPOUNDS

(75) Inventors: Immacolata Conte, Pomezia (IT); Joerg Habermann, Pomezia (IT); Angela Mackay, Pomezia (IT); Frank Narjes, Pomezia (IT); Maria del Rosario Rico Ferreira, Pomezia (IT); Ian Stansfield, Pomezia (IT)

(73) Assignee: Istituto di Ricerche di Biologia Molecolare P. Angeletti SpA, Rome (IT)

( * ) Notice: Subject to any disclaimer, the term of this patent is extended or adjusted under 35 U.S.C. 154(b) by 345 days.

(21) Appl. No.: 12/218,425

(22) Filed: Jul. 15, 2008

(65) Prior Publication Data

US 2009/0048239 A1 Feb. 19, 2009

Related U.S. Application Data

(63) Continuation-in-part of application No. PCT/GB2008/050555, filed on Jul. 9, 2008.

(60) Provisional application No. 61/008,231, filed on Dec. 19, 2007.

(30) Foreign Application Priority Data

Jul. 17, 2007 (GB) .............................. GB0713865.4
Dec. 19, 2007 (GB) .............................. GB0724635.8

(51) Int. Cl.
| | |
|---|---|
| C07D 513/18 | (2006.01) |
| C07D 513/22 | (2006.01) |
| C07D 515/22 | (2006.01) |
| A61K 31/4155 | (2006.01) |
| A61K 31/454 | (2006.01) |
| A61K 31/5517 | (2006.01) |
| A61P 31/12 | (2006.01) |

(52) U.S. Cl. .................. 514/183; 514/214.03; 514/219; 514/233.2; 514/250; 514/338; 514/406; 514/410; 540/457

(58) Field of Classification Search .................. 514/183, 514/214.03, 219, 233.2, 250, 338, 406, 410; 540/457

See application file for complete search history.

(56) References Cited

U.S. PATENT DOCUMENTS

| | | | |
|---|---|---|---|
| 3,480,613 A | 11/1969 | Walton | |
| 4,182,623 A | 1/1980 | Kloek | |
| 5,206,382 A | 4/1993 | Costa et al. | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,184 B2 | 10/2005 | Friedrichs et al. | |
| 7,153,848 B2 | 12/2006 | Hudyma et al. | |
| 7,348,425 B2 | 3/2008 | Hudyma et al. | |
| 7,470,664 B2 | 12/2008 | Holloway et al. | |
| 7,662,809 B2 * | 2/2010 | Ercolani et al. ............... 514/183 |
| 7,767,660 B2 | 8/2010 | Stansfield et al. | |
| 7,781,422 B2 | 8/2010 | Stansfield et al. | |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2005/0119318 A1 | 6/2005 | Hudyma et al. | |
| 2005/0239767 A1 | 10/2005 | Chan et al. | |
| 2006/0100262 A1 | 5/2006 | Conte et al. | |
| 2006/0257980 A1 | 11/2006 | Li | |
| 2007/0027071 A1 | 2/2007 | Holloway et al. | |
| 2007/0049593 A1 | 3/2007 | Oka et al. | |

(Continued)

FOREIGN PATENT DOCUMENTS

EP 1719773 A1 11/2006

(Continued)

OTHER PUBLICATIONS

V. Lohmann et al., "Replication of Subgenomic Hepatitis C Virus RNAs in a Hepatoma Cell Line," 285 Science 110-13 (1999).
Volker Lohmann et al., "Selective stimulation of Hepatitis C Virus and Pestivirus NS5B RNA Polymerase Activity by GTP," 274(16) The Journal of Biological Chemistry 10807-15 (1999).
W. Clark Still et al., "Rapid Chromatographic Technique for Preparative Separations with Moderate Resolution," 43(14) Journal of Organic Chemistry 2923-25 (1978).

(Continued)

*Primary Examiner* — Bruck Kifle
(74) *Attorney, Agent, or Firm* — Sheldon O. Heber; Julia M. Lake

(57) ABSTRACT

A class of macrocyclic compounds of formula (I), wherein $R^7$, A, Ar, B, D, F, M, $Q^1$, $Q^2$, W, X, Y and Z are defined herein, that are useful as inhibitors of viral proteases, particularly the hepatitis C virus (HCV) NS3 protease, are provided. Also provided are processes for the synthesis and use of such macrocyclic compounds for treating or preventing HCV infection.

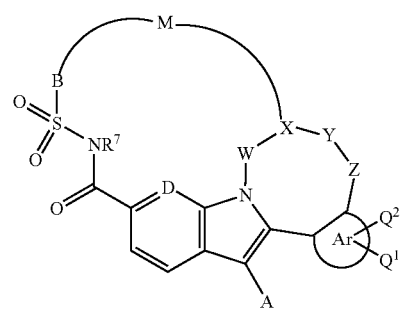

(I)

24 Claims, No Drawings

U.S. PATENT DOCUMENTS

2007/0060565 A1    3/2007    Meanwell et al.

FOREIGN PATENT DOCUMENTS

| | | |
|---|---|---|
| GB | 2337262 A | 11/1999 |
| GB | 2430621 A | 4/2007 |
| WO | WO9300334 A1 | 1/1993 |
| WO | WO9637619 A1 | 11/1996 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | WO0068216 A1 | 11/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | WO0259321 A2 | 8/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | WO03099824 A1 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | WO2004065367 A1 | 8/2004 |
| WO | WO2004087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | WO2005080388 A1 | 9/2005 |
| WO | WO2005080399 A1 | 9/2005 |
| WO | 2006/008556 A1 | 1/2006 |
| WO | WO2006007693 A1 | 1/2006 |
| WO | WO2006020082 A1 | 2/2006 |
| WO | 2006/021341 A1 | 3/2006 |
| WO | 2006/027628 A2 | 3/2006 |
| WO | WO2006029912 A1 | 3/2006 |
| WO | WO2006046030 A2 | 5/2006 |
| WO | WO2006046039 A1 | 5/2006 |
| WO | WO2006052013 A1 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | WO2007029029 A2 | 3/2007 |
| WO | WO2007033032 A1 | 3/2007 |
| WO | WO2007033175 A1 | 3/2007 |
| WO | WO2007054741 A1 | 5/2007 |
| WO | 2007/131966 A1 | 11/2007 |
| WO | WO2007129119 A1 | 11/2007 |
| WO | WO2007131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/075103 A1 | 6/2008 |
| WO | WO2008101665 A1 | 8/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

J.M. Travins & F.A. Etzkorn, "Facile synthesis of D-amino acids from an L-serine-derived axiridine," 39 Tetrahedron Letters 9389-92 (1998).

Tim Mosmann, "Rapid Colorimetric Assay for Cellular Growth and Survival: Application to Proliferation and Cytotoxicity Assays," 65 Journal of Immunological Methods 55-63 (1983).

Paul Blaney et al., "Fused and bridged bi- and tri-cyclic lactams via sequential metallo-azomethine ylide cycloaddition-lactamisation," 58(9) Tetrahedron 1719(37) (2002).

Jean-Yves Winum et al., "N-(tert-Butoxycarbonyl)-N-[4-(dimethylazaniumylidene)-1,4-dihydropyridin-1-ylsulfonyl] azanide: A New Sulfamoylating Agent. Structure and Reactivity toward Amines," 3(14) Organic Letters 2241-2243 (2001).

Eric P. Gillis & Martin D. Burke, "A Simple and Modular Strategy for Small Molecule Synthesis: Iterative Suzuki-Miyaura Coupling of B-Protected Haloboronic Acid Building Blocks," 129(21) Journal of the American Chemical Society 6716-17 (2007).

Ana Martinez et al., "Benzothiadiazine Dioxides (BTD) Derivatives as Non-nucleoside Human Cytomegalovirus (HCMV) Inhibitors. Study of Structural Requirements for Biological Activity," 11(11) Bioorganic & Medicinal Chemistry 2395-402 (2003).

A. Srikrishna et al., "Enantiospecific construciton of the BC-ring system of taxanes," 45(14) Tetrahedron Letters 2939-42 (2004).

Nathalie Goudreau & Montse Llinas-Brunet, "The therapeutic potential of NS3 protease inhibitors in HCV infection," 14(9) Expert Opinion on Investigational Drugs 1129-44 (2005).

Gennadiy Koev & Warren Kati, "The emerging field of HCV drug resistance," 17(3) Expert Opinion on Investigational Drugs 303-19 (2008).

R. Jennifer Randall, "Hepatitis C Virus Infection and Long-Term Survivors of Childhood Cancer: Issues for the Pediatric Oncology Nurse," 18(1) Journal of Pediatric Oncology Nursing 4-15 (2001).

Michael J. Szymonifka & James V. Heck, "The Synthesis and Reactions of 4-Carbomethoxy Betat-Sultams," 30(22) Tetrahedron Letters 2869-72 (1989).

Albert Padwa et al., "Transmutation of 1,3-Dipoles. The Conversion of Alpha-Diazo Ketones into Azomethine Ylides via Carbonyl Ylides," 114(2) Journal of the American Chemical Society 593-601 (1992).

Gulam A. Bahadur et al., "The Reactions of Four Derivatives of Pyrrolo[1,2-a]indole with Arene-sulfonyl Azides," 12 Journal of the American Chemical Society: Perkins Transactions 1 2870-77 (1980).
"Prophylactic treatment from online medical dictionary," http://cancerweb.nc.ac.uk/cgi-bin/omd?prophylactic+treatment, accessed May 7, 2007.
Stacey R. Vlahakis, "Human Immunodeficiency Virus (HIV) Disease: Human Immunodeficiency Virus and Hepatitis C Virus Coinfection," 54(2) Lebanese Medical Journal 106-10 (2006).
T. Asselah et al., "Steatosis in Chronic Hepatitis C: Why Does It Really Matter," 55 Gut 123-30 (2006).
Brian W Dymock et al., "Novel Approaches to the Treatment of Hepatitis C Virus Infection," 11 Antiviral Chemistry & Chemotherapy 79-96 (2000).
Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
Scott J. Miller et al., "Application of Ring-Closing Metathesis to the Synthesis of Rigidified Amino Acids and Peptides," 118 J. Am. Chem. Soc. 9606-14 (1996).
Jason S. Kingsbury et al., "A Recyclable Ru-Based Metathesis Catalyst," 121 J. Am. Chem. Soc. 791-99 (1999).
Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).
Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
Ashok Arasappan et al., "P2-P4 Macrocyclic inhibitors of hepatitis C virus NS3-4A serine protease," 16 Bioorganic & Medicinal Chemistry Letters 3960-65 (2006).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)-Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).
Marc-Andre Poupart et al., "Solid-Phase Synthesis of Peptidomimetic Inhibitors for the Hepatitis C Virus NS3 Protease," 66(14) J. Org. Chem. 4743-51 (2001).
Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).
T. K. Chakaborty et al., "Alpha-Phenylglycinol as chiral auxilliary in diastereoselective Strecker synthesis of alpha-amino acids," 51(33) Tetrahedron 9179-90 (1995).
John A. McCauley et al., "Bismacrocyclic Inhibitors of Hepatitis C NS3/4a Protease," 47 Angew. Chem. Int. Ed. 9104-07 (2008).
Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).
Paul Aeberli et al., "Neuropharmacological investigation of N-benzylsulfamides," 10(4) J. Med. Chem. 636-42 (1967).
Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).
Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).
Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).
Kevin X. Chen et al. "Novel Potent Hepatitis C Virus NS3 Serine Protease Inhibitors Derived from Proline-Based Macrocycles," 49 J. Med. Chem. 995-1005 (2006).
Yuri Goldberg et al., "Highly regioselective bromination of 2,3-dimethylanisole with N-bromosuccinimide," 57 J. Org. Chem. 6374-76 (1992).
Manfred Schlosser et al., "8-Methoxyisoquinoline derivatives through ortho-selective metallation of 2-(3-methoxyphenyl)ethylamines," 32(17) Tetrahedron Letters 1965-66 (1991).
Angela Casini et al., "Carbonic Anhydrase inhibitors inhibition of cytosolic isozymes I and II with sulfamide derivatives," 13(5) Bioorg. Med. Chem. Lett. 837-40 (2003).
Kiyotaka Onisuka et al., "A novel route to 2,3-disubstituted indoles via palladium-catalyzed three-component coupling of aryl iodide, o-alkenlyphenyl isocyanide and amine," 43 Tetrahedron Letters 6197-99 (2002).
Duane E. Rudisill & J. K. Stille, "Palladium-catalyzed synthesis of 2-substituted indoles," 54(25) J. Org. Chem. 5856-66 (2002).
Youwei YAN et al., Complex of NS3 protease and NS4A peptide of BK strain hepatitis C virus: A 2.2 Angstrom resolution structure in a hexagonal crystal form, 7 Protein Science 837 (1998).
Non-Final Office Action mailed on Nov. 19, 2009 in U.S. Appl. No. 12/002,996.
Amendment filed on Feb. 17, 2010 in U.S. Appl. No. 12/002,996.

* cited by examiner

THERAPEUTIC COMPOUNDS

CROSS REFERENCE TO RELATED APPLICATION

This application is a continuation-in-part of International Application No. PCT/GB2008/050555, entitled "Therapeutic Compounds" filed Jul. 9, 2008, and claims priority under 35 U.S.C. §119(a) to GB Application No. 0713865.4, filed Jul. 17, 2007 and to GB Application No. 0724635.8, filed Dec. 19, 2007, and claims priority under 35 U.S.C. §119(e) to U.S. Provisional Application Ser. No. 61/008,231, filed Dec. 19, 2007, each of the prior applications, including the International Application, are herein incorporated by reference in their entirety.

BACKGROUND OF THE INVENTION

The present invention relates to macrocyclic indole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit.

Published International applications WO2006/046030 and WO2006/046039 (both Istituto Di Ricerche Di Biologia Molecolare P. Angeletti SpA) disclose certain tetracyclic indole derivatives:

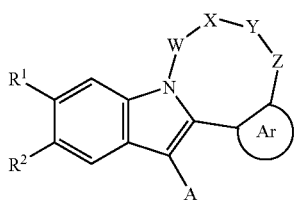

wherein $R^1$, $R^2$, A, Ar, W, X, Y, and Z are defined therein, useful for the treatment or prevention of infection by hepatitis C virus. Published International applications WO2007/029029 and WO2007/054741 (both Istituto Di Ricerche Di Biologia Molecolare P. Angeletti SpA) disclose structurally related tetracyclic indole derivatives, useful for the treatment or prevention of infection by hepatitis C virus.

SUMMARY OF THE INVENTION

We have now discovered a class of macrocyclic indole derivatives useful for the treatment or prevention of infection by hepatitis C virus.

Thus, the present invention provides the compound of the formula (I):

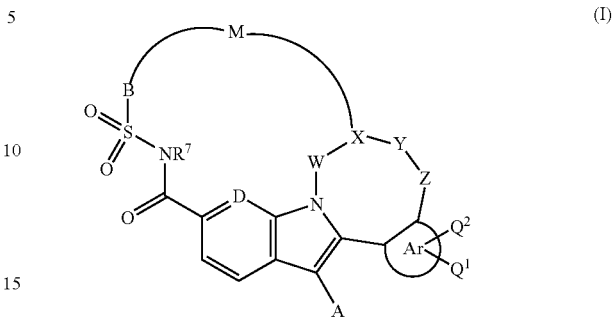

(I)

wherein Ar is a moiety containing at least one aromatic ring and possesses 5-, 6-, 9- or 10-ring atoms optionally containing 1, 2 or 3 heteroatoms independently selected from N, O and S, $Q^1$ is hydrogen, halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^cR^d$; $R^a$ and $R^b$ are each independently selected from hydrogen, $C_{1-4}$ alkyl and $C(O)C_{1-4}$ alkyl; or $R^a$, $R^b$ and the nitrogen atom to which they are attached form a heteroaliphatic ring of 4 to 7 ring atoms, where said ring is optionally substituted by halogen, hydroxy, $C_{1-4}$ alkyl or $C_{1-4}$ alkoxy; $R^c$ and $R^d$ are each independently selected from hydrogen, $C_{1-6}$ alkyl or $C_{1-6}$ alkoxy; or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$ alkyl or $C_{1-4}$ alkoxy; and wherein said alkyl, alkoxy and aryl groups are optionally substituted by halogen or hydroxy; $R^e$ is hydrogen or $C_{1-6}$ alkyl; $R^f$ is hydrogen, $C_{1-6}$alkyl; $Q^2$ is hydrogen, halogen, hydroxy, $C_{1-4}$alkyl or $C_{1-4}$ alkoxy, where said $C_{1-4}$ alkyl and $C_{1-4}$ alkoxy groups are optionally substituted by halogen or hydroxy; or $Q^1$ and $Q^2$ may be linked by a bond or a heteroatom selected from N, O and S to form a ring of 4 to 7 atoms, where said ring is optionally substituted by halogen, hydroxy, $C_{1-4}$ alkyl or $C_{1-4}$ alkoxy;

A is $C_{3-6}$ alkyl or $C_{2-6}$ alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$ alkyl or $C_{1-4}$ alkoxy;

D is N or $CR^8$; $R^8$ is hydrogen, fluorine, chlorine, $C_{1-4}$ alkyl, $C_{2-4}$ alkenyl or $C_{1-4}$ alkoxy, where said $C_{1-4}$ alkyl, $C_{2-4}$ alkenyl and $C_{1-4}$ alkoxy groups are optionally substituted by hydroxy or fluorine;

W is a bond, C=O, O, $S(O)_{0-2}$ or $-(CR^{10}R^{11})-(CR^{12}R^{13})_{0-1}-$;

Y is a bond, C=O, O, $-CR^{14}R^{15}-$ or $NR^{14}$;

Z is a bond, C=O, O, $S(O)_{0-2}$, $-(CR^{10}R^{11})-(CR^{12}R^{13})_{0-1}-$ or $NR^{10}$;

and none, one or two of W, Y and Z are a bond;

X is $-C(R^9)-$ or N;

$R^9$, $R^{10}$, $R^{11}$, $R^{12}$, $R^{13}$, $R^{14}$ and $R^{15}$ are each independently selected from hydrogen, hydroxy, fluoro, $C_{1-6}$ alkyl, $C_{2-6}$ alkenyl, $C_{1-6}$ alkoxy, $C(O)C_{1-6}$ alkyl, a heteroaliphatic ring of 4 to 7 ring atoms, which ring may contain 1, 2 or 3 heteroatoms selected from N, O or S or a group S(O), $S(O)_2$, NH or $NC_{1-4}$alkyl $(CH_2)_{0-3}NR^{16}R^{17}$, $C(O)(CH_2)_{0-3}NR^{16}R^{17}$, NHC $(O)(CH_2)_{0-3}NR^{16}R^{17}$, $O(CH_2)_{1-3}NR^{16}R^{17}$, $S(O)_{0-2}(CH_2)_{0-3}NR^{16}R^{17}$ and $C(O)(CH_2)_{0-3}OR^{16}$; or one of $R^{10}$, $R^{14}$ and $R^9$ is linked to $R^{20}$ or $R^{21}$ to form a ring of 4 to 10 atoms, where said ring is optionally substituted by halogen, hydroxy, $C_{1-4}$ alkyl or $C_{1-4}$ alkoxy; or, when X is —$CR^9$— and Z is —$CR^{10}R^{11}$— or $NR^{10}$, $R^{10}$ is joined to $R^9$ to form a —$(CH_2)$—$_{1-4}$ group, optionally substituted by $C_{1-4}$ alkyl; or when X is —$CR^9$—, $R^9$ is joined with an atom of the linker M to form an aliphatic ring of 4-7 ring atoms, said aliphatic ring optionally containing one or two heteroatoms selected from O, N or S or a group $S(O)$, $S(O)_2$, NH or $NC_{1-4}$alkyl;

$R^{16}$ and $R^{17}$ are independently selected from hydrogen, $C_{1-6}$ alkyl and $(CH_2)_{0-4}NR^{18}R^{19}$; or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$ alkyl, and which ring is optionally substituted by halogen, hydroxy, $C_{1-4}$ alkyl or $C_{1-4}$ alkoxy;

$R^{18}$ and $R^{19}$ are independently selected from hydrogen and $C_{1-6}$alkyl; or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$ alkyl, and which ring is optionally substituted by halogen, hydroxy, $C_{1-4}$ alkyl or $C_{1-4}$ alkoxy;

$R^7$ is hydrogen or $C_{1-6}$ alkyl;

B is $N(R^{20})$— and M is $C_{3-7}$ alkylene or $C_{3-7}$ alkenylene, optionally substituted by $R^{21}$, where 1 or 2 of the carbon atoms in the $C_{3-7}$ alkylene or $C_{3-7}$ alkenylene groups is optionally replaced by O, $NR^{22}$, S, SO, $SO_2$, piperidinyl, piperazinyl, homopiperazinyl or pyrrolidinyl, where $R^{20}$ and $R^{22}$ are each independently hydrogen, $C_{1-6}$ alkyl, $C_{2-6}$ alkenyl, $(CH_2)_{0-3}C_{3-6}$ cycloalkyl, $(CH_2)_{1-3}OH$, $C_{1-6}$ alkoxy, $C(O)C_{1-6}$ alkyl, $(CH_2)_{0-3}$aryl, $(CH_2)_{0-3}Het$, $(CH_2)_{0-3}$heteroaryl, $(CH_2)_{1-3}NR^{16}R^{17}$, $C(O)(CH_2)_{1-3}NR^{16}R^{17}$, $S(O)_{0-2}(CH_2)_{1-3}NR^{16}R^{17}$, $C(O)(CH_2)_{1-3}OR^{16}$, $(CH_2)_{1-3}$—$O$—$(CH_2)_{0-3}$aryl, or $R^{20}$ is linked to one of $R^{10}$, $R^{14}$ and $R^9$ to form a ring of 4 to 10 atoms as hereinbefore described; or where 1 or 2 of the carbon atoms in the $C_{3-7}$alkylene or $C_{3-7}$ alkenylene group are replaced by $NR^{22}$, then the $R^{20}$ and $R^{22}$ groups can be joined to form a —$(CH_2)$—$_{1-3}$ group, optionally substituted by $C_{1-2}$alkyl, where $R^{21}$ is halo, $C_{1-4}$alkyl, $(CH_2)_{0-3}C_{3-8}$cycloalkyl, $(CH_2)_{0-3}$aryl, $(CH_2)_{0-3}$heteroaryl, $(CH_2)_{0-3}$Het, oxo or $(CH_2)_{0-3}NR^{16}R^{17}$, or $R^{21}$ is linked to one of $R^{10}$, $R^{14}$ and $R^9$ to form a ring of 4 to 10 atoms as hereinbefore described;

and pharmaceutically acceptable salts thereof.

DETAILED DESCRIPTION OF THE INVENTION

In one embodiment of the present invention, Ar is a five- or six-membered aromatic ring optionally containing 1, 2 or 3 heteroatoms independently selected from N, O and S, and which ring is optionally substituted by groups $Q^1$ and $Q^2$ as hereinbefore defined.

Preferably, Ar is a five- or six-membered aromatic ring optionally containing 1 or 2 heteroatoms independently selected from N, O or S, such as phenyl, pyridyl, pyridazinyl, pyrimidinyl, pyrazinyl, furanyl, pyrazolyl, imidazolyl and thienyl, which ring is optionally substituted by groups $Q^1$ and $Q^2$ as hereinbefore defined. More preferably, Ar is phenyl, pyridyl, or furanyl, particularly phenyl, optionally substituted by groups $Q^1$ and $Q^2$ as hereinbefore defined.

Suitably, A is unsubstituted or substituted by fluorine, chlorine, methyl or methoxy, particularly fluorine. More suitably, A is unsubstituted or substituted by fluorine. Examples of suitable A groups include cyclohexyl, cyclopentyl and fluorocyclohexyl, especially 2-fluorocyclohexyl. Preferably A is cyclohexyl.

In a further embodiment, D is $CR^8$ where $R^8$ is as hereinbefore defined. Preferably, $R^8$ is hydrogen or $C_{1-4}$ alkyl. More preferably, $R^8$ is hydrogen.

In a preferred embodiment, the present invention provides the compound of the formula (II):

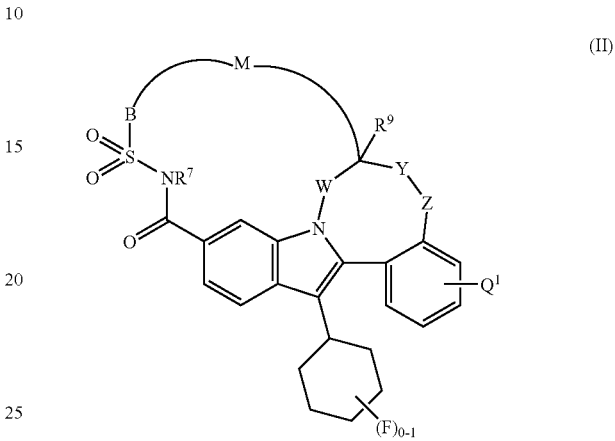

(II)

wherein $Q^1$ is hydrogen, halogen, hydroxy, a group $(O)_{0-1}(CR^gR^h)_{0-4}R^i$ wherein $R^g$ is hydrogen or $C_{1-6}$ alkyl; $R^h$ is hydrogen or $C_{1-6}$ alkyl; and $R^i$ is hydrogen, $C_{1-5}$alkyl optionally substituted by $C_{3-6}$ cycloalkyl, or $R^i$ is aryl, $C_{1-6}$ alkoxy, heteroaryl or a 4-, 5-, 6- or 7-membered heteroaliphatic ring optionally substituted by halogen, hydroxy, $C_{1-4}$ alkyl or $C_{1-4}$ alkoxy, or a group $NR^jR^k$, or $CONR^jR^k$, wherein $R^j$ and $R^k$ are each independently selected from hydrogen, $C_{1-4}$ alkyl and $C(O)C_{1-4}$ alkyl; or $R^j$, $R^k$ and the nitrogen atom to which they are attached form a heteroaliphatic ring of 4 to 7 ring atoms optionally substituted by halogen, hydroxy, $C_{1-4}$ alkyl or $C_{1-4}$ alkoxy; and wherein said alkyl, alkoxy, heteroaryl and aryl groups are optionally substituted by halogen or hydroxy;

$A^1$ is cyclohexyl, cyclopentyl or fluorocyclohexyl, especially 2-fluorocyclohexyl;

W is a bond, C=O, O, $S(O)_{0-2}$ or —$(CR^{10}R^{11})$—$(CR^{12}R^{13})_{0-1}$—;

Y is a bond, C=O, O, —$CR^{14}R^{15}$— or $NR^{14}$;

Z is a bond, C=O, O, $S(O)_{0-2}$, —$(CR^{10}R^{11})$—$(CR^{12}R^{13})_{0-1}$— or $NR^{10}$;

and none, one or two of W, Y and Z are a bond;

$R^9$ is a bond, hydrogen, fluoro or hydroxyl;

$R^{10}$, $R^{11}$, $R^{12}$, $R^{13}$, $R^{14}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, a heteroaliphatic ring of 4 to 7 ring atoms containing 1, 2 or 3 heteroatoms selected from N, O or S or a group $S(O)$, $S(O)_2$, NH or $NC_{1-4}$alkyl, $(CH_2)_{0-3}NR^{16}R^{17}$, or $R^{10}$, $R^{11}$, $R^{12}$, $R^{13}$, $R^{14}$ and $R^{15}$ are each independently selected from $(CH_2)_{0-3}NR^{16}R^{17}$, $C(O)(CH_2)_{0-3}NR^{16}R^{17}$, $NR^1C(O)(CH_2)_{0-3}NR^{16}R^{17}$ where $R^1$ is hydrogen or $C_{1-4}$ alkyl, such as methyl, $O(CH_2)_{1-3}NR^{16}R^{17}$, $S(O)_{0-2}(CH_2)_{0-3}NR^{16}R^{17}$, $C(O)(CH_2)_{0-3}OR^{16}$ and $NMeC(O)(CH_2)_{0-3}NR^{16}R^{17}$; or one of $R^{10}$, $R^{14}$ and $R^9$ is linked to $R^{20}$ or $R^{21}$ to form a 4-10 membered carbocyclic ring, where said ring is optionally substituted by halogen, hydroxy, $C_{1-4}$alkyl or $C_{1-4}$alkoxy; or, when Z is —$CR^{10}R^{11}$— or $NR^{10}$, $R^{10}$ is joined to $R^9$ to form a —$(CH_2)$—$_{1-4}$ group, optionally substituted by $C_{1-4}$alkyl; or $R^9$ is joined with an atom of the linker M to form an aliphatic ring of 4-7 ring atoms, said aliphatic ring optionally containing one or two heteroatoms selected from O, N or S or a group S(O), S(O)$_2$, NH or NC$_{1-4}$alkyl;
R$^{16}$ and R$^{17}$ are independently selected from hydrogen, C$_{1-6}$alkyl and (CH$_2$)$_{0-4}$NR$^{18}$R$^{19}$; or R$^{16}$, R$^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
R$^{18}$ and R$^{19}$ are independently selected from hydrogen and C$_{1-6}$alkyl; or R$^{18}$, R$^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
R$^7$ is hydrogen or C$_{1-6}$alkyl;
B is N(R$^{20}$)— and R$^{20}$ is hydrogen, C$_{1-6}$alkyl optionally substituted by 1-3 fluoro, C$_{2-6}$alkenyl, (CH$_2$)$_{0-3}$C$_{3-6}$cycloalkyl, (CH$_2$)$_{1-3}$OH, C$_{1-6}$alkoxy, C(O)C$_{1-6}$alkyl, (CH$_2$)$_{0-3}$aryl, (CH$_2$)$_{0-3}$Het, (CH$_2$)$_{0-3}$heteroaryl, (CH$_2$)$_{1-3}$NR$^{16}$R$^{17}$, C(O)(CH$_2$)$_{1-3}$NR$^{16}$R$^{17}$, S(O)$_{0-2}$(CH$_2$)$_{1-3}$NR$^{16}$R$^{17}$, C(O)(CH$_2$)$_{1-3}$OR$^{16}$, (CH$_2$)$_{1-3}$—O—(CH$_2$)$_{0-3}$aryl, or R$^{20}$ is linked to one of R$^{10}$, R$^{14}$ and R$^9$ to form a ring of 4 to 10 atoms as hereinbefore described, or R$^{20}$ and one of the R$^{21}$ groups can be joined to form a —(CH$_2$)—$_{1-3}$ group, optionally substituted by C$_{1-2}$alkyl;
and M is C$_{3-7}$alkylene or C$_{3-7}$alkenylene, optionally substituted by one or two groups R$^{21}$, which can be substituents on the same carbon atom, where R$^{21}$ is halo, C$_{1-4}$ alkyl optionally substituted by 1-3 fluoro, (CH$_2$)$_{0-3}$C$_{3-8}$cycloalkyl, (CH$_2$)$_{0-3}$ aryl, (CH$_2$)$_{0-3}$heteroaryl, (CH$_2$)$_{0-3}$Het, oxo or (CH$_2$)$_{0-3}$ NR$^{16}$R$^{17}$, or R$^{21}$ is linked to one of R$^{10}$, R$^{14}$ and R$^9$ to form a ring of 4 to 10 atoms as hereinbefore described or R$^{20}$ and one of the R$^{21}$ groups can be joined to form a —(CH$_2$)—$_{1-3}$ group, optionally substituted by C$_{1-2}$alkyl as herebefore described;
and 1, 2 or 3 of the carbon atoms in the C$_{3-7}$alkylene or C$_{3-7}$alkenylene groups is optionally replaced by O, NR$^{22}$, S, SO, SO$_2$, piperidinyl, piperazinyl, homopiperazinyl or pyrrolidinyl;
and each group R$^{22}$ is independently hydrogen, C$_{1-6}$ alkyl optionally substituted with 1-3 fluoro, C$_{2-6}$ alkenyl, (CH$_2$)$_{0-3}$ C$_{3-6}$cycloalkyl, (CH$_2$)$_{1-3}$OH, C$_{1-6}$ alkoxy, C(O)C$_{1-6}$ alkyl, (CH$_2$)$_{0-3}$aryl, (CH$_2$)$_{0-3}$Het, (CH$_2$)$_{0-3}$heteroaryl, (CH$_2$)$_{1-3}$ NR$^{16}$R$^{17}$, C(O)(CH$_2$)$_{1-3}$NR$^{16}$R$^{17}$, (CH$_2$)$_{1-3}$C(O)NR$^{16}$R$^{17}$, S(O)$_{0-2}$(CH$_2$)$_{0-3}$NR$^{16}$R$^{17}$, C(O)(CH$_2$)$_{1-3}$OR$^{16}$, (CH$_2$)$_{1-3}$O (CH$_2$)$_{0-4}$aryl, or where 1, 2 or 3 of the carbon atoms in the C$_{3-7}$alkylene or C$_{3-7}$ alkenylene group are replaced by NR$^{22}$, then the R$^{20}$ and R$^{22}$ groups can be joined to form a —(CR$_2$)—$_{1-3}$ group, optionally substituted by C$_{1-2}$alkyl;
and pharmaceutically acceptable salts thereof.
Preferably, Q$^1$ is hydrogen, halogen, hydroxy, C$_{1-6}$ alkyl, C$_{1-6}$alkoxy
or O$_{0-1}$(CH$_2$)$_{0-3}$R$^{23}$ where R$^{23}$ is a 5- or 6-membered heteroaliphatic ring, such as pyrrolidine or piperidine, or heteroaryl, such as pyridyl. More preferably, Q$^1$ is hydrogen, O—CH$_2$-(2-pyridyl), O—CH$_2$CH$_2$-(1-pyrrolidine), halogen, hydroxy, C$_{1-4}$ alkyl or C$_{1-4}$ alkoxy. Most preferably, Q$^1$ is hydrogen, O—CH$_2$-(2-pyridyl), O—CH$_2$CH$_2$-(1-pyrrolidine), fluorine, chlorine, methyl or methoxy. Suitable examples of Q$^1$ groups, when this is other than hydrogen, are O—CH$_2$-(2-pyridyl), O—CH$_2$CH$_2$-(1-pyrrolidine), methoxy, methyl and fluorine.
Preferably, Q$^2$ is hydrogen.
When a group Q is other than hydrogen, examples of preferred Q positions are:

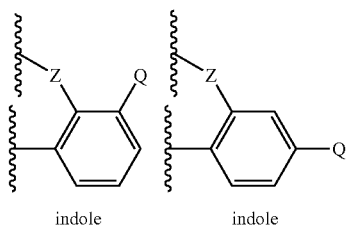

indole    indole

Preferably R$^7$ is hydrogen.
Preferably R$^9$ is hydrogen.
Preferably A$^1$ is cyclohexyl.
Suitably R$^{20}$ is hydrogen, C$_{1-6}$alkyl optionally substituted by 1-3 fluoro
or R$^{20}$ and one of the R$^{21}$ groups or R$^{20}$ and R$^{22}$ can be joined to form a —(CH$_2$)—$_{1-3}$ group, optionally substituted by C$_{1-2}$alkyl. More suitably, R$^{20}$ is methyl or R$^{20}$ and one of the R$^{21}$ groups or R$^{20}$ and R$^{22}$ can be joined to form a —(CH$_2$)$_2$— group.
Preferably R$^{20}$ is methyl.
In a further embodiment, W is a bond, C=O or —(CR$^{10}$R$^{11}$)—(CR$^{12}$R$^{13}$)$_{0-1}$— where R$^{10}$, R$^{11}$, R$^{12}$ and R$^{13}$ are as hereinbefore defined. Preferably, W is —(CR$^{10}$R$^{11}$)—(CR$^{12}$R$^{13}$)$_{0-1}$—. More preferably, W is —CH$_2$— or —CH$_2$CH$_2$—. Most preferably, W is —CH$_2$—.
In a further embodiment, Z is a bond, C=O, O, —(CR$^{10}$R$^{11}$)—(CR$^{12}$R$^{13}$)$_{0-1}$— or NR$^{10}$ where R$^{10}$, R$^{11}$, R$^{12}$ and R$^{13}$ are as hereinbefore defined. Preferably, Z is a bond, O or —(CR$^{10}$R$^{11}$)—(CR$^{12}$R$^{13}$)$_{0-1}$—. More preferably, Z is a bond, O, —H$_2$— or NR$^{10}$— wherein R$^{10}$ is as hereinbefore defined. Preferably R$^{10}$ is methyl. Most preferably, Z is O, Suitable examples of Z groups are O, NCH$_3$ and CH$_2$.
In a further embodiment, Y is a bond, C=O, O, —CR$^{14}$R$^{15}$— or NR$^{14}$ where R$^{14}$ and R$^{15}$ are as hereinbefore defined. Preferably, Y is C=O, O, CR$^{14}$R$^{15}$— or —NR$^{14}$. More preferably, Y is O, —CR$^{14}$R$^{15}$— or NR$^{14}$. Most preferably, Y is —CH$_2$—, NH, N(C$_{1-6}$alkyl), NCH$_2$CH$_2$N(C$_{1-6}$alkyl)$_2$ or NC(O)(CH$_2$)$_{1-2}$N(C$_{1-6}$alkyl)$_2$. Especially, Y is —CH$_2$—, NH, N(C$_{1-4}$alkyl), N(CH$_2$)$_2$N(C$_{1-4}$alkyl)$_2$ or NC(O)CH$_2$N(C$_{1-4}$alkyl)$_2$. More especially, Y is —CH$_2$—, NCH$_3$ or N(CH$_2$)$_2$N(CH$_3$)$_2$. Most especially, Y is —CH$_2$—. Suitable examples of Y groups are CH$_2$ and a bond.
In a further embodiment, M is C$_{3-7}$ alkylene, optionally substituted by one or two halo such as fluoro, C$_{1-4}$ alkyl or oxo, and where one or two of the carbon atoms in the C$_{3-7}$ alkylene group is optionally replaced by O, NR$^{22}$, S, SO or SO$_2$, where R$^{22}$ is as hereinbefore defined. Preferably, M is C$_{3-7}$alkylene, optionally substituted by one or two halo, such as fluoro, C$_{1-4}$alkyl, such as methyl, or oxo, and where one or two of the carbon atoms in the C$_{3-7}$ alkylene group is optionally replaced by O, NR$^{22}$, S, SO or SO$_2$, where R$^{22}$ is hydrogen, C$_{1-6}$alkyl optionally substituted by one, two or three fluoro, (CH$_2$)$_{0-3}$C$_{3-6}$cycloalkyl, (CH$_2$)$_{1-3}$OH, (CH$_2$)$_{0-3}$aryl, (CH$_2$)$_{0-3}$heteroaryl such as pyrazolyl, (CH$_2$)$_{1-3}$NR$^{16}$R$^{17}$, C(O)(CH$_2$)$_{1-3}$NR$^{16}$R$^{17}$, (CH$_2$)$_{1-3}$C(O)NR$^{16}$R$^{17}$ or (CH$_2$)$_{1-3}$O (CH$_2$)$_{0-3}$aryl, where R$^{16}$ and R$^{17}$ are as hereinbefore defined. More preferably, M is C$_{3-7}$ alkylene, optionally substituted by methyl or gem dimethyl or gem difluoro, and where one or two of the carbon atoms in the C$_{3-7}$alkylene group is replaced by O or NR$^{22}$, where R$^{22}$ is hydrogen, C$_{1-4}$ alkyl, (CH$_2$)C$_{3-6}$ cycloalkyl, (CH$_2$)$_2$OH, CH$_2$phenyl, CH$_2$pyridyl, (CH$_2$)$_2$ NR$^{16}$R$^{17}$, C(O)CH$_2$NR$^{16}$R$^{17}$, CH$_2$C(O)NR$^{16}$R$^{17}$, (CH$_2$) pyrazolyl, (CH$_2$)$_2$F or (CH$_2$)$_2$OCH$_2$-phenyl, where R$^{16}$ and R$^{17}$ are each hydrogen or C$_{1-4}$ alkyl or R$^{16}$ and R$^{17}$ are linked to form a nitrogen containing heteroaliphatic ring containing 4 to 7 ring members. Preferably M is a chain of six or seven atoms chosen from carbon, nitrogen and oxygen optionally substituted as hereinbefore described, at least one of the atoms being nitrogen and optionally one of the atoms being nitrogen or oxygen, the rest being carbon. In one embodiment of the invention, there is a nitrogen atom in the chain two atoms from B and a nitrogen or oxygen atom adjacent to X, the other atoms being carbon.

Examples of suitable B-M-X combinations (where X is —CR$^9$—) are:

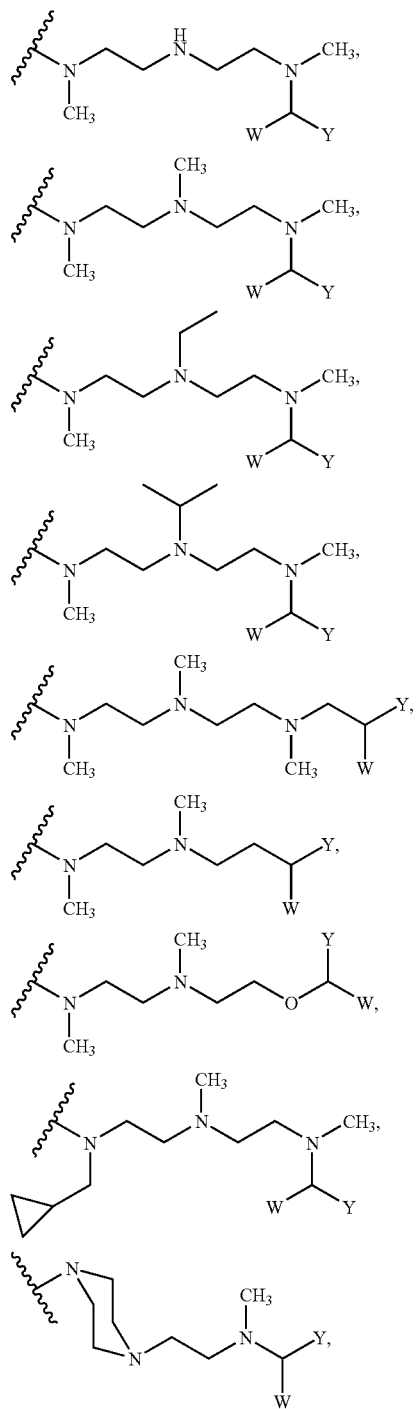

-continued

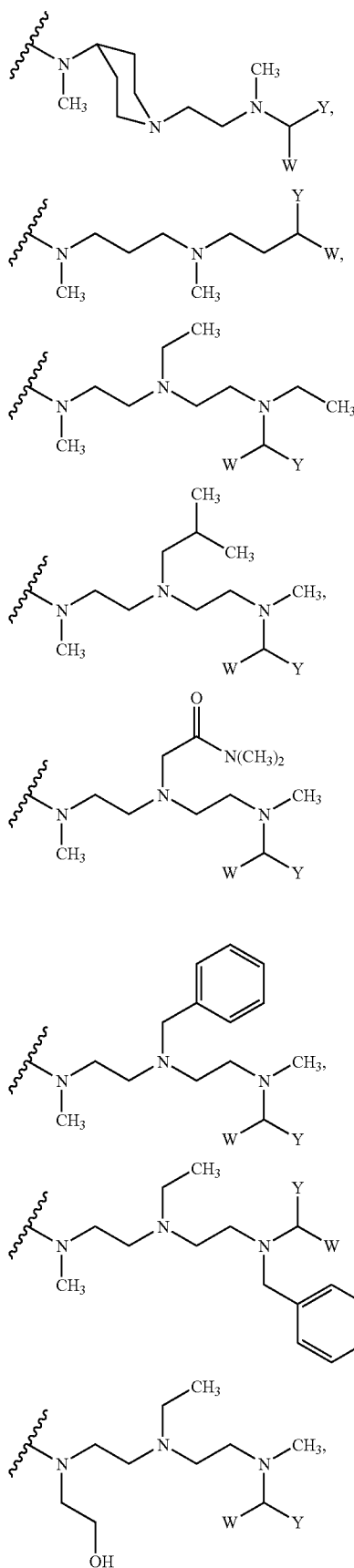

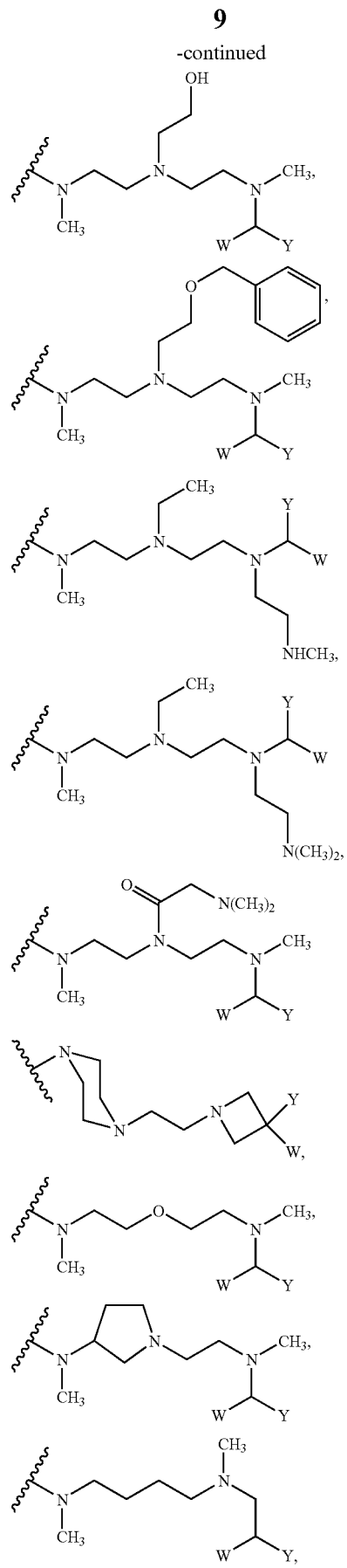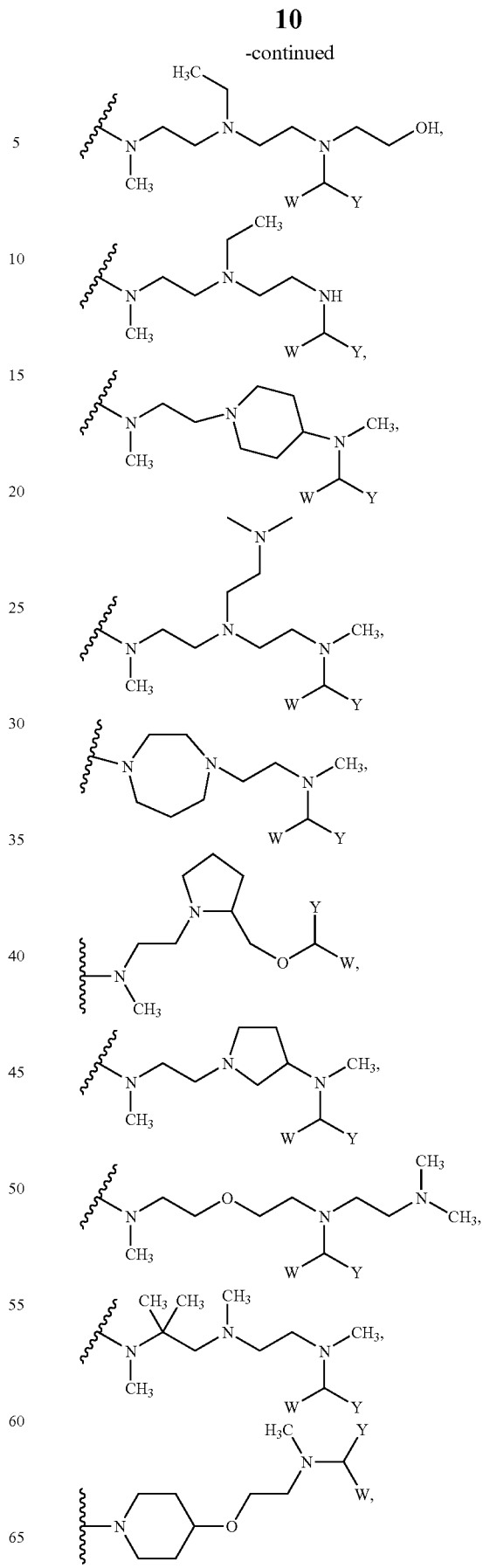

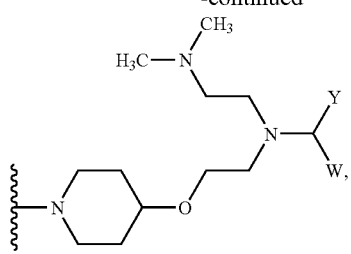
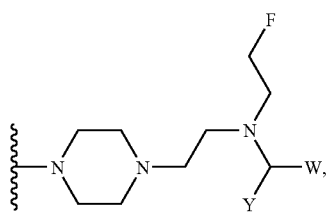
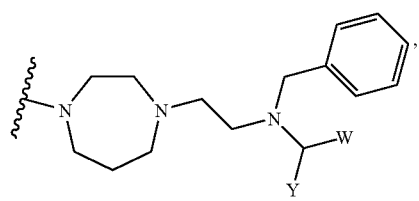
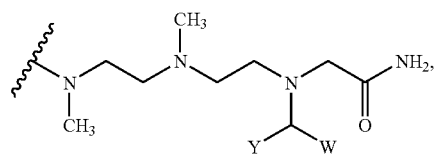
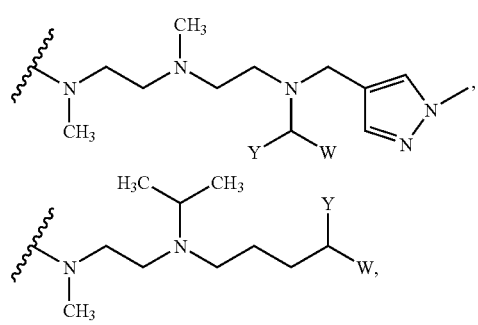
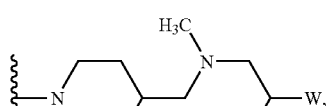
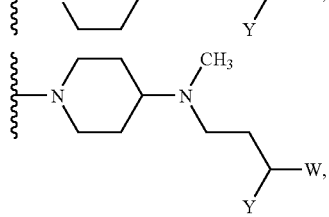
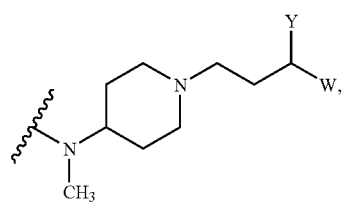
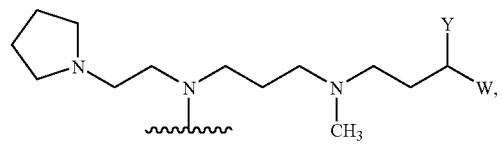
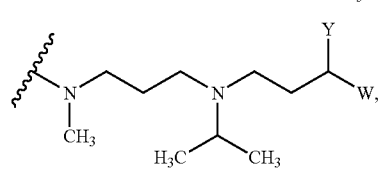
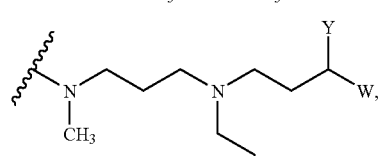
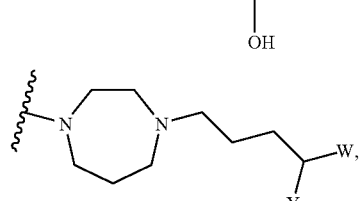
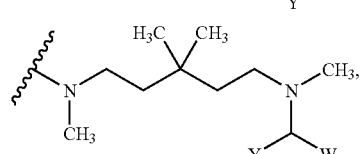
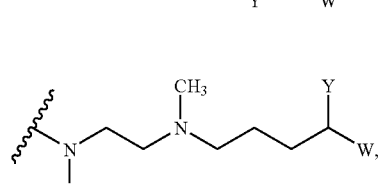
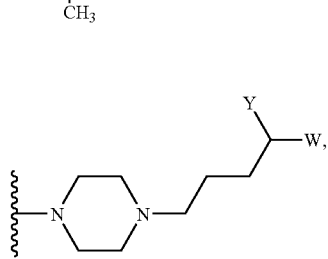
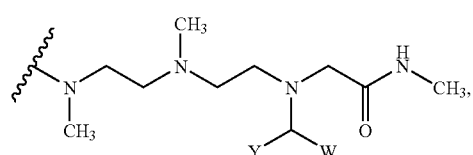
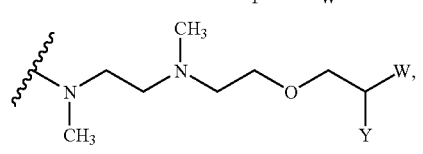
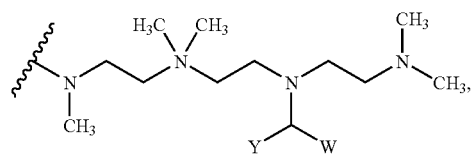

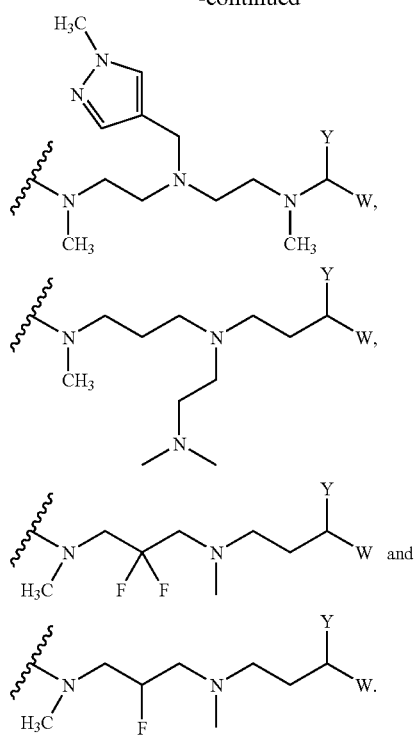
More suitable B-M-X combinations (where X is —CR$^9$—) are:
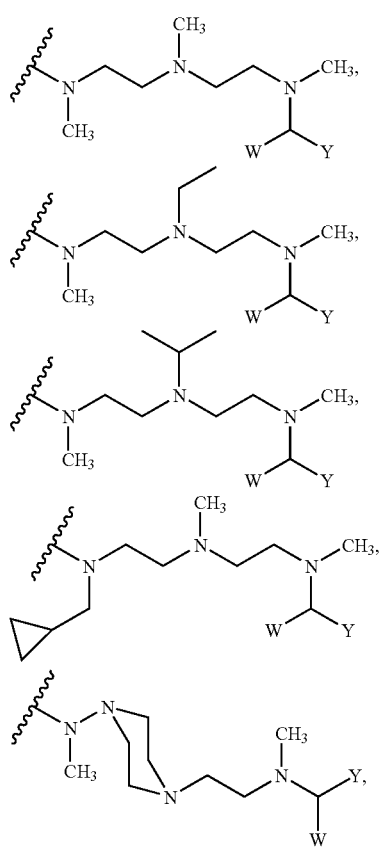
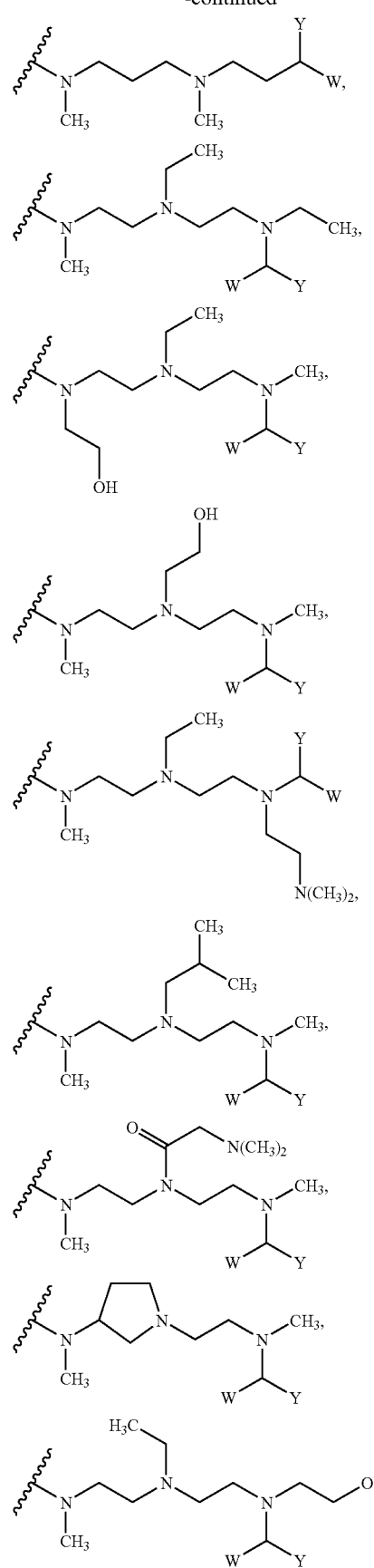

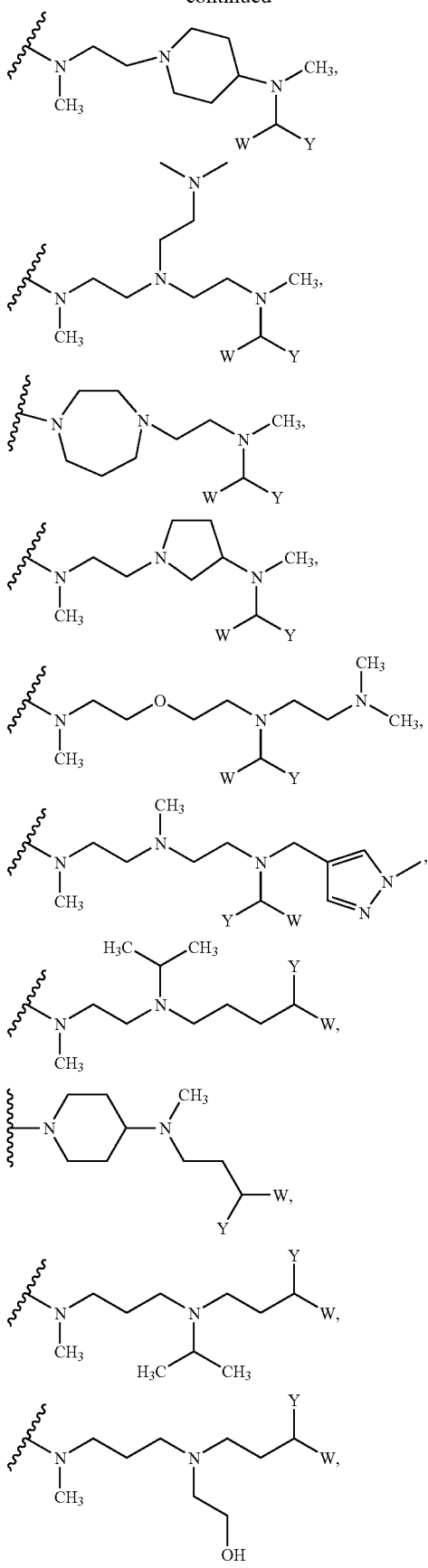
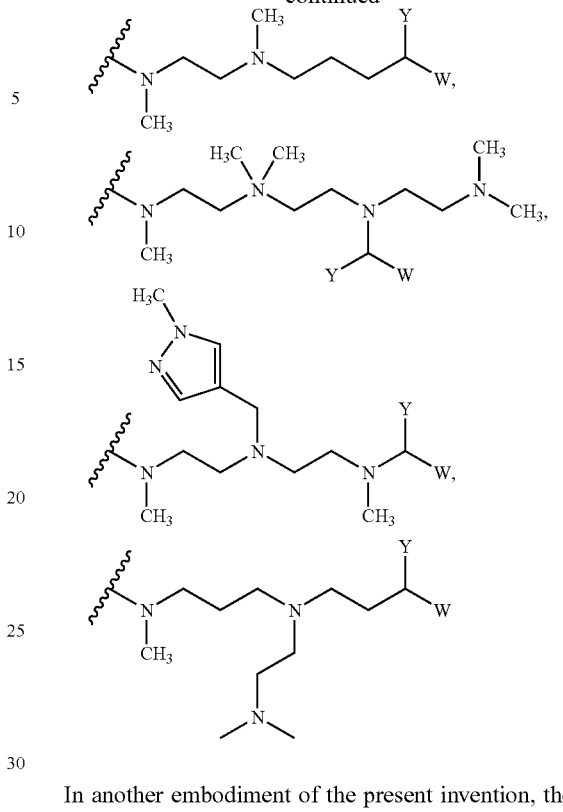

In another embodiment of the present invention, there is provided the compound of formula (Ia):

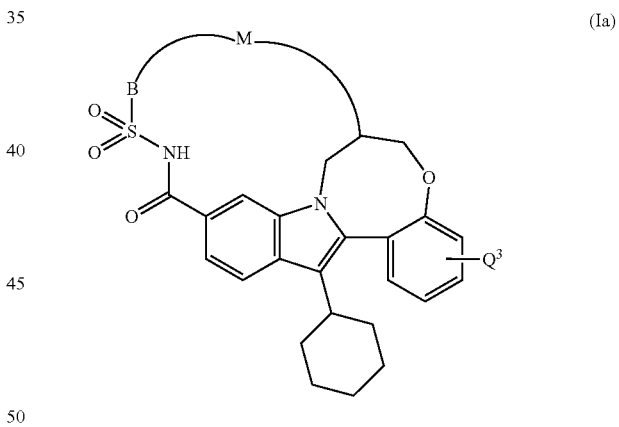

(Ia)

or a pharmaceutically acceptable salt thereof, wherein M and B are as defined in relation to formula (I) and $Q^3$ is hydrogen, O—CH$_2$-(2-pyridyl), O—CH$_2$CH$_2$-(1-pyrrolidine), halogen, hydroxy, $C_{1-4}$ alkyl or $C_{1-4}$ alkoxy. In one embodiment $Q^3$ is hydrogen.

When any variable occurs more than one time in formula (I) or in any substituent, its definition on each occurrence is independent of its definition at every other occurrence.

As used herein, the term "alkyl", "alkenyl", "alkynyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkenyl groups include vinyl and allyl. A suitable alkynyl group is propargyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl.

As used herein, the term "alkylene" means that the alkyl group links two separate groups and may be straight or branched. Examples of suitable alkylene groups include ethylene [—$CH_2$—$CH_2$—] and propylene [—$CH_2$—$CH_2H_2$—, —$CH(CH_3)$—$CH_2$— or —$CH_2$—$CH(CH_3)$—]. The terms "alkenylene" and "alkynylene" shall be construed in an analogous manner.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolinyl and isoquinolinyl.

Where a compound or group is described as "optionally substituted" none, one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include:

(7R)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18-(cyclopropylmethyl)-21,24-dimethyl-7,8-dihydro-6H-7,11-(epiminoethanoiminoethanoiminothioiminomethano)indolo[1,2-e][1,5]benzoxazocin-15-one 17,17-dioxide;

(20R)-30-cyclohexyl-21-methyl-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(7S)-14-cyclohexyl-18,21-dimethyl-7,8-dihydro-6H-7,11-(epoxyethanoiminoethanoiminothioiminomethano)indolo[1,2-e][1,5]benzoxazocin-15-one 17,17-dioxide;

(7R)-14-cyclohexyl-18,21,24-trimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide;

13-cyclohexyl-5,17,20,23-tetramethyl-6,7-dihydro-5H-10,6-(methanoiminothioiminoethanoiminoethanoiminomethano)indolo[1,2-d][1,4]benzodiazepin-14-one 16,16-dioxide;

13-cyclohexyl-3-methoxy-17,20-dimethyl-6,7-dihydro-5H-6,10-(ethanoiminoethanoiminothioiminomethano)indolo[2,1-a][2]benzazepin-14-one 16,16-dioxide;

(7R)-14-cyclohexyl-3-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-3-fluoro-18-methyl-7,8-dihydro-6H-7,11-(epiminoethanoiminoethanoiminothioiminomethano)-indolo[1,2-e][1,5]benzoxazocin-15-one 17,17-dioxide;

(+)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(−)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(7S)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R,S)-14-[(1R,2S) or (1S,2R)-2-fluorocyclohexyl]-18,23-dimethyl-7,8-dihydro-6H-11,7-(methanoiminothioiminobutanoiminomethano)indolo[1,2-e][1,5]benzoxazocin-15-one 17,17-dioxide;

(20S)-31-cyclohexyl-10-methyl-19,22-dioxa-9-thia-1,8,10,13-tetraazahexacyclo[18.9.1.1$^{2,6}$.1$^{3,29}$.0$^{13,17}$.0$^{23,28}$]dotriaconta-2(32),3,5,23,25,27,29(31)-heptaen-7-one 9,9-dioxide;

(18R)-29-cyclohexyl-10,17-dimethyl-20-oxa-9-thia-1,8,10,14,17-pentaazahexacyclo[16.9.1.1$^{2,6}$.1$^{3,27}$.1$^{11,14}$.0$^{21,26}$]hentriaconta-2(31),3,5,21,23,25,27(29)-heptaen-7-one 9,9-dioxide;

(7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,24-dimethyl-7,8-dihydro-6H-7,11-(epiminoethanooxyethanoiminothioiminomethano)indolo[1,2-e][1,5]benzoxazocin-15-one 17,17-dioxide;

(16S,18R)-29-cyclohexyl-10,17-dimethyl-20-oxa-9-thia-1,8,10,13,17-pentaazahexacyclo[16.9.1$^{2,6}$.1$^{3,27}$.1$^{13,16}$.0$^{21,26}$]hentriaconta-2(31),3,5,21,23,25,27(29)-heptaen-7-one 9,9-dioxide;

(7R)-14-cyclohexyl-21-ethyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide;

31-cyclohexyl-8-oxa-24-thia-1,4,16,23,25-pentaazaheptacyclo[23.2.2.1$^{4,6}$.1$^{6,16}$.1$^{15,18}$.1$^{17,21}$.0$^{9,14}$]tritriaconta-9,11,13,15(31),17(30),18,20-heptaen-22-one 24,24-dioxide;

(7R)-14-cyclohexyl-18,19,19,21,24-pentamethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-21-ethyl-18,24-dimethyl-4-(piperidin-1-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]-N-methylacetamide;

(7R)-14-cyclohexyl-24-[2-(dimethylamino)ethyl]-18,21,21-trimethyl-7,8-dihydro-6H-7,11-(epiminopentanoiminothioiminomethano)indolo[1,2-e][1,5]benzoxazocin-15-one 17,17-dioxide;

(7R)-14-cyclohexyl-18,21,24-trimethyl-4-(2-pyrrolidin-1-ylethoxy)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,22-dimethyl-7,8-dihydro-6H-7,11-(ethanoiminopropanoiminothioiminomethano)indolo[1,2-e][1,5]benzoxazocin-15-one 17,17-dioxide;

30-cyclohexyl-18-oxa-2-thia-1,3,10,24-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(−)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(+)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide;

(−)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide;

14-[(1R,2S) or (1S,2R)-2-fluorocyclohexyl]-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R or 7S)-14-cyclohexyl-18,21-dimethyl-7,8-dihydro-6H-7,11-(methanooxyethanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-18,21-dimethyl-7,8-dihydro-6H-17,17-(propanoiminoethanoiminothioiminomethano)indolo[1,2-e][1,5]benzoxazocin-15-one 17,17-dioxide;

14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(7R)-21-[2-(benzyloxy)ethyl]-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-(2-hydroxyethyl)-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isobutyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-(N,N-dimethylglycyl)-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18-(2-hydroxyethyl)-24-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21,24-diethyl-18-methyl-7,8-dihydro-6H-7,11-(epiminoethanoiminoethanoiminothioiminomethano)indolo[1,2-e][1,5]benzoxazocin-15-one 17,17-dioxide;

20-benzyl-13-cyclohexyl-17,23-dimethyl-6,7-dihydro-5H-6,10-(epiminoethanoiminoethanoiminothioiminomethano)indolo[2,1-a][2]benzazepin-14-one 16,16-dioxide;

(7R)-14-cyclohexyl-2-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-2-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-2-fluoro-18-methyl-24-(pyridin-3-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-3-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18-methyl-24-[2-(methylamino)ethyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-2-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18,24-dimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,21,24-trimethyl-4-propyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isopropyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-24-(2-hydroxyethyl)-3,18-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-3,18,21,24-tetramethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-18-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isopropyl-3,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-4,18-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-[2-(dimethylamino)ethyl]-18,24-dimethyl-7,8-dihydro-6H-7,11-(epiminoethanoiminoethanoiminothioiminomethano)indolo[1,2-e][1,5]benzoxazocin-15-one 17,17-dioxide;

(18R)-29-cyclohexyl-10,17-dimethyl-20-oxa-9-thia-1,8,10,13,17-pentaazahexacyclo[16.9.1.1$^{2,6}$.1$^{3,27}$.1$^{13,16}$.0$^{21,26}$]hentriaconta-2(31),3,5,21,23,25,27(29)-heptaen-7-one 9,9-dioxide;

(3R)-31-cyclohexyl-2,22-dimethyl-5-oxa-21-thia-2,13,20,22,25-pentaazahexacyclo[23.2.2.1$^{3,13}$.1$^{12,15}$.1$^{14,18}$.0$^{6,11}$]dotriaconta-6,8,10,12(31),14(30),15,17-heptaen-19-one 21,21-dioxide;

(5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31), 16(30), 17,19-heptaen-21-one 23,23-dioxide;

(20R)-31-cyclohexyl-21-methyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

(5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31),16(30),17,19-heptaen-21-one 23,23-dioxide;

(20R)-31-cyclohexyl-21-methyl-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide;

(20R)-31-cyclohexyl-21-[2-(dimethylamino)ethyl]-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide;

(20R)-30-cyclohexyl-21-(2-fluoroethyl)-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(20R)-21-benzyl-31-cyclohexyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

(7S)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-18-methyl-7,8-dihydro-6H-7,11-(epiminoethanooxyethanoiminothioiminomethano)indolo[1,2-e][1,5]benzoxazocin-15-one 17,17-dioxide;

(7R)-4-allyl-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-4-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18,24-dimethyl-4-(trifluoromethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-(cyclopropylmethyl)-18,21,24-trimethyl-7,8-dihydro-6H-7,11-(epiminoethanoiminoethanoiminothioiminomethano)indolo[1,2-e][1,5]benzoxazocin-15-one 17,17-dioxide;

2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]acetamide;

(7R)-14-cyclohexyl-18,21-dimethyl-24-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,24-dimethyl-4-(morpholin-4-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-4-(benzyloxy)-14-cyclohexyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-18,21,24-trimethyl-7,8-dihydro-6H-7,11-(epiminoethanoiminoethanoiminothioiminomethano)indolo[1,2-e][1,5]benzoxazocin-15-one 17,17-dioxide;

14-[(1R,2S) or (1S,2R)-2-fluorocyclohexyl]-18,22-dimethyl-7,8-dihydro-6H-7,11-(ethanoiminopropanoiminothioiminomethano)indolo[1,2-e][1,5]benzoxazocin-15-one 17,17-dioxide;

30-[(1R,2S) or (1S,2R)-2-fluorocyclohexyl]-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-[(1R,2S) or (1S,2R)-2-fluorocyclohexyl]-22-methyl-18-oxa-2-thia-1,3,10,22-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-cyclohexyl-23-methyl-6-oxa-22-thia-1,14,21,23-tetraazahexacyclo[22.2.2.1$^{4,14}$.1$^{13,16}$.1$^{15,19}$.0$^{7,12}$]hentriaconta-7,9,11,13(30),15(29),16,18-heptaen-20-one 22,22-dioxide;

(7R) or (7S)-14-cyclohexyl-22-methyl-18-(2-pyrrolidin-1-ylethyl)-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-isopropyl-18-methyl-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-(2-hydroxyethyl)-18-methyl-7,8-dihydro-6H-7,11-(ethanoiminopropanoiminothioiminomethano)indolo[1,2-e][1,5]benzoxazocin-15-one 17,17-dioxide;

31-cyclohexyl-18-oxa-2-thia-1,3,10,24-tetraazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

14-cyclohexyl-21-isopropyl-18-methyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4-methoxy-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21,21,24-tetramethyl-7,8-dihydro-6H-7,11-(epiminopentanoiminothioiminomethano)indolo[1,2-e][1,5]benzoxazocin-15-one 17,17-dioxide;

14-[(1R,2S) or (1S2R)-2-fluorocyclohexyl]-18,22-dimethyl-7,8-dihydro-6H-7,11-(ethanoiminopropanoiminothioiminomethano)indolo[1,2-e][1,5]benzoxazocin-15-one 17,17-dioxide;

30-[(1R,2S)-2-fluorocyclohexyl]-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-[(1R,2S)-2-fluorocyclohexyl]-22-methyl-18-oxa-2-thia-1,3,10,22-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-cyclohexyl-23-methyl-6-oxa-22-thia-1,14,21,23-tetraazahexacyclo[22.2.2.1$^{4,14}$.1$^{13,16}$.1$^{15,19}$.0$^{7,12}$]hentriaconta-7,9,11,13(30),15(29),16,18-heptaen-20-one 22,22-dioxide;

(7R) or (7S)-14-cyclohexyl-22-methyl-18-(2-pyrrolidin-1-ylethyl)-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-isopropyl-18-methyl-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-(2-hydroxyethyl)-18-methyl-7,8-dihydro-6H-7,11-(ethanoiminopropanoiminothioiminomethano)indolo[1,2-e][1,5]benzoxazocin-15-one 17,17-dioxide;

31-cyclohexyl-18-oxa-2-thia-1,3,10,24-tetraazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

14-cyclohexyl-21-isopropyl-18-methyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4-methoxy-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21,21,24-tetramethyl-7,8-dihydro-6H-7,11-(epiminopentanoiminothioiminomethano)indolo[1,2-e][1,5]benzoxazocin-15-one 17,17-dioxide;

(7R)-14-[(1R,2S)-2-fluorocyclohexyl]-4,18,21-trimethyl-7,8-dihydro-6H-7,11-(propanoiminoethanoiminothioiminomethano)indolo[1,2-e][1,5]benzoxazocin-15-one 17,17-dioxide;

2-[(7R)-14-cyclohexyl-4,18,24-trimethyl-17,17-dioxido-15-oxo-7,8-dihydro-6H-7,11-(epiminoethanoiminoethanoiminothioiminomethano)indolo[1,2-e][1,5]benzoxazocin-21-yl]-N,N-dimethylacetamide;

(7R)-14-cyclohexyl-4,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,21,24-tetramethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,24-trimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclopentyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-7,8-dihydro-6H-7,11-(epiminoethanooxyethanoiminothioiminomethano)indolo[1,2-e][1,5]benzoxazocin-15-one 17,17-dioxide;

(7R)-14-cyclohexyl-4,18,21-trimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4,18,22-trimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-22-[2-(dimethylamino)ethyl]-4,18-dimethyl-7,8-dihydro-6H-7,11-(ethanoiminopropanoiminothioiminomethano)indolo[1,2-e][1,5]benzoxazocin-15-one 17,17-dioxide;

(20R)-30-cyclohexyl-15-methoxy-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(7R)-14-cyclohexyl-20,20-difluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-20-fluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

The present invention also provides a compound of formula (I) or a pharmaceutically acceptable salt thereof for treatment or prevention of infection by hepatitis C virus in a human or animal.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 1 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) may be prepared by internal ring closure of the compound of formula (III):

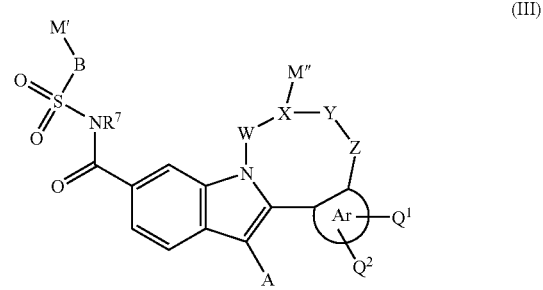

(III)

where A, Ar, $Q^1$, $Q^2$, B, $R^7$, X, W, Y and Z are as defined in relation to formula (I), X is $CR^9$ and M' and M" have suitable precursor functionality to form group M as defined in relation to formula (I). For instance, when M is —$CH_2$—$CH_2$—NH—$CH_2$—$CH_2$—N($CH_3$)—, M' can be —$CH_2$—CHO and M" can be —N($CH_3$)—$CH_2$—$CH_2$—$NH_2$, where the reaction is carried out in the presence of a mild reducing agent, such as sodium cyanoborohydride, in a suitable solvent mixture, such as aqueous methanol, at pH 5-6.

According to a general process (b), compounds of formula (I) may be prepared by internal ring closure of the compound of formula (IV):

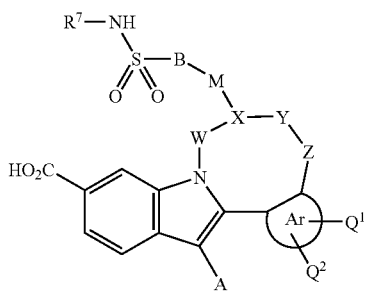
(IV)

where A, Ar, B, M, $Q^1$, $Q^2$, $R^1$, X, W, Y and Z are as defined in relation to formula (I). The reaction is conveniently carried out in the presence of a coupling reagent, such as EDC, and an additive, such as DMAP, in a suitable solvent such as DMF, DCM and mixtures thereof.

Compounds of formulae (III) and (IV) are either known in the art or may be prepared by conventional methodology well known to one of ordinary skill in the art using, for instance, procedures described in the accompanying Descriptions and Examples, or by alternative procedures which will be readily apparent.

Compounds of formula (I) can be converted into other compounds of formula (I) using synthetic methodology well known in the art. For instance, the compound of formula (I) where M comprises an N—H group may be converted into the compound of formula (I) where M comprises an N—CH$_3$ group by methylation using formaldehyde followed by a mild reducing agent, such as sodium borohydride. By analogy, using similar conditions, the compound of formula (I) where M comprises an N—H group may be converted into the compound of formula (I) where M comprises an N—CH$_2$CH$_3$ or an N—CH(CH$_3$)$_2$ group by using acetaldehyde or acetone, respectively. Alternatively, alkylation of the N—H group may be carried out using a suitable alkyl halide and a base, such as potassium carbonate, in a suitable solvent, such as acetone, MeCN or DMF.

General Synthetic schemes

Three general strategies were employed for assembly of compounds from the macrocyclic class (Methods A, B and C); Method B can be regarded as an extension of Method A.

Method A

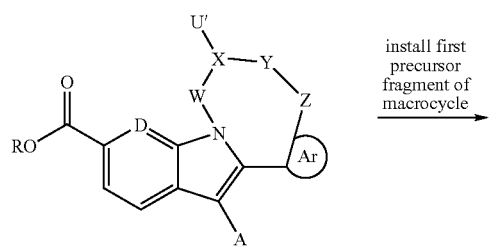

install first precursor fragment of macrocycle

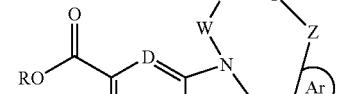

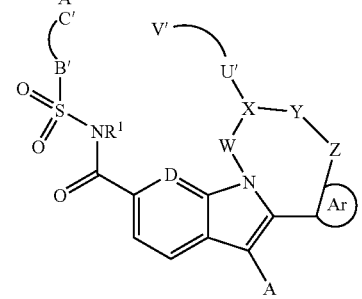

1) unmask acid
2) functionalise acid to install second precursor fragment to macrocycle

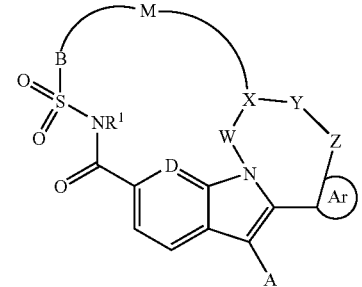

1) Functional group manipulation
2) ring closure

A suitably functionalised tether was assembled first (as described in published International patent applications WO2006/046030, WO2006/046039 and WO2007/054741). A precursor fragment to one section of the macrocycle was installed on the tether, with subsequent unmasking of the acid at C6 and functionalisation to introduce a precursor fragment to the remaining segment of the macrocycle. Functional group manipulation and macrocyclisation (e.g., via amide bond formation, alkylation, reductive amination, metathesis etc) set up the macrocycle. Potentially, the bond formed in ring closure could be at almost any point around the macrocyclic linker (e.g., forming the acylsulfonylurea bond could also be the ring closing step).

Method B

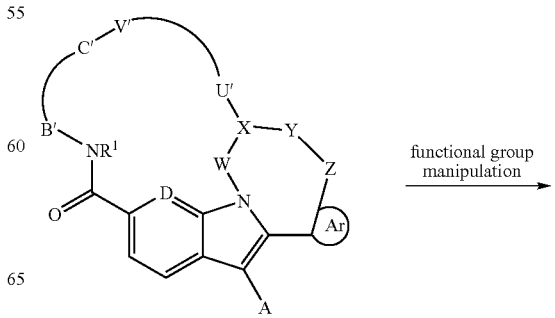

functional group manipulation

-continued

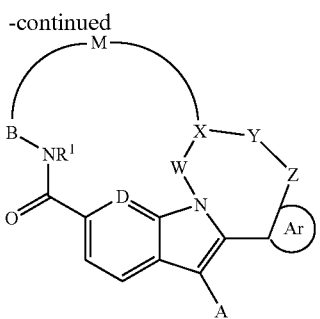

Functional groups on the macrocycle were manipulated post-closure, e.g., via reductive amination, alkylation, amide reduction, amide formation etc. Potentially, sidechains can branch from any point around the macrocyclic linker.

The present invention is illustrated further by the following non-limiting examples.

The compounds of the invention were tested for inhibitory activity against the HCV RNA dependent RNA polymerase (NS5B) in an enzyme inhibition assay as described in example i). The compounds generally have $IC_{50}$'s below 100 nM in this assay.

The potential for compounds of the invention to inhibit HCV replication may be demonstrated using a cell based sub-genomic replication assay as described in example 11).

Compound names in the examples were generated using software from ACDLabs (version 8.0).

i) In-Vitro HCV NS5B Enzyme Inhibition Assay

Published International patent application WO 96/37619 describes the production of recombinant HCV RdRp from insect cells infected with recombinant baculovirus encoding the enzyme. The purified enzyme was shown to possess in

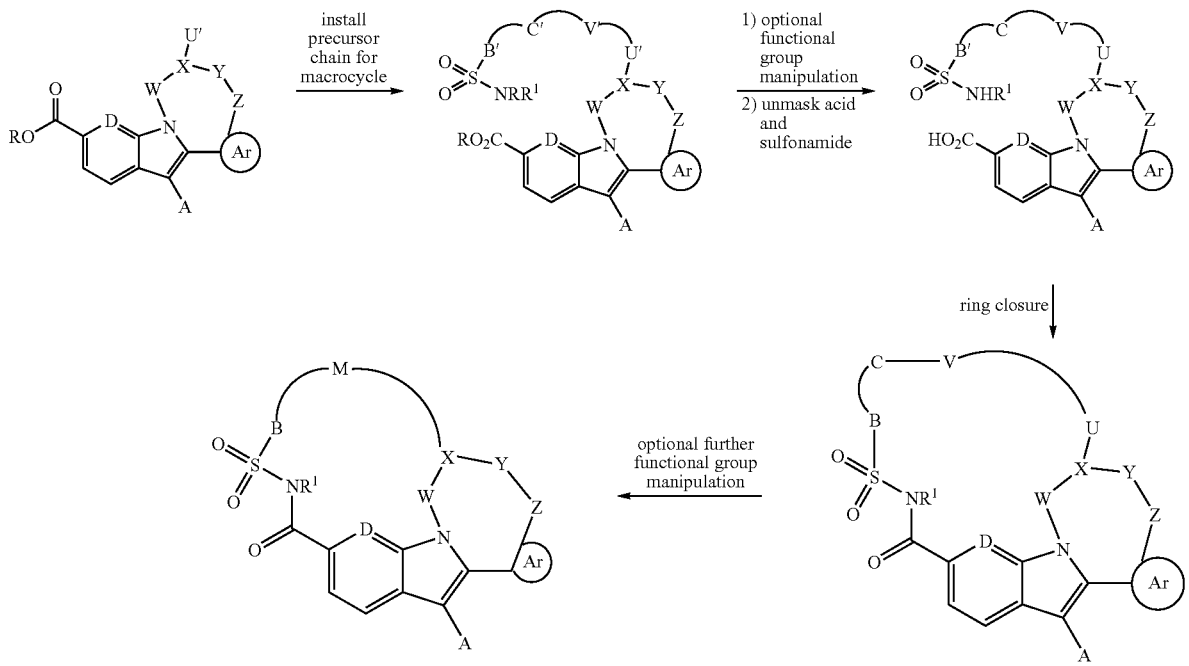

A suitably functionalised tether was assembled first (as described in published International patent applications WO 2006/046030, WO 2006/046039 and WO 2007/054741). A precursor fragment to the macrocycle was installed on the tether (either step-wise or as a single transformation). Optionally, functionality on this precursor to the macrocycle could be modified prior to unmasking of the acid at C6 of the indole and, if appropriate the sulfonamide moiety, followed by macrocyclisation (e.g., via amide bond formation) to set up the macrocycle.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 4th edition, 2007. The protecting groups may be removed at a convenient subsequent stage using methods known from the art.

vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

$$\% \text{ Residual activity} = 100/(1 + [I]/IC_{50})^S$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International application WO 02/59321). Cells were seeded into 96 well plates at a density of $10^4$ cells per well in a final volume of 0.1 ml of DMEM/10% FCS. Two hours after plating, 50 µl of DMEM/10% FCS containing a 3× concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS+0.1% Triton X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition} = 1 - (Ai-b)/(A_0-b) = [I]^n/([I]^n + IC_{50})$$

where:
- $Ai$=absorbance value of HBI10 cells supplemented with the indicated inhibitor concentration.
- $A_0$=absorbance value of HBI10 cells incubated without inhibitor.
- $b$=absorbance value of Huh-7 cells plated at the same density in the same microtiter plates and incubated without inhibitor.
- $n$=Hill coefficient.

Representative data for compounds of this invention are reported in Tables A and 1-5. To determine cytotothe cellular toxicity of the compounds, a standard MTT assay as described by T. Mosmann (Rapid colorimetric assay for cellular growth and survival: application to proliferation and cytotoxicity assays; J Immunol Methods. 1983, 65, 55-63) was used. The assay is based on the capacity of mitochondrial dehydrogenase enzymes in living cells to convert the yellow water-soluble substrate 3-(4,5-dimethilthiazol-2-yl)-2,5-diphenyl tetrazolium bromide (MTT) into a dark blue formazan product, which is insoluble in water. The amount of formazan produced is directly proportional to the cell number in a range of cell line.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage corporation and Jones Flashmaster II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a Perkin Elmer API 100, or Waters MicroMass ZQ, operating in negative ($ES^-$) or positive ($ES^+$) ionization mode and results are reported as the ratio of mass over charge (m/z) for the parent ion only. Preparative scale HPLC separations were carried out on a Waters Delta Prep 4000 separation module, equipped with a Waters 486 absorption detector or on an automated Waters Fraction Lynx or Gilson preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; aq.: aqueous; Ar: aryl; atm: atmosphere; 9-BBN: 9-borabicyclo[3.3.1]nonane; cat.: catalytic; dioxan(e): 1,4-dioxane; dppf: (1,1'-bisdiphenylphosphino)ferrocene; DAST: diethylaminosulfur trifluoride; 1,2-DCE: 1,2-dichloroethane; DCM: dichloromethane; DIAD: diisopropylazodicarboxylate; DIC: 1,3-diisopropyl carbodiimide; DIPEA: diisopropylethyl amine; DMA: N,N-dimethylacetamide; DMAP: N,N-dimethylpyridin-4-amine; DME: dimethoxyethane; DMF: dimethylformamide; DMS: dimethylsulfide; DMSO: dimethylsulfoxide; DMP: Dess-Martin Periodinane; DPPA: diphenylphosphorylazide; EDC: 1-ethyl-(3-dimethylaminopropyl)carbodiimide HCl salt; eq: equivalent(s); $Et_3N$: triethylamine; EtOAc: ethyl acetate; $Et_2O$: diethyl ether; EtOH: ethanol; $Et_3SiH$: triethylsilane; FC: Flash Chromatography; h: hour(s); HOAc: acetic acid; HATU: O-(7-azabenzotriazol-1-yl)-N,N,N',N'-tetramethyluronium hexafluorophosphate; HOBt: 1 hydroxybenzotriazole; Me: methyl; MeCN: acetonitrile; MeOH: methanol; min: minute(s); Ms: methanesulfonyl; MS: mass spectrum; NBS: N-bromo succinimide; PE: petroleum ether; Ph: phenyl; quant.: quantitative; RP-HPLC: reversed phase high-pressure liquid chromatography; RT: room temperature; sat.: saturated; sec: second(s); SFC: Super-critical fluid chromatography; sat. aq.: saturated solution; TBAF: tetrabutyl ammonium fluoride; TBTU: O-benzotriazol-1-yl-N,N,N',N'-tetramethyluronium tetrafluoroborate; TFA: trifluoroacetic acid; THF: tetrahydrofuran; THP: tetrahydropyranyl; TMS: trimethylsilyl; Ts: para-toluene sulfonyl.

Example 1

(7R)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide

Step 1: N-(2,2-dimethoxyethyl)-N-methylsulfamide

Sulfamide (5 eq) was added to a solution of 2,2-dimethoxy-N-methylethanamine in dioxane (0.12 M). The reaction was stirred at reflux overnight. The solvent was removed in vacuo, the residue taken up in EtOAc and washed with $H_2O$, brine, before being dried ($Na_2SO_4$), filtered and concentrated in vacuo to give the crude material. DCM was added and a precipitated formed, that was collected by filtration. Further trituration of the filtrate with DCM afforded clean product (67%). $^1$H NMR (300 MHz, DMSO-$d_6$, 300 K) δ 2.67 (s, 3H), 2.98 (d, J 5.3, 2H), 3.28 (s, 6H), 4.48 (t, J 5.3, 1H), 6.7 (s, 2H).

Step 2: tert-butyl (2R)-2-({[(4-nitrophenyl)sulfonyl]oxy}methyl)aziridine-1-carboxylate A solution of tert-butyl (2R)-2-({[tert-butyl(dimethyl)silyl]oxy}methyl)aziridine-1-carboxylate (prepared following literature procedures: Travins, J. M.; Etzkorn, F. A. *Tetrahedron Lett.* 1998, 39, 9389-9392) in THF/$Et_2O$ (1/1) (0.17 M) was cooled in an ice bath and treated dropwise over 20 min with 1 M TBAF in THF (1.05 eq). The resulting solution was stirred in the ice bath for 30 min, before being quenched by the addition of sat. aq. $NaHCO_3$ and extracted into $Et_2O$/PE (4/1). The organic layers were collected, washed with brine, dried over $Na_2SO_4$, filtered and concentrated in vacuo. The residue was taken up in dry DCM (0.17 M) and $Et_3N$ (1.3 eq) introduced prior to cooling to 0° C. DMAP (0.1 eq) and 4-nitrobenzenesulfonyl chloride (1.1 eq) were added and the resulting mixture left to stir at RT overnight. The reaction mixture was diluted with DCM and washed with sat. aq. $NaHCO_3$, water and brine before drying over $Na_2SO_4$, filtering and concentrating in vacuo. The crude was purified by FC (PE/EtOAc 8:2) to afford the title compound as an off-white solid (57%). ($ES^+$) m/z 359 $(M+H)^+$.

Step 3: methyl (7R)-7-[(tert-butoxycarbonyl)amino]-14-cyclohexyl-7,8-dihydro-6H-indolo[1,2-e][1,5]benzoxazocine-11-carboxylate A solution of methyl 3-cyclohexyl-2-(2-hydroxyphenyl)-1H-indole-6-carboxylate (prepared as described in published International patent application WO2006/046030) (0.15 M) in DMF was treated with CsF (4 eq) in one portion; the resulting mixture was stirred for 20 min at RT then treated via dropping funnel over 30 min with a solution of tert-butyl (2R)-2-({[(4-nitrophenyl)sulfonyl]oxy}methyl)aziridine-1-carboxylate (1.3 eq) in DMF (0.5 M). The resulting solution was stirred at RT overnight. The reaction mixture was then placed into an ice bath and powdered KO$^t$Bu (1.4 eq) added slowly to the reaction mixture. After 1.5 h, the reaction was quenched with sat. aq. $NH_4Cl$ and extracted into EtOAc. The combined organic layers were washed with water and brine, before being dried over $Na_2SO_4$, filtered and concentrated in vacuo. The crude material was purified by FC (PE/EtOAc 8:2) affording the product as an off-white foam (85%). ($ES^+$) m/z 505 $(M+H)^+$.

Step 4: methyl (7R)-7-amino-14-cyclohexyl-7,8-dihydro-6H-indolo[1,2-e][1,5]benzoxazocine-11-carboxalate Methyl (7R)-7-[(tert-butoxycarbonyl)amino]-14-cyclohexyl-7,8-dihydro-6H-indolo[1,2-e][1,5]benzoxazocine-11-carboxylate (0.14 M) in DCM was treated with TFA (10 eq) and stirred at RT for 1 h. The reaction was diluted with DCM and cautiously basified with aq. $NaHCO_3$, before separating the phases and extracting the aqueous with DCM. The combined organics were washed with brine, dried over $Na_2SO_4$, filtered and concentrated in vacuo to afford the product as an off-white foam (100%) that was used without further purification. ($ES^+$) m/z 405 $(M+H)^+$; $[\alpha]_D^{20}$+42.3 (c=1.0, MeOH).

Step 5: methyl (7R)-14-cyclohexyl-7-(methylamino)-7,8-dihydro-6H-indolo[1,2-e][1,5]benzoxazocine-11-carboxylate A solution of methyl (7R)-7-amino-14-cyclohexyl-7,8-dihydro-6H-indolo[1,2-e][1,5]benzoxazocine-11-carboxylate (0.35 M) in THF was treated dropwise with 2,2,2-trifluoroethyl formate (1.2 eq) and stirred overnight at RT. The volatiles were removed in vacuo and the residue dissolved (0.11 M) in THF and treated dropwise with $BH_3$DMS complex (2M in THF; 5 eq). The resulting solution was stirred at RT for 20 h. The reaction was quenched by the careful addition of HCl/MeOH (1.25 M) and the resulting solution refluxed for 2 h. The volatiles were then removed in vacuo and the residue partitioned between sat. aq. $NaHCO_3$ and EtOAc. The combined organics were washed with brine, dried over $Na_2SO_4$, filtered and concentrated in vacuo. The crude was purified by FC (EtOAc/PE 80:20+1% $NEt_3$) to afford the product (79%). ($ES^+$) m/z 419 $(M+H)^+$; $[\alpha]_D^{20}$+47.4 (c=0.46, $CHCl_3$).

Step 6: methyl (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate To a solution of tert-butyl (2-oxoethyl)carbamate (1 eq; 0.38 M) in dry MeOH was added a mixture of methyl (7R)-14-cyclohexyl-7-(methylamino)-7,8-dihydro-6H-indolo[1,2-e][1,5]benzoxazocine-11-carboxylate (0.14 M), acetic acid (2 eq) and sodium acetate (1 eq) in dry MeOH, and the mixture stirred at RT for 15 min. Then Pd/C (0.3 weight eq) was added as a slurry in MeOH under $N_2$. The atmosphere in the reaction vessel was charged with $H_2$ and the reaction stirred vigorously under a $H_2$ atmosphere (balloon) at 60° C. overnight. The reaction was allowed to cool to RT, flushed with $N_2$ and filtered through a plug of celite. The filtrate was concentrated in vacuo and the residue purified by FC (PE/EtOAc 2.5:1 to 1.5:1 gradient) to afford the title compound (82%). ($ES^+$) m/z 562 $(M+H)^+$; $[\alpha]_D^{20}$+67.1 (c=0.67, $CHCl_3$).

Step 7: (7R)-7-{2-[(tert-butoxycarbonyl)amino]ethyl}(methyl)amino]-14-cyclohexyl-7,8-dihydro-6H-indolo[1,2-e][1,5]benzoxazocine-11-carboxylic acid 2N NaOH (aq) (6 eq) was added to a solution of methyl (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate (0.02 M) in MeOH/THF (3/1) and the reaction stirred vigorously at 60° C. for 4 h. The reaction was allowed to cool to RT before reducing the volume of MeOH/THF in vacuo. The residue was partitioned between 1N HCl (aq) and EtOAc, ensuring the aqueous phase was acidic. The aqueous was extracted a second time with EtOAc and the combined organics washed with water, brine before being dried ($Na_2SO_4$), filtered and concentrated in vacuo. The material was taken on without further purification. MS ($ES^+$) m/z 548 (M+H)$^+$.

Step 8: tert-butyl {2-{[(7R)-14-cyclohexyl-11-[({[(2,2-dimethoxyethyl)(methyl)amino]sulfonyl}amino)carbonyl]-7,8-dihydro-6H-indolo[1,2-e][1,5]benzoxazocin-7-yl}(methyl)amino]ethyl}carbamate To a solution of (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylic acid (0.15 M) in DCM were added sequentially EDC (1.8 eq), N-(2,2-dimethoxyethyl)-N-methylsulfamide (1.8 eq) (prepared as described in Step 1) and DMAP (1.2 eq). The mixture was stirred at 40° C. for 1.5 hours. Further EDC (0.48 eq) and sulfamide (0.5 eq) were introduced and heating continued for 1 h. The reaction was left to cool with stirring overnight. The reaction was diluted with EtOAc and washed with 1N HCl (aq). The aqueous was extracted with EtOAc and the organics combined, washed with brine, dried ($Na_2SO_4$), filtered and concentrated in vacuo to leave a brown gum. The residue was purified by RP-HPLC (Waters Xterra column; MeCN/$H_2O$/0.1% TFA gradient). Fractions containing the pure compound were combined and lyophilized to afford the product as a white powder (44%). MS ($ES^+$) m/z 728 (M+H)$^+$.

Step 9: (7R)-7-[(2-aminoethyl)(methyl)amino]-14-cyclohexyl-N-{[methyl(2-oxoethyl)amino]sulfonyl}-7,8-dihydro-6H-indolo[1,2-e][1,5]benzoxazocine-11-carboxamide A solution of tert-butyl {2-[{(7R)-14-cyclohexyl-11-[({[(2,2-dimethoxyethyl)-(methyl)amino]sulfonyl}amino)carbonyl]-7,8-dihydro-6H-indolo[1,2-e][1,5]-benzoxazocin-7-yl}(methyl)amino]ethyl}carbamate (0.03 M) in DCM was treated with TFA (100 eq) and water (180 eq) at RT and the resulting mixture stirred vigorously for 3 h at 40° C. The volatiles were removed in vacuo and the residue diluted with $Et_2O$ and re-evaporated to drive off excess TFA. The product was used in the subsequent step without further purification. MS ($ES^+$) m/z 582 (M+H)$^+$; 600 (M+$H_2O$+H)$^+$.

Step 10: (7R)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide Catalytic HOAc was added to a solution of methyl (7R)-7-[(2-aminoethyl)(methyl)amino]-14-cyclohexyl-N-{[methyl(2-oxoethyl)amino]sulfonyl}-7,8-dihydro-6H-indolo[1,2-e][1,5]benzoxazocine-11-carboxamide (0.006 M) in MeOH at RT, followed by $NaCNBH_3$ (5 eq) and the reaction stirred for 30 mins. Additional $NaCNBH_3$ (5 eq) was introduced and the reaction stirred for 30 mins. Volatiles were removed in vacuo and the residue taken up in MeCN, filtered to remove insoluble material and concentrated in vacuo. The residue was purified by RP-HPLC (Waters Xterra column; MeCN/$H_2O$/0.1% TFA gradient). Fractions containing the pure compound were combined and lyophilized to afford the product as a white powder (15%). $^1$H NMR (500 MHz, DMSO-$d_6$+TFA, 335 K) δ 1.14-1.22 (m, 1H), 1.31-1.40 (m, 2H), 1.53-1.57 (m, 1H), 1.68-1.75 (m, 2H), 1.91-2.07 (m, 4H), 2.39 (s, 3H), 2.63-2.68 (m, 1H), 2.97 (s, 3H), 3.04-3.45 (m, 7H), 3.47-3.49 (m, 1H), 3.98-4.15 (m, 2H), 4.16-4.18 (m, 1H), 4.45-4.59 (m, 1H), 4.61-4.64 (m, 1H), 7.31-7.44 (m, 4H), 7.55-7.58 (m, 1H), 7.92 (d, J 8.7, 1H), 8.03 (s, 1H); ($ES^+$) m/z 566 (M+H)$^+$. $[α]_D^{20}$=+73.2 (c=0.7, DMSO).

Example 2

(7R)-14-cyclohexyl-18,21,24-trimethyl-7,8-dihydro-6H-7,11-(epiminoethanoiminoethanoiminothioiminomethano)indolo[1,2-e][1,5]benzoxazocin-15-one 17,17-dioxide Formaldehyde (10 eq) (37 wt % aq solution) was added to a methanolic solution of (7R)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide (Example 1), followed by HOAc (cat.) and $NaCNBH_3$ (5 eq). After 30 min a further 5 eq $NaCNBH_3$ and HCHO (37% aqueous solution) were added. Volatiles were removed in vacuo and the residue treated with MeCN. The insoluble residue was filtered off and the resultant MeCN solution concentrated in vacuo. Purification was by automated RP-HPLC, eluting with MeCN/TFA buffered with 0.1% TFA gradient. Fractions containing the product were combined and freeze dried to afford the product as a white powder (26%). $^1$H NMR (600 MHz, DMSO-$d_6$+TFA, 300 K) δ 1.12-1.20 (m, 1H), 1.28-1.41 (m, 2H), 1.45-1.51 (m, 1H), 1.66-1.74 (m, 2H), 1.82-1.88 (m, 1H), 1.89-2.00 (m, 3H), 2.64-2.71 (m, 4H), 2.92 (s, 3H), 3.03 (s, 3H), 3.37-3.62 (m, 7H), 3.69-3.77 (m, 1H), 3.91-3.99 (m, 1H), 4.07-4.16 (m, 1H), 4.21-4.28 (m, 1H), 4.39-4.48 (m, 1H), 4.68-4.74 (m, 1H), 7.28-7.39 (m, 3H), 7.5 (d, J 8.3, 1H), 7.55-7.59 (m, 1H), 7.94 (d, J 8.3, 1H), 8.09 (s, 1H); ($ES^+$) m/z 580 (M+H)$^+$.

Example 3

(7R)-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide Acetaldehyde (10 eq) was added to a methanolic solution of (7R)-14-cyclohexyl-18,24-dimethyl-7,8-dihydro-6H-7,11-(epiminoethanoiminoethanoiminothioiminomethano)-indolo[1,2-e][1,5]benzoxazocin-15-one 17,17-dioxide (Example 1), followed by HOAc (cat.) and $NaCNBH_3$ (5 eq). After 30 mins, volatiles were removed in vacuo and the residue treated with MeCN as described in Example 1. Purification was by automated RP-HPLC, eluting with MeCN/TFA buffered with 0.1% TFA gradient. Fractions containing the product were combined and freeze dried to afford the product as a white powder (24%). $^1$H NMR (400 MHz, DMSO-$d_6$, 300 K) δ 1.14-1.23 (m, 4H), 1.28-1.37 (m, 2H), 1.40-1.47 (m, 1H), 1.64-1.72 (m, 2H), 1.80-1.87 (m, 1H), 1.89-1.98 (m, 3H), 2.32 (s, 3H), 2.62-2.69 (m, 1H), 2.91-3.00 (m, 2H), 3.02 (s, 3H), 3.12-3.58 (m, 8H), 3.82-3.97 (m, 2H), 4.01-4.07 (m, 1H), 4.34-4.39 (m, 1H), 4.54-4.59 (m, 1H), 7.31-7.39 (m, 3H), 7.46 (d, J 8.8, 1H), 7.54-7.59 (m, 1H), 7.91 (d, J 8.8, 1H), 8.05 (s, 1H); ($ES^+$) m/z 594 (M+H)$^+$.

Example 4

(7R)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide Acetone (130 eq) was added to a methanolic solution of (7R)-14-cyclohexyl-18,24-dimethyl-7,8-dihydro-6H-7,11-

(epiminoethanoiminoethanoiminothioiminomethano)-indolo[1,2-e][1,5]benzoxazocin-15-one 17,17-dioxide (Example 1), followed by HOAc (cat.) and NaCNBH$_3$ (40 eq). The reaction was warmed to 40° C. for 2 h before being left to stir overnight at RT. Volatiles were removed in vacuo and the residue treated with MeCN. Insolubles were filtered off and the resultant MeCN solution concentrated in vacuo. Purification was by automated RP-HPLC, eluting with MeCN/TFA buffered with 0.1% TFA gradient. Fractions containing the product were combined and freeze dried to afford the product as a white powder (22%). $^1$H NMR (600 MHz, DMSO-d$_6$+ TFA, 320 K) δ 1.12-1.22 (m, 4H), 1.28-1.39 (m, 5H), 1.40-1.47 (m, 1H), 1.65-1.72 (m, 2H), 1.80-1.88 (m, 1H), 1.89-1.98 (m, 3H), 2.42 (s, 3H), 2.65-2.72 (m, 1H), 3.04 (s, 3H), 3.12-3.30 (m, 3H), 3.32-3.44 (m, 2H), 3.47-3.61 (m, 3H), 3.67-3.75 (m, 1H), 3.91-4.02 (m, 2H), 4.08-4.15 (m, 1H), 4.38-4.43 (m, 1H), 4.60-4.66 (m, 1H), 7.32-7.40 (m, 3H), 7.48 (d, J 8.4, 1H), 7.54-7.59 (m, 1H), 7.92 (d, J 8.4, 1H), 8.09 (s, 1H); (ES$^+$) m/z 608 (M+H)$^+$. [α]$_D^{20}$=+51.6 (c=1.2, MeOH).

Example 5

(7R)-14-cyclohexyl-18-(cyclopropylmethyl)-21,24-dimethyl-7,8-dihydro-6H-7,11-(epiminoethanoiminoethanoiminothioiminomethano)indolo[1,2-e][1,5]benzoxazocin-15-one 17,17-dioxide Step 1: N-(cyclopropylmethyl)-(2,2-dimethoxyethanamine)

A solution of cyclopropanecarboxaldehyde in MeOH (0.2 M) was treated with 2,2-dimethoxyethylamine (1.2 eq). The solution was cooled with an ice/water bath and treated portionwise with NaCNBH$_3$ (1.0 eq). The pH of the resulting solution was adjusted to 6 with AcOH, and the reaction left at RT for 24 h. The mixture was concentrated, diluted with EtOAc, washed with sat. aq. NaHCO$_3$, brine, dried (Na$_2$SO$_4$), filtered and concentrated in vacuo to afford the product (61%). $^1$H NMR (300 MHz, DMSO-d$_6$, 300 K) δ 0.05-0.07 (m, 2H), 0.15-0.17 (m, 2H), 0.87-0.93 (m, 1H), 2.39-2.41 (m, 2H), 2.64-2.66 (m, 2H), 3.3 (s, 6H), 4.46 (t, J 3.0, 1H), 5.38 (m, 1H).

Step 2: N-(cyclopropylmethyl)-N-(2,2-dimethoxyethyl)sulfamide

Sulfamide (5 eq) was added to a solution of N-(cyclopropylmethyl)-(2,2-dimethoxyethanamine) in dioxane (0.12 M). The reaction was stirred at reflux overnight. The solvent was removed in vacuo, the residue taken up in EtOAc and washed with H$_2$O, brine, before being dried (Na$_2$SO$_4$), filtered and concentrated in vacuo to give the crude material. DCM was added and the resultant precipitate removed by filtration, while the filtrate was concentrated in vacuo to afford the product (68%). $^1$H NMR (300 MHz, DMSO-d$_6$, 300 K) δ 0.15-0.19 (m, 2H), 0.44-0.47 (m, 2H), 1.03-1.05 (m, 1H), 2.95-2.98 (m, 2H), 3.17-3.19 (m, 2H), 3.28 (s, 6H), 4.51 (t, J 5.0, 1H), 6.63 (s, 2H).

Step 3: (7R)-14-cyclohexyl-18-(cyclopropylmethyl)-21,24-dimethyl-7,8-dihydro-6H-7,11-(epiminoethanoiminoethanoiminothioiminomethano)indolo[1,2-e][1,5]benzoxazocin-15-one 17,17-dioxide The synthesis to afford the title compound was directly analogous to Examples 1 and 2, using N-(cyclopropylmethyl)-N-(2,2-dimethoxyethyl)sulfamide in place of N-(2,2-dimethoxyethyl)-N-methylsulfamide. $^1$H NMR (600 MHz, DMSO-d$_6$+TFA, 300 K) δ 0.23-0.35 (m, 2H), 0.42-0.58 (m, 2H), 0.91-1.09 (m, 1H), 1.14-1.43 (m, 3H), 1.49-1.51 (m, 1H), 1.62-1.73 (m, 2H), 1.82-2.01 (m, 4H), 2.58-2.87 (m, 4H), 2.92 (s, 3H), 3.23-3.25 (m, 1H), 3.31-3.75 (m, 9H), 3.95-3.99 (m, 1H), 4.05-4.15 (m, 1H), 4.20-4.26 (m, 1H), 4.27-4.41 (m, 1H), 4.68-4.70 (m, 1H), 7.26-7.37 (m, 3H), 7.51 (d, J 8.4, 1H), 7.48-7.54 (m, 1H), 7.93 (d, J 8.4, 1H), 8.09 (s, 1H); (ES$^+$) m/z 620 (M+H)$^+$.

Example 6

(20R)-30-cyclohexyl-21-methyl-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide Step 1: tert-butyl 4-(aminosulfonyl)piperazine-1-carboxylate Sulfamide (5 eq) was added to a solution of tert-butyl piperazine-1-carboxylate in dioxane (0.12 M). The reaction was stirred at reflux overnight. The solvent was removed in vacuo, the residue taken up in EtOAc and washed with H$_2$O, brine, before being dried (Na$_2$SO$_4$), filtered and concentrated in vacuo to give the crude material. Purification was by automated FC (EtOAc:PE:Et$_3$N 40:60:0.02) to afford the title compound (70%). $^1$H NMR (300 MHz, DMSO-d$_6$, 300 K) δ 1.39 (s, 9H), 2.88-2.90 (m, 4H), 3.37-3.39 (m, 4H), 6.78 (s, 2H).

Step 2: methyl (7R)-7-[(2-chloroethyl)(methyl)amino]-14-cyclohexyl-7,8-dihydro-6H-indolo[1,2-e][1,5]benzoxazocine-11-carboxylate HOAc (cat.) was added to a stirred mixture of methyl (7R)-14-cyclohexyl-7-(methylamino)-7,8-dihydro-6H-indolo[1,2-e][1,5]benzoxazocine-11-carboxylate (prepared as described in Example 1, Step 5) (0.03 M) and chloroacetaldehyde (50 wt % in water; 1.5 eq) in MeOH. NaCNBH$_3$ (1.5 eq) was introduced and the reaction heated at 60° C. for 2 h. The reaction was allowed to cool to RT and partitioned between water and EtOAc. The organics were washed with saturated NaHCO$_3$ (aq), brine before being dried (Na$_2$SO$_4$) filtered and concentrated in vacuo. The material was taken on without further purification. (ES$^+$) m/z 480 (M+H)$^+$; 482 (M+H)$^+$.

Step 3: (7R)-7-[(2-chloroethyl)(methyl)amino]-14-cyclohexyl-7,8-dihydro-6H-indolo[1,2-e][1,5]benzoxazocine-1-carboxylic acid BBr$_3$ (1 M solution in DCM; 6 eq) was added to a solution of methyl (7R)-7-[(2-chloroethyl)(methyl)amino]-14-cyclohexyl-7,8-dihydro-6H-indolo[1,2-e][1,5]benzoxazocine-11-carboxylate (0.03 M) in DCM at 0° C. Following complete addition, the cooling bath was removed and the reaction stirred at RT for 15 min. The reaction was then partitioned between 1N HCl (aq) and EtOAc. The organics were washed with brine, dried (Na$_2$SO$_4$), filtered and concentrated in vacuo. The resultant carboxylic acid was taken on without further purification. (ES⁺) m/z 466 (M+H)⁺; 468 (M+H)⁺.

Step 4: tert-butyl 4-{[({(7R)-[(2-chloroethyl)(methyl)amino]-14-cyclohexyl-7,8-dihydro-6H-indolo[1,2-e][1,5]benzoxazocin-1-yl}carbonyl)amino]sulfonyl}piperazine-1-carboxylate To a solution of (7R)-7-[(2-chloroethyl)(methyl)amino]-14-cyclohexyl-7,8-dihydro-6H-indolo[1,2-e][1,5]benzoxazocine-11-carboxylic acid (0.15 M) in DCM were added sequentially EDC (1.5 eq), tert-butyl 4-(aminosulfonyl)piperazine-1-carboxylate (1.5 eq) (prepared as described in Step 1) and DMAP (3 eq). The mixture was stirred at 40° C. for 2 h. Further EDC (1.5 eq) and protected (aminosulfonyl)piperazine (1 eq) were introduced and heating continued for 2 h. Additional EDC (0.5 eq) and protected (aminosulfonyl)piperazine (0.5 eq) were introduced and heating continued for 1 h. The reaction was allowed to cool before being partitioned between EtOAc and 1N HCl (aq). The aqueous was extracted with EtOAc and the organics combined, washed with saturated NaHCO₃ (aq), brine, dried (Na₂SO₄), filtered and concentrated in vacuo to leave a yellow gum. (ES⁺) m/z 713 (M+H)⁺; 715 (M+H)⁺.

Step 5: (7R)-7-[(2-chloroethyl)(methyl)amino]-14-cyclohexyl-N-piperazin-1-ylsulfonyl)-7,8-dihydro-6H-indolo[1,2-e][1,5]benzoxazocine-11-carboxamide TFA (100 eq) was added to a stirred solution of tert-butyl 4-{[({(7R)-7-[(2-chloroethyl)(methyl)amino]-14-cyclohexyl-7,8-dihydro-6H-indolo[1,2-e][1,5]benzoxazocin-11-yl}carbonyl)amino]sulfonyl}piperazine-1-carboxylate (0.12 M) in DCM. The reaction was warmed at 40° C. for 1.5 h. The reaction was allowed to cool to RT and the volatiles were then removed in vacuo, diluting with Et₂O and re-concentrating to drive off excess TFA. The material was taken on without further purification. (ES⁺) m/z 613 (M+H)⁺; 615 (M+H)⁺

Step 6: (20R)-30-cyclohexyl-21-methyl-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide DIPEA (20 eq) was added to a solution of (7R)-7-[(2-chloroethyl)(methyl)amino]-14-cyclohexyl-N-(piperazin-1-ylsulfonyl)-7,8-dihydro-6H-indolo[1,2-e][1,5]benzoxazocine-11-carboxamide (0.001 M) in MeCN and the mixture irradiated in a microwave (SmithCreator) at 150° C. for 5 mins. The volatiles were removed in vacuo and the residue purified by RP-HPLC, eluting with MeCN/TFA buffered with 0.1% TFA gradient. Fractions containing the product were combined and freeze dried to afford the product as a white powder (26% overall for steps 2 through to 6). ¹H NMR (600 MHz, DMSO-d₆+TFA, 330 K) δ 1.12-1.20 (m, 1H), 1.29-1.37 (m, 2H), 1.47-1.49 (m, 1H), 1.68-1.72 (m, 2H), 1.82-1.99 (m, 4H), 2.43 (s, 3H), 2.69-2.74 (m, 1H), 2.96-2.99 (m, 1H), 3.12-3.19 (m, 1H), 3.31-3.61 (m, 8H), 3.71-3.89 (m, 2H), 4.03-4.07 (m, 1H), 4.11-4.18 (m, 2H), 4.52-4.58 (m, 1H), 4.62-4.68 (m, 1H), 7.32-7.35 (m, 2H), 7.40-7.42 (m, 1H), 7.48 (d, J 8.4, 1H), 7.55-7.58 (m, 1H), 7.91 (d, J 8.4, 1H), 7.95 (s, 1H); (ES⁺) m/z 592 (M+H)⁺.

Example 7

(7S)-14-cyclohexyl-18,21-dimethyl-7,8-dihydro-6H-7,11-(epoxyethanoiminoethanoiminothioiminomethano)indolo[1,2-e][1,5]benzoxazocin-15-one 17,17-dioxide Step 1: N-benzyl-2-chloro-N-methylethanaminium chloride 2-[benzyl(methyl)amino]ethanol was added dropwise to an excess of SOCl₂ (50 eq) and the mixture heated at 35° C. for 16 h. Volatiles were removed in vacuo and the residual oil triturated with Et₂O to give the title compound as a white solid in quantitative yield. (ES⁺) m/z 184 (M+H)⁺; 186 (M+H)⁺.

Step 2: N-benzyl-2-{[(7S)-11-carboxy-14-cyclohexyl-7,8-dihydro-6H-indolo[1,2-e][1,5]benzoxazocin-7-yl]oxy}-N-methylethanaminium chloride To a suspension of methyl (7S)-14-cyclohexyl-7-hydroxy-7,8-dihydro-6H-indolo[1,2-e][1,5]benzoxazocine-11-carboxylate (prepared as described in International patent application WO2006/046030) in toluene (0.05 M), were added 10 eq of 30% w/w aq. NaOH followed by 0.25 eq of NBu₄Br. After stirring for 30 min, 2.5 eq of N-benzyl-2-chloro-N-methylethanaminium chloride were added and the reaction mixture was stirred at 60° C. for 16 h. The reaction mixture was concentrated in vacuo, and the residue purified by RP-HPLC (Waters Xterra prep. C18 column, 5 um, 19×100 mm. Mobile phase: MeCN/H₂O buffered with 0.1% TFA). Fractions containing the pure compound were combined and freeze dried in the presence of HCl to afford the title compound (25%) as a white powder. (ES⁺) m/z 539 (M+H)⁺.

Step 3: (7S)-7-{2-[benzyl(methyl)amino]ethoxy}-14-cyclohexyl-N-{[(2,2-dimethoxyethyl)(methyl)amino]sulfonyl}-7,8-dihydro-6H-indolo[1,2-e][1,5]benzoxazocine-11-carboxamide A solution (0.06 M) of N-benzyl-2-{[(7S)-11-carboxy-14-cyclohexyl-7,8-dihydro-6H-indolo[1,2-e][1,5]benzoxazocin-7-yl]oxy}-N-methylethanaminium chloride and DMAP (3 eq) in anhydrous DCM, was treated with EDC (1.5 eq) and N-(2,2-dimethoxyethyl)-N-methylsulfamide (prepared as described in Example 1, Step 1). The mixture was stirred at 40° C. for 14 h, and then diluted with EtOAc, washed with aqueous sat. aq. NaHCO₃ and brine. The organic layer was dried (Na₂SO₄), filtered and concentrated in vacuo to give the title compound. The product was used in the next step without further purification. (ES⁺) m/z 719 (M+H)⁺.

Step 4: (7S)-14-cyclohexyl-N-{[(2,2-dimethoxyethyl)(methyl)amino]sulfonyl}-7-[2-(methylamino)ethoxy]-7,8-dihydro-6H-indolo[1,2-e][1,5]benzoxazocine-11-carboxamide Pd/C (1 eq) was added to a solution of (7S)-7-{2-[benzyl(methyl)amino]ethoxy}-14-cyclohexyl-N-{[(2,2-dimethoxyethyl)(methyl)amino]sulfonyl}-7,8-dihydro-6H-indolo[1,2-e][1,5]benzoxazocine-11-carboxamide (0.06 M) in MeOH. The resulting mixture was stirred for 12 h under H₂ atmosphere. The mixture was filtered and then concentrated in vacuo to afford the title compound. The product was used in the next step without further purification. (ES⁺) m/z 629 (M+H)⁺.

Step 5: (7S)-14-cyclohexyl-7-[2-(methylamino) ethoxy]-N-{[methyl(2-oxoethyl)amino]sulfonyl}-7, 8-dihydro-6H-indolo[1,2-e][1,5]benzoxazocine-11-carboxamide A solution of (7S)-14-cyclohexyl-N-{[(2,2-dimethoxyethyl)(methyl)amino]sulfonyl}-7-[2-(methylamino)ethoxy]-7,8-dihydro-6H-indolo[1,2-e][1,5]benzoxazocine-11-carboxamide (0.06 M) in DCM was treated with an excess of TFA and $H_2O$ (>50 eq). The mixture was stirred at 40° C. for 30 min. All the volatiles were concentrated in vacuo to give the title compound, which was taken on without further purification. $(ES^+)$ m/z 583 $(M+H)^+$.

Step 6: (7S)-14-cyclohexyl-18,21-dimethyl-7,8-dihydro-6H-7,11-(epoxyethanoiminoethanoiminothioiminomethano)indolo[1,2-e][1,5]benzoxazocin-15-one 17,17-dioxide A solution (4 mM) of (7S)-14-cyclohexyl-7-[2-(methylamino)ethoxy]-N-{[methyl(2-oxoethyl)amino]sulfonyl}-7,8-dihydro-6H-indolo[1,2-e][1,5]benzoxazocine-11-carboxamide in MeOH was treated with $NaBH_3CN$ (10 eq). The mixture was stirred at RT overnight, then quenched with few drops of aqueous sat. aq. $NaHCO_3$ and concentrated in vacuo. The crude was purified by automated RP-MS-HPLC (Waters Xterra prep. C18 column, 5 um, 19×100 mm. Mobile phase: $MeCN/H_2O$ buffered with 0.1% TFA). Fractions containing the pure compound were combined and freeze dried to afford the title compound as a white powder (5%; over steps 3-6). $^1H$ NMR (600 MHz, DMSO-$d_6$+TFA, 335 K) δ 1.10-1.40 (m, 4H), 1.50-1.60 (m, 1H), 1.60-1.70 (m, 2H), 1.80-1.90 (m, 1H), 1.90-2.0 (m, 2H), 2.60-2.75 (m, 1H), 2.80 (s, 3H), 3.05 (s, 3H), 3.20-3.60 (m, 4H), 3.70-4.00 (m, 6H), 4.00-4.10 (m, 1H), 4.10-4.30 (m, 1H), 4.85-4.95 (m, 1H), 7.15-7.25 (m, 2H), 7.25-7.35 (m, 1H), 7.35-7.45 (m, 1H), 7.45-7.55 (m, 1H), 7.85 (d, J 8.4, 1H), 8.25 (s, 1H); $(ES^+)$ m/z 567 $(M+H)^+$.

Example 8

(7R)-14-cyclohexyl-18,21,24-trimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide

Step 1: 4-bromo-3-hydroxyphenyl 4-methylbenzenesulfonate $K_2CO_3$ (3 eq) was added to a stirred mixture of 4-bromoresorcinol (0.35 M) and TsCl (1.2 eq) in acetone and the mixture stirred at 50° C. for 18 h. Volatiles were removed in vacuo and the residue partitioned between 6 N HCl (aq) and EtOAc. The combined organic fractions were washed with brine, dried ($Na_2SO_4$), filtered and evaporated in vacuo to give the title compound. The product was used in the next step without further purification. $(ES^+)$ m/z 343, 345 $(M+H)^+$.

Step 2: 4-bromo-3-(methoxymethoxy)phenyl 4-methylbenzenesulfonate

A solution of 4-bromo-3-hydroxyphenyl 4-methylbenzenesulfonate in dry DMF (1.0 M) was treated with NaH (1.2 eq of a 60% dispersion in mineral oil) and the mixture was stirred at RT for 30 min. Chloromethyl methyl ether (1.2 eq) was then added dropwise and the mixture was stirred at RT overnight. The mixture was diluted with EtOAc and the organic phase washed with 1 N HCl and brine before drying ($Na_2SO_4$), filtering and concentrating in vacuo. The crude was purified by FC (PE/EtOAc 1/9) to afford the title compound (77%). $(ES^+)$ m/z 387, 389 $(M+H)^+$.

Step 3: (2-(methoxymethoxy)-4-{[(4-methylphenyl) sulfonyl]oxy}phenyl)boronic acid To a solution (0.30 M) of 4-bromo-3-(methoxymethoxy) phenyl 4-methylbenzenesulfonate in a mixture (1:3) of THF/ toluene, triisopropyl borate was added and then the mixture cooled to −78° C. To the cold solution, n-BuLi (2.5 M in hexane; 1.5 eq) was added via syringe pump over 1.5 h. The mixture was stirred at −78° C. for a further 2 h and then left to warm to RT overnight. The mixture was diluted with EtOAc and washed with 1 N HCl, extracting the aqueous fraction a further two times with EtOAc. The combined organics were washed with sat. aq. $NaHCO_3$ and brine, dried ($Na_2SO_4$), filtered and concentrated in vacuo to afford the product, that could be used directly as crude or purified by FC (PE/EtOAc 9/1) to afford the title compound (43%). $^1H$ NMR (400 MHz, DMSO-$d_6$, 300 K) δ 2.42 (s, 3H), 3.31 (s, 3H), 5.06 (s, 2H), 6.64-6.69 (m, 2H), 7.44-7.49 (m, 3H), 7.74 (d, J 8.3, 2H); $(ES^+)$ m/z 353 $(M+H)^+$.

Step 4: methyl 3-cyclohexyl-2-(2-(methoxymethoxy)-4-{[(4-methylphenyl)sulfonyl] oxy}phenyl)-1H-indole-6-carboxylate Methyl 2-bromo-3-cyclohexyl-1H-indole-6-carboxylate (prepared as in International patent application WO 2004/ 087714), (2-(methoxymethoxy)-4-{[(4-methylphenyl)-sulfonyl]oxy}phenyl)boronic acid (1 eq) and bis(triphenylphosphinepalladium(II) chloride (0.1 eq) were dissolved in dioxane (0.08M). The solution was degassed and flushed with argon. A 2M aqueous solution of $Na_2CO_3$ (1 eq) was added and the mixture was heated to 100° C. After 3 h the temperature was raised to 110° C. Heating was continued overnight. All volatiles were evaporated and the residual material was dissolved in EtOAc. The solution was washed with 1N aqueous HCl, sat. aq. $NaHCO_3$ and brine. After drying over $Na_2SO_4$ all volatiles were evaporated in vacuo. The residual material was subjected to FC (PE:EtOAc, 8:2). After evaporation of the product fractions the product was obtained as a light orange amorphous solid (58%). $(ES^+)$ m/z 564 $(M+H)^+$.

Step 5: methyl 3-cyclohexyl-2-[4-hydroxy-2-(methoxymethoxy)phenyl]-1H-indole-6-carboxylate Methyl 3-cyclohexyl-2-(2-(methoxymethoxy)-4-{[(4-methylphenyl)sulfonyl]oxy}-phenyl)-1H-indole-6-carboxylate was suspended in MeOH 0.18 M) and NaOMe (5 eq) was added. The mixture was warmed in a closed vessel to 80° C. After 4 h additional NaOMe (5 eq) was added. The mixture was warmed overnight. The mixture was cooled to RT and 1N aqueous HCl was added to the mixture. After dilution with $H_2O$ the mixture was extracted with EtOAc. The organic phase was separated and washed with sat. aq. $NaHCO_3$ and brine. After drying over $Na_2SO_4$ all volatiles were evaporated in vacuo. The residual material was filtered with PE:EtOAc (8:2) through a pad of silica gel. The product was obtained as a yellowish amorphous solid (49%). $(ES^+)$ m/z 410 $(M+H)^+$.

Step 6: methyl 3-cyclohexyl-2-[2-(methoxymethoxy)-4-(pyridin-2-ylmethoxy)phenyl]-1H-indole-6-carboxylate Methyl 3-cyclohexyl-2-[4-hydroxy-2-(methoxymethoxy) phenyl]-1H-indole-6-carboxylate was dissolved in DMF (0.17 M) and Cs$_2$CO$_3$ (1.05 eq) was added. The mixture was stirred for 20 min, then 2-bromomethylpyridine (1.05 eq) was added and the suspension was stirred at RT. After 4 h Cs$_2$CO$_3$ (0.3 eq) was added and the mixture was stirred overnight. Since the reaction was incomplete the mixture was warmed for 30 min to 35° C. The mixture was diluted with EtOAc and extracted with 1N aqueous HCl, sat. aq. NaHCO$_3$ and brine. After drying over Na$_2$SO$_4$ all volatiles were evaporated in vacuo. The product was obtained as a beige amorphous solid (89%). (ES$^+$) m/z 501 (M+H)$^+$.

Step 7: methyl 3-cyclohexyl-2-[2-hydroxy-4-(pyridin-2-ylmethoxy)phenyl]-1H-indole-6-carboxylate Methyl 3-cyclohexyl-2-[2-(methoxymethoxy)-4-(pyridin-2-ylmethoxy)phenyl]-1H-indole-6-carboxylate was dissolved in MeOH (0.5 M). 3N HCl (2 eq) was added, followed by more MeOH. The mixture was warmed to 80° C. for 6 h. By this time a clear solution had formed. All volatiles were evaporated in vacuo and the residual material was dissolved in DCM. The solution was washed with sat. aq. NaHCO$_3$ and brine. After drying over Na$_2$SO$_4$ all volatiles were evaporated in vacuo leaving a beige amorphous solid (quant). (ES$^+$) m/z 457 (M+H)$^+$.

Step 8: methyl 3-cyclohexyl-2-[2-[2S)-oxiran-2-ylmethoxy]-4-(pyridin-2-ylmethoxy)phenyl]-1H-indole-6-carboxylate Methyl 3-cyclohexyl-2-[2-hydroxy-4-(pyridin-2-ylmethoxy)phenyl]-1H-indole-6-carboxylate was dissolved in DMF (0.1 M) and CsF (3 eq) was added. The resulting mixture was warmed to 30° C. The fluorescent mixture was treated with (S)-(+)-glycidyl tosylate (1.2 eq) and stirred at 30° C. overnight The mixture was diluted with EtOAc and extracted with H$_2$O, sat. aq. NaHCO$_3$ and brine. After drying over Na$_2$SO$_4$ all volatiles were evaporated in vacuo. A brownish sticky residue was obtained (99%). (ES$^+$) m/z 513 (M+H)$^+$.

Step 9: methyl (7S)-14-cyclohexyl-7-hydroxy-3-(pyridin-2-ylmethoxy)-7,8-dihydro-6H-indolo[1,2-e][1,5]benzoxazocine-11-carboxylate Methyl 3-cyclohexyl-2-[2-[(2S)-oxiran-2-ylmethoxy]-4-(pyridin-2-ylmethoxy)phenyl]-1H-indole-6-carboxylate was dissolved in DMF (0.1 M) and the solution was added slowly to a suspension of Cs$_2$CO$_3$ (0.5 eq) in DMF at 65° C. After 1 h the mixture was diluted with Et$_2$O. The solution was extracted with H$_2$O, sat. aq. NaHCO$_3$ and brine. After drying over Na$_2$SO$_4$ all volatiles were evaporated in vacuo to leave an orange amorphous solid. The product was purified by FC (PE:EtOAc, 1:1+1% NEt$_3$ to wash away remaining starting material, then EtOAc:MeOH, 9:1+1% NEt$_3$). The product was obtained as a yellowish amorphous solid (62%). (ES$^+$) m/z 513 (M+H)$^+$.

Step 10: methyl (7R)-7-azido-14-cyclohexyl-3-(pyridin-2-ylmethoxy)-7,8-dihydro-6H-indolo[1,2-e][1,5]benzoxazocine-11-carboxylate Methyl (7S)-14-cyclohexyl-7-hydroxy-3-(pyridin-2-ylmethoxy)-7,8-dihydro-6H-indolo[1,2-e][1,5]benzoxazocine-11-carboxylate was dissolved in THF (60 mM) and PPh$_3$ (1.2 eq) was added. The solution was cooled to 0° C. and treated with DIPEA (1 eq), followed by slow addition of DIAD (1.2 eq). The mixture was left stirring at this temperature for 5 min, then a solution of DPPA in THF (1.2 eq) was added dropwise. After complete addition the mixture was stirred at 0° C. for further 30 min, then stirring was continued at RT. Since no reaction was observed after 1 h more PPh$_3$ in THF (1.2 eq), DIAD in THF (1.2 eq) and DPPA in THF (0.6 eq) were added at RT. The formation of a precipitate was observed. Stirring was continued for 1 h at RT after which time HPLC-MS indicated complete conversion. The mixture was used without further treatment in the next reaction (quant). (ES$^+$) m/z 538 (M+H)$^+$.

Step 11: methyl (7R)-7-amino-14-cyclohexyl-3-(pyridin-2-ylmethoxy)-7,8-dihydro-6H-indolo[1,2-e][1,5]benzoxazocine-11-carboxylate The reaction from the previous step was treated with a solution of PPh$_3$ in THF (1.3 eq). After 3 h H$_2$O was added. The mixture was warmed to 50° C. overnight. The mixture was diluted with EtOAc, then extracted with H$_2$O, sat. aq. NaHCO$_3$ and brine. After drying over Na$_2$SO$_4$ all volatiles were evaporated in vacuo to leave a yellowish oil. The material was dissolved in THF/MeOH (2:1). The mixture was diluted with water and 3N aqueous HCl was added. The resulting mixture was washed thoroughly with EtOAc. The combined organic phases were discarded. The aqueous phase was basified by addition of solid Na$_2$CO$_3$ to pH=8. The resulting mixture was extracted twice with EtOAc. The combined organic phases were dried over Na$_2$SO$_4$ and evaporated in vacuo. The product was obtained as a yellowish amorphous solid (61%). (ES$^+$) m/z 512 (M+H)$^+$.

Step 12: methyl (7R)-7-({2-[(tert-butoxycarbonyl)(methyl)amino]ethyl}amino)-14-cyclohexyl-3-(pyridin-2-ylmethoxy)-7,8-dihydro-6H-indolo[1,2-e][1,5]benzoxazocine-11-carboxylate Methyl (7R)-7-amino-14-cyclohexyl-3-(pyridin-2-ylmethoxy)-7,8-dihydro-6H-indolo[1,2-e][1,5]benzoxazocine-11-carboxylate was dissolved in HC(OMe)$_3$ (50 eq) and a solution of tert-butyl methyl(2-oxoethyl)carbamate (1.6 eq, prepared according to *Tetrahedron* 2002, 58, 1719-1737) in HC(OMe)$_3$ (50 eq) was added. The mixture was stirred overnight at RT to allow formation of the imine. All volatiles were evaporated and the residual material was dissolved in MeOH/HOAc (0.05 M). NaCNBH$_3$ (1 eq) was added and the mixture was stirred at RT for 1 h. Some formation of the N-formyl product was observed alongside formation of the desired product. The solution was used directly in the next step. (ES$^+$) m/z 669 (M+H)$^+$.

Step 13: methyl (7R)-7-[{2-[(tert-butoxycarbonyl)(methyl)amino]ethyl}(methyl)amino]-14-cyclohexyl-3-(pyridin-2-ylmethoxy)-7,8-dihydro-6H-indolo[1,2e][1,5]benzoxazocine-11-carboxylate To the solution of methyl (7R)-7-({2-[(tert-butoxycarbonyl)(methyl)amino]ethyl}amino)-14-cyclohexyl-3-(pyridin-2-ylmethoxy)-7,8-dihydro-6H-indolo[1,2-e][1,5]benzoxazocine-11-carboxylate in MeOH/HOAc containing NaCNBH$_3$ from the previous step was added a 37% solution of HCHO in water (1 eq) and stirring at RT was continued. After 1 h all volatiles were evaporated. The residual material was taken up with Et$_2$O and the resulting solution was washed with sat. aq. NaHCO$_3$ and with brine. After drying over Na$_2$SO$_4$ all volatiles were evaporated in vacuo. The yellow residue was subjected to FC (PE:EtOAc, 6:4+1% NEt$_3$). After evaporation of the solvents the product was obtained as a colourless solid (44%). The material was used without further characterisation in the next reaction. (ES+) m/z 683 (M+H)+.

Step 14: (7R)-7-[{2-[(tert-butoxycarbonyl) (methyl) amino]ethyl}(methyl)amino]-14-cyclohexyl-3-(pyridin-2-ylmethoxy)-7,8-dihydro-6H-indolo[1,2-e][1,5]benzoxazocine-11-carboxylic acid To the solution of methyl (7R)-7-[{2-[(tert-butoxycarbonyl)(methyl)amino]-ethyl}(methyl)amino]-14-cyclohexyl-3-(pyridin-2-ylmethoxy)-7,8-dihydro-6H-indolo[1,2-e][1,5]benzoxazocine-11-carboxylate in dioxane (0.1 M) was added 2M KOH solution (3 eq). The mixture was warmed to 60° C. After 4 days the mixture was neutralised by addition of 1N HCl and all volatiles were evaporated in vacuo. The residual material was dried in vacuo and used without further purification. (ES+) m/z 669 (M+H)+.

Step 15: tert-butyl {2-[[(7R)-14-cyclohexyl-11-[({[(2,2-dimethoxyethyl)(methyl)amino]sulfonyl}amino)carbonyl]-3-(pyridin-2-ylmethoxy)-7,8-dihydro-6H-indolo[1,2-e][1,5]benzoxazocin-7-yl](methyl)amino]ethyl}methylcarbamate (7R)-7-[{2-[(tert-butoxycarbonyl)(methyl)amino]ethyl}(methyl)amino]-14-cyclohexyl-3-(pyridin-2-ylmethoxy)-7,8-dihydro-6H-indolo[1,2-e][1,5]benzoxazocine-11-carboxylic acid, N-(2,2-dimethoxyethyl)-N-methylsulfamide (2 eq, see Example 1, Step 1) and DMAP (5 eq) were dissolved in DCM (24 mM) and EDC (3 eq) was added. The mixture was warmed to 40° C. After 2 h the mixture was diluted with DCM and extracted twice with $H_2O$, sat. aq. $NH_4Cl$ and brine. The organic phase was dried over $Na_2SO_4$ and evaporated in vacuo. The product was obtained as a yellowish sticky solid and used without further purification (91%). (ES+) m/z 849 (M+H)+.

Step 16: (7R)-14-cyclohexyl-7-{methyl[2-(methylamino)ethyl]amino}-N-{[methyl(2-oxoethyl)amino]sulfonyl}-3-(pyridin-2-ylmethoxy)-7,8-dihydro-6H-indolo[1,2-e][1,5]benzoxazocine-11-carboxamide tert-butyl {2-[[(7R)-14-cyclohexyl-11-[({[(2,2-dimethoxyethyl)(methyl)amino]-sulfonyl}amino)carbonyl]-3-(pyridin-2-ylmethoxy)-7,8-dihydro-6H-indolo[1,2-e][1,5]benzoxazocin-7-yl](methyl)amino]ethyl}methylcarbamate was dissolved in DCM/$H_2O$/TFA (8:1:3, 15 mM). The mixture was warmed to 40° C. After 30 min all volatiles were evaporated in vacuo and the residual material was coevaporated twice with toluene. The remaining yellow oil was used in the next reaction without further purification.

Step 17: (7R)-14-cyclohexyl-18,21,24-trimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide (7R)-14-cyclohexyl-7-{methyl[2-(methylamino)ethyl]amino}-N-{[methyl(2-oxoethyl)amino]sulfonyl}-3-(pyridin-2-ylmethoxy)-7,8-dihydro-6H-indolo[1,2-e][1,5]benzoxazocine-11-carboxamide was dissolved in MeOH (1.7 mM), $NEt_3$ (3.3 eq) and HOAc (6.6 eq) were added, followed by $NaCNBH_3$ (2 eq). After 1 h all volatiles were evaporated in vacuo. The material was dissolved in DMSO and purified by prep RP-HPLC. After lyophilisation of the product fractions the product was obtained as a colourless amorphous material (27%, TFA-salt). $^1$H NMR (400 MHz, DMSO-$d_6$, 300 K, TFA-salt) δ 8.62 (d, 1H, J 4.52), 7.99 (s, 1H), 7.89 (d, 2H, 8.60), 7.60 (d, 1H, J 7.80), 7.44-7.38 (m, 2H), 7.28 (d, 1H, J 8.20), 7.03-7.01 (m, 2H), 5.30 (d, 1H, J 12.80), 5.25 (d, 1H, J 12.80), 4.55-4.51 (m, 1H), 4.34-4.32 (m, 1H), 4.10-4.05 (m, 1H), 3.98-3.85 (m, 2H), 3.51-3.45 (m, 2H), 3.33-3.10 (m, 5H), 3.00 (s, 3H), 2.99-2.90 (m, 1H), 2.83 (s, 3H), 2.66-2.62 (m, 1H), 2.34 (s, 3H), 1.92-1.67 (m, 6H), 1.45-1.13 (m, 4H); (ES+) m/z 687 (M+H)+.

Example 9

13-cyclohexyl-5,17,20,23-tetramethyl-6,7-dihydro-5H-10,6-(methanoiminothioiminoethanoiminoethanoiminomethano)indolo[1,2-d][1,4]benzodiazepin-14-one 16,16-dioxide Step 1: dimethyl 13-cyclohexyl-6,7-dihydro-5H-indolo[1,2-d][1,4]benzodiazepine-6,10-dicarboxylate Methyl 2-bromo-3-cyclohexyl-indole-6-carboxylate (prepared as described in International patent application WO 2004/087714), 2-(4,4,5,5-tetramethyl-1,3,2-dioxaborolan-2-yl)aniline (1.4 eq) and $Pd(PPh_3)_2Cl_2$ (0.1 eq) were dissolved in dioxane (0.08M) and 2M $Na_2CO_3$ solution (1 eq) was added. The mixture was degassed and flushed with Ar. The mixture was heated to 100° C. under Ar atmosphere. After 6 h the mixture was cooled to RT and all volatiles were evaporated in vacuo. The residual material was dissolved in DCM and PE was added. The mixture was left stirring for 3 days. The resulting precipitate was filtered off and dissolved again in DCM. The product methyl-2-(2-aminophenyl)-3-cyclohexyl-1H-indole-6-carboxylate was precipitated from this solution with PE and obtained after filtration and drying in vacuo as a beige powder (68%). (ES+) m/z 349 (M+H)+.

The foregoing compound was dissolved in MeCN (0.07M) and $Bu_4NBr$ (0.3 eq) was added followed by $K_2CO_3$ (6 eq). Ethyl α-chloroacrylate (1.7 eq) was added to the mixture which was then heated overnight to 60° C. All volatiles were evaporated in vacuo and the residual material was mixed with EtOAc. The suspension was extracted with 10% citric acid, sat. aq. $NaHCO_3$ and brine. After drying over $Na_2SO_4$ all volatiles were evaporated in vacuo. The residual material was subjected to purification by FC (PE, then PE:EtOAc, 9:1; then PE:EtOAc, 8:2).

After evaporation of the solvents the product was obtained as a yellowish solid (84%). (ES+) m/z 433 (M+H)+.

Step 2: Dimethyl 13-cyclohexyl-5-methyl-6,7-dihydro-5H-indolo[1,2-d][1,4]benzodiazepine-6,10-dicarboxylate Dimethyl 13-cyclohexyl-6,7-dihydro-5H-indolo[1,2-d][1,4]benzodiazepine-6,10-dicarboxylate was dissolved in anhydrous MeOH (0.05M) and HOAc was added. The mixture was treated with a 37% solution of HCHO in water (1.2 eq), then $NaCNBH_3$ (1.2 eq) was added. The solution was stirred for 2 h at RT. The product was isolated by FC (PE:EtOAc, 9:1, 0.5% $NEt_3$). After evaporation of the solvents a colourless solid was obtained (quant.). (ES+) m/z 447 (M+H)+.

Step 3: Methyl 13-cyclohexyl-6-(hydroxymethyl)-5-methyl-6,7-dihydro-5H-indolo[1,2-d][1,4]benzodiazepine-10-carboxylate Dimethyl 13-cyclohexyl-5-methyl-6,7-dihydro-5H-indolo[1,2-d][1,4]benzodiazepine-6,10-dicarboxylate was dissolved in anhydrous THF (0.05M) and $LiBH_4$ (1 eq) was added. The mixture was stirred at RT. After 1 h only marginal conversion to the product was observed. BH$_3$-THF complex (1 eq) was added and the mixture was stirred at RT. After 2 h a further equivalent of BH$_3$-THF complex was added and the mixture was stirred for 2 h. The mixture was quenched by addition of silica gel and all volatiles were evaporated in vacuo. The product was isolated by FC (PE:EtOAc, 8:2). After evaporation of the solvents the product was obtained as a colourless solid (80%). (ES$^+$) m/z 419 (M+H)$^+$.

Step 4: Methyl 13-cyclohexyl-6-formyl-5-methyl-6, 7-dihydro-5H-indolo[1,2-d][1,4]benzodiazepine-10-carboxylate DMSO (5 eq) was dissolved in DCM and the solution was cooled to −78° C. At this temperature a 2M solution of oxalylchloride in DCM (2.5 eq) was added slowly and the mixture was stirred for 25 min at −78° C. A solution of dimethyl 13-cyclohexyl-5-methyl-6,7-dihydro-5H-indolo[1,2-d][1,4] benzodiazepine-6,10-dicarboxylate (1 eq) in DCM (0.09M) was added slowly at −78° C. and stirring was continued for 25 min at this temperature. Then NEt$_3$ (8 eq) was added and the resulting slurry was placed into an ice bath at 0° C. The mixture was left stirring for 90 min, then diluted with DCM and extracted with sat. aq. NH$_4$Cl, sat. aq. NaHCO$_3$ and brine. After drying over Na$_2$SO$_4$ all volatiles were evaporated in vacuo. The product was obtained as a deep-yellow solid, which was filtered with DCM over a pad of silica. After evaporation of the solvent the product was obtained as a yellowish solid (quant.). (ES$^+$) m/z 417 (M+H)$^+$.

Step 5: 6-{[{2-[(tert-butoxycarbonyl)(methyl)amino] ethyl}(methyl)amino]methyl}-13-cyclohexyl-5-methyl-6,7-dihydro-5H-indolo[1,2-d][1,4]benzodiazepine-10-carboxylic acid Methyl 13-cyclohexyl-6-formyl-5-methyl-6,7-dihydro-5H-indolo[1,2-d][1,4]benzodiazepine-10-carboxylate was dissolved in MeOH (0.09M) and HOAc was added. N,N'-dimethylethylendiamine (4 eq) was added and the mixture was stirred for 5 min. NaCNBH$_3$ (1.5 eq) was added and the mixture was stirred overnight. All volatiles were then evaporated in vacuo and the residual material was dissolved in EtOAc. The solution was extracted with sat. aq. NH$_4$Cl, sat. aq. NaHCO$_3$ and brine. After drying over Na$_2$SO$_4$ all volatiles were evaporated in vacuo. The crude residue of methyl 13-cyclohexyl-5-methyl-6-({methyl[2-(methylamino)ethyl] amino}methyl)-6,7-dihydro-5H-indolo[1,2-d][1,4]benzodiazepine-10-carboxylate was dissolved in dioxane (0.05M) and di-tert-butyl dicarbonate$_2$O (2 eq) was added. The mixture was stirred for 1 h. All volatiles were then evaporated in vacuo and the residual material was taken up in EtOAc. The solution was extracted with sat. aq. NH$_4$Cl, sat. aq. NaHCO$_3$ and with brine. After drying over Na$_2$SO$_4$ all volatiles were evaporated in vacuo. The residual material was filtered through a pad of silica gel (PE:EtOAc, 7:3). After evaporation of the solvents, the crude mixture of methyl 6-{[{2-[(tert-butoxycarbonyl)(methyl)amino]ethyl}-(methyl)amino]methyl}-13-cyclohexyl-5-methyl-6,7-dihydro-5H-indolo[1,2-d][1,4]benzodiazepine-10-carboxylate was dissolved in dioxane (0.05M) and 1M KOH solution (2 eq) was added. The mixture was warmed to 60° C. After 12 h, EtOAc was added and the mixture was extracted with 10% aqueous citric acid solution and brine. After drying the organic phase over Na$_2$SO$_4$ all volatiles were evaporated in vacuo. The residual solid (6-{[{2-[(tert-butoxycarbonyl)(methyl)amino]ethyl}-(methyl)amino]methyl}-13-cyclohexyl-5-methyl-6,7-dihydro-5H-indolo[1,2-d][1,4]benzodiazepine-10-carboxylic acid) was used without further purification in the next reaction (67% over 3 steps). (ES$^+$) m/z 575 (M+H)$^+$.

Step 6: 13-cyclohexyl-5-methyl-6-({methyl[2-(methylamino)ethyl]amino}methyl)-N-{[methyl(2-oxoethyl)amino]sulfonyl}-6,7-dihydro-5H-indolo[1,2-d] [1,4]benzodiazepine-10-carboxamide 6-{[{2-[(tert-butoxycarbonyl)(methyl)amino]ethyl}(methyl)amino]methyl}-13-cyclohexyl-5-methyl-6,7-dihydro-5H-indolo[1,2-d][1,4]benzodiazepine-10-carboxylic acid, N-(2,2-dimethoxyethyl)-N-methylsulfamide (2 eq, Example 1, Step 1) and DMAP (5 eq) were dissolved in DCM (0.06M) and EDC (3 eq) was added. The mixture was warmed to 40° C. Within 5 min the clear yellow solution turned dark brown. The mixture was stirred overnight. After dilution with DCM the solution was extracted with 1N HCl, sat. aq. NaHCO$_3$ and brine. After drying the organic phase over Na$_2$SO$_4$ the solution was discoloured with activated charcoal. All volatiles were evaporated in vacuo leaving tert-butyl {2-[({13-cyclohexyl-10-[({[(2,2-dimethoxyethyl)(methyl)amino]sulfonyl}-amino)carbonyl]-5-methyl-6,7-dihydro-5H-indolo[1, 2-d][1,4]benzodiazepin-6-yl}methyl)(methyl)amino] ethyl}methylcarbamate as a glassy brownish solid (MS (ES$^+$) m/z 755 (m+H)$^+$). The material was dissolved in DCM (0.03M) and water was added. To the biphasic system TFA was added and then the vigorously stirred mixture was warmed to 40° C. After 2 h the acetal was completely cleaved, while some N-Boc-protected material was still around. More TFA was added until a monophasic system was obtained. Heating was continued for 3 h. Then all volatiles were evaporated in vacuo and the residual material was coevaporated three times with toluene. The residual sticky material was digested with Et$_2$O leaving a dark red powder. This material was used without further purification in the next reaction. (ES$^+$) m/z 609 (M+H)$^+$.

Step 7: 13-cyclohexyl-5,17,20,23-tetramethyl-6,7-dihydro-5H-10,6-(methanoiminothioiminoethanoiminoethanoiminomethano)indolo[1,2-d][1,4]benzodiazepin-14-one 16,16-dioxide 13-cyclohexyl-5-methyl-6-({methyl[2-(methylamino) ethyl]amino}methyl)-N-{[methyl(2-oxoethyl)amino]sulfonyl}-6,7-dihydro-5H-indolo[1,2-d][1,4]benzodiazepine-10-carboxamide was dissolved in MeOH (1.5 mM), NEt$_3$ (3.3 eq) and HOAc (6.6 eq) were added, followed by NaCNBH$_3$ (2 eq). The solution was stirred at RT overnight. All volatiles were evaporated in vacuo and the residual material was dissolved in EtOAc. The solution was washed with 1N HCl, sat. aq. NH$_4$Cl, sat. aq. NaHCO$_3$ and brine. The organic phase was dried over Na$_2$SO$_4$ and evaporated in vacuo. The acidic aqueous phases were basified with sat. aq. NaHCO$_3$ and extracted with EtOAc. The organic phase was evaporated in vacuo and the residual material unified with the previously obtained material. The material was dissolved in DMSO and purified by prep RP-HPLC. After lyophilisation of the product fractions the product was obtained as a yellowish amorphous material (11%). $^1$H NMR (400 MHz, DMSO-d$_6$, 300 K, TFA-salt) δ 8.20 (s, 1H), 7.91 (d, 1H, J 8.62), 7.53 (d, 1H, J 8.37), 7.45-7.42 (m, 1H), 7.28-7.25 (m, 2H), 7.16-7.12 (m, 1H), 4.73 (d, 1H, J 14.86), 3.96 (d, 1H, J 14.86), 3.87-3.67 (m, 1H), 3.56-3.19 (m, 5H), 3.04 (s, 3H), 3.02-2.98 (m, 1H), 2.92-2.67 (m, 9H), 2.45-2.39 (m, 2H), 2.05-1.86 (m, 6H), 1.72-1.62 (m, 2H), 1.55-1.14 (m, 6H); (ES$^+$) m/z 593 (M+H)$^+$.

Example 10

13-cyclohexyl-3-methoxy-17,20-dimethyl-6,7-dihydro-5H-6,10-(ethanoiminoethanoiminothioiminomethano)indolo[2,1-a][2]benzazepin-14-one 16,16-dioxide

Step 1: (2-bromo-5-methoxyphenyl)methanol

2-Bromo-5-methoxy benzoic acid (1 eq) was dissolved in anhydrous THF (0.55M solution) and $BH_3SMe_2$ complex (2M in THF, 1 eq) was added dropwise to the solution. The mixture was stirred overnight, then HCl in MeOH was added and the mixture was warmed to 60° C. All volatiles were evaporated and the residual material was dissolved in DCM. The solution was washed with 1N HCl and with brine, then dried over $Na_2SO_4$ and evaporated in vacuo. A colourless oil was obtained (94%), which was used without further characterization in the next reaction.

Step 2: [(2-bromo-5-methoxybenzyl)oxy](triisopropyl)silane (2-Bromo-5-methoxyphenyl)methanol (1 eq) was dissolved in anhydrous DMF (1.1M solution) and imidazole (1.05 eq) was added. To the stirred solution triisopropylsilyl chloride (1.1 eq) was added and the resulting mixture was stirred at RT for 8 h. All volatiles were evaporated in vacuo and the residual material was filtered with PE/EtOAc (9:1) over a pad of silica gel. After evaporation in vacuo the product was obtained as a colourless oil (94%), which was used without further characterization in the next reaction.

Step 3: (4-methoxy-2-{[(triisopropylsilyl)oxy]methyl}phenyl)boronic acid

[(2-bromo-5-methoxybenzyl)oxy](triisopropyl)silane (1 eq) was dissolved in anhydrous THF (0.43M solution) and the solution was cooled to −78° C. A solution of n-BuLi (1.6M in hexanes, 1.05 eq) was added and the resulting mixture was stirred for 1 h at −78° C. Then triisopropyl borate (50% in THF, 1.3 eq) was added dropwise and the mixture was allowed to warm to RT overnight. 1N HCl was added and the resulting mixture was stirred at RT for 30 min. THF was removed in vacuo and replaced with $Et_2O$. The organic phase was washed with water and with brine, then dried over $Na_2SO_4$ and evaporated in vacuo. The product was obtained as a colourless oil (64% yield, 65% pure) which was used without further purification in the next reaction.

Step 4: methyl 3-cyclohexyl-2-(4-methoxy-2-{[(triisopropylsilyl)oxy]methyl}phenyl)-1H-indole-6-carboxylate Methyl-2-bromo-3-cyclohexyl-1H-indole-6-carboxylate (prepared as described in International patent application WO2004/087714 from commercially available methyl indole-6-carboxylate) and (4-methoxy-2-{[(triisopropylsilyl)oxy]methyl}phenyl)boronic acid (1.1 eq) were dissolved in dioxane (0.125M solution) and 2M aq. $Na_2CO_3$ solution (3.3 eq) was added. The mixture was degassed and flushed with argon. Then $Pd(PPh_3)_2Cl_2$ (0.1 eq) was added and the mixture was heated under argon atmosphere to 110° C. After 5 h at this temperature all volatiles were evaporated in vacuo and the residual material was dissolved in EtOAc. The solution was extracted with water and with brine, then dried over $Na_2SO_4$ and evaporated in vacuo. The residual material was purified by FC (PE:EtOAc, 9:1). After evaporation of the solvents the product was obtained as an off-white foam (81%). The material was used without further characterization in the next reaction.

Step 5: methyl 1-allyl-3-cyclohexyl-2-(4-methoxy-2-{[(triisopropylsilyl)oxy]methyl}phenyl)-1H-indole-6-carboxylate Methyl 3-cyclohexyl-2-(4-methoxy-2-{[(triisopropylsilyl)oxy]methyl}phenyl)-1H-indole-6-carboxylate (1 eq) was dissolved in DMF (0.34M solution) and the solution was degassed. NaH (60% dispersion in mineral oil; 1.1 eq) was added and the mixture was stirred for 5 min. Allyl bromide (1.2 eq) was added and stirring was continued for 5 h. All volatiles were evaporated in vacuo and the residual material was dissolved in $Et_2O$. The solution was washed with 0.5N HCl, saturated aq. $NaHCO_3$ solution and with brine. After drying the organic phase over $Na_2SO_4$ all volatiles were evaporated in vacuo and the residual material was purified by FC (PE:EtOAc, 10:1). After evaporation of the solvents the product was obtained as a colourless sticky solid (84%). The material was used without further characterization in the next reaction.

Step 6: methyl 1-allyl-3-cyclohexyl-2-[2-(hydroxymethyl)-4-methoxyphenyl]-1H-indole-6-carboxylate Methyl 1-allyl-3-cyclohexyl-2-(4-methoxy-2-{[(triisopropylsilyl)oxy]methyl}phenyl)-1H-indole-6-carboxylate (1 eq) was dissolved in THF (0.28M solution) and a 1M solution of tetrabutylammonium fluoride in THF (1 eq) was added. The mixture was stirred at RT for 2 h, then all volatiles were evaporated in vacuo and the residual material was dissolved in $Et_2O$. The solution was washed with 1N HCl, saturated aq. $NaHCO_3$ solution and with brine. The organic phase was dried over $Na_2SO_4$ and evaporated in vacuo. The residual material was purified by FC (PE:EtOAc, 8:2). After evaporation of the solvents the product was obtained as colourless foam (88%). ($ES^+$): m/z 434.2 $(M+H)^+$.

Step 7: methyl 1-allyl-3-cyclohexyl-2-(2-formyl-4-methoxyphenyl)-1H-indole-6-carboxylate DMSO (5 eq) was dissolved in DCM and the solution was cooled to −78° C. To the stirred solution oxalylchloride (2.5 eq) was added and the mixture was left stirring for 30 min. A solution of methyl 1-allyl-3-cyclohexyl-2-[2-(hydroxymethyl)-4-methoxyphenyl]-1H-indole-6-carboxylate (1 eq) in DCM (0.25M solution) was added and the mixture was stirred for 30 min at −78° C. $Et_3N$ (8 eq) was added and the mixture was allowed to warm to 0° C. At this temperature stirring was continued for 2 h, and then stirring was continued at RT overnight. The mixture was diluted with DCM, and then washed with water, 1N HCl, saturated aq. $NaHCO_3$ solution and with brine. After drying over $Na_2SO_4$ all volatiles were evaporated in vacuo. The residual material was purified by FC (PE:EtOAc, 9:1). After evaporation of the solvents the product was obtained as a yellow foam (88%). ($ES^+$): m/z 432.1 $(M+H)^+$.

Step 8: methyl rel-(3aS,14bS)-10-cyclohexyl-13-methoxy-1-methyl-1,2,3,3a,4,14b-hexahydroindolo[2,1-a]pyrrolo[3,2-d][2]benzazepine-7-carboxylate Methyl 1-allyl-3-cyclohexyl-2-(2-formyl-4-methoxyphenyl)-1H-indole-6-carboxylate (1 eq) was dissolved in toluene (0.05M solution) and sarcosine (1.1 eq) was added. After heating to 110° C. for 90 min 20 vol-% DMF were added and heating was continued for 2 h. After cooling to RT the mixture was diluted with EtOAc and the resulting solution was extracted with 1N HCl, sat. aq. NaHCO₃ solution and with brine. After drying over Na₂SO₄ all volatiles were evaporated in vacuo. The residual material was purified by FC (PE:EtOAc, 8:2). The product was obtained as colourless foam (61%) which was used without further characterization in the next reaction.

Step 9: Methyl 13-cyclohexyl-3-methoxy-6-[2-(methylamino)ethyl]-6,7-dihydro-5H-indolo[2,1-a][2]benzazepine-10-carboxylate To a 0.06 M solution of methyl 10-cyclohexyl-13-methoxy-1-methyl-1,2,3,3a,4,14b-hexahydroindolo[2,1-a]pyrrolo[3,2-d][2]benzazepine-7-carboxylate in EtOAc and MeOH 1:1, was added Pd/C (10 wt. %, 0.5 eq) and the mixture was stirred under hydrogen atmosphere for 18 h at RT. Since only traces of desired compound were detected the mixture was heated at 50° C. for 8 h. After filtration on a celite pad the solvent was removed in vacuo and the residual material was used in the next step without further purification. MS (ES⁺) m/z 461 (M+H)⁺.

Step 10: Methyl 6-{2-[(tert-butoxycarbonyl)(methyl)amino]ethyl}-13-cyclohexyl-3-methoxy-6,7-dihydro-5H-indolo[2,1-a][2]benzazepine-10-carboxylate Di-tert-butyl dicarbonate (1.5 eq) and Et₃N (3 eq) were added to a 0.1 M solution of methyl 13-cyclohexyl-3-methoxy-6-[2-(methylamino)ethyl]-6,7-dihydro-5H-indolo[2,1-a][2]benzazepine-10-carboxylate in DCM and the mixture was stirred at RT for 1 h. All volatiles were removed in vacuo and the residual material was dissolved in EtOAc. The resulting solution was washed with sat. aq. NaHCO₃ and brine. The organic phase was dried over Na₂SO₄ and evaporated in vacuo. The residual material was subjected to FC (PE:EtOAc 2:1). After evaporation of the solvent the product was obtained as white solid (45% yield, two steps). (ES⁺) m/z 561 (M+H)⁺.

Step 11: 6-{2-[(tert-butoxycarbonyl)(methyl)amino]ethyl}-13-cyclohexyl-3-methoxy-6,7-dihydro-5H-indolo[2,1-a][2]benzazepine-10-carboxylic acid To a 0.05M solution of methyl 6-{2-[(tert-butoxycarbonyl)(methyl)amino]ethyl}-13-cyclohexyl-3-methoxy-6,7-dihydro-5H-indolo[2,1-a][2]benzazepine-10-carboxylate in dioxane, 1M aqueous KOH solution (10 eq) was added and the mixture was heated to 70° C. After 2 h the mixture was neutralised with 1N HCl and then all volatiles were removed in vacuo. The residue was taken up with DCM and filtered to remove salts. The crude material was used without purification in the next step. (ES⁺) m/z 547 (M+H)⁺.

Step 12: Tert-butyl (2-{13-cyclohexyl-10-[({[(2,2-dimethoxyethyl)(methyl)amino]sulfonyl}amino)carbonyl]-3-methoxy-6,7-dihydro-5H-indolo[2,1-a][2]benzazepin-6-yl}ethyl)methylcarbamate To a solution of 6-{2-[(tert-butoxycarbonyl)(methyl)amino]ethyl}-13-cyclohexyl-3-methoxy-6,7-dihydro-5H-indolo[2,1-a][2]benzazepine-10-carboxylic acid in DCM (0.07M), N-(2,2-dimethoxyethyl)-N-methylsulfamide (2 eq, Example 1, Step 1), EDC (3 eq) and DMAP (5 eq) were added. The mixture was stirred at 40° C. for 3 h, then diluted with EtOAc and washed with 1N HCl, 1N NaOH solution and brine. The organic phase was dried over Na₂SO₄ and evaporated in vacuo and the residual material was used in the next step without purification. (ES⁺) m/z 727 (M+H)⁺.

Step 13: 13-cyclohexyl-3-methoxy-17,20-dimethyl-6,7-dihydro-5H-6,10-(ethanoiminoethanoiminothioiminomethano)indolo[2,1-a][2]benzazepin-14-one 16,16-dioxide To a 0.02 M solution of tert-butyl (2-{13-cyclohexyl-10-[({[(2,2-dimethoxyethyl)(methyl)amino]sulfonyl}amino)carbonyl]-3-methoxy-6,7-dihydro-5H-indolo[2,1-a][2]benzazepin-6-yl}ethyl)methylcarbamate in DCM:H₂O (99:1) TFA (170 eq) was added and the mixture was stirred at 40° C. for 1 h. All volatiles were removed in vacuo and the residual material was triturated with Et₂O. (ES⁺) m/z 581 (M+H)⁺. The crude material was then dissolved in MeOH (0.1 M) and HOAc (5 eq) was added followed by Et₃N (3 eq) and NaCNBH₃ (2 eq). After stirring at RT for 2 h the volatiles were removed in vacuo and the product was isolated by mass-guided RP-HPLC. After lyophilisation a white solid was obtained (12% yield, 4 steps). ¹H NMR (400 MHz, DMSO-d₆, TFA-d, 300 K) δ 8.25 (s, 1H), 7.89 (d, 1H, J 8.4), 7.49 (d, 1H, J 8.26), 7.41 (d, 1H, J 8.26), 7.06-7.05 (m, 1H), 7.01-7.00 (m, 1H), 4.40 (d, 1H, J 15.54), 4.01-3.96 (m, 1H), 3.85 (s, 3H), 3.82-3.75 (m, 1H), 3.67-3.55 (m, 3H), 3.42-3.38 (m, 2H), 2.96 (s, 3H), 2.86-2.73 (m, 4H), 2.28-2.24 (m, 1H), 2.04 (s, 3H), 2.01-1.77 (m, 3H), 1.75-1.67 (m, 3H), 1.55-1.48 (m, 2H), 1.42-1.35 (m, 2H), 1.22-1.18 (m, 1H); MS (ES⁺): m/z 565.5

Example 11

(7R)-14-cyclohexyl-3-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide Step 1: methyl 3-cyclohexyl-2-(4-fluoro-2-hydroxyphenyl)-1H-indole-6-carboxylate The compound was prepared in analogy to Example 8, Step 4, substituting (2-(methoxymethoxy)-4-{[(4-methylphenyl)sulfonyl]oxy}phenyl)boronic acid with (4-fluoro-2-hydroxyphenyl)boronic acid (97%). (ES⁺) m/z 368 (M+H)⁺.

Step 2: (7R)-14-cyclohexyl-3-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide The title compound was prepared using chemistry analogous to that described for Example 8, Steps 8-17, substituting methyl 3-cyclohexyl-2-[2-hydroxy-4-(pyridin-2-ylmethoxy)phenyl]-1H-indole-6-carboxylate with methyl 3-cyclohexyl-2-(4-fluoro-2-hydroxyphenyl)-1H-indole-6-carboxylate ¹H NMR (400 MHz, DMSO-d₆, 300 K) δ 1.10-1.20 (m, 1H), 1.27-1.38 (m, 2H), 1.40-1.47 (m, 1H), 1.62-1.73 (m, 2H), 1.78-1.86 (m, 1H), 1.86-1.98 (m, 3H), 2.34 (s, 3H), 2.82 (s, 3H), 3.01 (s, 3H), 3.25-3.50 (m, 5H), 3.50-3.62 (m, 3H), 3.85-3.98 (m, 2H), 4.05-4.15 (m, 1H), 4.30-4.39 (m, 1H), 4.48-4.58 (m, 1H), 7.16-7.23 (m, 1H), 7.28 (br d, J 9.8, 1H), 7.37-7.47 (m, 3H), 7.91 (d, J 8.6, 1H), 8.00 (s, 1H), 11.69 (br s, 1H); (ES⁺) m/z 598 (M+H)⁺.

Example 12

(7R)-14-cyclohexyl-24-[2-(dimethylamino)ethyl]-21-ethyl-3-fluoro-18-methyl-7,8-dihydro-6H-7,11-(epiminoethanoiminoethanoiminothioiminomethano)-indolo[1,2-e][1,5]benzoxazocin-15-one 17,17-dioxide

Step 1: methyl (7R)-7-(benzylamino)-14-cyclohexyl-3-fluoro-7,8-dihydro-6H-indolo[1,2-e][1,5]benzoxazocine-11-carboxylate Methyl (7R)-7-amino-14-cyclohexyl-3-fluoro-7,8-dihydro-6H-indolo[1,2-e][1,5]benzoxazocine-11-carboxylate (Example 11, Step 5) was dissolved in HC(OMe)$_3$ (50 eq) and a solution of benzaldehyde (1.1 eq) in HC(OMe)$_3$ (50 eq) was added. The mixture was stirred overnight at RT to allow formation of the imine. All volatiles were evaporated and the residual material was dissolved in MeOH/HOAc (0.05 M). NaCNBH$_3$ (1.1 eq) was added and the mixture was stirred at RT for 1 h. The solution was used directly in the next step. (ES$^+$) m/z 513 (M+H)$^+$.

Step 2: methyl (7R)-7-(benzyl{2-[(tert-butoxycarbonyl)amino]ethyl}amino)-14-cyclohexyl-3-fluoro-7,8-dihydro-6H-indolo[1,2-e][1,5]benzoxazocine-11-carboxylate To the solution of methyl (7R)-7-(benzylamino)-14-cyclohexyl-3-fluoro-7,8-dihydro-6H-indolo[1,2-e][1,5]benzoxazocine-11-carboxylate in MeOH/HOAc containing NaCNBH$_3$ from the previous step was added N-Boc-2-aminoacetaldehyde (1.5 eq) and the solution was stirred at RT. After 1 h all volatiles were evaporated. The residual material was taken up with EtOAc and the resulting solution was washed with sat. aq. NaHCO$_3$ and brine. After drying over Na$_2$SO$_4$ all volatiles were evaporated in vacuo. The yellow residue was subjected to FC (PE:EtOAc, 8:2+1% NEt$_3$). After evaporation of the solvents the product was obtained as a colourless solid (71%). (ES$^+$) m/z 656 (M+H)$^+$.

Step 3: (7R)-7-(benzyl{2-[(tert-butoxycarbonyl)amino]ethyl}amino)-14-cyclohexyl-3-fluoro-7,8-dihydro-6H-indolo[1,2-e][1,5]benzoxazocine-11-carboxylic acid To a solution of methyl (7R)-7-(benzyl{2-[(tert-butoxycarbonyl)amino]ethyl}amino)-14-cyclohexyl-3-fluoro-7,8-dihydro-6H-indolo[1,2-e][1,5]benzoxazocine-11-carboxylate in dioxane (0.1 M) was added 2M KOH aqueous solution (3 eq). The mixture was warmed to 60° C. After 2 h the mixture was neutralized by addition of 1N aqueous HCl and all volatiles were evaporated in vacuo. The residual material was taken up with EtOAc and water. The organic phase was separated and the aqueous layer was extracted with EtOAc. After drying the organic phases over Na$_2$SO$_4$ all volatiles were evaporated in vacuo (97%). (ES$^+$) m/z 652 (M+H)$^+$.

Step 4: tert-butyl [2-(benzyl{(7R)-14-cyclohexyl-11-[({[(2,2-dimethoxyethyl)(methyl)amino]sulfonyl}amino)carbonyl]-3-fluoro-7,8-dihydro-6H-indolo[1,2-e][1,5]benzoxazocin-7-yl}amino)ethyl]carbamate The compound was prepared in analogy to Example 8, Step 15 (95%); (ES$^+$) m/z 822 (M+H)$^+$.

Step 5: (7R)-7-[(2-aminoethyl)(benzyl)amino]-14-cyclohexyl-3-fluoro-N-{[methyl(2-oxoethyl)amino]sulfonyl}-7,8-dihydro-6H-indolo[1,2-e][1,5]benzoxazocine-11-carboxamide Tert-butyl [2-(benzyl{(7R)-14-cyclohexyl-11-[({[(2,2-dimethoxyethyl)(methyl)amino]sulfonyl}amino)carbonyl]-3-fluoro-7,8-dihydro-6H-indolo[1,2-e][1,5]benzoxazocin-7-yl}amino)ethyl]carbamate was dissolved in THF (50 mM) and 3M aqueous HCl (10 eq) was added. The solution was warmed to 60° C. and stirred for 2 h. The solution was then used directly in the next step. (ES$^+$) m/z 676 (M+H)$^+$.

Step 6: (7R)-24-benzyl-14-cyclohexyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide The solution of (7R)-7-[(2-aminoethyl)(benzyl)amino]-14-cyclohexyl-3-fluoro-N-{[methyl(2-oxoethyl)amino]sulfonyl}-7,8-dihydro-6H-indolo[1,2-e][1,5]benzoxazocine-11-carboxamide in THF from the previous step was diluted with MeOH (10 mM) and pH was adjusted to 5 with 2M NaOH in MeOH. NaCNBH$_3$ (2 eq) was added in one portion and the resulting mixture was stirred at RT for 45 min. All volatiles were evaporated. The residual material was taken up with EtOAc and the resulting solution was washed with sat. aq. NaHCO$_3$ and brine. After drying over Na$_2$SO$_4$ all volatiles were evaporated in vacuo (94%). (ES$^+$) m/z 660 (M+H)$^+$.

Step 7: (7R)-24-benzyl-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide (7R)-24-benzyl-14-cyclohexyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide was dissolved in MeOH/THF/HOAc (0.05 M) and acetaldehyde (5 eq) was added followed by NaCNBH$_3$ (2 eq). The resulting mixture was stirred at RT for 2 h then all volatiles were evaporated. The residual material was taken up with EtOAc and the resulting solution was washed with sat. aq. NaHCO$_3$ and brine. After drying over Na$_2$SO$_4$ all volatiles were evaporated in vacuo. The yellow residue was subjected to FC (EtOAc:MeOH, 95:5+1% NEt$_3$). After evaporation of the solvents the product was obtained as a colourless solid (43%). (ES$^+$) m/z 688 (M+H)$^+$.

Step 8: (7R)-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide (7R)-24-benzyl-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide was dissolved in MeOH (30 mM) and the solution treated with 1.25 M HCl in MeOH (3 eq). The resulting mixture was warmed to 40° C. and Pd/C (10% w/w, 1 eq) was added. The slurry was stirred under hydrogen atmosphere for 2 h then the catalyst was filtered off with Celite®. All volatiles were then evaporated in vacuo; the residue was partitioned between EtOAc and aq. sat. NaHCO$_3$ and the organic phase was collected. After drying over Na$_2$SO$_4$ all volatiles were evaporated in vacuo (quant.). (ES$^+$) m/z 598 (M+H)$^+$.

Step 9: tert-butyl {2-[(7R)-14-cyclohexyl-21-ethyl-3-fluoro-18-methyl-17,17-dioxido-15-oxo-7,8-dihydro-6H-7,11-(epiminoethanoiminoethanoiminothioiminomethano)indolo[1,2-e][1,5]benzoxazocin-24-yl]ethyl}methylcarbamate The compound was prepared from (7R)-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide in analogy to Step 7 substituting MeCHO with tert-butyl methyl(2-oxoethyl)carbamate (prepared according to *Tetrahedron* 2002, 58, 1719-1737) (quant.). (ES$^+$) m/z 755 (M+H)$^+$.

Step 10: (7R)-14-cyclohexyl-21-ethyl-3-fluoro-18-methyl-24-[2-(methylamino)ethyl]-7,8-dihydro-6H-7,11-(epiminoethanoiminoethanoiminothioiminomethano)indolo[1,2-e][1,5]benzoxazocin-15-one 17,17-dioxide Tert-butyl {2-[(7R)-14-cyclohexyl-21-ethyl-3-fluoro-18-methyl-17,17-dioxido-15-oxo-7,8-dihydro-6H-7,11-(epiminoethanoiminoethanoiminothioiminomethano)indolo[1,2-e][1,5]benzoxazocin-24-yl]ethyl}methylcarbamate was dissolved in a 3:1 mixture of DCM and TFA and the resulting solution was stirred at RT for 1 h then all volatiles were evaporated under reduced pressure (quant.). (ES$^+$) m/z 655 (M+H)$^+$.

Step 11: (7R)-14-cyclohexyl-24-[2-(dimethylamino)ethyl]-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide The compound was prepared from (7R)-14-cyclohexyl-21-ethyl-3-fluoro-18-methyl-24-[2-(methylamino)ethyl]-7,8-dihydro-6H-7,11-(epiminoethanoiminoethanoiminothioiminomethano)-indolo[1,2-e][1,5]benzoxazocin-15-one 17,17-dioxide in analogy to Step 7 substituting MeCHO with HCHO (37% in water). The crude material was dissolved in DMSO and purified by prep RP-HPLC. After lyophilisation of the product fractions the product was obtained as a colourless amorphous material (12%, TFA-salt). $^1$H NMR (400 MHz, DMSO-d$_6$, 330 K) δ 1.13-1.22 (m, 1H), 1.22 (t, J 9.8, 3H), 1.29-1.37 (m, 2H), 1.40-1.47 (m, 1H), 1.62-1.73 (m, 2H), 1.80-1.89 (m, 1H), 1.90-1.98 (m, 3H), 2.62-2.83 (m, 4H), 2.84 (s, 6H), 2.96-3.46 (m, 7H), 3.07 (s, 3H), 3.46-3.61 (m, 3H), 3.85-4.04 (m, 4H), 4.15-4.24 (m, 1H), 4.55 (d, J 14.7, 1H), 7.09-7.21 (m, 2H), 7.37-7.43 (m, 1H), 7.53 (d, J 8.4, 1H), 7.90 (d, J 8.4, 1H), 8.19 (s, 1H), 9.30 (br s, 1H); (ES$^+$) m/z 669 (M+H)$^+$.

Example 13

(+)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide Step 1: methyl 14-cyclohexyl-7-methylene-7,8-dihydro-6H-indolo[1,2-e][1,5]benzoxazocine-11-carboxylate A solution of methyl 3-cyclohexyl-2-(2-hydroxyphenyl)-1H-indole-6-carboxylate (prepared as described in International patent application WO2006/046030) (0.12 M) in DMF was treated with KO$^t$Bu (2.1 eq) in one portion; the resulting mixture was stirred for 30 min at RT then treated dropwise with 3-chloro-2-(chloromethyl)prop-1-ene (1.1 eq). The resulting solution was stirred at RT overnight before being quenched by addition of HCl (1N) and extracted into EtOAc. The combined organic layers were washed with sat. aq. NaHCO$_3$ and brine, before being dried (Na$_2$SO$_4$), filtered and concentrated in vacuo. The crude material was purified by FC (PE/EtOAc 85:15) affording the product as a yellow oil (97%). (ES$^+$) m/z 402 (M+H)$^+$.

Step 2: methyl (7R,S)-14-cyclohexyl-7-(hydroxymethyl)-7,8-dihydro-6H-indolo[1,2-e][1,5]benzoxazocine-1-carboxylate A solution of methyl 14-cyclohexyl-7-methylene-7,8-dihydro-6H-indolo[1,2-e][1,5]benzoxazocine-11-carboxylate (0.14 M) in THF was cooled to 0° C. and treated with 0.5 M 9-BBN in THF (5 eq). The resulting solution was warmed to RT and stirred for 3 h before re-cooling to 0° C. 1N NaOH (3 eq) and H$_2$O$_2$ (2 eq) were added and the solution warmed to RT for 2 h before diluting with EtOAc. The organic layers were washed with water then brine, before being dried (Na$_2$SO$_4$), filtered and concentrated in vacuo. The material was taken on without further purification. (ES$^+$) m/z 420 (M+H)$^+$.

Step 3: methyl (7R,S)-14-cyclohexyl-7-({[(4-methylphenyl)sulfonyl]oxy}methyl)-7,8-dihydro-6H-indolo[1,2-e][1,5]benzoxazocine-11-carboxylate A solution of methyl 14-cyclohexyl-7(R,S)-(hydroxymethyl)-7,8-dihydro-6H-indolo[1,2-e][1,5]benzoxazocine-11-carboxylate (0.14 M) in DCM was treated with TsCl (3.5 eq) and pyridine (35 eq) and the resulting mixture was stirred overnight at RT. The reaction was quenched by addition of HCl (1N) and extracted into EtOAc. The combined organic layers were washed with sat. aq. NaHCO$_3$ and brine, before being dried (Na$_2$SO$_4$), filtered and concentrated in vacuo. The crude material was purified by FC (PE/EtOAc 9:1) affording the product as a yellow oil (95%, over steps 2, 3). (ES$^+$) m/z 574 (M+H)$^+$.

Step 4: methyl 7(R,S)-(cyanomethyl)-14-cyclohexyl-7,8-dihydro-6H-indolo[1,2-e][1,5]benzoxazocine-11-carboxylate A solution of methyl 14-cyclohexyl-7(R,S)-({[(4-methylphenyl)sulfonyl]oxy}methyl)-7,8-dihydro-6H-indolo[1,2-e][1,5]benzoxazocine-11-carboxylate (0.35 M) in DMF was treated with NaCN (1.2 eq) and the resulting mixture was stirred overnight at RT. The reaction was quenched by addition of sat. aq. NaHCO$_3$ and extracted into EtOAc. The combined organic layers were washed with brine, before being dried (Na$_2$SO$_4$), filtered and concentrated in vacuo. The crude material was purified by FC (PE/EtOAc 9:1) affording the product as a yellow foam (90%). (ES$^+$) m/z 429 (M+H)$^+$.

Step 5: methyl 7(R,S)-(2-aminoethyl)-14-cyclohexyl-7,8-dihydro-6H-indolo[1,2-e][1,5]benzoxazocine-11-carboxylate Platinum(IV) oxide (0.5 eq) was added to a solution of methyl 7(R,S)-(cyanomethyl)-14-cyclohexyl-7,8-dihydro-6H-indolo[1,2-e][1,5]benzoxazocine-11-carboxylate (0.20 M) in MeOH. The atmosphere in the reaction vessel was exchanged for H$_2$ and the reaction stirred vigorously at RT for 4 h. The reaction vessel was flushed with N₂ and the reaction mixture filtered through a plug of celite (washing well with MeOH and EtOAc). Volatiles were removed in vacuo to afford the crude product which was purified by FC (EtOAc/MeOH/Et₃N 93:5:2) affording the product as a yellow oil (12%). (ES⁺) m/z 433 (M+H)⁺.

Step 6: methyl 7(R,S)-(2-{[N-(tert-butoxycarbonyl)-β-alanyl]amino}ethyl)-14-cyclohexyl-7,8-dihydro-6H-indolo[1,2-e][1,5]benzoxazocine-11-carboxylate A solution of methyl 7(R,S)-(2-aminoethyl)-14-cyclohexyl-7,8-dihydro-6H-indolo[1,2-e][1,5]benzoxazocine-11-carboxylate (0.14 M) in DCM was treated with N-(tert-butoxycarbonyl)-β-alanine (2 eq) followed by HATU (1.3 eq) and DIPEA (2.5 eq) and the resulting mixture was stirred overnight at RT. The reaction was diluted with EtOAc and the combined organic layers were washed with sat. aq. NaHCO₃, HCl (1N) and brine, before being dried (Na₂SO₄), filtered and concentrated in vacuo. The product was used directly in the next step without further purification. (ES⁺) m/z 604 (M+H)⁺.

Step 7: methyl 7(R,S)-{2-[[N-(tert-butoxycarbonyl)-N-methyl-β-alanyl](methyl)amino]ethyl}-14-cyclohexyl-7,8-dihydro-6H-indolo[1,2-e][1,5]benzoxazocine-11-carboxylate A solution of methyl 7(R,S)-(2-{[N-(tert-butoxycarbonyl)-β-alanyl]amino}ethyl)-14-cyclohexyl-7,8-dihydro-6H-indolo[1,2-e][1,5]benzoxazocine-11-carboxylate (0.18 M) in DMF was treated with sodium hydride (2.4 eq) and the resulting solution stirred for 15 min at RT. Methyl iodide (2.2 eq) was then added and the reaction stirred at RT for 90 min. The reaction was not complete so further NaH (60% dispersion in mineral oil; 2 eq) and MeI (1.5 eq) were added and stirring continued for 1 h. The reaction was diluted with EtOAc and the combined organic layers were washed twice with HCl (1N) and then brine, before being dried (Na₂SO₄), filtered and concentrated in vacuo. The crude material was purified by FC (PE/EtOAc 8:2 to 6:4) affording the product as a yellow oil (49%, over steps 6, 7). (ES⁺) m/z 632 (M+H)⁺.

Step 8: methyl 14-cyclohexyl-7(R,S)-{2-[methyl(N-methyl-β-alanyl)amino]ethyl}-7,8-dihydro-6H-indolo[1,2-e][1,5]benzoxazocine-11-carboxylate A solution of methyl 7(R,S)-{2-[[N-(tert-butoxycarbonyl)-N-methyl-β-alanyl](methyl)amino]ethyl}-14-cyclohexyl-7,8-dihydro-6H-indolo[1,2-e][1,5]benzoxazocine-11-carboxylate (0.09 M) in DCM was treated with TFA (20 eq) and the resulting mixture was stirred overnight at RT. The reaction was diluted with EtOAc and the combined organic layers were washed with sat. aq. NaHCO₃ then brine, before being dried (Na₂SO₄), filtered and concentrated in vacuo. The product was used directly in the next step without further purification. (ES⁺) m/z 532 (M+H)⁺.

Step 9: methyl 14-cyclohexyl-7(R,S)-(2-{methyl[3-(methylamino)propyl]amino}ethyl)-7,8-dihydro-6H-indolo[1,2-e][1,5]benzoxazocine-11-carboxylate A solution of methyl 14-cyclohexyl-7(R,S)-{2-[methyl(N-methyl-β-alanyl)amino]ethyl}-7,8-dihydro-6H-indolo[1,2-e][1,5]benzoxazocine-11-carboxylate (0.02 M) in THF was treated dropwise with BH₃-DMS complex (2M in THF; 10 eq). The resulting solution was stirred at RT for 3 h. The reaction was quenched by the careful addition of HCl/MeOH (1.25 M) and the resulting solution refluxed for 2 h. The mixture was cooled before concentrating in vacuo. The crude material was purified by FC (EtOAc/MeOH/Et₃N 90:8:2) affording the product as a yellow oil (48%, over steps 8, 9). (ES⁺) m/z 518 (M+H)⁺.

Step 10: methyl 14-cyclohexyl-7R-(2-{methyl[3-(methylamino)propyl]amino}ethyl)-7,8-dihydro-6H-indolo[1,2-e][1,5]benzoxazocine-11-carboxylate and methyl 14-cyclohexyl-7S-(2-{methyl[3-(methylamino)propyl]amino}ethyl)-7,8-dihydro-6H-indolo[1,2-e][1,5]benzoxazocine-11-carboxylate Methyl 14-cyclohexyl-7(R,S)-(2-{methyl[3-(methylamino)propyl]amino}ethyl)-7,8-dihydro-6H-indolo[1,2-e][1,5]benzoxazocine-11-carboxylate was dissolved in MeOH and the enantiomers were separated by SFC chromatography (stationary phase: Chiralcel OD-H 250×10 mm; mobile phase: 25% EtOH containing 0.4% diethylamine/CO₂; flow rate 10 mL/min; column pressure: 100 bar; column temperature: 35° C.; detection UV 254 nm). The enantiomeric excess of the two fractions thus obtained (compound recovery 60%) were determined by SFC analysis using the same conditions as described above: Isomer A (retention time 6.95 min, e.e.>98%) $[\alpha]_D^{20}$=−30.9 (c=0.14, MeOH); Isomer B (retention time 9.07 min, e.e. 98%) $[\alpha]_D^{20}$=+21.0 (c=0.2, MeOH).

Step 11: methyl 7R or 7S-{2-[{3-[{[(tert-butoxycarbonyl)amino]sulfonyl}(methyl)amino]propyl}(methyl)amino]ethyl}-14-cyclohexyl-7,8-dihydro-6H-indolo[1,2-e][1,5]benzoxazocine-11-carboxylate A solution of methyl 14-cyclohexyl-(7R or 7S)-(2-{methyl[3-(methylamino)propyl]amino}ethyl)-7,8-dihydro-6H-indolo[1,2-e][1,5]benzoxazocine-11-carboxylate (Isomer A from SFC separation) (0.09 M) in THF was treated with N-[1-{[(tert-butoxycarbonyl)amino]sulfonyl}pyridin-4(1H)-ylidene]-N-methylmethanaminium chloride (1.5 eq) (prepared following literature procedures: Organic Letters 2001, 3, 2241) and stirred overnight at RT. The reaction was partitioned between HCl (1N) and EtOAc and the layers separated. The combined organics were washed with brine, dried (Na₂SO₄), filtered and concentrated in vacuo. The crude material was purified by FC (EtOAc/PE 8:2) affording the product as a colourless oil (91%). (ES⁺) m/z 697 (M+H)⁺.

Step 12: 7R or 7S-{2-[{3-[{[(tert-butoxycarbonyl)amino]sulfonyl}(methyl)amino]propyl}(methyl)amino]ethyl}-14-cyclohexyl-7,8-dihydro-6H-indolo[1,2-e][1,5]benzoxazocine-11-carboxylic acid 2N NaOH (aq) (10 eq) was added to a solution of methyl (7R or 7s)-{2-[{3-[{[(tert-butoxycarbonyl)amino]sulfonyl}(methyl)amino]propyl}(methyl)amino]ethyl}-14-cyclohexyl-7,8-dihydro-6H-indolo[1,2-e][1,5]benzoxazocine-11-carboxylate (0.08 M) in MeOH and the reaction stirred at 60° C. for 2 h. The reaction was cooled to RT before diluting with EtOAc. The combined organic layers were washed with sat. aq. NH₄Cl and then brine, before being dried (Na₂SO₄), filtered and concentrated in vacuo. The material was taken on without further purification. (ES⁺) m/z 683 (M+H)⁺.

Step 13: 7R or 7S-{2-[{3-[(aminosulfonyl)(methyl)amino]propyl}(methyl)amino]ethyl}-14-cyclohexyl-7,8-dihydro-6H-indolo[1,2-e][1,5]benzoxazocine-11-carboxylic acid A solution of (7R or 7S)-{2-[{3-[{[(tert-butoxycarbonyl)amino]sulfonyl}(methyl)amino]propyl}(methyl)amino]

ethyl}-14-cyclohexyl-7,8-dihydro-6H-indolo[1,2-e][1,5]benzoxazocine-11-carboxylic acid (0.07 M) in DCM was treated with TFA (20 eq) and the resulting mixture was stirred overnight at RT. The reaction was not complete therefore further TFA (20 eq) was added and stirring continued for 3 h. The reaction was concentrated in vacuo and the residue evaporated 3 times from HCl/Et$_2$O. The product was used directly in the next step without further purification. (ES$^+$) m/z 583 (M+H)$^+$.

Step 14: 7R or 7S-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide A solution of (7R or 7S)-{2-[{3-[(aminosulfonyl)(methyl)amino]propyl}(methyl)amino]ethyl}-14-cyclohexyl-7,8-dihydro-6H-indolo[1,2-e][1,5]benzoxazocine-11-carboxylic acid (0.009 M) in DCM was treated with EDC (1.5 eq) and DMAP (5 eq) and the resulting mixture was stirred for 72 h at RT then 40° C. for 2 h before concentrating in vacuo. The residue was purified by RP-HPLC (Waters Xterra column; MeCN/H$_2$O/0.1% TFA gradient). Fractions containing the pure compound were combined and lyophilized in the presence of HCl to afford the product as a white powder (9%; over steps 12, 13, 14); This material was characterized as a 2:1* mixture of isomers (due to chiral nitrogen upon protonation) by $^1$H NMR. $^1$H NMR (400 MHz, DMSO-d$_6$+TFA, 330 K) δ 1.19-1.33 (m, 5H), 1.46-1.72 (m, 4H), 1.82-2.04 (m, 4H), 2.10-2.15* and 2.27-2.34 (m, 2H), 2.63-2.72 (m, 1H), 2.77 and 2.81* (s, 3H), 3.03 and 3.07* (s, 3H), 3.13-3.18 (m, 1H), 3.23-3.35 (m, 1H), 3.55-4.08 (m, 7H), 4.38-4.41 and 4.67-4.71* (m, 1H), 7.14-7.24 (m, 1H), 7.27-7.40 (m, 2H), 7.42-7.51 (m, 1H), 7.53-7.60 (m, 1H), 7.86-7.93 (m, 1H), 8.04 and 8.47* (s, 1H); (ES$^+$) m/z 565 (M+H)$^+$; [α]$_D^{20}$=+22.0 (c=0.1, MeOH).

Example 14

(−)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide The title compound was prepared using chemistry analogous to that described for Example 13, Steps 11-14, starting from methyl 14-cyclohexyl-(7R or 7S)-(2-{methyl[3-(methylamino)propyl]amino}ethyl)-7,8-dihydro-6H-indolo[1,2-e][1,5]benzoxazocine-11-carboxylate (Isomer B from SFC separation) prepared as described in Example 13, Steps 1-10. (ES$^+$) m/z 565 (M+H)$^+$; [α]$_D^{20}$=−21.0 (c=0.1, MeOH).

Example 15

(7S)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide The title compound was prepared using chemistry analogous to that described for Example 1, Steps 1-10, starting from tert-butyl (2S)-2-({[tert-butyl(dimethyl)silyl]oxy}methyl)aziridine-1-carboxylate (prepared in line with literature procedures: Travins, J. M.; Etzkom, F. A. *Tetrahedron Lett.* 1998, 39, 9389-9392). (ES$^+$) m/z 566 (M+H)$^+$; [α]$_D^{20}$=75.3 (c=0.1, DMSO).

Example 16

(7R,S)-14-[(1R,2S) or (1S,2R)-2-fluorocyclohexyl]-18,23-dimethyl-7,8-dihydro-6H-11,7-(methanoiminothioiminobutanoiminomethano)indolo[1,2-e][1,5]benzoxazocin-15-one 17,17-dioxide Step 1: methyl (7R,S)-14-[(1R,2S) or (1S,2R)-2-fluorocyclohexyl]-7-({[(4-methylphenyl)sulfonyl]oxy}methyl)-7,8-dihydro-6H-indolo[1,2-e][1,5]benzoxazocine-11-carboxylate The title compound was prepared using chemistry analogous to that described for Example 13, Steps 1-3, starting from methyl 3-[(1R,2S) or (1S,2R)-2-fluorocyclohexyl]-2-(2-hydroxyphenyl)-1H-indole-6-carboxylate (prepared as described in International patent application WO2007/054741) (23%). (ES$^+$) m/z 592 (M+H)$^+$.

Step 2: methyl (7R,S)-14-[(1R,2S) or (1S,2R)-2-fluorocyclohexyl]-7-[(methylamino)methyl]-7,8-dihydro-6H-indolo[1,2-e][1,5]benzoxazocine-11-carboxylate Methyl (7R,S)-14-[(1R,2S) or (1S,2R)-2-fluorocyclohexyl]-7-({[(4-methylphenyl)sulfonyl]oxy}methyl)-7,8-dihydro-6H-indolo[1,2-e][1,5]benzoxazocine-11-carboxylate (0.5 M) in THF was treated with an equal volume of a 27% solution of MeNH$_2$ in MeOH (excess). The resulting mixture was stirred at 65° C. in a sealed tube overnight. The reaction mixture was concentrated and the residue was purified by FC (50-100% EtOAc in PE) to afford the title compound (72%). (ES$^+$) m/z 451 (M+H)$^+$.

Step 3: methyl (7R,S)-7-{[{4-[(tert-butoxycarbonyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate To a mixture of methyl (7R,S)-14-[(1R,2S) or (1S,2R)-2-fluorocyclohexyl]-7-[(methylamino)methyl]-7,8-dihydro-6H-indolo[1,2-e][1,5]benzoxazocine-11-carboxylate (0.05 M) and 4-[(tert-butoxycarbonyl)amino]butanoic acid (1.1 eq) in THF was added HATU (1.05 eq), and the resulting mixture was stirred overnight at RT. The reaction was quenched with water, extracted with EtOAc and the organic layer dried (Na$_2$SO$_4$), filtered and concentrated in vacuo. The residue was purified by FC (25-50% EtOAc in PE) to afford the desired compound (44%). (ES$^+$) m/z 636 (M+H)$^+$.

Step 4: (7R,S)-7-{[{4-[(tert-butoxycarbonyl)(methyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid To a suspension of NaH (60% dispersion in mineral oil; 4.5 eq) in THF (0.3 M) was added a solution of methyl (7R,S)-7-{[{4-[(tert-butoxycarbonyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate in THF (0.1 M). The mixture was stirred for 1 h at RT before introducing MeI (4.5 eq). The resulting mixture was stirred for 2 days. The reaction was quenched with H$_2$O and extracted with EtOAc. The organic layer was separated, dried (Na$_2$SO$_4$), filtered and concentrated in vacuo. The residue was used directly in the next step. (ES$^+$) m/z 636 (M+H)$^+$.

Step 5: benzyl (7R,S)-7-{[{4-[(tert-butoxycarbonyl)(methyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate To a mixture of (7R,S)-7-{[{4-[(tert-butoxycarbonyl)(methyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid (0.02 M) and $K_2CO_3$ (4.5 eq) in acetone, was added benzyl bromide (4.5 eq). The resulting mixture was stirred for 3~4 h at RT before being quenched with water and extracted with EtOAc. The organic layer was separated, dried ($Na_2SO_4$), filtered and concentrated in vacuo. The residue was purified by FC (EtOAc/PE, 1:1) to afford the title compound (86% over steps 4 and 5). ($ES^+$) m/z 726 $(M+H)^+$.

Step 6: benzyl (7R,S)-14-[(1R,2S) or (1S,2R)-2-fluorocyclohexyl]-7-({methyl[4-(methylamino)butanoyl]amino}methyl)-7,8-dihydro-6H-indolo[1,2-e][1,5]benzoxazocine-11-carboxylate To a solution of benzyl (7R,S)-7-{[{4-[(tert-butoxycarbonyl)(methyl)amino]butanoyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate-(0.02 M) in DCM was added TFA (>350 eq). The resulting mixture was stirred for 1-2 h, then the volatiles were removed in vacuo and the residue partitioned between sat. aq. $NaHCO_3$ and EtOAc. The organics were dried ($Na_2SO_4$), filtered and concentrated in vacuo. The residue was used directly in the next step.

Step 7: benzyl (7R,S)-14-[(1R,2S) or (1S,2R)-2-fluorocyclohexyl]-7-({methyl[4-(methylamino)butyl]amino}methyl)-7,8-dihydro-6H-indolo[1,2-e][1,5]benzoxazocine-11-carboxylate $BH_3 \cdot Me_2S$ (2M in THF; 1.05 eq.) was added to a solution of benzyl (7R,S)-14-[(1R,2S) or (1S,2R)-2-fluorocyclohexyl]-7-({methyl[4-(methylamino)butanoyl]amino}methyl)-7,8-dihydro-6H-indolo[1,2-e][1,5]benzoxazocine-11-carboxylate (0.013 M) in THF. The resulting mixture was stirred overnight at RT. After quenching the reaction with MeOH and dilute HCl, the mixture was basified with sat. aq. $NaHCO_3$ and extracted with EtOAc. The organic layer was separated, dried ($Na_2SO_4$), filtered and concentrated in vacuo. The residue was used directly in the next step.

Step 8: benzyl (7R,S)-7-{[{4-[{[(tert-butoxycarbonyl)amino]sulfonyl}(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate (tert-butoxycarbonyl){[4-(dimethylamino)pyridinium-1-yl]sulfonyl}azanide (1.8 eq) (prepared following literature procedures: *Organic Letters* 2001, 3, 2241) was added to a solution of benzyl (7R,S)-14-[(1R,2S) or (1S,2R)-2-fluorocyclohexyl]-7-({methyl[4-(methylamino)butyl]amino}methyl)-7,8-dihydro-6H-indolo[1,2-e][1,5]benzoxazocine-11-carboxylate (0.013 M) in THF. The resulting mixture was stirred for 2~3 h at RT. The reaction mixture was concentrated in vacuo, and the residue was purified by FC (25-50% EtOAc/PE) to afford the title compound (54% over steps 6-8). ($ES^+$) m/z 791 $(M+H)^+$.

Step 9: (7R,S)-7-{[{4-[{[(tert-butoxycarbonyl)amino]sulfonyl}(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid $Pd(OH)_2$/C (0.25 wt eq) was added to benzyl (7R,S)-7-{[{4-[{[(tert-butoxycarbonyl)amino]sulfonyl}(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylate (0.01 M) in THF. The resulting mixture was hydrogenated overnight at RT and atmospheric pressure. The catalyst was then filtered off and the filtrate concentrated in vacuo to give the title compound (98%). ($ES^+$) m/z 701 $(M+H)^+$.

Step 10: (7R,S)-7-{[{4-[(aminosulfonyl)(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid To a solution of (7R,S)-7-{[{4-[{[(tert-butoxycarbonyl)amino]sulfonyl}(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid (0.01 M) in DCM was added TFA (>600 eq). The resulting mixture was stirred for 1~2 h, before removing the volatiles in vacuo to afford the product, which was used directly in the next step. ($ES^+$) m/z 601 $(M+H)^+$.

Step 11: (7R,S)-14-[(1R,2S) or (1S,2R)-2-fluorocyclohexyl]-18,23-dimethyl-7,8-dihydro-6H-11,7-(methanoiminothioiminobutanoiminomethano)indolo[1,2-e][1,5]benzoxazocin-15-one 17,17-dioxide A mixture of (7R,S)-7-{[{4-[(aminosulfonyl)(methyl)amino]butyl}(methyl)amino]methyl}-14-[(1R,2S) or (1S,2R)-2-fluorocyclohexyl]-7,8-dihydro-6H-indolo[1,2-e][1,5]benzoxazocine-11-carboxylic acid (0.002 M), EDC (5.2 eq), DMAP (12.3 eq) and $Et_3N$ (19.8 eq) in THF was stirred at RT for 2~3 days. The volatiles were evaporated in vacuo and the residue was purified by preparative HPLC (Sepax GP C18 30×150 mm; TFA: 0.1%; $CH_3CN/H_2O$: 45~80%). Fractions containing the pure compound were combined and lyophilized in the presence of HCl to afford the HCl salt of the title compound as a mixture of diastereoisomers (24%). $^1H$ NMR (600 MHz, DMSO-$d_6$, 320 K) δ1.06-2.28 (m, 13H), 2.52-5.18 (m, 18H), 7.11-7.60 (m, 5H), 7.83-8.49 (m, 2H), 9.91-10.29 (m, 1H), 11.13-11.78 (m, 1H); ($ES^+$) m/z 583 $(M+H)^+$.

Example 17

(20S)-31-cyclohexyl-10-methyl-19,22-dioxa-9-thia-1,8,10,13-tetraazahexacyclo[18.9.1.1$^{2,6}$.1$^{3,29}$.0$^{13,17}$.0$^{23,28}$]dotriaconta-2(32),3,5,23,25,27,29(31)-heptaen-7-one 9,9-dioxide Step 1: benzyl 1-benzylprolinate Benzyl bromide (2 eq.) and $K_2CO_3$ (2.5 eq) were added to a solution (0.6 M) of DL-proline in DMF. The reaction was stirred at 100° C. overnight. The solution was allowed to cool to RT and then diluted with EtOAc and washed with 1 N HCl, brine, before being dried ($Na_2SO_4$), filtered and concentrated in vacuo. The crude material was purified by FC (PE/EtOAc 90:10) to afford the product (43%). (ES$^+$) m/z 296 (M+H)$^+$ Step 2: (1-benzylpyrrolidin-2-yl)methanol A solution (0.06M) of benzyl 1-benzylprolinate in THF was cooled in an ice bath and treated with LiAlH$_4$ (3 eq). The resulting mixture was stirred at RT for 3 h, before being quenched by the addition of H$_2$O. The resulting mixture was stirred at RT for 30 min and then filtered through a pad of Solka-Floc and the filtrate concentrated in vacuo. The crude was purified by FC (PE/EtOAc 6:4+1% NEt$_3$) to afford the title compound as an off-white solid (62%). $^1$H NMR (400 MHz, CDCl$_3$) δ1.66-1.81 (m, 2H), 1.82-1.97 (m, 2H), 2.25-2.34 (m, 1H), 2.40-2.53 (m, 1H), 2.71-2.77 (m, 1H), 2.94-3.01 (m, 1H), 3.34-3.39 (m, 1H), 3.40-3.45 (m, 1H), 3.63-3.68 (m, 1H), 3.95-3.99 (m, 1H), 7.26-7.30 (m, 5H).

Step 3: 1-benzyl-2-(chloromethyl)pyrrolidinium chloride (1-benzylpyrrolidin-2-yl)methanol was slowly added to thionyl chloride (45 eq) and the resulting mixture was stirred for 15 h at 35° C. All the volatiles were removed in vacuo. The yellow oil residue was treated with Et$_2$O and re-evaporated to drive off excess thionyl chloride. The crude material was then dried at the high vacuum pump for 2 h to afford the product (100%). $^1$H NMR (400 MHz, CDCl$_3$) δ1.85-2.01 (m, 1H), 2.15-2.32 (m, 3H), 2.85-3.05 (m, 1H), 3.43-3.54 (m, 1H), 3.65-3.79 (m, 1H), 3.92-4.02 (m, 2H), 4.20-4.22 (m, 1H), 4.41-4.43 (m, 1H), 7.44-7.62 (m, 5H).

Step 4: methyl (7S)-7-[(1-benzylpyrrolidin-2-yl) methoxy]-14-cyclohexyl-7,8-dihydro-6H-indolo[1,2-e][1,5]benzoxazocine-11-carboxylate Methyl (7S)-14-cyclohexyl-7-hydroxy-7,8-dihydro-6H-indolo[1,2-e][1,5]benzoxazocine-11-carboxylate (prepared as described in International patent application WO2006/046030) in toluene (0.17 M) was treated with 30% NaOH (aq) (10 eq) and tetrabutylammonium bromide (0.25 eq). The solution was stirred at RT for 30 min, then 1-benzyl-2-(chloromethyl)pyrrolidinium chloride (2.5 eq) was added to the solution and the resulting mixture was stirred at 60° C. over night. Toluene was eliminated in vacuo; the residue was taken up in EtOAc and washed with 1 N HCl (aq), brine, before being dried (Na$_2$SO$_4$), filtered and concentrated in vacuo. The crude material was purified by FC (PE/EtOAc 50:50+1% NEt$_3$) to afford the product (80%). (ES$^+$) m/z 579 (M+H)$^+$ Step 5: methyl (7S)-14-cyclohexyl-7-(pyrrolidin-2-ylmethoxy)-7,8-dihydro-6H-indolo[1,2-e][1,5]benzoxazocine-11-carboxylate To a solution of methyl (7S)-7-[(1-benzylpyrrolidin-2-yl) methoxy]-14-cyclohexyl-7,8-dihydro-6H-indolo[1,2-e][1,5] benzoxazocine-11-carboxylate (0.07 M) in EtOAc, was added an excess of AcOH (>50 eq) and Pd(OH)$_2$/C. The atmosphere in the reaction flask was charged with H$_2$ and the reaction stirred vigorously under a H$_2$ atmosphere (balloon) at RT for 2 d. The mixture was filtered and the filtrate concentrated in vacuo. The crude was purified by FC (gradient from EtOAc/PE 6:4+1% NEt$_3$ to EtOAc/PE 8:2+1% NEt$_3$+ 5% MeOH) to afford the product (50%). (ES$^+$) m/z 489 (M+H)$^+$.

Step 6: methyl (7S)-7-[(1-{2-[(tert-butoxycarbonyl) (methyl)amino]ethyl}pyrrolidin-2-yl)methoxy]-14-cyclohexyl-7,8-dihydro-6H-indolo[1,2-e][1,5]benzoxazocine-11-carboxylate To a solution (0.02 M) of methyl (7S)-14-cyclohexyl-7-(pyrrolidin-2-ylmethoxy)-7,8-dihydro-6H-indolo[1,2-e][1,5]benzoxazocine-11-carboxylate in MeOH/THF (2/1), AcOH (cat.) was added followed by tert-butyl methyl(2-oxoethyl)carbamate (2 eq, prepared as described in *Tetrahedron* 2002, 58, 1719-1737). The reaction was stirred at RT for 30 min at which point NaCNBH$_3$ (2 eq) was added and the mixture was stirred at 40° C. for 1 h. Additional tert-butyl methyl(2-oxoethyl)carbamate (1 eq) and NaCNBH$_3$ (5 eq) were added and the reaction was stirred for further 30 min at 40° C. The reaction was quenched by adding sat. aq. NaHCO$_3$. The aqueous phase was extracted with EtOAc and the combined organics washed with brine before being dried (Na$_2$SO$_4$), filtered and concentrated in vacuo. The product was used in the subsequent step without further purification. (ES$^+$) m/z 646 (M+H)$^+$ Step 7: methyl (7S)-14-cyclohexyl-7-({1-[2-(methylamino)ethyl]pyrrolidin-2-yl}methoxy)-7,8-dihydro-6H-indolo[1,2-e][1,5]benzoxazocine-11-carboxylate A solution of methyl (7S)-7-[(1-{2-[(tert-butoxycarbonyl) (methyl)amino]ethyl}pyrrolidin-2-yl)methoxy]-14-cyclohexyl-7,8-dihydro-6H-indolo[1,2-e][1,5]benzoxazocine-11-carboxylate (0.06 M) in DCM was treated with an excess of TFA (>50 eq). The mixture was stirred at RT for 2 h. Volatiles were removed in vacuo and the residue partitioned between EtOAc and sat. aq. NaHCO$_3$. The aqueous was extracted with EtOAc and the organics combined, washed with brine, dried (Na$_2$SO$_4$), filtered and concentrated in vacuo to afford the product (82%). The material was taken on without further purification. (ES$^+$) m/z 546 (M+H)$^+$.

Step 8: methyl (7S)-7-[(1-{2-[{[(tert-butoxycarbonyl)amino]sulfonyl}(methyl)amino]ethyl}pyrrolidin-2-yl)methoxy]-14-cyclohexyl-7,8-dihydro-6H-indolo [1,2-e][1,5]benzoxazocine-1-carboxylate To a solution of methyl (7S)-14-cyclohexyl-7-({1-[2-(methylamino)ethyl]pyrrolidin-2-yl}methoxy)-7,8-dihydro-6H-indolo[1,2-e][1,5]benzoxazocine-11-carboxylate (0.05 M) in THF was added (tert-butoxycarbonyl){[4-(dimethylamino) pyridinium-1-yl]sulfonyl}azanide (prepared following literature procedures: *Organic Letters* 2001, 3, 2241) (1.2 eq) and the resulting mixture was stirred for 2.5 h at RT. The solution was diluted in EtOAc and washed with 1 N HCl, brine, before being dried (Na$_2$SO$_4$), filtered and concentrated in vacuo. The crude was purified by FC (EtOAc/PE 85:15+ 1% NEt$_3$) to afford the product (14%). (ES$^+$) m/z 725 (M+H)$^+$.

Step 9: (7S)-7-[(1-{2-[{[(tert-butoxycarbonyl)amino] sulfonyl}(methyl)amino]ethyl}pyrrolidin-2-yl)methoxy]-14-cyclohexyl-7,8-dihydro-6H-indolo[1,2-e][1,5]benzoxazocine-11-carboxylic acid A solution of methyl (7S)-7-[(1-{2-[{[(tert-butoxycarbonyl)amino]sulfonyl}(methyl)amino]ethyl}pyrrolidin-2-yl) methoxy]-14-cyclohexyl-7,8-dihydro-6H-indolo[1,2-e][1,5] benzoxazocine-11-carboxylate (7 mM) in MeOH was treated with 2 N NaOH (10 eq). The mixture was stirred at 60° C. for 3 h. MeOH was eliminated in vacuo, the residue was dissolved in EtOAc and neutralized by adding 6 N HCl. The aqueous was extracted with EtOAc and the organics combined, washed with brine, dried ($Na_2SO_4$), filtered and concentrated in vacuo to afford the product. The material was taken on without further purification. ($ES^+$) m/z 711 (M+H)$^+$.

Step 10: (7S)-7-[(1-{2-[(aminosulfonyl)(methyl) amino]ethyl}pyrrolidin-2-yl)methoxy]-14-cyclohexyl-7,8-dihydro-6H-indolo[1,2-e][1,5]benzoxazocine-11-carboxylic acid A solution of (7S)-7-[(1-{2-[{[(tert-butoxycarbonyl) amino]sulfonyl}(methyl)amino]ethyl}-pyrrolidin-2-yl) methoxy]-14-cyclohexyl-7,8-dihydro-6H-indolo[1,2-e][1,5]benzoxazocine-11-carboxylic acid (7 mM) in DCM was treated with an excess of TFA (>100 eq). The mixture was stirred at RT for 3.5 h. Volatiles were removed in vacuo. The residue was dissolved in toluene and re-evaporated to drive off excess TFA. The material was taken on without further purification. ($ES^+$) m/z 611 (M+H)$^+$.

Step 11: (20S)-31-cyclohexyl-10-methyl-19,22-dioxa-9-thia-1,8,10,13-tetraazahexacyclo[18.9.1. 1$^{2,6}$.1$^{3,29}$.0$^{13,17}$.0$^{23,28}$]dotriaconta-2(32),3,5,23,25, 27,29(31)-heptaen-7-one 9,9-dioxide To a solution (7 mM) of (7S)-7-[(1-{2-[(aminosulfonyl) (methyl)amino]ethyl}pyrrolidin-2-yl)methoxy]-14-cyclohexyl-7,8-dihydro-6H-indolo[1,2-e][1,5]benzoxazocine-11-carboxylic acid in DCM, DMAP (5 eq) and EDC (2 eq) were added and the resulting mixture heated at 40° C. for 2 h and then at RT over night. Volatiles were eliminated in vacuo and the residue redissolved in DMSO. Purification was by RP-HPLC (stationary phase: column Waters XTERRA prep. C18, 5 um, 19×100 mm) eluting with MeCN/TFA buffered with 0.1% TFA gradient. Fractions containing the product were combined and freeze dried to afford the product as a white powder (34%) as a mixture of isomers. $^1$H NMR (600 MHz, DMSO-d$_6$+TFA, 320 K) δ 1.15-2.02 (m, 14H), 2.68-2.70 (m, 1H), 2.94-3.08 (m, 3H), 3.14-4.11 (m, 1H), 4.32-4.61 (m, 2H), 4.81-4.90 (m, 1H), 7.16-7.39 (m, 2H), 7.40-7.49 (m, 1H), 7.50-7.57 (m, 2H), 7.85-7.94 (m, 1H), 8.13-8.43 (m, 1H); ($ES^+$) m/z 593 (M+H)$^+$.

Example 18

(18R)-29-cyclohexyl-10,17-dimethyl-20-oxa-9-thia-1,8,10,14,17-pentaazahexacyclo[16.9.1.1$^{2,6}$.1$^{3,27}$. 1$^{11,14}$.0$^{21,26}$]hentriaconta-2(31),3,5,21,23,25,27(29)-heptaen-7-one 9,9-dioxide Step 1: tert-butyl[1-(2-chloroethyl)pyrrolidin-3-yl] methylcarbamate To a solution of tert-butyl methyl(pyrrolidin-3-yl)carbamate (1 eq) in MeOH chloroacetaldehyde (50% wt in $H_2O$) (2.4 eq) was added, the pH adjusted to 6 with HOAc and the solution left stirring for 1 h. NaCNBH$_3$ (1.5 eq) was then added and the solution left stirring for 3 h. The reaction was treated with sat. aq. NaHCO$_3$, diluted with DCM and washed with $H_2O$ and brine, dried over $Na_2SO_4$ and evaporated in vacuo to obtain the title compound as yellow oil (98%). ($ES^+$) m/z 263 (M+H)$^+$.

Step 2: methyl (7R)-7-[(2-{3-[(tert-butoxycarbonyl) (methyl)amino]pyrrolidin-1-yl}ethyl)(methyl) amino]-14-cyclohexyl-7,8-dihydro-6H-indolo[1,2-e] [1,5]benzoxazocine-11-carboxylate A solution of methyl (7R)-14-cyclohexyl-7-(methylamino)-7,8-dihydro-6H-indolo[1,2-e][1,5]benzoxazocine-11-carboxylate (1 eq) in MeCN was treated with tert-butyl[1-(2-chloroethyl)pyrrolidin-3-yl]methylcarbamate (2.4 eq) and NEt$_3$ (2 eq) and heated at 140° C. in a microwave oven. The solvent was removed in vacuo and the residue purified by FC (Biotage; DCM/MeOH) to get the title compound as a white powder (64%). ($ES^+$) m/z 645 (M+H)$^+$.

Step 3: methyl (7R)-14-cyclohexyl-7-(methyl{2-[3-(methylamino)pyrrolidin-1-yl]ethyl}amino)-7,8-dihydro-6H-indolo[1,2-e][1,5]benzoxazocine-11-carboxylate Methyl (7R)-7-[(2-{3-[(tert-butoxycarbonyl)(methyl) amino]pyrrolidin-1-yl}ethyl)(methyl)amino]-14-cyclohexyl-7,8-dihydro-6H-indolo[1,2-e][1,5]benzoxazocine-11-carboxylate was dissolved in DCM and treated with TFA. The solution was stirred for 2 h at RT. The solvents were removed in vacuo to leave the product as pale yellow foam. ($ES^+$) m/z 545 (M+H)$^+$.

Step 4: methyl (7R)-7-[(2-{3-[{[(tert-butoxycarbonyl)amino]sulfonyl}(methyl)amino]pyrrolidin-1-yl}ethyl)(methyl)amino]-14-cyclohexyl-7,8-dihydro-6H-indolo[1,2-e][1,5]-benzoxazocine-1-carboxylate Tert-BuOH/DCM (2M, 1.1 eq) was added to a stirred mixture of chlorosulfonyl isocyanate (1.1 eq) in dry DCM cooled to 0° C. The mixture was left stirring at 0° C. for 90 min. A solution of methyl (7R)-14-cyclohexyl-7-(methyl{2-[3-(methylamino)pyrrolidin-1-yl]ethyl}amino)-7,8-dihydro-6H-indolo[1,2-e][1,5]benzoxazocine-11-carboxylate (1.0 eq) and NEt$_3$ (3.0 eq) in dry DCM was added and the mixture was stirred at 0° C. for 1 h and at RT further 2 h. The residue obtained after evaporation of all volatiles was taken into EtOAc, diluted with HCl (1N), washed with brine, dried and concentrated in vacuo and the residue purified by FC (Biotage; DCM/MeOH) to get the title compound as a white powder (52%). ($ES^+$) m/z 724 (M+H)$^+$.

Step 5: (7R)-7-[(2-{3-[{[(tert-butoxycarbonyl) amino]sulfonyl}(methyl)amino]pyrrolidin-1-yl}ethyl)(methyl)amino]-14-cyclohexyl-7,8-dihydro-6H-indolo[1,2-e][1,5]benzoxazocine-11-carboxylic acid A solution of methyl (7R)-7-[(2-{3-[{[(tert-butoxycarbonyl)amino]sulfonyl}(methyl)amino]pyrrolidin-1-yl}ethyl) (methyl)amino]-14-cyclohexyl-7,8-dihydro-6H-indolo[1,2-e][1,5]benzoxazocine-11-carboxylate in dioxane was treated with aqueous KOH (1M) (3 eq) and heated at 70° C. for 1 h. The residue obtained after evaporation of all volatiles was taken into EtOAc, acidified with HCl (1N), and the organics washed with brine, dried and concentrated in vacuo to get the title compound as a white powder. ($ES^+$) m/z 710 (M+H)$^+$.

Step 6: (7R)-7-[(2-{3-[(aminosulfonyl)(methyl) amino]pyrrolidin-1-yl}ethyl)(methyl)amino]-14-cyclohexyl-7,8-dihydro-6H-indolo[1,2-e][1,5]benzoxazocine-11-carboxylic acid A solution of (7R)-7-[(2-{3-[{[(tert-butoxycarbonyl) amino]sulfonyl}(methyl)amino]pyrrolidin-1-yl}ethyl)(methyl)amino]-14-cyclohexyl-7,8-dihydro-6H-indolo[1,2-e][1, 5]benzoxazocine-11-carboxylic acid in DCM was treated with TFA and the solution was left stirring for 1 h. All volatiles were removed in vacuo to leave the product as pale yellow foam. (ES⁺) m/z 610 (M+H)⁺.

Step 7: (18R)-29-cyclohexyl-10,17-dimethyl-20-oxa-9-thia-1,8,10,14,17-pentaazahexacyclo[16.9.1.1²,⁶.1³,²⁷.1¹¹,¹⁴.0²¹,²⁶]hentriaconta-2(31), 3,5,21,23, 25,27(29)-heptaen-7-one 9,9-dioxide A solution of (7R)-7-[(2-{3-[(aminosulfonyl)(methyl)amino]pyrrolidin-1-yl}ethyl)(methyl)amino]-14-cyclohexyl-7,8-dihydro-6H-indolo[1,2-e][1,5]benzoxazocine-11-carboxylic acid in DCM was treated with EDC (2 eq) and DMAP (3 eq) and the solution was left stirring for 1 h at 35° C. The residue obtained after evaporation of all volatiles was purified by automated RP-HPLC to obtain the title compound as bis TFA salt and as a mixture of two diastereoisomers (a/b) in a 1:1 ratio (55%). ¹H NMR (600 MHz, DMSO-d₆, 300 K, bis TFA-salt) δ 8.36-8.23 (bs, 1H-a), 7.94-7.83 (m, 1H-a, 1H-b), 7.82-7.74 (bs, 1H-b), 7.59-7.48 (m, 2H-a, 1H-b), 7.41-7.28 (m, 3H-a, 4H-b), 4.92-4.78 (m, 2H-a, 1H-b), 4.62-4.46 (m, 2H-b, 1H-a), 4.15-3.82 (m, 2H-a, 2H-b), 3.60-3.40 (m, 2H-a, 2H-b), 3.22-3.11 (m, 1H-a), 2.98 (s, 3H-a), 3.50-2.79 (m, 6H-a, 6H-b), 2.97-2.89 (m, 1H-b), 2.86 (s, 3H-b), 2.78-2.61 (m, 1H-a, 1H-b), 2.24 (s, 3H-a), 2.21 (s, 3H-b), 2.34-2.09 (m, 2H-a, 2H-b), 2.02-1.82 (m, 4H-a, 4H-b), 1.78-1.65 (m, 2H-a, 2H-b), 1.54-1.42 (m, 1H-a, 1H-b), 1.40-1.29 (m, 2H-a, 2H-b), 1.22-1.11 (m, 1H-a, 1H-b); (ES⁺) m/z 592 (M+H)⁺.

Example 19

(7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide Step 1: 1-(methoxymethoxy)-2-methylbenzene To a suspension of NaH (60% dispersion in mineral oil; 1.2 eq) in Et₂O/DMF (5:1, 0.2M) a solution of o-cresol in Et₂O (1 eq, 2M) was added dropwise over 15 min. A solution of MOMCl in Et₂O (1.1 eq, 2M) was added and the mixture was stirred for 30 min then poured into H₂O and extracted with Et₂O. The combined organic extracts were washed with 1N NaOH, H₂O and brine, dried over Na₂SO₄, filtered and evaporated in vacuo to give the title compound. The product was used in the next step without further purification.

Step 2: [2-(methoxymethoxy)-3-methylphenyl]boronic acid

To a solution of 1-(methoxymethoxy)-2-methylbenzene in diethyl ether (0.3M) cooled at −60° C. tBuLi in pentane (1.7M, 1.4 eq) was added dropwise and the mixture was stirred for 1 h while warming gradually to 0° C. then for further 2 h at 0° C. The mixture was cooled to −78° C. and a solution of B(OMe)₃ in THF (3 eq, 3.0M) was added dropwise and the mixture was allowed to reach RT and stirred overnight. The mixture was cooled to 0° C. and 1N HCl was added, then the reaction mixture was stirred for 2 h. All volatiles were removed under reduced pressure and the residue was extracted with EtOAc. The combined extracts were washed with H₂O and brine, dried over Na₂SO₄, filtered and evaporated in vacuo to give a yellow solid which was triturated with PE to give a white solid which was used in the next step without further purification.

Step 3: methyl 3-cyclohexyl-2-[2-(methoxymethoxy)-3-methylphenyl]-1H-indole-6-carboxylate The compound was prepared in analogy to Example 8, Step 4, substituting (2-(methoxymethoxy)-4-{[(4-methylphenyl)sulfonyl]oxy}phenyl)boronic acid with [2-(methoxymethoxy)-3-methylphenyl]boronic acid (83%). (ES⁺) m/z 408 (M+H)⁺.

Step 4: (7R)-14-cyclohexyl-4,18,24-trimethyl-7,8-dihydro-6H-7,11-(epiminoethanoiminoethanoiminothioiminomethano)indolo[1,2-e][1,5]benzoxazocin-15-one 17,17-dioxide The title compound was prepared using chemistry analogous to that described for Example 8, Steps 7-17, (ES⁺) m/z 580 (M+H)⁺

Step 5: (7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide Acetaldehyde (10 eq) was added to the reaction from the previous step followed by HOAc (cat.) and NaCNBH₃ (5 eq). After 30 min, all volatiles were removed in vacuo and the residue taken in EtAOc and washed with sat. aq. NaHCO₃ and brine. After drying over Na₂SO₄ the crude was by purified by automated RP-HPLC, eluting with a MeCN/H₂O gradient (buffered with 0.1% TFA). Fractions containing the product were combined and lyophilised to afford the product as a white powder (25% bis TFA salt).
¹H NMR (400 MHz, DMSO-d₆, 300 K) δ 1.02-1.17 (m, 1H), 1.21 (t, J 6.7, 3H), 1.30-1.52 (m, 3H), 1.78-1.86 (m, 2H), 1.86-1.98 (m, 4H), 2.37 (s, 3H), 2.60 (s, 3H), 3.03 (s, 3H), 3.13-3.33 (m, 3H), 3.33-3.50 (m, 5H), 3.50-3.63 (m, 2H), 3.64-3.79 (m, 1H), 3.83-3.99 (m, 1H), 3.99-4.14 (m, 2H), 4.31-4.41 (m, 1H), 4.61 (d, J 14.8, 11H), 7.12-7.31 (m, 2H), 7.40-7.52 (m, 2H), 7.91 (d, J 8.5, 1H), 8.08 (s, 1H), 11.7 (br s, 1H); (ES⁺) m/z 608 (M+H)⁺.

Example 20

(7R)-14-cyclohexyl-18,24-dimethyl-7,8-dihydro-6H-7,11-(epiminoethanoooxyethanoiminothioiminomethano)indolo[1,2-e][1,5]benzoxazocin-15-one 17,17-dioxide Step 1: methyl (7R)-7-[{2-[2-(benzyloxy)ethoxy]ethyl}(tert-butoxycarbonyl)amino]-14-cyclohexyl-7,8-dihydro-6H-indolo[1,2-e][1,5]benzoxazocine-11-carboxylate

[2-(benzyloxy)ethoxy]acetaldehyde was prepared by Swern oxidation of commercially available 2-[2-(benzyloxy)ethoxy]ethanol. A 0.15M solution of the foregoing aldehyde and methyl (7R)-7-amino-14-cyclohexyl-7,8-dihydro-6H-indolo[1,2-e][1,5]benzoxazocine-11-carboxylate (prepared as described in Example 1, Step 4) in CH(OMe)₃ was stirred overnight at RT; the residue obtained after removing volatiles in vacuo was dissolved in MeOH (0.15M solution), NaCNBH₃ (2.3 eq) was added and the mixture was left stirring for 4 h. All volatiles were evaporated and the residual material was dissolved in EtOAc and washed with sat. aq. NaHCO₃ and brine. After drying over Na₂SO₄ all volatiles were evaporated in vacuo; FC (Biotage, PE/EtOAc 1:1 to 1:3 with 0.5%

NEt₃) afforded 35% of methyl (7R)-7-({2-[2-(benzyloxy)ethoxy]ethyl}amino)-14-cyclohexyl-7,8-dihydro-6H-indolo[1,2-e][1,5]benzoxazocine-11-carboxylate.

A 1M solution of the latter in THF was treated with di-tert-butyl dicarbonate (1.5 eq) overnight at 40° C.; the residue obtained after evaporation was dissolved in EtOAc and washed with sat. aq. NaHCO₃ and brine, dried over Na₂SO₄ and concentrated; the crude (quantitative) was used without further purification.

Step 2: methyl (7R)-7-((tert-butoxycarbonyl){2-[2-(methylamino)ethoxy]ethyl}amino)-14-cyclohexyl-7,8-dihydro-6H-indolo[1,2-e][1,5]benzoxazocine-11-carboxylate Methyl (7R)-7-[{2-[2-(benzyloxy)ethoxy]ethyl}(tert-butoxycarbonyl)amino]-14-cyclohexyl-7,8-dihydro-6H-indolo[1,2-e][1,5]benzoxazocine-11-carboxylate was dissolved in MeOH/AcOH 10:1 (0.06M) and palladium on carbon (10%, 0.25 eq) was added. The mixture was degassed and hydrogen atmosphere was applied. The mixture was left stirring at RT. After 2 days all volatiles were evaporated in vacuo and the residue was filtered on celite using EtOAc and MeOH as solvents. After evaporation of the solvents in vacuo methyl (7R)-7-{(tert-butoxycarbonyl)[2-(2-hydroxyethoxy)ethyl]amino}-14-cyclohexyl-7,8-dihydro-6H-indolo[1,2-e][1,5]benzoxazocine-11-carboxylate was obtained. DMAP (0.2 eq) and MsCl (1.2 eq) was added to a 0.06M solution of previous crude and NEt₃ (1.5 eq)) in dry DCM and the mixture was stirred at RT for 90 min. After quenching with sat NaHCO₃ the mixture was extracted with DCM and the combined organic phases washed with 1N HCl and brine, dried and concentrated. A 0.07M solution of crude mesylate and NEt₃ (4 eq) was treated with 2M MeNH₂/THF (22 eq) at 80° C. overnight, evaporation gave a residue that was used as such. Yield 70% (three steps). (ES⁺) m/z 606 (M+H)⁺.

Step 3: methyl (7R)-7-[(tert-butoxycarbonyl)(2-{2-[{[(tert-butoxycarbonyl)amino]sulfonyl}(methyl)amino]ethoxy}ethyl)amino]-14-cyclohexyl-7,8-dihydro-6H-indolo[1,2-e][1,5]benzoxazocine-11-carboxylate Chlorosulfonyl isocyanate (1.2 eq) was dissolved in dry DCM (0.2M) and 1.3 eq of a 2M solution of t-BuOH in ether was added at 0° C., after stirring for 1 h a 1 M solution of methyl (7R)-7-((tert-butoxycarbonyl){2-[2-(methylamino)ethoxy]ethyl}amino)-14-cyclohexyl-7,8-dihydro-6H-indolo[1,2-e][1,5]benzoxazocine-11-carboxylate (1 eq) and NEt₃ (3 eq) in dry DCM was added dropwise, and stirring was continued for 30 min at 0° C. and then at RT for 2 h. All volatiles were evaporated in vacuo and the residue was taken in EtOAc, washed with 1N HCl and brine, dried and concentrated; the crude material was purified by FC (Biotage, gradient of PE/EtOAc 1:1 to 1:3) to afford 40% of the title compound. (ES⁺) m/z 785 (M+H)⁺.

Step 4: (7R)-14-cyclohexyl-18-methyl-7,8-dihydro-6H-7,11-(epiminoethanooxyethanoiminothioiminomethano)indolo[1,2-e][1,5]benzoxazocin-15-one 17,17-dioxide Methyl (7R)-7-[(tert-butoxycarbonyl)(2-{2-[{[(tert-butoxycarbonyl)amino]sulfonyl}(methyl)amino]ethoxy}ethyl)amino]-14-cyclohexyl-7,8-dihydro-6H-indolo[1,2-e][1,5]benzoxazocine-11-carboxylate was dissolved in dioxane (0.07M) and 1M KOH solution (10 eq) was added. The mixture was left stirring at 75° C. for 3 h. After cooling to 0° C. the pH of the solution was adjusted with 1M HCl to pH 6 and all volatiles were removed in vacuo. The residue was extracted with EtOAc. The combined organic phases were washed with H₂O and brine and dried over Na₂SO₄. All volatiles were evaporated in vacuo. The residual material was dissolved in dry DCM, TFA (35 eq) was added and the mixture was left stirring at RT. After 2 h all volatiles were evaporated in vacuo. The residue (TFA salt of (7R)-7-[(2-{2-[(aminosulfonyl)(methyl)amino]ethoxy}ethyl)amino]-14-cyclohexyl-7,8-dihydro-6H-indolo[1,2-e][1,5]benzoxazocine-11-carboxylic acid) was taken in dry DCM (0.07M), DMAP (3 eq) and EDC (2 eq) were added and the mixture was stirred at 40° C. for 1 h, some crystals of EDC were added and stirring was continued for 1 h. The residue obtained after evaporation was extracted with EtOAc. The combined organic phases were washed with sat. aq. NH₄Cl and brine, dried over Na₂SO₄ and concentrated to afford the title compound which was used without further purification. Yield: quantitative as crude. (ES⁺) m/z 553 (M+H)⁺.

Step 4: (7R)-14-cyclohexyl-18,24-dimethyl-7,8-dihydro-6H-7,11-(epiminoethanooxyethanoiminothioiminomethano)indolo[1,2-e][1,5]benzoxazocin-15-one 17,17-dioxide NaCNBH₃ (2 eq) was added to a stirred solution (0.05M) of (7R)-14-cyclohexyl-18-methyl-7,8-dihydro-6H-7,11-(epiminoethanooxyethanoiminothioiminomethano)indolo[1,2-e][1,5]benzoxazocin-15-one 17,17-dioxide, HCHO (3 eq) and AcOH (10 eq) in MeOH and the mixture was stirred at RT for 2 h. Evaporation gave a residue that was taken in DMSO and purified by prep. RP-HPLC. After lyophilisation of the fractions the title compound was obtained as a white solid (35%). ¹H NMR (500 MHz, DMSO-d₆, 330 K, bis TFA-salt) δ 7.97 (b.s, 1H), 7.95 (d, 1H, J 8.4), 7.58 (t, 1H, J 7.7), 7.48 (b.d, 1H, J 8.4), 7.41 (d, 1H, J 6.3), 7.36-7.33 (m, 2H), 4.90 (d, 1H, J 15.2), 4.49 (b.s, 1H), 4.35 (dd, 1H, J 8.3, 12.3), 4.28 (b.s., 1H), 3.93-3.86 (m, 1H), 3.82-3.68 (m, 5H), 3.61-3.50 (m, 2H), 3.42-3.35 (m, 1H), 3.01 (s, 3H), 2.92 (s, 3H), 2.75-2.66 (m, 1H), 1.99-1.82 (m, 4H), 1.74-1.66 (m, 2H), 1.50 (b.d, 1H, J 11.8), 1.41-1.29 (m, 2H), 1.21-1.10 (m, 1H); (ES⁺) m/z 567 (M+H)⁺.

Example 21

(16S,18R)-29-cyclohexyl-10,17-dimethyl-20-oxa-9-thia-1,8,10,13,17-pentaazahexacyclo[16.9.1.1$^{2,6}$.1$^{3,27}$.1$^{13,16}$.0$^{21,26}$]hentriaconta-2(31),3,5,21,23,25,27(29)-heptaen-7-one 9,9-dioxide Step 1: methyl (7R)-7-[[(3S)-1-(tert-butoxycarbonyl)pyrrolidin-3-yl](methyl)amino]-14-cyclohexyl-7,8-dihydro-6H-indolo[1,2-e][1,5]benzoxazocine-11-carboxylate AcOH (4 eq) was added to a stirred mixture of tert-butyl 3-oxopyrrolidine-1-carboxylate (1.5 eq) and methyl (7R)-7-amino-14-cyclohexyl-7,8-dihydro-6H-indolo[1,2-e][1,5]benzoxazocine-11-carboxylate (1 eq, prepared as described in Example 1, Step 4) in dry DCE (1M); after 30 min Na(OAc)₃BH (1.8 eq) was added and the mixture was stirred at RT for 4 h. Evaporation to dryness gave a residue that was taken in EtOAc, washed with sat. aq. NaHCO₃ and brine, dried and concentrated in vacuo. AcOH (4 eq) was added to a stirred mixture of foregoing crude (1 eq) and a 37% solution of HCHO in H₂O (2 eq) in dry MeOH (1M); NaCNBH₃ (1.6 eq) was added and the mixture was stirred at RT for 3 h. Evaporation to dryness gave a residue that was taken in EtOAc, washed with sat. aq. NaHCO$_3$ and brine, then dried and concentrated in vacuo. The crude material was purified by FC (Biotage, PE:EtOAc:toluene, 4:3:3) to afford methyl (7R)-7-[[(3S)-1-(tert-butoxycarbonyl)pyrrolidin-3-yl](methyl)amino]-14-cyclohexyl-7,8-dihydro-6H-indolo[1,2-e][1,5]benzoxazocine-11-carboxylate (43%) and its diastereoisomer methyl (7R)-7-[[(3R)-1-(tert-butoxycarbonyl)pyrrolidin-3-yl](methyl)amino]-14-cyclohexyl-7,8-dihydro-6H-indolo[1,2-e][1,5]benzoxazocine-11-carboxylate (43%). (ES$^+$) m/z 588 (M+H)$^+$.

Step 2: tert-butyl (3S)-3-[{(7R)-14-cyclohexyl-11-[({[(2,2-dimethoxyethyl)(methyl)amino]sulfonyl}amino)carbonyl]-7,8-dihydro-6H-indolo[1,2-e][1,5]benzoxazocin-7-yl}(methyl)amino]pyrrolidine-1-carboxylate 1M KOH (3.5 eq) was added to a 0.3M solution of methyl (7R)-7-[[(3S)-1-(tert-butoxycarbonyl)pyrrolidin-3-yl](methyl)amino]-14-cyclohexyl-7,8-dihydro-6H-indolo[1,2-e][1,5]benzoxazocine-11-carboxylate (1 eq) in dioxane and the mixture was stirred at 75° C. for 12 h. The pH was adjusted at 0° C. by addition of 1N HCl (until pH=6), then all volatiles were evaporated, the solid residue was taken in CHCl$_3$ and salt was filtered off. The filtrate was concentrated in vacuo to afford a residue that was taken in dry DCM (0.05M); DMAP (3.5 eq), EDC (1.5 eq) and N-(2,2-dimethoxyethyl)-N-methylsulfamide (1.5 eq; prepared as described in Example 1, step 1) were added and the mixture was stirred at 40° C. for 1 h. The residue obtained after evaporation was extracted with EtOAc. The combined organic phases were washed with 1M HCl, sat. aq. NaHCO$_3$ and brine, dried over Na$_2$SO$_4$ and concentrated to afford the title compound which was used without further purification. (ES$^+$) m/z 754 (M+H)$^+$.

Step 3: (16S,18R)-29-cyclohexyl-10,17-dimethyl-20-oxa-9-thia-1,8,10,13,17-pentaazahexacyclo [16.9.1.1$^{2,6}$.1$^{3,27}$.1$^{13,16}$.0$^{21,26}$]hentriaconta-2(31),3,5,21,23,25,27(29)-heptaen-7-one 9,9-dioxide A 0.05M solution of tert-butyl (3S)-3-[{(7R)-14-cyclohexyl-11-[({[(2,2-dimethoxyethyl)(methyl)amino]sulfonyl}amino)carbonyl]-7,8-dihydro-6H-indolo[1,2-e][1,5]benzoxazocin-7-yl}(methyl)amino]pyrrolidine-1-carboxylate in DCM/TFA 3:1 was stirred at RT for 1.5 h. The residue obtained by evaporation was dissolved in MeOH, NEt$_3$ (5 eq) was added, followed by NaCNBH$_3$ (3 eq) and AcOH (10 eq) and the mixture was stirred for 4 h at RT.

The residue obtained after removing MeOH in vacuo was taken in sat. aq. NaHCO$_3$ and EtOAc and extracted with EtOAc; without further washings the organic phase was dried over Na$_2$SO$_4$ and concentrated, and the residue purified by RP-HPLC to afford after lyophilisation of the fractions the title compound as a white solid (6%). $^1$H NMR (400 MHz, DMSO-d$_6$) δ 8.04 (s, 1H), 7.77 (d, 1H, J 8.4), 7.64 (d, 1H, J 8.4), 7.52 (t, 1H, J 7.6), 7.34-7.27 (m, 3H), 4.66 (d, 1H, J 15.6), 4.23 (dd, 1H, J 4.6, 11.2), 4.05 (b.t, 1H, J 11.2), 3.90-3.80 (m, 2H), 3.70-3.00 (m, 7H, partially obscured by water signal), 2.98-2.90 (m, 1H), 2.80-2.60 (m, 2H), 2.75 (s, 3H), 2.32-2.18 (m, 1H), 2.22 (s, 3H), 1.98-1.87 (m, 3H), 1.84-1.65 (m, 4H), 1.50-1.45 (m, 1H), 1.37-1.27 (m, 2H), 1.15-1.08 (m, 1H); (ES$^+$) m/z 592 (M+H)$^+$.

Example 22

(7R)-14-cyclohexyl-21-ethyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide Step 1: methyl 2-[2-(allyloxy)phenyl]-3-cyclohexyl-1H-indole-6-carboxylate Methyl 3-cyclohexyl-2-(2-hydroxyphenyl)-1H-indole-6-carboxylate (prepared as described in published International patent application WO 2006/046030) was suspended in MeCN/DCM (1:1, 0.1M) and K$_2$CO$_3$ (1 eq) was added. To the stirred mixture allyl bromide (1.1 eq) was added and the mixture was warmed to 50° C. After 4 h a further 0.5 eq of allyl bromide were added and heating was continued over night. The mixture was filtered and the filter cake was extracted with hot ethyl acetate. The combined filtrates were evaporated in vacuo. The residual material was dissolved in hot DCM and precipitated by addition of PE. The precipitate was collected and dried in vacuo. The product was obtained as a beige crystalline powder. (81%). (ES$^+$) m/z 390 (M+H)$^+$.

Step 2: methyl 2-(3-allyl-2-hydroxyphenyl)-3-cyclohexyl-1H-indole-6-carboxylate

Methyl 2-[2-(allyloxy)phenyl]-3-cyclohexyl-1H-indole-6-carboxylate was heated neat to 220° C. The starting material liquified at about 190° C. and turned dark brown. After 1 h the starting material was consumed. The brown liquid solidified upon cooling to RT. The product was isolated by FC (biotage column, PE:EtOAc, 9:1). After evaporation of the solvents the product was obtained as a beige amorphous solid (80%). (ES$^+$) m/z 390 (M+H)$^+$.

Step 3: methyl 3-cyclohexyl-2-(2-hydroxy-3-propylphenyl)-1H-indole-6-carboxylate Methyl 2-(3-allyl-2-hydroxyphenyl)-3-cyclohexyl-1H-indole-6-carboxylate was dissolved in EtOAc (0.08M). After adding Pd/C (10%) HOAc was added and the mixture was degassed and flushed with Ar. After degassing, H$_2$-atmosphere was applied and the mixture was left stirring at RT. After 30 min the reaction was complete and the catalyst was filtered off. After evaporation of the solvents the product was obtained as a yellowish solid (98%). (ES$^+$) m/z 392 (M+H)$^+$.

Step 4: (7R)-7-[(2-aminoethyl)(methyl)amino]-14-cyclohexyl-N-{[methyl(2-oxoethyl)amino]sulfonyl}-4-propyl-7,8-dihydro-6H-indolo[1,2-e][1,5]benzoxazocine-11-carboxamide The title compound was prepared using chemistry analagous to that described for Example 1, Steps 3-9. (ES$^+$) m/z 624 (M+H)$^+$.

Step 5: (7R)-14-cyclohexyl-21-ethyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide (7R)-7-[(2-aminoethyl)(methyl)amino]-14-cyclohexyl-N-{[methyl(2-oxoethyl)amino]sulfonyl}-4-propyl-7,8-dihydro-6H-indolo[1,2-e][1,5]benzoxazocine-11-carboxamide was dissolved in MeOH (0.9 mM), NEt$_3$ and HOAc were added, followed by NaCNBH$_3$. After 30 min the ring-closed intermediate with [M+H]+=608 had formed and MeCHO was added. After one night all volatiles were evaporated in vacuo and the residual material was dissolved in MeCN. The product was isolated by mass-guided RP-HPLC. After lyophilisation a colourless powder was obtained (6%). $^1$H NMR (400 MHz, DMSO-d$_6$) δ 8.09 (s, 1H), 7.91 (d, 1H, J 8.6), 7.47-7.45 (m, 2H), 7.30-7.27 (m, 1H), 7.21-7.19 (m, 1H), 4.62 (d, 1H, J 14.9), 4.41-4.36 (m, 1H), 3.98-3.84 (m, 3H), 3.58-3.13 (m, 8H), 3.04-2.98 (m, 4H), 2.67 (q, 3H, J 7.26), 2.63-2.56 (m, 1H), 2.34 (s, 3H), 1.95-1.65 (m, 10H), 1.48-1.09 (m, 8H), 0.98 (t, 3H, J 7.26); (ES+) m/z 636 (M+H)+.

Example 23

31-cyclohexyl-8-oxa-24-thia-1,4,16,23,25-pentaazaheptacyclo[23.2.2.1$^{4,6}$.1$^{6,16}$.1$^{15,18}$.1$^{17,21}$.0$^{9,14}$]tritriaconta-9,11,13,15(31),17(30),18,20-heptaen-22-one 24,24-dioxide

Step 1: 5,5-bis(bromomethyl)-2,2-dimethyl-1,3-dioxane

TsOH monohydrate (0.1 eq) was added at 0° C. to a 0.2M solution of 2,2-bis(bromomethyl)propane-1,3-diol in acetone/2,2-dimethoxypropane (10:1) and the solution was stirred for 2 h at RT. Filtration over a pad of neutral alumina with EtOAc afforded the title compound as a white solid after evaporation of the solvent in vacuo (quant). $^1$H NMR (300 MHz, CDCl$_3$, 300 K) δ 3.80 (s, 4H), 3.58 (s, 4H), 1.42 (s, 6H).

Step 2: methyl 14'-cyclohexyl-2,2-dimethylspiro[1,3-dioxane-5,7'-indolo[1,2-e][1,5]benzoxazocine]-11'-carboxylate NaH (5 eq, 60% dispersion in mineral oil) was added to a degassed solution of methyl 3-cyclohexyl-2-(2-hydroxyphenyl)-1H-indole-6-carboxylate (prepared as described in published International patent application WO2006/046030) in DMF (0.2 M) and the solution was allowed to stir for 20 min at RT. The mixture was then placed in an oil bath preheated at 70° C., a degassed solution of 5,5-bis(bromomethyl)-2,2-dimethyl-1,3-dioxane (1.5 eq) in dry DMF (0.4M) was added and the mixture was stirred for 1 h; additional electrophile (1.5 eq) was added and stirring was continued for 3 h at 70° C. The reaction was quenched with sat. aq. NH$_4$Cl, acidified with 1N HCl and extracted with Et$_2$O; the organic layer was washed with H$_2$O and brine, dried over Na$_2$SO$_4$ and the solvent was removed in vacuo. The crude was purified by FC (PE/EtOAc) to afford the title compound (50%) and recovered starting material (44%). (ES+) m/z 490 (M+H)+.

Step 3: Methyl 1-{2-[4-(aminosulfonyl)piperazin-1-yl]ethyl}-14'-cyclohexylspiro[azetidine-3,7'-indolo[1,2-e][1,5]benzoxazocine]-11'-carboxylate Cat. TsOH monohydrate was added to a suspension of methyl 14'-cyclohexyl-2,2-dimethylspiro[1,3-dioxane-5,7'-indolo[1,2-e][1,5]benzoxazocine]-11'-carboxylate in MeOH/THF 1:2 (0.03 M), and the solution was stirred at RT for 3 h. Filtration on a pad of neutral alumina using EtOAc as eluent afforded after evaporation of the solvent in vacuo methyl 14-cyclohexyl-7,7-bis(hydroxymethyl)-7,8-dihydro-6H-indolo[1,2-e][1,5]benzoxazocine-11-carboxylate (quant). This material was dissolved in dry MeCN (0.2M) and DIPEA (4.0 eq) and trifluoromethane sulfonic anhydride (3.5 eq) was added at 0° C. The mixture was stirred at 0° C. for 15 min, then more DIPEA (4 eq) was added at RT. Tert-butyl 4-(2-aminoethyl)piperazine-1-carboxylate (2 eq) was added, and the mixture was stirred at 70° C. for 1 h. After removal of the solvent in vacuo EtOAc was added, the solution was washed with H$_2$O and brine, dried over Na$_2$SO$_4$ and the solvent was removed in vacuo. The crude methyl 1-{2-[4-(tert-butoxycarbonyl)piperazin-1-yl]ethyl}-14'-cyclohexylspiro[azetidine-3,7'-indolo[1,2-e][1,5]benzoxazocine]-11'-carboxylate was taken in DCM/TFA 3:1 (0.13M) and stirred at RT for 2 h. The mixture was evaporated to dryness and the residual material was dissolved in EtOAc. The solution was washed with sat. aq. NaHCO$_3$ and brine. The organic phase was dried over Na$_2$SO$_4$ and the solvent evaporated in vacuo. The residue was dissolved in dry dioxane (0.06M) and sulfamide (5 eq) was added. The mixture was stirred at reflux for 3 h, then overnight at RT. The residue obtained after evaporation was purified by FC (EtOAc/MeOH, 9:1) to afford the title compound in 40% yield. (ES+) m/z 622 (M+H)+.

Step 4: 31-cyclohexyl-8-oxa-24-thia-1,4,16,23,25-pentaazaheptacyclo[23.2.2.1$^{4,6}$.1$^{6,16}$.1$^{15,18}$.1$^{17,21}$.0$^{9,14}$]tritriaconta-9,11,13,15(31),17(30),18,20-heptaen-22-one 24,24-dioxide 0.1M aq KOH (3 eq) was added to a 0.1M solution of methyl 1-{2-[4-(aminosulfonyl)piperazin-1-yl]ethyl}-14'-cyclohexylspiro[azetidine-3,7'-indolo[1,2-e][1,5]benzoxazocine]-11'-carboxylate in dioxane and the mixture was stirred at 70° C. for 150 min. 1M HCl was added until pH=6, the compound was extracted with EtOAc, washed with brine, dried over Na$_2$SO$_4$ and concentrated. The residue was dissolved in DCM (0.05M) and treated with DMAP (3 eq) and EDC (1.5 eq) for 90 min at 40° C. The residue obtained after evaporation was purified by RP-HPLC to afford the title compound as bis-TFA salt (15%). $^1$H NMR (400 MHz, DMSO-d$_6$, 300 K) δ 8.17 (b.s, 1H), 7.89 (d, 1H, J 8.3), 7.46 (b.s, 2H), 7.24-7.16 (m, 3H), 5.15 (d, 1H, J 17.4), 4.16-4.05 (m, 2H), 4.05-3.78 (m, 2H), 3.78-3.15 (m, 6H), 3.15-2.40 (m, 10H, partially obscured by DMSO signal), 2.00-1.80 (m, 4H), 1.80-1.62 (m, 2H), 1.62-1.50 (m, 1H), 1.40-1.22 (m, 3H); (ES+) m/z 590 (M+H)+.

Example 24

(7R)-14-cyclohexyl-18,19,19,21,24-pentamethyl-7,8-dihydro-6H-7,11-(epiminoethanoiminoethanoiminothioiminomethano)indolo[1,2-e][1,5]benzoxazocin-15-one 17,17-dioxide

Step 1: tert-butyl (2-hydroxy-1,1-dimethylethyl)methylcarbamate

A solution of N-(tert-butoxycarbonyl)-N,2-dimethylalanine in THF (0.17 M) was treated at RT with BH$_3$-DMS complex in THF (10 eq., 2M) and the mixture was stirred at 45° C. for 8 h. The reaction was carefully quenched with H$_2$O and the pH adjusted to 9 with 2M aq. Na$_2$CO$_3$. The mixture was then extracted with EtOAc and washed with brine. After drying over Na$_2$SO$_4$, the crude material was purified by FC (10-50% EtOAc in PE) to afford the product. (ES+) m/z 204 (M+H)+.

Step 2: tert-butyl (1,1-dimethyl-2-oxoethyl)methylcarbamate

The foregoing compound was dissolved in DCM (0.1 M) and to the mixture was added DMP (1.5 eq,) in one portion. The mixture was stirred for 1 h, then it was diluted with Et$_2$O and treated with sat. aq. NaHCO₃ containing Na₂S₂O₃. The mixture was stirred for 5 min, then Et₂O was added and the layers were separated. The organic phase was washed with sat. aq. NaHCO₃ and H₂O, dried over Na₂SO₄ and evaporated. The crude product was used without further purification. (ES⁺) m/z 202 (M+H)⁺.

Step 3: methyl (7R)-7-[(2-aminoethyl)(methyl) amino]-14-cyclohexyl-7,8-dihydro-6H-indolo[1,2-e] [1,5]-benzoxazocine-11-carboxylate Methyl (7R)-7-[{2-[(tert-butoxycarbonyl)amino]ethyl} (methyl)amino]-14-cyclohexyl-7,8-dihydro-6H-indolo[1,2-e][1,5]benzoxazocine-11-carboxylate (Example 1, Step 6) was treated in analogy to Example 8, Step 11 (100%); (ES⁺) m/z 463 (M+H)⁺.

Step 4: methyl (7R)-7-[{2-{[2-[(tert-butoxycarbonyl) (methyl)amino]-2-methylpropyl}(methyl)amino] ethyl}(methyl)amino]-14-cyclohexyl-7,8-dihydro-6H-indolo[1,2-e][1,5]benzoxazocine-11-carboxylate The foregoing compound and the compound from step 2 were reacted in analogy to Example 8, Step 12 and 13 to give the title compound; (ES⁺) m/z 662 (M+H)⁺.

Step 5: methyl (7R)-14-cyclohexyl-7-[methyl(2-{[2-methyl-2-(methylamino)propyl]amino}ethyl)amino]-7,8-dihydro-6H-indolo[1,2-e][1,5]benzoxazocine-11-carboxylate The material was prepared from the foregoing compound in analogy to Example 1, Step 4 (100%); (ES⁺) m/z 562 (M+H)⁺.

Step 6: methyl (7R)-7-[{2-[{2-[{[(tert-butoxycarbonyl)amino]sulfonyl}(methyl)amino]-2-methylpropyl}(methyl)amino]ethyl}(methyl)amino]-14-cyclohexyl-7,8-dihydro-6H-indolo[1,2-e][1,5] benzoxazocine-11-carboxylate Chlorosulfonylisocyanate (1 eq.) and tBuOH (1.3 eq.) were stirred at 0° C. in DCM (0.1 M) for 90 minutes. A solution of the compound from step 6 and NEt₃ (5 eq.) in DCM (0.04 M) was added and the resulting mixture was stirred at RT for 1 h. All volatiles were removed in vacuo. The crude material was purified by FC (2-10% MeOH in EtOAc+ 2% NEt₃) to afford the title compound (59%); (ES⁺) m/z 741 (M+H)⁺.

Step 7: (7R)-7-[{2-[{2-[{[(tert-butoxycarbonyl) amino]sulfonyl}(methyl)amino]-2-methylpropyl} (methyl)amino]ethyl}(methyl)amino]-14-cyclohexyl-7,8-dihydro-6H-indolo[1,2-e][1,5] benzoxazocine-11-carboxylic acid The foregoing compound was reacted in analogy to Example 10, Step 11 (71%); (ES⁺) m/z 727 (M+H)⁺.

Step 8: (7R)-7-{[2-[{2-[(aminosulfonyl)(methyl) amino]-2-methylpropyl}(methyl)amino]ethyl}(methyl)amino]-14-cyclohexyl-7,8-dihydro-6H-indolo[1, 2-e][1,5]benzoxazocine-11-carboxylic acid The material was prepared from the compound prepared in step 8 in analogy to Example 1, Step 4 (100%); (ES⁺) m/z 627 (M+H)⁺.

Step 9: (7R)-14-cyclohexyl-18,19,19,21,24-pentamethyl-7,8-dihydro-6H-7,11-(epiminoethanoiminoethanoiminothioiminomethano)indolo[1,2-e][1,5]benzoxazocin-15-one 17,17-dioxide The foregoing compound was reacted in analogy to Example 8, Step 14 (23%, TFA-salt); ¹H NMR (400 MHz, DMSO-d₆+2% TFA, 300 K) δ 1.07-1.20 (m, 1H), 1.26-1.36 (m, 3H), 1.39 (s, 3H), 1.43-1.52 (m, 1H), 1.57 (s, 3H), 1.64-1.77 (m, 2H), 1.80-1.88 (m, 1H), 1.89-2.02 (m, 3H), 2.73 (s, 3H), 2.93 (s, 3H), 3.08 (s, 3H), 3.33-3.44 (m, 1H), 3.51-3.65 (m, 3H), 3.65-3.81 (m, 2H), 3.89-4.00 (m, 1H), 4.04-4.17 (m, 1H), 4.27 (apparent t, J 11.0, 1H), 4.43-4.56 (m, 1H), 4.73 (d, J 15.2, 1H), 7.31-7.44 (m, 3H), 7.53 (d, J 8.4, 1H), 7.58 (apparent t, J 7.8, 1H), 7.95 (d, J 8.4, 1H), 8.09 (s, 1H), 11.7 (br s, 1H); (ES⁺) m/z 608 (M+H)⁺.

Example 25

(7R)-14-cyclohexyl-18,21-dimethyl-7,8-dihydro-6H-7,11-(propanoiminoethanoiminothioiminomethano) indolo[1,2-e][1,5]benzoxazocin-15-one 17,17-dioxide (A25)

Step 1: (4S)-4-benzyl-3-pent-4-enoyl-1,3-oxazolidin-2-one

To a solution (0.49 M) of (4S)-4-benzyl 1,3-oxazolidinone in THF cooled to −78° C. was added dropwise n-BuLi in hexane (2.5 M, 1.1 eq). The resulting solution was stirred at −78° C. for 30 min, then a solution of 4-pentenoyl chloride in THF (4 M, 1.1 eq) was added dropwise. The resulting mixture was stirred at −78° C. for 20 min and then allowed to reach 0° C., where it was stirred for another 40 min. The reaction was quenched by addition of sat. aq. NH₄Cl before partitioning between H₂O and EtOAc. The layers were separated and the aqueous phase re-extracted with EtOAc. The combined organic extracts were washed with brine, dried over Na₂SO₄, filtered and concentrated in vacuo. The residue was purified by FC eluting with PE/EtOAc (10:1) to give the product as a colourless oil (72%). (ES⁺) m/z 260 (M+H)⁺.

Step 2: (4S)-4-benzyl-3-[2-(hydroxymethyl)pent-4-enoyl]-1,3-oxazolidin-2-one

The foregoing compound was dissolved in DCM (0.2 M) and cooled to 0° C. TiCl₄ (1.1 eq) was added dropwise to the mixture, followed by Hünig's base (1.1 eq) and the resulting deep red mixture was stirred at 0° C. for 40 min. s-Trioxane (1.1 eq) was added to the reaction mixture in one portion, followed by dropwise addition of TiCl₄ (1.1 eq). The reaction mixture was stirred for 3 h at 0° C. and then quenched by dropwise addition of sat. aq. NH₄Cl. The mixture was stirred for 30 min, poured into H₂O and extracted with DCM. The combined organic extracts were washed once with sat. aq. NH₄Cl, dried with Na₂SO₄, filtered and concentrated in vacuo. The resulting orange oil was used without further purification. (ES⁺) m/z 290 (M+H)⁺.

Step 3: (4S)-4-benzyl-3-[(2R)-2-({[tert-butyl(dimethyl)silyl]oxy}methyl)pent-4-enoyl]-1,3-oxazolidin-2-one The foregoing compound was dissolved in DCM (0.2 M) and at RT treated with DMAP (0.1 eq), NEt₃ (1.5 eq) and tert-butyldimethylchlorosilane (1.2 eq). The mixture was stirred at RT °C. for 18 h, then ethyl acetate was added and the resulting mixture was washed with HCl (1N), sat. aq. NaHCO$_3$, water and brine. The combined organic extracts were dried over Na$_2$SO$_4$, filtered and concentrated in vacuo. The residue was purified by FC eluting with PE/EtOAc (20:1) to give the product as a colourless oil (73% over two steps). (ES$^+$) m/z 404 (M+H)$^+$; [α]$_D^{20}$: +32.9° (c=1.3, CHCl$_3$).

Step 4: (2S)-2-({[tert-butyl(dimethyl)silyl]oxy}methyl)pent-4-en-1-ol

The foregoing compound was dissolved in Et$_2$O (0.19 M) and cooled to 0° C. Solid LiBH$_4$ (1.2 eq) was added in one portion followed by the dropwise addition of methanol (1.2 eq). The resulting mixture was stirred for 40 min at 0° C., then for 90 min at RT. The mixture was then cooled to 0° C. and sat. aq. NaHCO$_3$ was carefully added over 30 min. The biphasic mixture was stirred vigorously for 1 h at 0° C. and then poured into H$_2$O. The aqueous layer was extracted with EtOAc and the combined organic extracts were dried over Na$_2$SO$_4$, filtered and concentrated in vacuo. The residue was purified by FC eluting with PE/EtOAc (12:1) to give the product as a colourless oil (80%). (ES$^+$) m/z 231 (M+H)$^+$; [α]$_D^{20}$: −4.1° (c=1.4, CHCl$_3$).

Step 5: (2R)-2-({[tert-butyl(dimethyl)silyl]oxy}methyl)pent-4-en-1-yl methanesulfonate The foregoing compound was dissolved in DCM (0.5 M), N,N-diisopropylethylamine (2 eq) was added and the mixture was cooled to 0° C. MsCl (1.2 eq) was added dropwise and the mixture was stirred for 1 h at RT. The reaction mixture was then diluted with EtOAc and washed with HCl (1N), sat. aq. NaHCO$_3$ and brine. The organic layer was dried over Na$_2$SO$_4$, filtered and concentrated in vacuo. The residue was used without further purification (98%). (ES$^+$) m/z 309 (M+H)$^+$.

Step 6: methyl 2-(2-{[(2S)-2-({[tert-butyl(dimethyl)silyl]oxy}methyl)pent-4-en-1-yl]oxy}phenyl)-3-cyclohexyl-1H-indole-6-carboxylate A solution of methyl 3-cyclohexyl-2-(2-hydroxy-phenyl)-1H-indole-6-carboxylate (prepared as described in published International patent application WO2006/046030) in DMA (0.1 M) was treated with Cs$_2$CO$_3$ (1.2 eq) at and heated to 60° C. The mesylate from prepared in the foregoing step was added in as a DMA solution (0.5 M) over 30 min and the resulting mixture was heated to 65-70° C. and left for 15 h. After cooling to RT the solution was diluted with EtOAc and washed with H$_2$O (3×) and brine. The organic layer was dried over Na$_2$SO$_4$, filtered and evaporated to dryness. The residue was purified by FC eluting with PE/EtOAc (20:1) to give the product as a colourless solid (79%). (ES$^+$) m/z 562 (M+H)$^+$.

Step 7: methyl 3-cyclohexyl-2-(2-{[(2R)-2-(hydroxymethyl)pent-4-en-1-yl]oxy}phenyl)-1H-indole-6-carboxylate A solution of the foregoing compound in THF (0.1 M) was treated with TBAF (1.0 eq, 1.0 M in THF) at RT and stirred for 20 min. Most of the THF was removed in vacuo, and the residue was diluted with EtOAc. After washing with HCl (1N), water and brine, the organic layer was dried over Na$_2$SO$_4$, filtered and concentrated in vacuo. The residue was purified by FC eluting with PE/EtOAc (8:1 to 5:1) to give the product as a yellowish foam (93%). (ES$^+$) m/z 448 (M+H)$^+$; [α]$_D^{20}$: +13.40 (c=0.93, CHCl$_3$).

Step 8: methyl (7R)-7-allyl-14-cyclohexyl-7,8-dihydro-6H-indolo[1,2-e][1,5]benzoxazocine-11-carboxylate The foregoing compound was converted to its mesylate as described in step 5 and the crude product was dissolved in DMA (0.3 M) and added dropwise over 40 minutes to a suspension of Cs$_2$CO$_3$ (2 eq) in DMA (final concentration 0.080 M) heated at 65° C. After completion of the addition the mixture was stirred at that temperature for another 1.5 h, then cooled to RT, diluted with EtOAc and washed with H$_2$O (4×) and brine (2×). The combined organic extracts were dried over Na$_2$SO$_4$, filtered and concentrated in vacuo. The residue was purified by FC eluting with PE/EtOAc to give the product as a colourless foam (86%). (ES$^+$) m/z 430 (M+H)$^+$; [α]$_D^{20}$: +68.6° (c=0.7, CHCl$_3$).

Step 9: methyl (7R)-14-cyclohexyl-7-(3-hydroxypropyl)-7,8-dihydro-6H-indolo[1,2-e][1,5]benzoxazocine-11-carboxylate A solution of the foregoing compound in THF (1.0 M) was added to a solution of 9-BBN in THF (0.5 M, 2.5 eq) cooled to 0° C. The resulting mixture was stirred for 24 h at RT, and was then cooled to 0° C. Sodium hydroxide (1 M, 5 eq) was added, followed by dropwise addition of hydrogen peroxide (35%, 5 eq). The resulting mixture was stirred for 15 min at 0° C. and then for further 30 min at RT. Water was added and the mixture was extracted several times with EtOAc and DCM. The combined organic extracts were dried over Na$_2$SO$_4$, filtered and concentrated in vacuo. The residue was purified by FC eluting with PE/EtOAc (9:1 to 2:1, containing 2% MeOH) to give the product as a colourless solid (75%). (ES$^+$) m/z 448 (M+H)$^+$.

Step 10: methyl (7R)-7-{3-[{2-[(tert-butoxycarbonyl)(methyl)amino]ethyl}-(methyl)amino]propyl}-14-cyclohexyl-7,8-dihydro-6H-indolo[1,2-e][1,5]benzoxazocine-11-carboxylate The foregoing compound was dissolved in DCM (0.12 M) and oxidized to the corresponding aldehyde using DMP (1.5 eq). After stirring for 1 h at RT, the reaction was diluted with EtOAc and washed with a mixture of sat. aq. NaHCO$_3$ and sat. aq. Na$_2$S$_2$O$_3$ (1:1, v/v, 2×), water and brine. The organic layer was dried over Na$_2$SO$_4$, filtered and concentrated in vacuo. The crude aldehyde was dissolved in 1,2-DCE (0.12 M) at RT. To the resulting solution tert-butyl methyl[2-(methylamino)ethyl]carbamate (prepared as described in European patent application 1998/296811 from commercially available N,N'-dimethylethylenediamine) was added (1.5 eq), followed by sodium triacetoxyborohydride (1.4 eq). After 1.5 h sodium hydroxide (1 M, 2 eq) was added and the mixture stirred vigorously for 10 min). After dilution with EtOAc, the organic phase was washed with water and brine. The organic layer was dried over Na$_2$SO$_4$, filtered and concentrated in vacuo. The residue was purified by FC eluting with PE/EtOAc (1:1, containing 0.5% NEt$_3$ and 0.5% MeOH) to give the product as a sticky foam (69%). (ES$^+$) m/z 618 (M+H)$^+$.

Step 11: methyl (7R)-7-{3-[{2-[{[(tert-butoxycarbonyl)amino]-sulfonyl}(methyl)amino]ethyl}(methyl)amino]propyl}-14-cyclohexyl-7,8-dihydro-6H-indolo[1,2-e][1,5]benzoxazocine-11-carboxylate The foregoing compound was dissolved in DCM (0.08 M) and TFA was added (165 eq). After stirring for 30 min at RT, the reaction mixture was evaporated to dryness, taken into EtOAc and washed with sat. aq. NaHCO$_3$. The organic layer was dried over Na$_2$SO$_4$, filtered and concentrated in vacuo. The crude amine was dissolved in THF (0.2 M) and (tert-butoxycarbonyl) {[4-(dimethyliminio)pyridin-1(4H)-yl] sulfonyl}azanide (1.2 eq) (prepared following literature procedure: Winum, J.-Y. et al Org. Lett. 2001, 3, 2241-2243) was added. The resulting mixture was heated to 40° C. for 18 h, cooled to RT, diluted with EtOAc and washed with HCl (1 N), sat. aq. NaHCO$_3$ and brine. The organic layer was dried over Na$_2$SO$_4$, filtered and concentrated in vacuo to give the product as a yellow oil (91%), which was used without further purification. (ES$^+$) m/z 697 (M+H)$^+$.

Step 12: (7R)-7-{3-[{2-[{[(tert-butoxycarbonyl) amino]sulfonyl}(methyl)amino]-ethyl}(methyl) amino]propyl}-14-cyclohexyl-7,8-dihydro-6H-indolo[1,2-e][1,5]benzoxazocine-11-carboxylic acid The foregoing compound was dissolved in dioxane (0.07 M) and KOH (1 M, 10 eq) was added. The mixture was heated to 65° C. for 3.5 h, then cooled to RT and diluted with EtOAc. HCl (1 N) was added until the aq. phase had a pH of about 2. The aq. phase was separated, extracted with EtOAc and the combined extracts were washed with brine, dried over Na$_2$SO$_4$, filtered and concentrated in vacuo to give the product as a clear oil (99%), which was used without further purification. (ES$^+$) m/z 683 (M+H)$^+$.

Step 13: (7R)-7-{3-[{2-[(aminosulfonyl)(methyl) amino]ethyl}(methyl)amino]propyl}-14-cyclohexyl-7,8-dihydro-6H-indolo[1,2-e][1,5]benzoxazocine-11-carboxylic acid The foregoing compound in DCM (0.03 M) was treated with TFA (52 eq) and the mixture was heated to 50° C. After 20 min all the stirred volatiles were removed in vacuo and the residue partitioned between water and EtOAc. The organic layers was washed with brine, dried over Na$_2$SO$_4$, filtered and concentrated in vacuo to afford the product as a yellow solid (73%) which was used without further purification. (ES$^+$) m/z 583 (M+H)$^+$.

Step 14: (7R)-14-cyclohexyl-18,21-dimethyl-7,8-dihydro-6H-7,11-(propanoiminoethanoiminothioiminomethano)indolo[1,2-e][1,5]benzoxazocin-15-one 17,17-dioxide The title compound was prepared in analogy to Example 18, Step 7 from the foregoing compound using EDC (3 eq) and DMAP ((5 eq) and heating the mixture to 40° C. for 15 h). The residue obtained after evaporation of all volatiles was purified by automated RP-HPLC to obtain the title compound as its TFA salt (23%) and as a mixture of two isomers (8:1). $^1$H NMR (400 MHz, DMSO-d$_6$, 300 K, data for major isomer) δ 0.97-1.08 (m, 1H), 1.10-1.21 (m, 1H), 1.25-1.53 (m, 4H), 1.63-1.75 (m, 2H), 1.78-2.05 (m, 6H), 2.60-2.72 (m, 1H), 2.74-2.80 (m, 1H), 2.85 (bs, 3H), 3.08 (s, 3H), 3.1-3.49 (m, 5H, partially covered by water), 3.54-3.70 (m, 2H), 3.78-3.98 (m, 2H), 4.38 (d, J 14.5, 1H), 4.44 (bs, 1H), 7.29-7.40 (m, 3H), 7.47 (d, J 7.9 Hz, 1H), 7.58 (app. t, J 7.9 Hz, 1H), 7.91 (d, J 8.5, 1H); 8.02 (s, 1H), 9.89 (bs, 1H), 11.9 (bs, 1H); MS (ES$^+$) m/z 565 (M+H)$^+$; [α]$_D^{20}$: +22° (c=0.28, CH$_3$CN).

Example 26

(7R)-14-cyclohexyl-21-ethyl-18,24-dimethyl-4-(piperidin-1-ylmethyl)-7,8-dihydro-6H-7,11-(epiminoethanoiminoethanoiminothioiminomethano)indolo[1, 2-e][1,5]benzoxazocin-15-one 17,17-dioxide (A26)

Step 1: methyl 3-cyclohexyl-2-(3-formyl-2-methoxyphenyl)-1H-indole-6-carboxylate Methyl 2-bromo-3-cyclohexyl-1H-indole-6-carboxylate (prepared as in International patent application WO 2004/087714), (3-formyl-2-methoxyphenyl) boronic acid (1.5 eq) and Pd(PPh$_3$)$_2$Cl$_2$ (0.1 eq) were dissolved in dioxane (0.08M). The solution was degassed and flushed with Ar. 2M Na$_2$CO$_3$ solution (1 eq) was added and the mixture was heated to 110° C. for 2 h. All volatiles were evaporated in vacuo and the residual material was dissolved in EtOAc, filtered over Celite and evaporated in vacuo. The residual material was filtered over a plug of silica gel eluting with (PE/EtOAc 1:1). After evaporation of the fractions containing product and trituration with Et$_2$O methyl 3-cyclohexyl-2-(3-formyl-2-methoxyphenyl)-1H-indole-6-carboxylate was obtained as off-white solid (77%). (ES$^+$) m/z 392 (M+H)$^+$.

Step 2: methyl 3-cyclohexyl-2-(3-formyl-2-hydroxyphenyl)-1H-indole-6-carboxylate The foregoing compound e was dissolved in dry DCM (0.1 M) and treated dropwise with BBr$_3$ (1 M in DCM, 2 eq). After stirring for 1 h at RT, an excess of MeOH was added dropwise and stirring continued for 20 min. The volatiles were evaporated and the mixture partitioned between EtOAc and 1N HCl. The organic layer was washed with brine, dried over Na$_2$SO$_4$, filtered and concentrated in vacuo. Methyl 3-cyclohexyl-2-(3-formyl-2-hydroxyphenyl)-1H-indole-6-carboxylate (75%) was obtained pure after trituration with Et$_2$O. (ES$^+$) m/z 378 (M+H)$^+$.

Step 3: methyl 3-cyclohexyl-2-[2-hydroxy-3-(piperidin-1-ylmethyl)phenyl]-1H-indole-6-carboxylate A suspension of the foregoing compound and NaBH (OAc)$_3$ in 1,2-DCE was stirred overnight at RT. After addition of sat. aq. NaHCO$_3$ the mixture was extracted into EtOAc. The combined organic layers were washed with brine, dried over Na$_2$SO$_4$, filtered and concentrated in vacuo to afford the title compound which was used without further purification. (ES$^+$) m/z 447 (M+H)$^+$.

Step 4: methyl (7R)-7-[(tert-butoxycarbonyl)amino]-14-cyclohexyl-4-piperidin-1-ylmethyl)-7,8-dihydro-6H-indolo[1,2-e][1,5]benzoxazocine-11-carboxylate The compound was prepared in analogy to Example 1, Step 3 from methyl 3-cyclohexyl-2-[2-hydroxy-3-(piperidin-1-ylmethyl)phenyl]-1H-indole-6-carboxylate and tert-butyl (2R)-2-({[(4-nitrophenyl)sulfonyl]oxy}methyl)aziridine-1-carboxylate. The compound was used without further purification. (ES$^+$) m/z 602 (M+H)$^+$.

Step 5: methyl (7R)-7-amino-14-cyclohexyl-4-piperidin-1-ylmethyl)-7,8-dihydro-6H-indolo[1,2-e][1, 5]benzoxazocine-11-carboxylate The compound was prepared in analogy to Example 1, Step 4 from methyl (7R)-7-[(tert-butoxycarbonyl)amino]-14-cyclohexyl-4-(piperidin-1-ylmethyl)-7,8-dihydro-6H-indolo[1,2-e][1,5]benzoxazocine-11-carboxylate. (ES$^+$) m/z 502 (M+H)$^+$.

Step 6: methyl (7R)-14-cyclohexyl-7-(methylamino)-4-piperidin-1-ylmethyl)-7,8-dihydro-6H-indolo[1,2-e][1,5]benzoxazocine-11-carboxylate The compound was prepared in analogy to Example 1, Step 5 from methyl (7R)-7-amino-14-cyclohexyl-4-(piperidin-1-ylmethyl)-7,8-dihydro-6H-indolo[1,2-e][1,5]benzoxazocine-11-carboxylate. (ES$^+$) m/z 516 (M+H)$^+$.

Step 7: methyl (7R)-7-[{2-[(tert-butoxycarbonyl)amino]ethyl}(methyl)amino]-14-cyclohexyl-4-(piperidin-1-ylmethyl)-7,8-dihydro-6H-indolo[1,2-e][1,5]benzoxazocine-11-carboxylate The compound was prepared in analogy to Example 1, Step 6 from methyl (7R)-14-cyclohexyl-7-(methylamino)-4-(piperidin-1-ylmethyl)-7,8-dihydro-6H-indolo[1,2-e][1,5]benzoxazocine-11-carboxylate and tert-butyl (2-oxoethyl)carbamate. The compound was used without further purification. (ES$^+$) m/z 659 (M+H)$^+$.

Step 8: (7R)-7-[{2-[(tert-butoxycarbonyl)amino]ethyl}(methyl)amino-]14-cyclohexyl-4-(piperidin-1-ylmethyl)-7,8-dihydro-6H-indolo[1,2-e][1,5]benzoxazocine-11-carboxylic acid The compound was prepared in analogy to Example 1, Step 7 from methyl (7R)-7-[{2-[(tert-butoxycarbonyl)amino]ethyl}(methyl)amino]-14-cyclohexyl-4-(piperidin-1-ylmethyl)-7,8-dihydro-6H-indolo[1,2-e][1,5]benzoxazocine-11-carboxylate. The compound was used without further purification. (ES$^+$) m/z 645 (M+H)$^+$.

Step 9: tert-butyl {2-[[(7R)-14-cyclohexyl-11-[({[2,2-dimethoxyethyl)(methyl)amino]sulfonyl}amino)carbonyl]-4-piperidin-1-ylmethyl)-7,8-dihydro-6H-indolo[1,2-e][1,5]benzoxazocin-7-yl](methyl)amino]ethyl}carbamate The compound was prepared in analogy to Example 1, Step 8 from (7R)-7-[{2-[(tert-butoxycarbonyl)amino]ethyl}(methyl)amino]-14-cyclohexyl-4-(piperidin-1-ylmethyl)-7,8-dihydro-6H-indolo[1,2-e][1,5]benzoxazocine-11-carboxylic acid and N-(2,2-dimethoxyethyl)-N-methylsulfamide (prepared as described in Example 1, Step 1). The compound was used without further purification. (ES$^+$) m/z 826 (M+H)$^+$.

Step 10: (7R)-14-cyclohexyl-21-ethyl-18,24-dimethyl-4-(piperidin-1-ylmethyl)-7,8-dihydro-6H-7,11-(epiminoethanoiminoethanoiminothioiminomethano)indolo[1,2-e][1,5]benzoxazocin-15-one 17,17-dioxide The compound was prepared in one pot following the procedures described in Example 1, Steps 9 and 10 and in Example 3 from tert-butyl {2-[[(7R)-14-cyclohexyl-11-[({[(2,2-dimethoxyethyl)(methyl)amino]sulfonyl}amino)carbonyl]-4-(piperidin-1-ylmethyl)-7,8-dihydro-6H-indolo[1,2-e][1,5]benzoxazocin-7-yl](methyl)amino]ethyl}carbamate. Purification was done by automated RP-HPLC, eluting with MeCN/H$_2$O buffered with 0.1% TFA gradient. Fractions containing the product were combined and freeze dried to afford the product as a white powder (2%).

$^1$H NMR (400 MHz, DMSO-d$_6$, 300 K) δ 1.08-1.99 (m, 19H), 2.50-2.75 (m, 8H, partially obscured by DMSO signal), 2.89-3.61 (m, 17H), 3.85-4.54 (m, 3H), 7.36-7.52 (m, 2H), 7.55-7.79 (m, 2H), 7.91 (d, J 8.7, 1H), 8.12 (s, 1H) 9.30 (bs, 1H); (ES$^+$) m/z 691 (M+H)$^+$.

Example 27

(7R)-14-cyclohexyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide (A27)

Step 1: methyl 3-cyclohexyl-2-(2-hydroxy-3-methoxyphenyl)-1H-indole-6-carboxylate The compound was prepared in analogy to Example 8, Step 4, from (2-hydroxy-3-methoxyphenyl)boronic acid. 99% after FC (PE:EtOAc, 4:1 to 1:1). (ES$^+$) m/z 380 (M+H)$^+$.

Step 2: methyl 3-cyclohexyl-2-{3-methoxy-2-[(2S)-oxiran-2-ylmethoxy]phenyl}-1H-indole-6-carboxylate The compound was prepared in analogy to Example 8, Step 8, from methyl 3-cyclohexyl-2-(2-hydroxy-3-methoxyphenyl)-1H-indole-6-carboxylate (100%). (ES$^+$) m/z 436 (M+H)$^+$.

Step 3: methyl (7S)-14-cyclohexyl-7-hydroxy-4-methoxy-7,8-dihydro-6H-indolo[1,2-e][1,5]benzoxazocine-11-carboxylate The compound was prepared in analogy to Example 8, Step 9 (100% as crude, no purification was done). (ES$^+$) m/z 436 (M+H)$^+$.

Step 4: methyl (7R)-7-azido-14-cyclohexyl-4-methoxy-7,8-dihydro-6H-indolo[1,2-e][1,5]benzoxazocine-11-carboxylate The compound was prepared in analogy to Example 8, Step 10 (quant.); (ES$^+$) m/z 461 (M+H)$^+$.

Step 5: methyl (7R)-7-amino-14-cyclohexyl-4-methoxy-7,8-dihydro-6H-indolo[1,2-e][1,5]benzoxazocine-11-carboxylate The reaction mixture from the previous step was treated in analogy to Example 8, Step 11. (41%, extracted with EtOAc at acidic pH and precipitated pure from the organic layer). (ES$^+$) m/z 435 (M+H)$^+$.

Step 6: methyl (7R)-7-[{2-[(tert-butoxycarbonyl)amino]ethyl}(methyl)amino]-14-cyclohexyl-4-methoxy-7,8-dihydro-6H-indolo[1,2-e][1,5]benzoxazocine-11-carboxylate The compound was prepared in analogy to Example 8, Steps 12 and 13 using tert-butyl (2-oxoethyl)carbamate instead of tert-butyl methyl(2-oxoethyl)carbamate (75%; purified by FC, PE:EtOAc 2:1 to 1:1+0.2% NEt$_3$); (ES$^+$) m/z 592 (M+H)$^+$.

Step 7: (7R)-7-[{2-[(tert-butoxycarbonyl)amino]ethyl}(methyl)amino]-14-cyclohexyl-4-methoxy-7,8-dihydro-6H-indolo[1,2-e][1,5]benzoxazocine-11-carboxylic acid The compound was prepared in analogy to Example 8, Step 14 (74%); (ES$^+$) m/z 578 (M+H)$^+$.

Step 8: tert-butyl {2-[{(7R)-14-cyclohexyl-1-[({[(2,2-dimethoxyethyl)(methyl)amino]sulfonyl}amino)carbonyl]-4-methoxy-7,8-dihydro-6H-indolo[1,2-e][1,5]benzoxazocin-7-yl}(methyl)amino]ethyl}carbamate The compound was prepared in analogy to Example 8, Step 15 (100% as crude); (ES$^+$) m/z 758 (M+H)$^+$.

Step 9: (7R)-7-[(2-aminoethyl)(methyl)amino]-14-cyclohexyl-4-methoxy-N-{[methyl(2-oxoethyl)amino]sulfonyl}-7,8-dihydro-6H-indolo[1,2-e][1,5]benzoxazocine-11-carboxamide TFA (22 eq) was added to a 0.15M solution of the foregoing crude material in dry DCM and the mixture was stirred at RT for 1.5 h. Evaporation gave a residue that was used as such; (ES$^+$) m/z 612 (M+H)$^+$.

Step 10: (7R)-14-cyclohexyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide The compound was prepared in analogy to Example 8, Step 17 (16%). $^1$H NMR (400 MHz, DMSO-d$_6$, 300 K) δ 1.08-1.20 (m, 1H), 1.27-1.40 (m, 2H), 1.40-1.49 (m, 1H), 1.65-1.74 (m, 2H), 1.78-1.99 (m, 4H), 2.41 (s, 3H), 2.69 (br s, 1H), 2.98 (s, 3H), 3.25-3.45 (m, 8H), 3.91 (s, 3H), 3.96-4.15 (m, 3H), 4.51 (d, J 11.2, 1H), 4.64 (d, J 14.4, 1H), 6.94 (br d, J 6.0, 1H), 7.27-7.32 (m, 2H), 7.44 (d, J 8.0, 1H), 7.91 (d, J 8.0, 1H), 8.01 (s, 1H); (ES$^+$) m/z 596 (M+H)$^+$.

Example 28

(7R)-14-cyclohexyl-21-ethyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide (A28)

Prepared in analogy to Example 3 from the compound obtained in Example 27, Step 10 (35%). $^1$H NMR (400 MHz, DMSO-d$_6$, 300 K) δ 1.08-1.20 (m, 1H), 1.20-1.26 (m, 3H), 1.28-1.39 (m, 2H), 1.39-1.47 (m, 1H), 1.64-1.75 (m, 2H), 1.70-2.00 (m, 4H), 2.58 (s, 3H), 2.62-2.72 (m, 1H), 3.22 (s, 3H), 3.15-3.61 (m, 9H), 3.70-3.78 (m, 1H), 3.92 (s, 3H), 3.90-4.02 (m, 1H), 4.02-4.12 (m, 2H), 4.44-4.48 (m, 1H), 4.69 (d, J 15.6, 1H), 6.95 (br d, J 6.8, 1H), 7.27-7.34 (m, 2H), 7.49 (d, J 8.5, 1H), 7.93 (d, J 8.5, 1H), 8.06 (s, 1H); (ES$^+$) m/z 624 (M+H)$^+$.

Example 29

(7R)-14-cyclohexyl-4-methoxy-18,24-dimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide (A29)

Prepared in analogy to Example 3 from the compound obtained in Example 27, Step 10 and substituting acetaldehyde with 1-methyl-1H-pyrazole-4-carbaldehyde (35%). $^1$H NMR (400 MHz, DMSO-d$_6$, 300 K) δ 1.06-1.20 (m, 1H), 1.27-1.38 (m, 2H), 1.38-1.46 (m, 1H), 1.64-1.74 (m, 2H), 1.80-1.98 (m, 4H), 2.54 (s, 3H), 2.64-2.73 (m, 1H), 3.03 (s, 3H), 3.21-3.48 (m, 6H), 3.63-3.78 (m, 2H), 3.85 (s, 3H), 3.91 (s, 3H), 3.92-4.07 (m, 3H), 4.21 (br d, J 14.4, 1H), 4.33 (br d, J 14.4, 1H), 4.39-4.43 (m, 1H), 4.68 (d, J 14.8, 1H), 6.95 (d, J 6.8, 1H), 7.26-7.34 (m, 2H), 7.48 (d, J 8.2, 1H), 7.61 (s, 1H), 7.89 (s, 1H), 7.92 (d, J 8.2, 1H), 8.04 (s, 1H); (ES$^+$) m/z 690 (M+H)$^+$.

Example 30

2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]-N-methylacetamide (A30)

Step 1: methyl (7R)-7-(benzylamino)-14-cyclohexyl-7,8-dihydro-6H-indolo[1,2-e][1,5]benzoxazocine-11-carboxylate The title compound was prepared in analogy to Example 12, Step 1 from methyl (7R)-7-amino-14-cyclohexyl-7,8-dihydro-6H-indolo[1,2-e][1,5]benzoxazocine-11-carboxylate. (ES$^+$) m/z 495 (M+H)$^+$.

Step 2: methyl (7R)-7-(benzyl{2-[(tert-butoxycarbonyl)amino]ethyl}amino)-14-cyclohexyl-7,8-dihydro-6H-indolo[1,2-e][1,5]benzoxazocine-1-carboxylate The title compound was prepared in analogy to Example 12, Step 2 from methyl (7R)-7-(benzylamino)-14-cyclohexyl-7,8-dihydro-6H-indolo[1,2-e][1,5]benzoxazocine-11-carboxylate (72%). (ES$^+$) m/z 638 (M+H)$^+$.

Step 3: (7R)-7-(benzyl{2-[(tert-butoxycarbonyl)amino]ethyl}amino)-14-cyclohexyl-7,8-dihydro-6H-indolo[1,2-e][1,5]benzoxazocine-11-carboxylic acid The title compound was prepared in analogy to Example 12, Step 3 from methyl (7R)-7-(benzyl{2-[(tert-butoxycarbonyl)amino]ethyl}amino)-14-cyclohexyl-7,8-dihydro-6H-indolo[1,2-e][1,5]benzoxazocine-11-carboxylate. (ES$^+$) m/z 624 (M+H)$^+$.

Step 4: tert-butyl[2-(benzyl{(7R)-14-cyclohexyl-11-[({[(2,2-dimethoxyethyl)(methyl)amino]sulfonyl}amino)carbonyl]-7,8-dihydro-6H-indolo[1,2-e][1,5]benzoxazocin-7-yl}amino)ethyl]carbamate The title compound was prepared in analogy to Example 12, Step 4 from (7R)-7-(benzyl{2-[(tert-butoxycarbonyl)amino]ethyl}amino)-14-cyclohexyl-7,8-dihydro-6H-indolo[1,2-e][1,5]benzoxazocine-11-carboxylic acid. (ES$^+$) m/z 804 (M+H)$^+$.

Step 5: (7R)-7-[(2-aminoethyl)(benzyl)amino]-14-cyclohexyl-N-{[methyl(2-oxoethyl)amino]sulfonyl}-7,8-dihydro-6H-indolo[1,2-e][1,5]benzoxazocine-11-carboxamide The title compound was prepared in analogy to Example 12, Step 5 from tert-butyl[2-(benzyl{(7R)-14-cyclohexyl-11-[({[(2,2-dimethoxyethyl)(methyl)amino]sulfonyl}amino)

carbonyl]-7,8-dihydro-6H-indolo[1,2-e][1,5]benzoxazocin-7-yl}amino)ethyl]carbamate. (ES+) m/z 658 (M+H)+.

Step 6: (7R)-24-benzyl-14-cyclohexyl-18-methyl-7,8-dihydro-6H-7,11-(epiminoethanoiminoethanoiminothioiminomethano)indolo[1,2-e][1,5]benzoxazocin-15-one 17,17-dioxide The title compound was prepared in analogy to Example 12, Step 6 from (7R)-7-[(2-aminoethyl)(benzyl)amino]-14-cyclohexyl-N-{[methyl(2-oxoethyl)amino]sulfonyl}-7,8-dihydro-6H-indolo[1,2-e][1,5]benzoxazocine-11-carboxamide. (ES+) m/z 642 (M+H)+.

Step 7: (7R)-24-benzyl-14-cyclohexyl-18,21-dimethyl-7,8-dihydro-6H-7,11-(epiminoethanoiminoethanoiminothioiminomethano)indolo[1,2-e][1,5]benzoxazocin-15-one 17,17-dioxide The title compound was prepared in analogy to Example 12, Step 7 from (7R)-24-benzyl-14-cyclohexyl-18-methyl-7,8-dihydro-6H-7,11-(epiminoethanoiminoethanoiminothioiminomethano)indolo[1,2-e][1,5]benzoxazocin-15-one 17,17-dioxide and substituting formaldehyde for acetaldehyde (40%). (ES+) m/z 656 (M+H)+.

Step 8: (7R)-14-cyclohexyl-18,21-dimethyl-7,8-dihydro-6H-7,11-(epiminoethanoiminoethanoiminothioiminomethano)indolo[1,2-e][1,5]benzoxazocin-15-one 17,17-dioxide The title compound was prepared in analogy to Example 12, Step 8 from (7R)-24-benzyl-14-cyclohexyl-18,21-dimethyl-7,8-dihydro-6H-7,11-(epiminoethanoiminoethanoiminothioiminomethano)indolo[1,2-e][1,5]benzoxazocin-15-one 17,17-dioxide (quant.). (ES+) m/z 566 (M+H)+.

Step 9: [(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]acetic acid A solution of the foregoing compound in MeOH (0.1 M) was treated with HOAc until pH was 5. NaCNBH3 (2 eq) was added in one portion and the resulting mixture was stirred at RT for 90 min. All volatiles were evaporated in vacuo. The residual material was taken up with EtOAc and the resulting solution was washed with sat. aq. NaHCO3 and brine. After drying over Na2SO4 all volatiles were evaporated in vacuo. The crude material was used without further purification. (ES+) m/z 624 (M+H)+.

Step 10: 2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]-N-methylacetamide The foregoing compound was dissolved in DCM/DMA (2:1, 0.1 M) and to the resulting solution DMAP (5 eq) and EDC (1.5 eq) were added. The mixture was stirred for 5 min then MeNH2—HCl (2 eq) was added and stirring continued for 16 h. All volatiles were removed in vacuo and the residue was dissolved in DMSO and purified by mass-guided prep RP-HPLC. After lyophilisation the product was obtained as a colourless amorphous material (16%, TFA-salt). $^1$H NMR (400 MHz, DMSO-$d_6$+3% TFA, 330 K) δ 1.09-1.22 (m, 1H), 1.29-1.42 (m, 2H), 1.45-1.55 (m, 1H), 1.64-1.77 (m, 2H), 1.81-1.87 (m, 1H), 1.88-2.00 (m, 3H), 2.67 (s, 3H), 2.71 (m, 1H), 2.87 (s, 3H), 3.06 (s, 3H), 3.07-3.14 (m, 2H), 3.15-3.25 (m, 2H), 3.30 (s, 2H), 3.35-3.44 (m, 1H), 3.46-3.55 (m, 2H), 3.59-3.70 (m, 1H), 3.92 (br d, J 10.0 Hz, 1H), 3.93-4.03 (m, 2H), 4.47 (d, J 14.8 Hz, 1H), 4.49-4.58 (m, 1H), 7.30-7.41 (m, 3H), 7.46 (d, J 8.0 Hz, 1H), 7.56 (br t, J 7.4 Hz, 1H), 7.83 (br s, 1H), 7.90 (d, J 8.4 Hz, 1H), 8.06 (s, 1H); MS (ES+) m/z 637 (M+H)+.

Example 31

(7R)-14-cyclohexyl-24-[2-(dimethylamino)ethyl]-18,21,21-trimethyl-7,8-dihydro-6H-7,11-(epiminopentanoiminothioiminomethano)indolo[1,2-e][1,5]benzoxazocin-15-one 17,17-dioxide (A31)

Step 1: 3,3-dimethylpent-4-enal

The compound was prepared by Swern oxidation of 3,3-dimethylpent-4-en-1-ol as described in *Tetrahedron Lett* 2004, 45 (14), 2939-2942 (95%).

Step 2: methyl (7R)-7-[(tert-butoxycarbonyl)(3,3-dimethylpent-4-en-1-yl)amino]-14-cyclohexyl-7,8-dihydro-6H-indolo[1,2-e][1,5]-benzoxazocine-11-carboxylate The compound was prepared in analogy to Example 20, Step 1 substituting [2-(benzyloxy)ethoxy]acetaldehyde with 3,3-dimethylpent-4-enal, and purified by FC (PE/EtOAc 9:1 to 5:1). Yield 100%. (ES+) m/z 601 (M+H)+.

Step 3: methyl (7R)-7-[(tert-butoxycarbonyl)(5-hydroxy-3,3-dimethylpentyl)amino]-14-cyclohexyl-7,8-dihydro-6H-indolo[1,2-e][1,5]benzoxazocine-11-carboxylate BH3 DMS (3.4 eq) was added at 0° C. to a 1M solution of the foregoing compound in dry THF and the mixture was stirred at RT for 2 h. After cooling to 0° C. H2O was carefully added followed by sodium perborate tetrahydrate (10 eq) and the mixture was stirred at RT for 3 h. After diluting with H2O the reaction was extracted with EtOAc, washed with brine, dried and concentrated. The crude material was purified by FC (PE/EtOAc 2:1) to afford the title compound (72%). (ES+) m/z 619 (M+H)+.

Step 4: methyl (7R)-7-{(tert-butoxycarbonyl)[3,3-dimethyl-5-(methylamino)pentyl]amino}-14-cyclohexyl-7,8-dihydro-6H-indolo[1,2-e][1,5]benzoxazocine-11-carboxylate DMAP (0.1 eq) and MsCl (1.5 eq) was added to a 0.05M solution of the foregoing compound and NEt3 (3 eq) in dry MeCN and the mixture was stirred at RT for 3 h. This solution was treated with additional NEt3 (3 eq) and 2M MeNH2/THF (22 eq) at 85° C. overnight, evaporation gave a residue that was taken in EtOAc and washed with sat. aq. NaHCO3 and brine, dried and concentrated (97%). (ES+) m/z 632 (M+H)+.

Step 5: methyl (7R)-7-((tert-butoxycarbonyl){5-[{[(tert-butoxycarbonyl)amino]sulfonyl}(methyl)amino]-3,3-dimethylpentyl}amino)-14-cyclohexyl-7,8-dihydro-6H-indolo[1,2-e][1,5]benzoxazocine-11-carboxylate Prepared in analogy to Example 20, Step 3. (94% as crude). (ES+) m/z 833 (M+Na)+.

Step 6: (7R)-7-({5-[(aminosulfonyl)(methyl)amino]-3,3-dimethylpentyl}amino)-14-cyclohexyl-7,8-dihydro-6H-indolo[1,2-e][1,5]benzoxazocine-11-carboxylic acid 1M aq. KOH was added to a 0.2M solution of the previous crude in dry dioxane and the mixture was stirred at 75° C. overnight. After adding 1N HCl the reaction mixture was extracted with EtOAc and washed with brine, dried and concentrated. The residue was dissolved in dry DCM (0.2M) and treated with TFA (20 eq) at RT for 2 h, then all volatiles were removed in vacuo to give a residue that was used as such (95%). (ES$^+$) m/z 597 (M+H)$^+$.

Step 7: (7R)-7-{{5-[(aminosulfonyl)(methyl)amino]-3,3-dimethylpentyl}[2-(dimethylamino)ethyl]amino}-14-cyclohexyl-7,8-dihydro-6H-indolo[1,2-e][1,5]benzoxazocine-1-carboxylic acid NaCNBH$_3$ (2 eq) was added to a stirred mixture of the previous crude, Et$_3$N (5 eq) and tert-butyl (2-oxoethyl)carbamate (1.5 eq) in MeOH (0.08M); AcOH (11 eq) was added and the mixture was stirred at RT for 3 h. MeOH was evaporated, H$_2$O added and extracted with EtOAc, the organic phase was washed once with a small amount of brine, dried and concentrated, and this crude was taken in dry DCM (0.2M) and treated with TFA (20 eq) at RT for 2 h. Evaporation to dryness gave a residue that was taken in MeOH (0.1M); NEt$_3$ (6 eq), 37% aq. solution of HCHO (7 eq) and NaCNBH$_3$ (4 eq) were added, then AcOH (10 eq) was added and the mixture was stirred at RT for 3 h. All volatiles were evaporated in vacuo, H$_2$O and EtOAc were added. The phases were separated and the organic phase was washed once with a small amount of brine, dried and concentrated. The crude material was used as such (74%); (ES$^+$) m/z 668 (M+H)$^+$.

Step 8: (7R)-14-cyclohexyl-24-[2-(dimethylamino)ethyl]-18,21,21-trimethyl-7,8-dihydro-6H-7,1-(epiminopentanoiminothioiminomethano)indolo[1,2-e][1,5]benzoxazocin-15-one 17,17-dioxide EDC (2 eq) was added to a stirred mixture of previous crude and DMAP (4 eq) in dry DMF (0.04M) and the mixture was stirred at 65° C. for 90 min. DMF was partially evaporated, the residue taken in DMSO and purified by automated RP-HPLC to give the title compound (7%). $^1$H NMR (400 MHz, DMSO-d$_6$, 300 K) δ 0.88 (s, 3H), 0.93 (s, 3H), 1.10-1.20 (m, 1H), 1.21-1.39 (m, 4H), 1.42-1.63 (m, 2H), 1.64-1.76 (m, 2H), 1.80-2.00 (m, 4H), 2.14-2.25 (m, 1H), 2.50-2.87 (m, 5H, partially under DMSO signal), 2.83 (s, 6H), 3.01 (s, 3H), 3.05-3.13 (m, 1H), 3.13-3.25 (m, 2H), 3.26-3.38 (m, 1H), 3.47-3.59 (m, 1H), 3.86-3.97 (m, 1H), 3.97-4.08 (m, 1H), 4.21-4.30 (m, 1H), 4.60 (d, J 14.7, 1H), 7.28-7.38 (m, 3H), 7.47 (d, J 8.3, 1H), 7.54-7.58 (m, 1H), 7.90 (d, J 8.3, 1H), 8.08 (s, 1H), 11.66 (br s, 1H); (ES$^+$) m/z 650 (M+H)$^+$.

Example 32

(7R)-14-cyclohexyl-18,21,24-trimethyl-4-(2-pyrrolidin-1-ylethoxy)-7,8-dihydro-6H-7,11-(epiminoethanoiminoethanoiminothioiminomethano)indolo[1,2-e][1,5]benzoxazocin-15-one 17,17-dioxide (A32)

Step 1: 2-(benzyloxy)-6-bromophenol

Tert-butyl amine (2 eq) was dissolved in toluene (1M) and the solution was cooled to −30° C. Br$_2$ (1 eq) was added dropwise maintaining the temperature. The mixture was left stirring for 30 min, then it was cooled to −78° C. A solution of 2-benzyloxyphenol (1 eq) in DCM (6M) was added dropwise. The mixture was allowed to reach RT over the course of 3 h. The mixture was diluted with Et$_2$O and H$_2$O was added. The mixture was washed with 1N HCl, sat. aq. Na$_2$S$_2$O$_3$ and brine. After drying over Na$_2$SO$_4$ all volatiles were evaporated in vacuo. The residue was purified by FC (PE:EtOAc, 9:1). The colourless oil was used without further characterization in the next reaction. (ES$^−$) m/z 277, 279 (M−H)$^−$.

Step 2: methyl 3-cyclohexyl-2-(4,4,5,5-tetramethyl-1,3,2-dioxaborolan-2-yl)-1H-indole-6-carboxylate Methyl 2-bromo-3-cyclohexyl indole-6-carboxylate (prepared as described in International patent application WO 2004/087714) was dissolved in dioxane (0.4M) and to the solution were added NEt$_3$ (4 eq), Pd(OAc)$_2$ (0.05 eq) and 2-(dicyclohexyl)phosphino biphenyl (0.19 eq). Pinacoloborane (3 eq) was added dropwise and the mixture was heated at 80° C. for 1 h. The mixture was cooled to RT and then quenched with sat. aq. NH$_4$Cl. The mixture was extracted with Et$_2$O. The combined organic phases were washed with brine and dried over Na$_2$SO$_4$. All volatiles were evaporated in vacuo. The residual material was purified by FC (PE:EtOAc, 9:1). After evaporation of the product fractions a yellowish solid was obtained. This material was dissolved in DCM and PE was added to induce crystallisation. The product was obtained as a beige crystalline powder (44%). (ES$^+$) m/z 384 (M+H)$^+$.

Step 3: methyl 2-[3-(benzyloxy)-2-hydroxyphenyl]-3-cyclohexyl-1H-indole-6-carboxylate The foregoing compound and 2-(benzyloxy)-6-bromophenol (1.5 eq) were dissolved in dioxane (0.11M). The solution was degassed and Pd(PPh$_3$)$_2$Cl$_2$ (0.1 eq) was added followed by 2M Na$_2$CO$_3$ solution (6 eq). The mixture was warmed under Ar atmosphere to 100° C. After 1 h all volatiles were evaporated in vacuo and the residual material was dissolved in EtOAc. The resulting mixture was washed with 1N HCl, sat. aq. NaHCO$_3$ and brine. After drying over Na$_2$SO$_4$ all volatiles were evaporated in vacuo. The residual material was purified by FC (PE:EtOAc, 9:1). After evaporation of the solvents a colourless foam was obtained (45%). (ES$^+$) m/z 456 (M+H)$^+$.

Step 4: methyl (7R)-4-(benzyloxy)-7-[(tert-butoxycarbonyl)amino]-14-cyclohexyl-7,8-dihydro-6H-indolo[1,2-e][1,5]benzoxazocine-11-carboxylate The compound was prepared in analogy to Example 1, Step 3, from methyl 2-[3-(benzyloxy)-2-hydroxyphenyl]-3-cyclohexyl-1H-indole-6-carboxylate (76%). (ES$^+$) m/z 611 (M+H)$^+$.

Step 5: methyl (7R)-7-amino-4-(benzyloxy)-14-cyclohexyl-7,8-dihydro-6H-indolo[1,2-e][1,5]benzoxazocine-11-carboxylate The compound was prepared in analogy to Example 1, Step 4, from methyl (7R)-4-(benzyloxy)-7-[(tert-butoxycarbonyl)amino]-14-cyclohexyl-7,8-dihydro-6H-indolo[1,2-e][1,5]benzoxazocine-11-carboxylate (quant.). (ES$^+$) m/z 511 (M+H)$^+$.

Step 6: methyl (7R)-4-(benzyloxy)-14-cyclohexyl-7-(methylamino)-7,8-dihydro-6H-indolo[1,2-e][1,5]benzoxazocine-11-carboxylate The compound was prepared in analogy to Example 1, Step 5, from methyl (7R)-7-amino-4-(benzyloxy)-14-cyclohexyl-7,8-dihydro-6H-indolo[1,2-e][1,5]benzoxazocine-11-carboxylate (60%). ($ES^+$) m/z 525 $(M+H)^+$.

Step 7: methyl (7R)-4-(benzyloxy)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate To a solution of the foregoing compound in MeOH was added HOAc (2 eq), followed by N-Boc-aminoacetaldehyde (1.2 eq). The mixture was left stirring for 15 min, then NaBH(OAc)$_3$ (1.5 eq) was added and the resulting solution was left stirring at RT over night. A precipitate was observed. The mixture was diluted with DCM and the resulting solution was extracted with sat. aq. NaHCO$_3$ and brine. After drying over Na$_2$SO$_4$ all volatiles were evaporated in vacuo. The residual material was purified by FC (PE:EtOAc, 8:2). After evaporation of the solvents the product was obtained as a yellowish amorphous solid (78%). ($ES^+$) m/z 668 $(M+H)^+$.

Step 8: methyl (7R)-7-{[2-[(tert-butoxycarbonyl)amino]ethyl}(methyl)amino]-14-cyclohexyl-4-hydroxy-7,8-dihydro-6H-indolo[1,2-e][1,5]benzoxazocine-11-carboxylate To a solution of the foregoing compound in EtOAc/HOAc was added Pd/C (10%). After degassing, H$_2$ atmosphere was applied and the mixture was left stirring at RT for one night. The mixture was flushed with Ar and filtered. The filter cake was washed with EtOAc and the combined filtrates were evaporated in vacuo. The residual material was used without further characterisation in the next reaction (quant).

Step 9: methyl (7R)-7-[{2-[(tert-butoxycarbonyl)amino]ethyl}(methyl)amino]-14-cyclohexyl-4-(2-pyrrolidin-1-ylethoxy)-7,8-dihydro-6H-indolo[1,2-e][1,5]benzoxazocine-11-carboxylate The foregoing compound was dissolved in DMF (0.05M) and NaH (2.2 eq) was added. After stirring for 5 min RT 3-(2-chloroethyl)pyrrolidine hydrochloride (1.1 eq) was added and the mixture was warmed to 50° C. over night. The reaction was quenched by addition of sat. aq. NH$_4$Cl. The product was extracted with DCM. The combined organic phases were washed with brine. After drying over Na$_2$SO$_4$ all volatiles were evaporated in vacuo. The residual material was purified by FC (PE:EtOAc, 6:4+1% MeOH+1% NEt$_3$). After evaporation of the solvents the product was obtained as a colourless amorphous solid. (50%). ($ES^+$) m/z 675 $(M+H)^+$.

Step 10: (7R)-7-[{2-[(tert-butoxycarbonyl)amino]ethyl}(methyl)amino]-14-cyclohexyl-4-(2-pyrrolidin-1-ylethoxy)-7,8-dihydro-6H-indolo[1,2-e][1,5]benzoxazocine-11-carboxylic acid The compound was prepared in analogy to Example 1, Step 7, from methyl (7R)-7-[{2-[(tert-butoxycarbonyl)amino]ethyl}(methyl)amino]-14-cyclohexyl-4-(2-pyrrolidin-1-ylethoxy)-7,8-dihydro-6H-indolo[1,2-e][1,5]benzoxazocine-11-carboxylate (quant.). ($ES^+$) m/z 661 $(M+H)^+$.

Step 11: tert-butyl {2-[[(7R)-14-cyclohexyl-1-[({[(2,2-dimethoxyethyl)(methyl)amino]sulfonyl}amino)carbonyl]-4-(2-pyrrolidin-1-ylethoxy-7,8-dihydro-6H-indolo[1,2-e][1,5]benzoxazocin-7-yl](methyl)amino]ethyl}carbamate The compound was prepared in analogy to Example 1, Step 8, from (7R)-7-[{2-[(tert-butoxycarbonyl)amino]ethyl}(methyl)amino]-14-cyclohexyl-4-(2-pyrrolidin-1-ylethoxy)-7,8-dihydro-6H-indolo[1,2-e][1,5]benzoxazocine-11-carboxylic acid (79%). ($ES^+$) m/z 841 $(M+H)^+$.

Step 12: (7R)-7-[(2-aminoethyl)(methyl)amino]-14-cyclohexyl-N-{[(methyl(2-oxoethyl)amino]sulfonyl}-4-(2-pyrrolidin-1-ylethoxy)-7,8-dihydro-6H-indolo[1,2-e][1,5]benzoxazocine-11-carboxamide The compound was prepared in analogy to Example 1, Step 9, from tert-butyl {2-[[(7R)-14-cyclohexyl-11-[({[(2,2-dimethoxyethyl)(methyl)amino]sulfonyl}amino)carbonyl]-4-(2-pyrrolidin-1-ylethoxy)-7,8-dihydro-6H-indolo[1,2-e][1,5]benzoxazocin-7-yl](methyl)amino]ethyl}carbamate (quant.). The material was used without characterization in the next reaction.

Step 13: (7R)-14-cyclohexyl-18,21,24-trimethyl-4-(2-pyrrolidin-1-ylethoxy)-7,8-dihydro-6H-7,11-(epiminoethanoiminoethanoiminothioiminomethano)indolo[1,2-e][1,5]benzoxazocin-15-one 17,17-dioxide The compound was prepared in analogy to Example 22, Step 11, from (7R)-7-[(2-aminoethyl)(methyl)amino]-14-cyclohexyl-N-{[methyl(2-oxoethyl)amino]sulfonyl}-4-(2-pyrrolidin-1-ylethoxy)-7,8-dihydro-6H-indolo[1,2-e][1,5]benzoxazocine-11-carboxamide and using a 37% solution of formaldehyde in H$_2$O instead of acetaldehyde (11%). $^1$H NMR (400 MHz, DMSO-d$_6$) δ 8.04 (s, 1H), 7.93 (d, 1H, J 8.4), 7.48-7.46 (d, 1H, J 8.4), 7.36-7.31 (m, 2H), 7.03-6.98 (m, 2H), 4.60 (d, 1H, J 15.6), 4.44-4.33 (m, 3H), 4.00-3.90 (m, 3H), 3.71-3.69 (m, 4H), 3.41-3.31 (m, 2H), 3.25-3.15 (m, 3H), 3.04 (s, 3H), 2.86-2.83 (m, 3H), 2.67-2.65 (m, 1H), 2.32 (s, 3H), 2.07-1.89 (m, 10H), 1.73-1.65 (m, 2H), 1.43-1.31 (m, 4H), 1.14-1.10 (m, 2H); ($ES^+$) m/z 693 $(M+H)^+$.

Example 33

(7R)-14-cyclohexyl-4-methoxy-18,22-dimethyl-7,8-dihydro-6H-7,11-(ethanoiminopropanoiminothioiminomethano)indolo[1,2-e][1,5]benzoxazocin-15-one 17,17-dioxide (A33)

Step 1: methyl 4-azidobutanoate

To a solution of methyl-4-bromobutyrate in DMSO (0.6 M) was added with stirring NaN$_3$ (1.5 eq). The suspension was heated (45-50° C., oil bath) with stirring for 5 h. After cooling, H$_2$O was added and the mixture extracted with Et$_2$O. The organic extracts were washed with brine and dried over Na$_2$SO$_4$. The solvent was removed in vacuo and the crude oil used without further purification (99%).

Step 2: 4-azidobutanoic acid

Methyl 4-azidobutanoate was suspended in 1N NaOH (1.2 eq) and the minimum of MeOH was added to make the reaction mixture homogenous. After 1 h at RT temperature, MeOH was removed in vacuo. The aqueous solution was extracted with Et$_2$O and acidified to pH=0 with concentrated HCl. The acids were then extracted with ether and the organic phases dried over Na$_2$SO$_4$. The crude oil obtained was used without further purification (quant.).

Step 3: (4S)-3-(4-azidobutanoyl)-4-benzyl-1,3-oxazolidin-2-one

NEt$_3$ was added to a stirred mixture of 4-azidobutanoic acid in THF (0.3 M) cooled to −78° C. and stirring was continued at this temperature for 10 min. Pivaloyl chloride (1.3 eq) was added dropwise. The resulting mixture was warmed to 0° C. and stirred for 1 h before re-cooling to −78° C. In a separate flask, (4S)-4-benzyl-1,3-oxazolidin-2-one was dissolved in THF (0.8 M) and cooled to −78° C. before dropwise addition of N-BuLi (1.6M, 1.35 eq.) over 10 min. The mixture was stirred at −78° C. for 1 h and then transferred into the −78° C. solution of mixed anhydride using a syringe. The reaction was stirred at −78° C. for 1 h, then at RT for a further 1 h. The reaction was quenched by addition of sat. aq. NH$_4$Cl before partitioning between H$_2$O and EtOAc. The layers were separated and the aqueous phase re-extracted with EtOAc. The combined organic extracts were washed with brine, dried over Na$_2$SO$_4$, filtered and concentrated in vacuo. The residue was purified by FC eluting with 10 to 30% EtOAc/PE to give the product as a colourless oil (74%). (ES$^+$) m/z 289 (M+H)$^+$.

Step 4: (4S)-3-[(2R)-4-azido-2-(hydroxymethyl) butanoyl]-4-benzyl-1,3-oxazolidin-2-one The foregoing compound was dissolved in DCM (0.1 M) and cooled to −10° C. TiCl$_4$ (1.1 eq) was added dropwise to the mixture, such that the internal temperature did not rise above 0° C. The mixture was stirred an additional 30 min and then Hünig's base (1.15 equiv.) was added dropwise, such that the internal temperature did not rise above 0° C. The deep red solution was stirred an additional 45 min at −10° C. s-Trioxane (1.2 eq) was added to the reaction mixture in one portion, followed by dropwise addition of TiCl$_4$ (1.1 eq). The reaction mixture was stirred for 2 h at −10° C. and then quenched by dropwise addition of sat. aq. NaHCO$_3$. The mixture was stirred for 30 min, poured into H$_2$O and extracted with DCM. The combined organic extracts were washed once with sat. aq. NH$_4$Cl, dried with Na$_2$SO$_4$, filtered and concentrated in vacuo. The residue was purified by FC eluting with 30 to 70% EtOAc/PE to give the product as a colourless oil (61%). (ES$^+$) m/z 319 (M+H)$^+$; [α]$_D^{20}$: +42.90 (c=1, CHCl$_3$).

Step 5: (4S)-3-[(2R)-4-azido-2-({[tert-butyl(dimethyl)silyl]oxy}methyl)butanonyl]-4-benzyl-1,3-oxazolidin-2-one The foregoing compound was dissolved in DCM (0.17 M) and treated with DMAP (0.1 eq) and NEt$_3$ (1.8 eq). The solution was cooled to 0° C. and tert-butyldimethylchlorosilane (1.5 eq) was added in one portion. The mixture was stirred at 0° C. for 30 min, warmed to RT and stirred for an additional 18 h. The reaction mixture was poured into sat. aq. NaHCO$_3$ and extracted with DCM. The combined organic extracts were dried with Na$_2$SO$_4$, filtered and concentrated in vacuo. The residue was purified by FC eluting with 10 to 20% EtOAc/PE to give the product as a colourless oil (90%). (ES$^+$) m/z 433 (M+H)$^+$; [α]$_D^{20}$: +30.2° (c=1, CHCl$_3$).

Step 6: (2S)-4-azido-2-({[tert-butyl(dimethyl)silyl]oxy}methyl)butan-1-ol

The foregoing compound was dissolved in Et$_2$O (0.17 M), treated with MeOH (1.1 eq) and cooled to 0° C. LiBH$_4$ (1.1 eq) was added in one portion and the mixture was stirred for 30 min at 0° C. The mixture was warmed to RT and stirred for 1 h. The mixture was then cooled to 0° C. and sat. aq. NaHCO$_3$ was carefully added over 30 min. The biphasic mixture was stirred vigorously for 1 h at 0° C. and then poured into H$_2$O. The aqueous layer was extracted with EtOAc and the combined organic extracts were dried with Na$_2$SO$_4$, filtered and concentrated in vacuo. The residue was purified by FC eluting with 10 to 20% EtOAc/PE to give the product as a colourless oil (60%). (ES$^+$) m/z 260 (M+H)$^+$; [α]$_D^{20}$: −1.5° (c=1, CHCl$_3$).

Step 7: (2R)-4-azido-2-({[(tert-butyl(dimethyl)silyl]oxy}methyl)butyl methanesulfonate The foregoing compound was dissolved in DCM (0.13 M), N,N-diisopropylethylamine (2 eq) was added and the mixture was cooled to 0° C. MsCl (1.1 eq) was added dropwise and the mixture was stirred for 15 min at 0° C., then warmed to RT and stirred for an additional 15 min. The reaction mixture was then poured into 1N HCl and extracted with DCM. The combined organic extracts were washed once with sat. aq. NaHCO$_3$ and brine, dried with Na$_2$SO$_4$, filtered and concentrated in vacuo. The residue was used without further purification (95%).

Step 8: methyl 2-(2-{[(2S)-4-azido-2-{[tert-butyl(dimethyl)silyl]oxy}methyl)butyl]oxy}-3-methoxyphenyl)-3-cyclohexyl-1H-indole-6-carboxylate A solution of methyl 3-cyclohexyl-2-(2-hydroxy-3-methoxyphenyl)-1H-indole-6-carboxylate (Example 27, Step 1) in DMA (0.1 M) was treated with Cs$_2$CO$_3$ (1.0 eq) at 60° C. and stirred for 30 min. (2R)-4-azido-2-({[tert-butyl(dimethyl)silyl]oxy}methyl)butyl methanesulfonate was added in one portion and the mixture was stirred for 18 h at 60° C. After cooling the solution was diluted with EtOAc and washed with H$_2$O (×3) and brine. The organic layer was dried with Na$_2$SO$_4$, filtered and evaporated to dryness. The residue was purified by FC eluting with 10 to 30% EtOAc/PE to give the product as a colourless solid (69%). (ES$^+$) m/z 621 (M+H)$^+$; [α]$_D^{20}$+1.2° (c=1, CHCl$_3$).

Step 9: methyl 2-(2-{[(2R)-4-azido-2-(hydroxymethyl)butyl]oxy}-3-methoxyphenyl)-3-cyclohexyl-1H-indole-6-carboxylate A solution of the foregoing compound in THF (0.1 M) was treated with TBAF (1.1 eq, 1.0 M in THF) at RT and stirred for 1 h. Reaction mixture was poured into 1N HCl and extracted with DCM. The combined organic extracts were washed once with sat. aq. NaHCO$_3$ and brine, dried with Na$_2$SO$_4$, filtered and concentrated in vacuo. The residue was used without further purification (quant.). (ES$^+$) m/z 507 (M+H)$^+$;

Step 10: methyl 2-{2-[((2S)-4-azido-2-{[(methylsulfonyl)oxy]methyl}butyl)oxy]-3-methoxyphenyl}-3-cyclohexyl-1H-indole-6-carboxylate The title compound was prepared in analogy to Step 7 from methyl 2-(2-{[(2R)-4-azido-2-(hydroxymethyl)butyl]oxy}-

3-methoxyphenyl)-3-cyclohexyl-1H-indole-6-carboxylate. The residue was used without further purification (99%). (ES$^+$) m/z 585 (M+H)$^+$.

Step 11: methyl (7R)-7-(2-azidoethyl)-14-cyclohexyl-4-methoxy-7,8-dihydro-6H-indolo[1,2-e][1,5]benzoxazocine-11-carboxylate A solution of the foregoing compound in DMA (0.5 M) was added dropwise over 30 minutes to a suspension of Cs$_2$CO$_3$ in DMA (final concentration 0.050 M) heated at 60° C. 30 minutes after completion of the addition mixture was cooled to RT, diluted with EtOAc and washed with H$_2$O (×2) and brine (×2). The combined organic extracts were dried with Na$_2$SO$_4$, filtered and concentrated in vacuo. The residue was purified by FC eluting with 20 to 35% EtOAc/PE to give the product as a colourless solid (67%). (ES$^+$) m/z 489 (M+H)$^+$; [α]$_D^{20}$: +34.60 (c=1, CHCl$_3$).

Step 12: methyl (7R)-7-(2-aminoethyl)-14-cyclohexyl-4-methoxy-7,8-dihydro-6H-indolo[1,2-e][1,5]benzoxazocine-11-carboxylate The foregoing compound was dissolved in EtOAc/MeOH (1:1, 0.15 M). Pd/C (10% w/w, 0.1 eq.) was added and the mixture was stirred at RT under H$_2$ atmosphere overnight then filtered on a short pad of Celite® washing with MeOH. The residue was used without further purification (94%). (ES$^+$) m/z 463 (M+H)$^+$.

Step 13: methyl (7R)-14-cyclohexyl-4-methoxy-7-[2-(methylamino)ethyl]-7,8-dihydro-6H-indolo[1,2-e][1,5]benzoxazocine-11-carboxylate The title compound was prepared in analogy to Example 1, Step 5 from methyl (7R)-7-(2-aminoethyl)-14-cyclohexyl-4-methoxy-7,8-dihydro-6H-indolo[1,2-e][1,5]benzoxazocine-11-carboxylate. The crude product was used without further purification (99%). (ES$^+$) m/z 477 (M+H)$^+$.

Step 14: methyl (7R)-7-{2-[[N-(tert-butoxycarbonyl)-N-methyl-β-alanyl](methyl)amino]ethyl}-14-cyclohexyl-4-methoxy-7,8-dihydro-6H-indolo[1,2-e][1,5]benzoxazocine-11-carboxylate The title compound was prepared in analogy to Example 13, Step 6 from methyl (7R)-14-cyclohexyl-4-methoxy-7-[2-(methylamino)ethyl]-7,8-dihydro-6H-indolo[1,2-e][1,5]benzoxazocine-11-carboxylate and N-(tert-butoxycarbonyl)-N-methyl-β-alanine The crude product was purified by FC eluting with 50 to 75% EtOAc/PE to give the product as a colourless solid (63%). (ES$^+$) m/z 662 (M+H)$^+$.

Step 15: methyl (7R)-14-cyclohexyl-4-methoxy-7-(2-{methyl[3-(methylamino)propyl]amino}ethyl)-7,8-dihydro-6H-indolo[1,2-e][1,5]benzoxazocine-11-carboxylate The title compound was prepared in analogy to Example 13, Step 9 from methyl (7R)-7-{2-[[N-(tert-butoxycarbonyl)-N-methyl-β-alanyl](methyl)amino]ethyl}-14-cyclohexyl-4-methoxy-7,8-dihydro-6H-indolo[1,2-e][1,5]benzoxazocine-11-carboxylate. The crude product was used without further purification (quant.). (ES$^+$) m/z 549 (M+H)$^+$.

Step 16: methyl (7R)-7-{2-[{3-[{[(tert-butoxycarbonyl)amino]sulfonyl}(methyl)amino]propyl}(methyl)amino]ethyl}-14-cyclohexyl-4-methoxy-7,8-dihydro-6H-indolo[1,2-e][1,5]benzoxazocine-11-carboxylate The title compound was prepared in analogy to Example 18, Step 4 from methyl (7R)-14-cyclohexyl-4-methoxy-7-(2-{methyl[3-(methylamino)propyl]amino}ethyl)-7,8-dihydro-6H-indolo[1,2-e][1,5]benzoxazocine-11-carboxylate. The crude product was used without further purification (96%). (ES$^+$) m/z 728 (M+H)$^+$.

Step 17: (7R)-7-{2-[{3-[{[(tert-butoxycarbonyl)amino]sulfonyl}(methyl)amino]propyl}(methyl)amino]ethyl}-14-cyclohexyl-4-methoxy-7,8-dihydro-6H-indolo[1,2-e][1,5]benzoxazocine-11-carboxylic acid The title compound was prepared in analogy to Example 18, Step 5 from methyl (7R)-7-{2-[{3-[{[(tert-butoxycarbonyl)amino]sulfonyl}(methyl)amino]propyl}(methyl)amino]ethyl}-14-cyclohexyl-4-methoxy-7,8-dihydro-6H-indolo[1,2-e][1,5]benzoxazocine-11-carboxylate. The crude product was used without further purification (86%). (ES$^+$) m/z 714 (M+H)$^+$.

Step 18: (7R)-7-{2-[{3-[(aminosulfonyl)(methyl)amino]propyl}(methyl)amino]ethyl}-14-cyclohexyl-4-methoxy-7,8-dihydro-6H-indolo[1,2-e][1,5]benzoxazocine-11-carboxylic acid The title compound was prepared in analogy to Example 18, Step 6 from (7R)-7-{2-[{3-[{[(tert-butoxycarbonyl)amino]sulfonyl}(methyl)amino]propyl}(methyl)amino]ethyl}-14-cyclohexyl-4-methoxy-7,8-dihydro-6H-indolo[1,2-e][1,5]benzoxazocine-11-carboxylic acid. The crude product was used without further purification (quant.). (ES$^+$) m/z 614 (M+H)$^+$.

Step 18: (7R)-14-cyclohexyl-4-methoxy-18,22-dimethyl-7,8-dihydro-6H-7,11-(ethanoiminopropanoiminothioiminomethano)indolo[1,2-e][1,5]benzoxazocin-15-one 17,17-dioxide The title compound was prepared in analogy to Example 18, Step 7 from (7R)-7-{2-[{3-[(aminosulfonyl)(methyl)amino]propyl}(methyl)amino]ethyl}-14-cyclohexyl-4-methoxy-7,8-dihydro-6H-indolo[1,2-e][1,5]benzoxazocine-11-carboxylic acid. The residue obtained after evaporation of all volatiles was purified by automated RP-HPLC to obtain the title compound as bis TFA salt and as a mixture of two isomers (20%).

$^1$H NMR (400 MHz, DMSO-d$_6$+3% TFA, 300 K, data for major isomer) δ 1.05-1.21 (m, 1H), 1.25-1.38 (m, 2H), 1.39-1.47 (m, 1H), 1.56-1.77 (m, 4H), 1.79-1.86 (m, 1H), 1.87-2.00 (m, 3H), 2.01-2.13 (m, 1H), 2.20-2.33 (m, 1H), 2.60-2.72 (m, 1H), 2.74-2.80 (m, 1H), 2.81 (br s, 3H), 3.02 (s, 3H), 3.05-3.14 (m, 2H), 3.19-3.37 (m, 2H), 3.53-3.65 (m, 2H), 3.68-3.82 (m, 2H), 3.89 (s, 3H), 4.35 (d, J 14.8 Hz, 1H), 4.52 (m, 1H), 6.93 (d, J 7.6 Hz, 1H), 7.19-7.31 (m, 2H), 7.48 (d, J 8.6 Hz, 1H), 7.90 (d, J 8.6 Hz, 1H), 8.05 (br s, 1H); MS (ES$^+$) m/z 596 (M+H)$^+$.

Example 34

30-cyclohexyl-18-oxa-2-thia-1,3,10,24-tetraaza-hexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide (A34)

Step 1: methyl 14-cyclohexyl-7-formyl-7,8-dihydro-6H-indolo[1,2-e][1,5]benzoxazocine-1-carboxylate A solution (0.03 M) of methyl 14-cyclohexyl-7-(hydroxymethyl)-7,8-dihydro-6H-indolo[1,2-e][1,5]benzoxazocine-11-carboxylate (prepared as described in example 13, steps 1-2) in DCM was added to a solution of DMP (0.04 M; 1.25 eq) in DCM at RT. The reaction was then left to stir at RT for 1 h. The mixture was diluted with EtOAc and washed with a 1:1 mixture of sat. aq. NaHCO$_3$ and sodium thiosulfate (aq) (3×) before washing with brine, drying (Na$_2$SO$_4$), filtering and concentrating in vacuo to afford the product as a tinted glass (98%). The material was taken on without further purification. (ES$^+$) m/z 418 (M+H)$^+$; 436 (M+H$_2$O+H)$^+$.

Step 2: methyl 7-[3-tert-butoxy-3-oxoprop-1-en-1-yl]-14-cyclohexyl-7,8-dihydro-6H-indolo[1,2-e][1,5]benzoxazocine-1-carboxylate (tert-butoxycarbonylmethylene)triphenylphosphorane (1.12 eq) was added directly to methyl 14-cyclohexyl-7-formyl-7,8-dihydro-6H-indolo[1,2-e][1,5]benzoxazocine-11-carboxylate (0.02 M) in THF and the mixture stirred at RT overnight. The volatiles were removed in vacuo. The residue was partitioned between EtOAc and 1N HCl (aq). The organics were washed with 1N HCl (aq), sat. aq. NaHCO$_3$, brine and then dried (Na$_2$SO$_4$), filtered and concentrated in vacuo. The residue was purified by flash chromatography (10% EtOAc/PE) to afford the product (93%) as a mixture of double bond geometric isomers. (ES$^+$) m/z 516 (M+H)$^+$; 538 (M+Na)$^+$.

Step 3: methyl 7-(3-tert-butoxy-3-oxopropyl)-14-cyclohexyl-7,8-dihydro-6H-indolo[1,2-e][1,5]benzoxazocine-11-carboxylate Cobalt chloride hexahydrate (cat.; 0.12 eq) was added to a solution of methyl 7-[3-tert-butoxy-3-oxoprop-1-en-1-yl]-14-cyclohexyl-7,8-dihydro-6H-indolo[1,2-e][1,5]benzoxazocine-11-carboxylate in MeOH (0.02 M). Once the cobalt chloride was in solution, NaBH$_4$ (5.4 eq) was introduced. Vigorous effervescence was noted, along with a darkening of the solution to grey/black. After circa 5 min, effervescence had subsided and the dark colour in the reaction began to dissipate with the reaction returning to yellow within 10 min. The reaction mixture was partitioned between EtOAc and 1N HCl (aq). The organics were washed with sat. aq. NaHCO$_3$, water and brine before being dried (Na$_2$SO$_4$), filtered and concentrated in vacuo. The product was taken on without further purification (97%). (ES$^+$) m/z 518 (M+H)$^+$; 540 (M+Na)$^+$.

Step 4: 3-[14-cyclohexyl-11-(methoxycarbonyl)-7,8-dihydro-6H-indolo[1,2-e][1,5]benzoxazocin-7-yl]propanoic acid TFA (>150 eq) and a few drops of water were added to a stirred solution of methyl 7-(3-tert-butoxy-3-oxopropyl)-14-cyclohexyl-7,8-dihydro-6H-indolo[1,2-e][1,5]benzoxazocine-11-carboxylate (0.03 M) in DCM at RT. The reaction was heated at 60° C. (oil bath temp) for 1 h. Further TFA was introduced (circa 60 eq) and heating continued for 2 h. Volatiles were removed in vacuo. The residue was taken up in EtOAc and washed with 1N HCl (aq), brine before being dried (Na$_2$SO$_4$) filtered and concentrated in vacuo. Residual tert-BuOH was removed by sonication in Et$_2$O/PE to afford the product (45%). (ES$^+$) m/z 462 (M+H)$^+$; 484 (M+Na)$^+$.

Step 5: methyl 7-{3-[4-(tert-butoxycarbonyl)piperazin-1-yl]-3-oxopropyl}-14-cyclohexyl-7,8-dihydro-6H-indolo[1,2-e][1,5]benzoxazocine-11-carboxylate HATU (1.1 eq) was added to a stirred mixture of tert-butyl piperazine-1-carboxylate (1.1 eq), DIPEA (2.5 eq) and 3-[14-cyclohexyl-11-(methoxycarbonyl)-7,8-dihydro-6H-indolo[1,2-e][1,5]benzoxazocin-7-yl]propanoic acid (0.03 M) in DMF under N$_2$ at RT. The reaction was warmed at 50° C. for 10 min. The reaction was allowed to cool to RT before being partitioned between EtOAc and 1N HCl (aq). The organics were washed with 1N HCl (aq), sat. aq. NaHCO$_3$, water and brine before being dried (Na$_2$SO$_4$), filtered and concentrated in vacuo. The material was taken on without further purification (88%). (ES$^+$) m/z 630 (M+H)$^+$; 652 (M+Na)$^+$.

Step 6: methyl 14-cyclohexyl-7-(3-oxo-3-piperazin-1-ylpropyl)-7,8-dihydro-6H-indolo[1,2-e][1,5]benzoxazocine-11-carboxylate Methyl 7-{3-[4-(tert-butoxycarbonyl)piperazin-1-yl]-3-oxopropyl}-14-cyclohexyl-7,8-dihydro-6H-indolo[1,2-e][1,5]benzoxazocine-11-carboxylate (0.04 M) in DCM was treated with TFA (170 eq) and stirred at RT overnight. The volatiles were then removed in vacuo and the residue partitioned between sat. aq. NaHCO$_3$ and EtOAc. The combined organics were washed with brine, dried (Na$_2$SO$_4$), filtered and concentrated in vacuo to afford the product as an off-white foam (100%) that was used without further purification. (ES$^+$) m/z 530 (M+H)$^+$.

Step 7: methyl 14-cyclohexyl-7-(3-piperazin-1-ylpropyl)-7,8-dihydro-6H-indolo[1,2-e][1,5]benzoxazocine-11-carboxylate A solution of methyl 14-cyclohexyl-7-(3-oxo-3-piperazin-1-ylpropyl)-7,8-dihydro-6H-indolo[1,2-e][1,5]benzoxazocine-11-carboxylate (0.08 M) in THF was treated dropwise with BH$_3$ DMS complex (2M in THF; 10 eq). The resulting solution was stirred at RT for 2.5 h. The reaction was quenched by the careful addition of HCl/MeOH (1.25 M) and the resulting solution refluxed for 2 h. The volatiles were then removed in vacuo and the residue partitioned between sat. aq. NaHCO$_3$ and EtOAc. The combined organics were washed with brine, dried (Na$_2$SO$_4$), filtered and concentrated in vacuo to afford the product as a yellow foam (100%) that was used without further purification. (ES$^+$) m/z 516 (M+H)$^+$.

Step 8: methyl 7-[3-(4-{[(tert-butoxycarbonyl)(methyl)amino]sulfonyl}piperazin-1-yl)propyl]-14-cyclohexyl-7,8-dihydro-6H-indolo[1,2-e][1,5]benzoxazocine-11-carboxylate To a solution of methyl 14-cyclohexyl-7-(3-piperazin-1-ylpropyl)-7,8-dihydro-6H-indolo[1,2-e][1,5]benzoxazocine-11-carboxylate (0.11 M) in dry THF was added (tert-butoxycarbonyl){[4-(dimethyliminio)pyridin-1(4H)-yl]sulfonyl}azanide (1 eq) (prepared following literature procedure: Winum, J.-Y. et al *Org. Lett.* 2001, 3, 2241-2243) and the mixture stirred at 40° C. for 2 h. The reaction was allowed to cool to RT before diluting with EtOAc. The combined organics were washed with 1N HCl (aq), sat. aq. NaHCO$_3$ then brine, dried (Na$_2$SO$_4$), filtered and concentrated in vacuo to afford the product as a yellow foam (58%) that was used without further purification. (ES$^+$) m/z 695 (M+H)$^+$.

Step 9: 7-[3-(4-{[(tert-butoxycarbonyl)(methyl) amino]sulfonyl}piperazin-1-yl)propyl]-14-cyclohexyl-7,8-dihydro-6H-indolo[1,2-e][1,5]benzoxazocine-11-carboxylic acid 2N NaOH (aq) (30 eq) was added to a solution of methyl 7-[3-(4-{[(tert-butoxycarbonyl)(methyl)amino] sulfonyl}piperazin-1-yl)propyl]-14-cyclohexyl-7,8-dihydro-6H-indolo[1,2-e][1,5]benzoxazocine-11-carboxylate (0.06 M) in MeOH and the reaction stirred at 70° C. for 3 h. The reaction was allowed to cool to RT before reducing the volume of MeOH in vacuo. The residue was partitioned between 1N HCl (aq) and EtOAc, ensuring the aqueous phase was acidic. The aqueous was extracted a second time with EtOAc and the combined organics washed with brine before being dried (Na$_2$SO$_4$), filtered and concentrated in vacuo. The material was taken on without further purification. (ES$^+$) m/z 681 (M+H)$^+$.

Step 10: 7-{3-[4-(aminosulfonyl)piperazin-1-yl]propyl}-14-cyclohexyl-7,8-dihydro-6H-indolo[1,2-e][1,5]benzoxazocine-11-carboxylic acid 7-[3-(4-{[(tert-butoxycarbonyl)(methyl)amino] sulfonyl}piperazin-1-yl)propyl]-1,4-cyclohexyl-7,8-dihydro-6H-indolo[1,2-e][1,5]benzoxazocine-11-carboxylic acid (0.07 M) in DCM was treated with TFA (200 eq) and stirred at RT for 1 h. The volatiles were then removed in vacuo and the residue partitioned between 1N HCl (aq) and EtOAc. The combined organics were washed with brine, dried (Na$_2$SO$_4$), filtered and concentrated in vacuo. The residue was treated with 2M HCl in Et$_2$O to afford the product as a beige solid (65%) that was used without further purification. (ES$^+$) m/z 581 (M+H)$^+$.

Step 11: 30-cyclohexyl-18-oxa-2-thia-1,3,10,24-tetraazahexacyclo[22.2.2.1$^{5,9}$.1$^{8,11}$.1$^{10,20}$.0$^{12,17}$] hentriaconta-5(31),6,8,11(30),12,14,16-heptaen-4-one 2,2-dioxide To a solution of 7-{3-[4-(aminosulfonyl)piperazin-1-yl] propyl}-14-cyclohexyl-7,8-dihydro-6H-indolo[1,2-e][1,5] benzoxazocine-11-carboxylic acid (0.04 M) in DCM were added EDC (1.5 eq) and DMAP (3 eq). The mixture was stirred at 50° C. for 2 h before cooling to RT and evaporating all volatiles in vacuo. The residue was purified by RP-HPLC (Waters Sunfire column; MeCN/H$_2$O/0.1% TFA gradient). Fractions containing the pure compound were combined and lyophilized to afford the product as a white powder (19%). $^1$H NMR (400 MHz, DMSO-d$_6$+TFA, 335 K) δ1.16-1.23 (m, 2H), 1.31-1.39 (m, 2H), 1.47-1.50 (m, 1H), 1.69-1.73 (m, 2H), 1.83-2.19 (m, 7H), 2.64-2.66 (m, 1H), 3.29-3.36 (m, 4H), 3.49-3.74 (m, 7H), 3.89-3.93 (m, 2H), 4.28-4.39 (m, 1H), 4.40-4.44 (m, 1H), 7.28-7.32 (m, 1H), 7.35-7.37 (m, 1H), 7.45-7.47 (m, 1H), 7.52-7.56 (m, 1H), 7.90-7.92 (m, 2H); (ES$^+$) m/z 563 (M+H)$^+$.

Example 35

(−)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide (A35)

Step 1: 2-[4-methoxy-2-(methoxymethoxy)phenyl]-4,4,5,5-tetramethyl-1,3,2-dioxaborolane Boron pinacolate (3.5 eq), Et$_3$N (4 eq), Pd(OAc)$_2$ (0.05 eq) and 2-(dicyclohexylphosphino)biphenyl (0.19 eq) were added to a solution of 1-bromo-4-methoxy-2-(methoxymethoxy)benzene (prepared as described in *JACS*, 2007, 129, 6716-6717) in toluene (0.2 M). The reaction was heated to 80° C. for 1.5 h. The mixture was cooled, diluted with EtOAc, washed with 1 N HCl (aq), brine, dried (Na$_2$SO$_4$), filtered and the solvent was removed in vacuo to give the product, which was taken on without further purification (quant.). (ES$^+$) m/z 295 (M+H)$^+$.

Step 2: methyl 3-cyclohexyl-2-[4-methoxy-2-(methoxymethoxy)phenyl]-1H-indole-6-carboxylate A mixture of methyl 2-bromo-3-cyclohexyl-1H-indole-6-carboxylate (prepared as described in International patent application WO2004087714, from commercially available methyl indole-6-carboxylate), 2-[4-methoxy-2-(methoxymethoxy)phenyl]-4,4,5,5-tetramethyl-1,3,2-dioxaborolane (2 eq) and 2 M Na$_2$CO$_3$ (aq) (6 eq) in dioxane (0.15 M) was prepared. Then the mixture was degassed with nitrogen and bis(triphenylphosphine)palladium (II) chloride (0.2 eq) was added. The resulting mixture was immersed in a preheated oil bath at 110° C. for 2 h. The mixture was cooled, diluted with EtOAc, washed with 1 N HCl (aq), brine, dried (Na$_2$SO$_4$), filtered and the solvent removed in vacuo. The crude was purified by automated FC (PE/EtOAc 9:1) to afford the product (93%). (ES$^+$) m/z 424 (M+H)$^+$.

Step 3: methyl 3-cyclohexyl-2-(2-hydroxy-4-methoxyphenyl)-1H-indole-6-carboxylate 3 M HCl (aq) (4 eq) was added to a stirred mixture of methyl 3-cyclohexyl-2-[4-methoxy-2-(methoxymethoxy) phenyl]-1H-indole-6-carboxylate in MeOH (0.05 M) and the mixture was stirred at 80° C. for 2 h. The mixture was cooled, solvents were concentrated in vacuo and the residue diluted with EtOAc, washed with sat. aq. NaHCO$_3$, brine, dried (Na$_2$SO$_4$), filtered and the solvent was removed in vacuo to afford the title compound (95%). (ES$^+$) m/z 380 (M+H)$^+$.

Step 4: methyl 14-cyclohexyl-7-(hydroxymethyl)-3-methoxy-7,8-dihydro-6H-indolo[1,2-e][1,5]benzoxazocine-11-carboxylate The title compound was prepared starting from methyl 3-cyclohexyl-2-(2-hydroxy-4-methoxyphenyl)-1H-indole-6-carboxylate using the same methodology described for example 13 (steps 1-2) (41%). (ES$^+$) m/z 450 (M+H)$^+$.

Step 5: (+)- and (−)-methyl 14-cyclohexyl-7-(hydroxymethyl)-3-methoxy-7,8-dihydro-6H-indolo[1, 2-e][1,5]benzoxazocine-11-carboxylate The enantiomers of methyl 14-cyclohexyl-7-(hydroxymethyl)-3-methoxy-7,8-dihydro-6H-indolo[1,2-e][1,5]benzoxazocine-11-carboxylate were separated via chiral SFC (Chiralpak IA column, modifier 25% (MeOH; 0.2% Et$_2$NH), pressure 100 bar, temperature 35° C.) to afford the first eluting ([α]$_D^{20}$−24 (c=1, MeOH)) and second eluting ([α]$_D^{20}$+26 (c=1, MeOH)) isomers. (ES$^+$) m/z 450 (M+H)$^+$.

Step 6: (−)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide The title compound was prepared starting from (+)-methyl 14-cyclohexyl-7-(hydroxymethyl)-3-methoxy-7,8-dihydro-6H-indolo[1,2-e][1,5]benzoxazocine-11-carboxylate (second eluting isomer from SFC) using the same methodology described for example 13 (steps 3-9 and 11-14). Purification was by automated RP-HPLC, eluting with a MeCN/H$_2$O (buffered with 0.1% TFA) gradient. Fractions containing the pure compound were combined and lyophilized to afford the product as a white powder (26%). $^1$H NMR (600 MHz, Py-d$_5$, 320 K) δ1.12-1.26 (m, 3H), 1.35-1.41 (m, 3H), 1.69-1.70 (m, 2H), 1.75-1.77 (m, 1H), 1.86-1.88 (m, 1H), 2.05-2.27 (m, 10H), 2.56-2.62 (m, 2H), 2.99-3.03 (m, 1H), 3.34 (s, 3H), 3.56-3.68 (m, 4H), 3.90 (s, 3H), 4.13-4.15 (m, 1H), 4.19-4.21 (m, 1H), 6.93-6.97 (m, 2H), 7.40 (d, J 8.4, 1H), 7.92-7.93 (m, 1H), 8.09 (d, J 8.4, 1H), 8.21 (s, 1H). (ES$^+$) m/z 595 (M+H)$^+$; [α]$_D^{20}$−47 (c=0.1, MeOH).

Example 36

(+)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide (A36)

Step 1: 3-[14-cyclohexyl-3-methoxy-11-(methoxycarbonyl)-7,8-dihydro-6H-indolo[1,2-e][1,5]benzoxazocin-7-yl]propanoic acid The title compound was prepared starting from methyl 14-cyclohexyl-7-(hydroxymethyl)-3-methoxy-7,8-dihydro-6H-indolo[1,2-e][1,5]benzoxazocine-11-carboxylate (prepared as described in example 35, steps 1-4) using the same methodology described for example 34 (steps 1-4). (ES$^+$) m/z 492 (M+H)$^+$.

Step 2: methyl 7-{3-[{2-[(tert-butoxycarbonyl)(methyl)amino]ethyl}(methyl)amino]-3-oxopropyl}-14-cyclohexyl-3-methoxy-7,8-dihydro-6H-indolo[1,2-e][1,5]-benzoxazocine-11-carboxylate The title compound was prepared starting from 3-[14-cyclohexyl-3-methoxy-11-(methoxycarbonyl)-7,8-dihydro-6H-indolo[1,2-e][1,5]benzoxazocin-7-yl]propanoic acid applying the same methodology described for example 34 (step 5), using tert-butyl methyl[2-(methylamino)ethyl]carbamate (prepared as described in European patent application 1998/296811 from commercially available N,N'-dimethylethylenediamine) instead of tert-butyl piperazine-1-carboxylate. The product was taken on without further purification. (ES$^+$) m/z 662 (M+H)$^+$.

Step 3: (+)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide The title compound was prepared starting from methyl 7-{3-[{2-[(tert-butoxycarbonyl)(methyl)amino]ethyl}(methyl)amino]-3-oxopropyl}-14-cyclohexyl-3-methoxy-7,8-dihydro-6H-indolo[1,2-e][1,5]benzoxazocine-11-carboxylate, using the same methodology described for example 34 (steps 6-11). The product was purified by RP-HPLC (Waters Sunfire column C18 OBD 10 μM; 19×250 mm MeCN/H$_2$O/ 0.1% TFA gradient). Fractions containing the pure product were combined and lyophilized to afford the racemic mixture (8%); The racemic mixture was separated via chiral SFC (Chiralpak AS-H column, modifier 40% (iPrOH; 0.4% Et$_2$NH), pressure 100 bar, temperature 35° C.) to afford the first eluting (retention time 10.63 min) ([α]$_D^{20}$+18.0 (c=0.1, MeOH)) and second eluting (retention time 13.16 min) ([α]$_D^{20}$−18.0 (c=0.1, MeOH)) isomers. $^1$H NMR (600 MHzcryo, DMSO-d$_6$+TFA, 300 K) δ0.92-1.16 (m, 1H), 1.25-1.49 (m, 4H), 1.65-1.77 (m, 3H), 1.78-1.98 (m, 7H), 2.61-2.67 (m, 1H), 2.87 (s, 3H), 3.09 (s, 3H), 3.16-3.28 (m, 2H), 3.31-3.37 (m, 1H), 3.54-3.62 (m, 2H), 3.64-3.69 (m, 1H), 3.78-95 (m, 5H), 4.28-4.42 (m, 2H), 6.87-6.91 (m, 2H), 7.23-7.24 (m, 1H), 7.41-7.49 (m, 1H), 7.61 (d, J 8.2, 1H), 8.08 (s, 1H). (ES$^+$) m/z 595 (M+H)$^+$.

Example 37

(−)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide (A37)

Step 1: (−)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide The title compound was prepared as for example 36, and is the second eluting isomer from chiral SFC (Chiralpak AS-H column, modifier 40% (iPrOH; 0.4% Et$_2$NH), pressure 100 bar, temperature 35° C.). (retention time 13.16 min; [α]$_D^{20}$−18.0 (c=0.1, MeOH)). (ES$^+$) m/z 595 (M+H)$^+$.

Example 38

14-[(1R,2S) or (1S,2R)-2-fluorocyclohexyl]-3-methoxy-18,22-dimethyl-7,8-dihydro-6H-7,11-(ethanoiminopropanoiminothioiminomethano)indolo[1,2-e][1,5]benzoxazocin-15-one 17,17-dioxide (A38)

Step 1: methyl 14-[(1R,2S) or (1S,2R)-2-fluorocyclohexyl]-7-(hydroxymethyl)-3-methoxy-7,8-dihydro-6H-indolo[1,2-e][1,5]benzoxazocine-11-carboxylate The title compound was prepared starting from (−)-methyl 2-bromo-3-[(1R,2S) or (1S,2R)-2-fluorocyclohexyl]-1H-indole-6-carboxylate (isomer A—prepared as described in International patent application WO2007054741) using the same methodology described for example 35 (steps 1-4).

Step 2: 14-[(1R,2S) or (1S,2R)-2-fluorocyclohexyl]-3-methoxy-18,22-dimethyl-7,8-dihydro-6H-7,11-(ethanoiminopropanoiminothioiminomethano)indolo[1,2-e][1,5]benzoxazocin-15-one 17,17-dioxide The title compound was prepared starting from methyl 14-[(1R,2S) or (1S,2R)-2-fluorocyclohexyl]-7-(hydroxymethyl)-3-methoxy-7,8-dihydro-6H-indolo[1,2-e][1,5]benzoxazocine-11-carboxylate using the same methodology described for example 13 (steps 3-9 and 11-14). The residue was purified by RP-HPLC (Sepax GP C18 30×100 mm; gradient 40-75% CH$_3$CN in H$_2$O; solvents buffered with 0.1% TFA). Fractions containing the pure compound were combined and lyophilized in the presence of HCl to afford the HCl salt of the title compound as a mixture of diastereoisomers (5% overall). $^1$H NMR (300 MHz, CD$_3$CN, 300 K) δ1.11-2.40 (m, 13H), 2.62-3.38 (m, 11H), 3.61-4.09 (m, 7H), 4.36-4.68 (m, 2H), 4.88-5.32 (m, 1H), 6.64-7.18 (m, 2H), 7.34-7.62 (m, 2H), 7.69-8.21 (m, 2H); (ES$^+$) m/z 613 (M+H)$^+$.

Example 39

(7R or 7S)-14-cyclohexyl-18,21-dimethyl-7,8-dihydro-6H-7,11-(methanooxyethanoiminoethanoiminothioiminomethano)indolo[1,2-e][1,5]benzoxazocin-15-one 17,17-dioxide (A39)

Step 1: (+)- and (−)-methyl 14-cyclohexyl-7-(hydroxymethyl)-7,8-dihydro-6H-indolo[1,2-e][1,5]benzoxazocine-11-carboxylate The enantiomers of methyl 14-cyclohexyl-7-(hydroxymethyl)-7,8-dihydro-6H-indolo[1,2-e][1,5]benzoxazocine-11-carboxylate (prepared as described in example 13, steps 1-2) were separated via chiral SFC (Chiralpak AD column, modifier 40% MeOH, pressure 100 bar, temperature 35° C.) to afford the first eluting ([α]$_D^{20}$−43.5 (c=1, MeOH)) and second eluting ([α]$_D^{20}$+43.6 (c=1, MeOH)) isomers. (ES$^+$) m/z 420 (M+H)$^+$.

Step 2: (7R or 7S)-7-({2-[benzyl(methyl)amino]ethoxy}methyl)-14-cyclohexyl-7,8-dihydro-6H-indolo[1,2-e][1,5]benzoxazocine-11-carboxylic acid A solution of (+)-methyl 14-cyclohexyl-7-(hydroxymethyl)-7,8-dihydro-6H-indolo[1,2-e][1,5]benzoxazocine-11-carboxylate (second eluting isomer) in toluene (0.04 M) was treated with 30% w/v NaOH (10 eq) and tetrabutylammonium bromide (0.25 eq) followed by N-benzyl-2-chloro-N-methylethanaminium chloride (prepared as described in example 7 step 1) (2.5 eq). The resulting solution was stirred at 65° C. for 18 h. Toluene was removed in vacuo, the residue was taken up in EtOAc and washed with 1N HCl (aq) and brine before drying (Na$_2$SO$_4$), filtering and concentrating in vacuo to afford the product as an oil that was used without further purification. (ES$^+$) m/z 553 (M+H)$^+$.

Step 3: (7R or 7S)-7-({2-[benzyl(methyl)amino]ethoxy}methyl)-14-cyclohexyl-N-{[(2,2-dimethoxyethyl)(methyl)amino]sulfonyl}-7,8-dihydro-6H-indolo[1,2-e][1,5]benzoxazocine-11-carboxamide A solution of (7R or 7S)-7-({2-[benzyl(methyl)amino]ethoxy}methyl)-14-cyclohexyl-7,8-dihydro-6H-indolo[1,2-e][1,5]benzoxazocine-11-carboxylic acid in dry DCM (0.06 M) was treated with DMAP (3 eq), EDC (1.5 eq) and N-(2,2-dimethoxyethyl)-N-methylsulfamide (prepared as described in example 1 step 1). The mixture was stirred at 40° C. for 2 h, and then diluted with EtOAc, washed with 1N HCl (aq), sat. aq. NaHCO$_3$ and brine, dried (Na$_2$SO$_4$), filtered and concentrated in vacuo to give the title compound. The crude material was used in the next step without further purification. (ES$^+$) m/z 733 (M+H)$^+$.

Step 4: (7R or 7S)-14-cyclohexyl-N-{[(2,2-dimethoxyethyl)(methyl)amino]sulfonyl}-7-{[2-(methylamino)ethoxy]methyl}-7,8-dihydro-6H-indolo[1,2-e][1,5]benzoxazocine-11-carboxamide A solution of (7R or 7S)-7-({2-[benzyl(methyl)amino]ethoxy}methyl)-14-cyclohexyl-N-{[(2,2-dimethoxyethyl)(methyl)amino]sulfonyl}-7,8-dihydro-6H-indolo[1,2-e][1,5]benzoxazocine-11-carboxamide in MeOH (0.06 M) was treated with AcOH (1 eq) and Pd/C (2 eq). The resulting mixture was stirred for 12 h under an H$_2$ atmosphere. The mixture was filtered and then concentrated in vacuo to afford the title compound. The crude material was used in the next step without further purification. (ES$^+$) m/z 643 (M+H)$^+$.

Step 5: (7R or 7S)-14-cyclohexyl-7-{[2-(methylamino)ethoxy]methyl}-N-{[methyl(2-oxoethyl)amino]sulfonyl}-7,8-dihydro-6H-indolo[1,2-e][1,5]benzoxazocine-11-carboxamide A solution of (7R or 7S)-14-cyclohexyl-N-{[(2,2-dimethoxyethyl)(methyl)amino]sulfonyl}-7-{[2-(methylamino)ethoxy]methyl}-7,8-dihydro-6H-indolo[1,2-e][1,5]benzoxazocine-11-carboxamide (0.05 M) in DCM was treated with an excess of TFA and H$_2$O (>50 eq of each). The mixture was stirred at 40° C. for 40 min. The solution was allowed to cool to RT and used in the next step. (ES$^+$) m/z 597 (M+H)$^+$.

Step 6: (7R or 7S)-14-cyclohexyl-18,21-dimethyl-7,8-dihydro-6H-7,11-(methanooxyethanoiminoethanoiminothioiminomethano)indolo[1,2-e][1,5]benzoxazocin-15-one 17,17-dioxide DCM solution coming from previous step was diluted with anhydrous MeOH (to give a final substrate concentration of 0.01M) and the pH adjusted with Et$_3$N to pH 5-6. NaBH$_3$CN (10 eq) was introduced and the mixture was stirred at RT for 1 h, then quenched with few drops of sat. aq. NaHCO$_3$ and concentrated in vacuo. Purification was by automated RP-HPLC, eluting with a MeCN/H$_2$O (buffered with 0.1% TFA) gradient. Fractions containing the product were combined and freeze dried to afford the product as a white powder (7%, over preceding 5 steps). $^1$H NMR (600 MHz, DMSO-d$_6$+ TFA, 300 K) δ 1.12-1.20 (m, 1H), 1.26-1.39 (m, 2H), 1.44-1.55 (m, 1H), 1.63-1.74 (m, 2H), 1.79-1.86 (m, 1H), 1.88-2.00 (m, 3H), 2.30-2.40 (m, 1H), 2.65-2.75 (m, 1H), 2.90 (s, 3H), 3.06 (s, 3H), 3.20-3.30 (m, 1H), 3.37-3.43 (m, 1H), 3.44-3.53 (m, 3H), 3.54-3.65 (m, 2H), 3.66-3.95 (m, 5H), 4.40-4.48 (m, 1H), 4.55-4.65 (m, 1H), 7.20-7.27 (m, 1H), 7.29-7.34 (m, 1H), 7.36-7.43 (m, 2H), 7.52-7.58 (m, 1H), 7.88 (d, J 8.4, 1H), 8.08 (s, 1H); (ES$^+$) m/z 581 (M+H)$^+$; [α]$_D^{20}$+11 (c=0.1, MeOH).

Example 40

(7R)-14-[(1R,2S) or (1S,2R)-2-fluorocyclohexyl]-18,21-dimethyl-7,8-dihydro-6H-7,11-(propanoiminoethanoiminothioiminomethano)indolo[1,2-e][1,5]benzoxazocin-15-one 17,17-dioxide Step 1: (2S)-5-azido-2-({[tert-butyl(dimethyl)silyl]oxy}methyl)pentan-1-ol The title compound was prepared from methyl 5-bromopentanoate, in analogous fashion to that described for methyl 4-bromobutanoate in example 33, steps 1-6. Purification by flash chromatography (9:1 to 7:3 PE:EtOAc) afforded the product as a colourless oil (38%). $^1$H NMR (400 MHz, DMSO-d$_6$, 300 K) δ 0.03 (s, 6H), 0.87 (s, 9H), 1.28-1.33 (m, 2H), 1.48-1.53 (m, 1H), 1.53-1.61 (m, 2H), 3.28-3.31 (m, 2H), 3.32-3.36 (m, 2H), 3.50 (dd, J 10.0, 5.6, 1H), 3.57 (dd, J 10.0, 5.6, 1H), 4.34-4.36 (m, 1H); [α]D$_{20}$=−6.5 (c=2.2, CHCl$_3$).

Step 2: (2R)-5-azido-2-({[tert-butyl(dimethyl)silyl]oxy}methyl)pentyl methanesulfonate (2S)-5-Azido-2-({[tert-butyl(dimethyl)silyl]oxy}methyl) pentan-1-ol was treated in analogous fashion to example 33, step 7, to afford the title compound. $^1$H NMR (400 MHz, DMSO-$d_6$, 300 K) $\delta$0.05 (s, 6H), 0.87 (s, 9H), 1.28-1.43 (m, 2H), 1.56-1.63 (m, 2H), 1.82-1.88 (m, 1H), 3.16 (s, 3H), 3.31-3.35 (m, 2H), 3.52-3.62 (m, 2H), 4.16 (d, J 5.6, 2H).

Step 3: methyl (7R)-7-(3-azidopropyl)-14-[(1R,2S) or (1S,2R)-2-fluorocyclohexyl]-7,8-dihydro-6H-indolo[1,2-e][1,5]benzoxazocine-11-carboxylate The title compound was prepared from methyl 3-[(1R,2S) or (1S,2R)-2-fluorocyclohexyl]-2-(2-hydroxyphenyl)-1H-indole-6-carboxylate (prepared as described in International patent application WO2007054741) and (2R)-5-azido-2-({[tert-butyl(dimethyl)silyl]oxy}methyl)pentyl methanesulfonate, using the same methodology described for the 3-azidoethyl analog, example 33 steps 8-11, (25% overall). (ES$^+$) m/z 491 (M+H)$^+$; [$\alpha$]$_D^{20}$+47.9 (c=1.05, CHCl$_3$).

Step 4: methyl (7R)-7-(3-aminopropyl)-14-[(1R,2S) or (1S,2R)-2-fluorocyclohexyl]-7,8-dihydro-6H-indolo[1,2-e][1,5]benzoxazocine-11-carboxylate To a solution of methyl (7R)-7-(3-azidopropyl)-14-[(1R,2S) or (1S,2R)-2-fluorocyclohexyl]-7,8-dihydro-6H-indolo[1,2-e][1,5]benzoxazocine-11-carboxylate (0.23 M) in dry MeOH under N$_2$ was added acetic acid (1 eq), then Pd/C (0.15 weight eq). The atmosphere in the reaction vessel was charged with H$_2$ and the reaction stirred vigorously under a H$_2$ atmosphere (balloon) overnight. The reaction was flushed with N$_2$ and filtered through a plug of celite. The filtrate was then concentrated in vacuo and the residue partitioned between sat. aq. NaHCO$_3$ and EtOAc. The combined organics were washed with brine, dried (Na$_2$SO$_4$), filtered and concentrated in vacuo to afford the title compound (100%) which was used without further purification; (ES$^+$) m/z 465 (M+H)$^+$.

Step 5: methyl (7R)-14-[(1R,2S) or (1S,2R)-2-fluorocyclohexyl]-7-[3-(methylamino)propyl]-7,8-dihydro-6H-indolo[1,2-e][1,5]benzoxazocine-11-carboxylate A solution of methyl (7R)-7-(3-aminopropyl)-14-[(1R,2S) or (1S,2R)-2-fluorocyclohexyl]-7,8-dihydro-6H-indolo[1,2-e][1,5]benzoxazocine-11-carboxylate (0.17 M) in THF was treated dropwise with 2,2,2-trifluoroethyl formate (1.5 eq) and stirred overnight at RT. The volatiles were removed in vacuo and the residue dissolved (0.09 M) in THF and treated dropwise with BH$_3$ DMS complex (2M in THF; 5 eq). The resulting solution was stirred at RT for 3 h. The reaction was quenched by the careful addition of HCl/MeOH (1.25 M) and the resulting solution refluxed for 2 h. The volatiles were then removed in vacuo and the residue partitioned between sat. aq. NaHCO$_3$ and EtOAc. The combined organics were washed with brine, dried (Na$_2$SO$_4$), filtered and concentrated in vacuo. The crude product was used in the subsequent step without further purification (100%). (ES$^+$) m/z 479 (M+H)$^+$.

Step 6: methyl (7R)-7-{3-[{2-[(tert-butoxycarbonyl)(methyl)amino]ethyl}(methyl)amino]propyl}-14-[(1R,2S) or (1S,2R)-2-fluorocyclohexyl]-7,8-dihydro-6H-indolo[1,2-e][1,5]benzoxazocine-11-carboxylate tert-Butyl methyl(2-oxoethyl)carbamate (2 eq) (prepared as described in Tetrahedron. 2002, 58, 1719) was added to a solution of methyl (7R)-14-[(1R,2S) or (1S,2R)-2-fluorocyclohexyl]-7-[3-(methylamino)propyl]-7,8-dihydro-6H-indolo[1,2-e][1,5]benzoxazocine-11-carboxylate (0.17 M) in THF at RT followed by HOAc (cat.). After 1 h all volatiles were removed in vacuo and the residue redissolved (0.17 M) in MeOH. NaCNBH$_3$ (3 eq) were added and the resulting solution stirred for 2 h at RT. The reaction was diluted with EtOAc and washed with sat. aq. NaHCO$_3$. The combined organics were washed with brine, dried (Na$_2$SO$_4$), filtered and concentrated in vacuo. The crude product was used in the subsequent step without further purification (100%). MS (ES$^+$) m/z 636 (M+H)$^+$.

Step 7: methyl (7R)-14-[(1R,2S) or (1S,2R)-2-fluorocyclohexyl]-7-(3-{methyl[2-(methylamino)ethyl]amino}propyl)-7,8-dihydro-6H-indolo[1,2-e][1,5]benzoxazocine-11-carboxylate Methyl (7R)-7-{3-[{2-[(tert-butoxycarbonyl)(methyl)amino]ethyl}(methyl)amino]propyl}-14-[(1R,2S) or (1S,2R)-2-fluorocyclohexyl]-7,8-dihydro-6H-indolo[1,2-e][1,5]benzoxazocine-11-carboxylate (0.10 M) in DCM was treated with TFA (25 eq) and stirred at RT overnight. The volatiles were then removed in vacuo and the residue partitioned between sat. aq. NaHCO$_3$ and EtOAc. The combined organics were washed with brine, dried (Na$_2$SO$_4$), filtered and concentrated in vacuo to afford the product as a white foam (100%) that was used without further purification. (ES$^+$) m/z 536 (M+H)$^+$.

Step 8: (7R)-7-{3-[{2-[(aminosulfonyl)(methyl)amino]ethyl}(methyl)amino]propyl}-14-[(1R,2S) or (1S,2R)-2-fluorocyclohexyl]-7,8-dihydro-6H-indolo[1,2-e][1,5]benzoxazocine-11-carboxylic acid The title compound was prepared from methyl (7R)-14-[(1R,2S) or (1S,2R)-2-fluorocyclohexyl]-7-(3-{methyl[2-(methylamino)ethyl]amino}propyl)-7,8-dihydro-6H-indolo[1,2-e][1,5]benzoxazocine-11-carboxylate using the same methodology described in example 34 steps 8-10, (80% overall). (ES$^+$) m/z 601 (M+H)$^+$.

Step 9: (7R)-14-[(1R,2S) or (1S,2R)-2-fluorocyclohexyl]-21-methyl-7,8-dihydro-6H-7,11-(propanoiminoethanoiminothioiminomethano)indolo[1,2-e][1,5]benzoxazocin-15-one 17,17-dioxide To a solution of (7R)-7-{3-[{2-[(aminosulfonyl)(methyl)amino]ethyl}(methyl)amino]propyl}-14-[(1R,2S) or (1S,2R)-2-fluorocyclohexyl]-7,8-dihydro-6H-indolo[1,2-e][1,5]benzoxazocine-11-carboxylic acid (0.05 M) in DCM were added EDC (2 eq) and DMAP (3.5 eq). The mixture was stirred at 50° C. for 2 h before cooling to RT and diluting with EtOAc. The mixture was washed with 1N HCl (aq) then brine, dried over Na$_2$SO$_4$, filtered and concentrated in vacuo. The residue was purified by RP-HPLC (Waters Sunfire column; MeCN/H$_2$O/0.1% TFA gradient). Fractions containing the pure compound were combined and lyophilized to afford the product as a white powder (20%). $^1$H NMR (600 MHz, DMSO-$d_6$+TFA, 300 K) $\delta$0.98-1.14 (m, 2H), 1.42-1.64 (m, 5H), 1.74-1.83 (m, 1H), 1.88-2.09 (m, 3H), 2.20-2.27 (m, 1H), 2.42-2.50 (m, 1H), 2.79-2.84 (m, 1H), 2.87 (s, 3H), 3.10 (s, 3H), 3.16-3.26 (m, 2H), 3.30-3.39 (m, 1H), 3.59-3.69 (m, 3H), 3.84-3.98 (m, 2H), 4.38-4.49 (m, 2H), 5.10 (dm, J$_{HF}$ 50.7, 1H), 7.32-7.33 (m, 1H), 7.47-7.48 (m, 2H), 7.54-7.56 (m, 1H), 7.95 (d, J 8.4, 1H), 8.04 (s, 1H); (ES$^+$) m/z 583 (M+H)$^+$. [$\alpha$]$_D^{20}$+8.1 (c=0.88, MeOH).

Compounds A1-A40 were assayed in the above described cell-based HCV replication assay (example ii)) and results are reported as $IC_{50}$ activity ranges in Table A.

TABLE A

Inhibition of HCV subgenomic replication by compounds A1-A40.

| Compound | $IC_{50}$ (nM) |
| --- | --- |
| A1 | +++ |
| A2 | +++ |
| A3 | +++ |
| A4 | +++ |
| A5 | +++ |
| A6 | ++ |
| A7 | ++ |
| A8 | +++ |
| A9 | ++ |
| A10 | ++ |
| A11 | +++ |
| A12 | +++ |
| A13 | ++ |
| A14 | +++ |
| A15 | + |
| A16 | ++ |
| A17 | ++ |
| A18 | +++ |
| A19 | +++ |
| A20 | ++ |
| A21 | +++ |
| A22 | ++ |

TABLE A-continued

Inhibition of HCV subgenomic replication by compounds A1-A40.

| Compound | $IC_{50}$ (nM) |
| --- | --- |
| A23 | ++ |
| A24 | ++ |
| A25 | +++ |
| A26 | +++ |
| A27 | +++ |
| A28 | +++ |
| A29 | +++ |
| A30 | ++ |
| A31 | +++ |
| A32 | +++ |
| A33 | +++ |
| A34 | ++ |
| A35 | +++ |
| A36 | ++ |
| A37 | +++ |
| A38 | +++ |
| A39 | +++ |
| A40 | +++ |

Activity ranges:
+++: <25 nM;
++: 25-150 nM;
+: 150-500 nM;
* >500 nM

The following tables show some of these and further non-limiting examples:

TABLE 1

16 membered macrocycles

| Example no. | Compound name | $IC_{50}$* (nM) | procedure | m/z (ES+) |
| --- | --- | --- | --- | --- |
| 101 | 14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide | ++ | C | 565 |
| 102 | (7R)-21-[2-(benzyloxy)ethyl]-14-cyclohexyl-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 700 |
| 103 | (7R)-14-cyclohexyl-21-(2-hydroxyethyl)-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 610 |
| 104 | (7R)-14-cyclohexyl-21-isobutyl-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 622 |
| 105 | (7R)-14-cyclohexyl-21-(N,N-dimethylglycyl)-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 651 |
| 106 | (7R)-14-cyclohexyl-21-ethyl-18-(2-hydroxyethyl)-24-methyl-7,8-dihydro-6H-7,11-(epiminoethanoiminoethanoiminothioiminomethano)-indolo[1,2-e][1,5]benzoxazocin-15-one 17,17-dioxide | +++ | A, B | 624 |
| 107 | (7R)-14-cyclohexyl-21,24-diethyl-18-methyl-7,8-dihydro-6H-7,11-(epiminoethanoiminoethanoiminothioiminomethano)-indolo[1,2-e][1,5]benzoxazocin-15-one 17,17-dioxide | +++ | A, B | 608 |

*Inhibition of HCV subgenomic replication

TABLE 2

Various macrocycles

| Example no. | Compound name | IC$_{50}$* (nM) | Procedure | m/z (ES$^+$) |
|---|---|---|---|---|
| 201 | 20-benzyl-13-cyclohexyl-17,23-dimethyl-6,7-dihydro-5H-6,10-(epiminoethanoiminoethanoiminothioiminomethano)-indolo[2,1-a][2]benzazepin-14-one 16,16-dioxide | * | A | 640 |
| 202 | (7R)-14-cyclohexyl-2-fluoro-18,21,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A | 598 |
| 203 | (7R)-14-cyclohexyl-21-ethyl-3-fluoro-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 612 |
| 204 | (7R)-14-cyclohexyl-21-ethyl-3-fluoro-18-methyl-7,8-dihydro-6H-7,11-(epiminoethanoiminoethanoiminothioiminomethano)-indolo[1,2-e][1,5]benzoxazocin-15-one 17,17-dioxide | ++ | A, B | 598 |
| 205 | (7R)-14-cyclohexyl-21-ethyl-2-fluoro-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 612 |
| 206 | (7R)-14-cyclohexyl-21-ethyl-2-fluoro-18-methyl-24-(pyridin-3-ylmethyl)-7,8-dihydro-6H-7,11-(epiminoethanoiminoethanoiminothioiminomethano)-indolo[1,2-e][1,5]benzoxazocin-15-one 17,17-dioxide | +++ | A, B | 689 |
| 207 | (7R)-14-cyclohexyl-3-fluoro-21-isopropyl-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 626 |
| 208 | (7R)-14-cyclohexyl-21-ethyl-3-fluoro-18-methyl-24-[2-(methylamino)ethyl]-7,8-dihydro-6H-7,11-(epiminoethanoiminoethanoiminothioiminomethano)-indolo[1,2-e][1,5]benzoxazocin-15-one 17,17-dioxide | ++ | A, B | 655 |
| 209 | (7R)-14-cyclohexyl-2-fluoro-21-isopropyl-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 626 |
| 210 | (7R)-14-cyclohexyl-21-ethyl-3-methoxy-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 624 |
| 211 | (7R)-14-cyclohexyl-21-ethyl-18,24-dimethyl-3-(pyridin-2-ylmethoxy)-7,8-dihydro-6H-7,11-(epiminoethanoiminoethanoiminothioiminomethano)-indolo[1,2-e][1,5]benzoxazocin-15-one 17,17-dioxide | +++ | A, B | 701 |
| 212 | (7R)-14-cyclohexyl-18,21,24-trimethyl-4-propyl-7,8-dihydro-6H-7,11-(epiminoethanoiminoethanoiminothioiminomethano)-indolo[1,2-e][1,5]benzoxazocin-15-one 17,17-dioxide | ++ | A, B | 622 |
| 213 | (7R)-14-cyclohexyl-21-isopropyl-18,24-dimethyl-4-propyl-7,8-dihydro-6H-7,11-(epiminoethanoiminoethanoiminothioiminomethano)-indolo[1,2-e][1,5]benzoxazocin-15-one 17,17-dioxide | ++ | A, B | 650 |
| 214 | (7R)-14-cyclohexyl-21-ethyl-24-(2-hydroxyethyl)-3,18-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 638 |
| 215 | (7R)-14-cyclohexyl-21-ethyl-3,18,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 608 |

TABLE 2-continued

Various macrocycles

| Example no. | Compound name | $IC_{50}$* (nM) | Procedure | m/z (ES+) |
|---|---|---|---|---|
| 216 | (7R)-14-cyclohexyl-3,18,21,24-tetramethyl-7,8-dihydro-6H-7,11-(epiminoethanoiminoethanoiminothioiminomethano)-indolo[1,2-e][1,5]benzoxazocin-15-one 17,17-dioxide | +++ | A, B | 594 |
| 217 | (7R)-14-cyclohexyl-24-[2-(dimethylamino)ethyl]-21-ethyl-18-methyl-7,8-dihydro-6H-7,11-(epiminoethanoiminoethanoiminothioiminomethano)-indolo[1,2-e][1,5]benzoxazocin-15-one 17,17-dioxide | +++ | A, B | 651 |
| 218 | (7R)-14-cyclohexyl-21-isopropyl-3,18,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 622 |
| 219 | (7R)-14-cyclohexyl-24-[2-(dimethylamino)ethyl]-21-ethyl-4,18-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 665 |
| 220 | (7R)-14-cyclohexyl-21-[2-(dimethylamino)ethyl]-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 637 |

*Inhibition of HCV subgenomic replication

TABLE 3

Various macrocycles

| Example no. | Compound name | $IC_{50}$* (nM) | Procedure | m/z (ES+) |
|---|---|---|---|---|
| 301 | (18R)-29-cyclohexyl-10,17-dimethyl-20-oxa-9-thia-1,8,10,13,17-pentaazahexacyclo[16.9.1.1$^{2,6}$.1$^{3,27}$.1$^{13,16}$.0$^{21,26}$]hentriaconta-2(31),3,5,21,23,25,27(29)-heptaen-7-one 9,9-dioxide | +++ | A | 592 |
| 302 | (3R)-31-cyclohexyl-2,22-dimethyl-5-oxa-21-thia-2,13,20,22,25-pentaazahexacyclo[23.2.2.1$^{3,13}$.1$^{12,15}$.1$^{14,18}$.0$^{6,11}$]dotriaconta-6,8,10,12(31),14(30),15,17-heptaen-19-one 21,21-dioxide | +++ | A | 606 |
| 303 | (5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31),16(30),17,19-heptaen-21-one 23,23-dioxide | +++ | C | 606 |
| 304 | (20R)-31-cyclohexyl-21-methyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide | +++ | A | 592 |
| 305 | (5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31),16(30),17,19-heptaen-21-one 23,23-dioxide | +++ | C | 620 |
| 306 | (20R)-31-cyclohexyl-21-methyl-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide | + | C | 593 |
| 307 | (20R)-31-cyclohexyl-21-[2-(dimethylamino)ethyl]-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide | + | C | 650 |
| 308 | (20R)-30-cyclohexyl-21-(2-fluoroethyl)-18-oxa-2-thia-1,3,10,21,24-pentaazahexacyclo[22.2.2.1$^{5,9}$.1$^{8,11}$.1$^{10,20}$.0$^{12,17}$]hentriaconta- | ++ | A | 610 |

TABLE 3-continued

Various macrocycles

| Example no. | Compound name | IC$_{50}$* (nM) | Procedure | m/z (ES$^+$) |
|---|---|---|---|---|
| | 5(31),6,8,11(30),12,14,16-heptaen-4-one 2,2-dioxide | | | |
| 309 | (20R)-21-benzyl-31-cyclohexyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide | + | A | 668 |

*Inhibition of HCV subgenomic replication

TABLE 4

Various macrocycles

| Example no. | Compound name | IC$_{50}$* (nM) | Procedure | m/z (ES$^+$) |
|---|---|---|---|---|
| 401 | (7S)-14-cyclohexyl-18,24-dimethyl-7,8-dihydro-6H-7,11-(epiminoethanoiminoethanoiminothioiminomethano)-indolo[1,2-e][1,5]benzoxazocin-15-one 17,17-dioxide | ++ | A | 566 |
| 402 | (7R)-14-cyclohexyl-24-[2-(dimethylamino)ethyl]-18-methyl-7,8-dihydro-6H-7,11-(epiminoethanooxyethanoiminothioiminomethano)indolo[1,2-e][1,5]benzoxazocin-15-one 17,17-dioxide | +++ | C | 624 |
| 403 | (7R)-4-allyl-14-cyclohexyl-21-ethyl-18,24-dimethyl-7,8-dihydro-6H-7,11-(epiminoethanoiminoethanoiminothioiminomethano)-indolo[1,2-e][1,5]benzoxazocin-15-one 17,17-dioxide | ++ | A, B | 634 |
| 404 | (7R)-14-cyclohexyl-21-ethyl-4-fluoro-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 612 |
| 405 | (7R)-14-cyclohexyl-4-fluoro-21-isopropyl-18,24-dimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 626 |
| 406 | (7R)-14-cyclohexyl-21-ethyl-18,24-dimethyl-4-(trifluoromethyl)-7,8-dihydro-6H-7,11-(epiminoethanoiminoethanoiminothioiminomethano)-indolo[1,2-e][1,5]benzoxazocin-15-one 17,17-dioxide | + | A, B | 662 |
| 407 | (7R)-14-cyclohexyl-4-(cyclopropylmethyl)-18,21,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 634 |
| 408 | 2-[(7R)-14-cyclohexyl-18,21-dimethyl-17,17-dioxido-15-oxo-7,8-dihydro-6H-7,11-(epiminoethanoiminoethanoiminothioiminomethano)-indolo[1,2-e][1,5]benzoxazocin-24-yl]acetamide | ++ | A, B | 623 |
| 409 | (7R)-14-cyclohexyl-18,21-dimethyl-24-[(1-methyl-1H-pyrazol-4-yl)methyl]-7,8-dihydro-6H-7,11-(epiminoethanoiminoethanoiminothioiminomethano)-indolo[1,2-e][1,5]benzoxazocin-15-one 17,17-dioxide | +++ | A, B | 660 |
| 410 | (7R)-14-cyclohexyl-18,24-dimethyl-4-(morpholin-4-ylmethyl)-7,8-dihydro-6H-7,11-(epiminoethanoiminoethanoiminothioiminomethano)-indolo[1,2-e][1,5]benzoxazocin-15-one 17,17-dioxide | ++ | A, B | 665 |
| 411 | (7R)-4-(benzyloxy)-14-cyclohexyl-18,21,24-trimethyl-7,8-dihydro-6H-7,11-(epiminoethanoiminoethanoiminothioiminomethano)-indolo[1,2-e][1,5]benzoxazocin-15-one 17,17-dioxide | ++ | A, B | 686 |
| 412 | (7R)-14-cyclohexyl-4-methoxy-18,21,24-trimethyl-7,8-dihydro-6H-7,11-(epiminoethanoiminoethanoiminothioiminomethano)- | +++ | A, B | 610 |

TABLE 4-continued

Various macrocycles

| Example no. | Compound name | IC$_{50}$* (nM) | Procedure | m/z (ES$^+$) |
|---|---|---|---|---|
| | indolo[1,2-e][1,5]benzoxazocin-15-one 17,17-dioxide | | | |
| 413 | (7R)-14-[(1R,2S) or (1S,2R)-2-fluorocyclohexyl]-18,21,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 598 |

*Inhibition of HCV subgenomic replication

TABLE 5

Various macrocycles

| Example no. | Compound name | IC$_{50}$* (nM) | Procedure | m/z (ES$^+$) |
|---|---|---|---|---|
| 501 | 14-[(1R,2S) or (1S,2R)-2-fluorocyclohexyl]-18,22-dimethyl-7,8-dihydro-6H-7,11-(ethanoiminopropanoiminothioiminomethano)indolo[1,2-e][1,5]benzoxazocin-15-one 17,17-dioxide | ++ | C | 583 |
| 502 | 30-[(1R,2S) or (1S,2R)-2-fluorocyclohexyl]-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide | ++ | A | 595 |
| 503 | 30-[(1R,2S) or (1S,2R)-2-fluorocyclohexyl]-22-methyl-18-oxa-2-thia-1,3,10,22-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide | ++ | C | 595 |
| 504 | 30-cyclohexyl-23-methyl-6-oxa-22-thia-1,14,21,23-tetraazahexacyclo[22.2.2.1$^{4,14}$.1$^{13,16}$.1$^{15,19}$.0$^{7,12}$]hentriaconta-7,9,11,13(30),15(29),16,18-heptaen-20-one 22,22-dioxide | ++ | C | 577 |
| 505 | (7R) or (7S)-14-cyclohexyl-22-methyl-18-(2-pyrrolidin-1-ylethyl)-7,8-dihydro-6H-7,11-(ethanoiminopropanoiminothioiminomethano)indolo[1,2-e][1,5]benzoxazocin-15-one 17,17-dioxide | ++ | C | 648 |
| 506 | (7R) or (7S)-14-cyclohexyl-22-isopropyl-18-methyl-7,8-dihydro-6H-7,11-(ethanoiminopropanoiminothioiminomethano)indolo[1,2-e][1,5]benzoxazocin-15-one 17,17-dioxide | +++ | C | 593 |
| 507 | (7R) or (7S)-14-cyclohexyl-22-(2-hydroxyethyl)-18-methyl-7,8-dihydro-6H-7,11-(ethanoiminopropanoiminothioiminomethano)indolo[1,2-e][1,5]benzoxazocin-15-one 17,17-dioxide | +++ | C, B | 595 |
| 508 | 31-cyclohexyl-18-oxa-2-thia-1,3,10,24-tetraazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide | ++ | C | 577 |
| 509 | 14-cyclohexyl-21-isopropyl-18-methyl-7,8-dihydro-6H-7,11-(propanoiminoethanoiminothioiminomethano)indolo[1,2-e][1,5]benzoxazocin-15-one 17,17-dioxide | +++ | C | 593 |
| 510 | (7R)-14-cyclohexyl-4-methoxy-18,21-dimethyl-7,8-dihydro-6H-7,11-(propanoiminoethanoiminothioiminomethano)indolo[1,2-e][1,5]benzoxazocin-15-one 17,17-dioxide | +++ | C | 595 |
| 511 | (7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide | +++ | A, B | 678 |
| 512 | (7R)-14-cyclohexyl-18,21,21,24-tetramethyl-7,8-dihydro-6H-7,11-(epiminopentanoiminothioiminomethano)indolo[1,2-e][1,5]benzoxazocin-15-one 17,17-dioxide | + | C | 593 |
| 513 | (7R)-14-[(1R,2S)-2-fluorocyclohexyl]-4,18,21-trimethyl-7,8-dihydro-6H-7,11-(propanoiminoethanoiminothioiminomethano)indolo[1,2-e][1,5]benzoxazocin-15-one 17,17-dioxide | +++ | C | 597 |
| 514 | 2-[(7R)-14-cyclohexyl-4,18,24-trimethyl-17,17-dioxido-15-oxo-7,8-dihydro-6H-7,11- | +++ | A, B | 665 |

TABLE 5-continued

Various macrocycles

| Example no. | Compound name | IC$_{50}$* (nM) | Procedure | m/z (ES$^+$) |
|---|---|---|---|---|
| | (epiminoethanoiminoethanoiminothioiminomethano)-indolo[1,2-e][1,5]benzoxazocin-21-yl]-N,N-dimethylacetamide | | | |
| 515 | (7R)-14-cyclohexyl-4,18,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A | 580 |
| 516 | (7R)-14-cyclohexyl-4,18,21,24-tetramethyl-7,8-dihydro-6H-7,11-(epiminoethanoiminoethanoiminothioiminomethano)-indolo[1,2-e][1,5]benzoxazocin-15-one 17,17-dioxide | +++ | A, B | 594 |
| 517 | (7R)-14-cyclohexyl-4,18,24-trimethyl-21-[(1-methyl-1H-pyrazol-4-yl)methyl]-7,8-dihydro-6H-7,11-(epiminoethanoiminoethanoiminothioiminomethano)-indolo[1,2-e][1,5]benzoxazocin-15-one 17,17-dioxide | +++ | A, B | 674 |
| 518 | (7R)-14-cyclopentyl-18,21,24-trimethyl-7,8-dihydro-6H-7,11-(epiminoethanoiminoethanoiminothioiminomethano)-indolo[1,2-e][1,5]benzoxazocin-15-one 17,17-dioxide | +++ | A, B | 566 |
| 519 | (7R)-14-cyclohexyl-4-methoxy-18,24-dimethyl-7,8-dihydro-6H-7,11-(epiminoethanooxyethanoiminothioiminomethano)indolo[1,2-e][1,5]benzoxazocin-15-one 17,17-dioxide | ++ | C | 597 |
| 520 | (7R)-14-cyclohexyl-4,18,21-trimethyl-7,8-dihydro-6H-7,11-(propanoiminoethanoiminothioiminomethano)indolo[1,2-e][1,5]benzoxazocin-15-one 17,17-dioxide | +++ | C | 579 |
| 521 | (7R)-14-cyclohexyl-4,18,22-trimethyl-7,8-dihydro-6H-7,11-(ethanoiminopropanoiminothioiminomethano)indolo[1,2-e][1,5]benzoxazocin-15-one 17,17-dioxide | +++ | C | 579 |
| 522 | (7R)-14-cyclohexyl-22-[2-(dimethylamino)ethyl]-4,18-dimethyl-7,8-dihydro-6H-7,11-(ethanoiminopropanoiminothioiminomethano)indolo[1,2-e][1,5]benzoxazocin-15-one 17,17-dioxide | +++ | C | 636 |
| 523 | (20R)-30-cyclohexyl-15-methoxy-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide | +++ | C | 607 |
| 524 | (7R)-14-cyclohexyl-20,20-difluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide | + | C | 631 |
| 525 | (7R)-14-cyclohexyl-20-fluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide | +++ | C | 613 |

*Inhibition of HCV subgenomic replication

What is claimed is:

1. A compound of the formula (I):

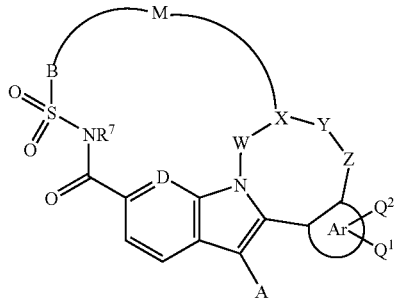

wherein Ar is a moiety containing at least one aromatic ring and possesses 5-, 6-, 9- or 10-ring atoms optionally containing 1, 2 or 3 heteroatoms independently selected from N, O and S, $Q^1$ is hydrogen, halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^cR^d$; $R^a$ and $R^b$ are each independently selected from hydrogen, $C_{1-4}$ alkyl and $C(O)C_{1-4}$ alkyl; or $R^a$, $R^b$ and the nitrogen atom to which they are attached form a heteroaliphatic ring of 4 to 7 ring atoms, where said ring is optionally substituted by halogen, hydroxy, $C_{1-4}$ alkyl or $C_{1-4}$ alkoxy; $R^c$ and $R^d$ are each independently selected from hydrogen, $C_{1-6}$ alkyl or $C_{1-6}$ alkoxy; or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$ alkyl or $C_{1-4}$ alkoxy; and wherein said alkyl, alkoxy and aryl groups are optionally substituted by halogen or hydroxy; $R^e$ is hydrogen or $C_{1-6}$ alkyl; $R^f$ is hydrogen, $C_{1-6}$ alkyl; $Q^2$ is hydrogen, halogen, hydroxy, $C_{1-4}$alkyl or $C_{1-4}$alkoxy, where said $C_{1-4}$ alkyl and $C_{1-4}$ alkoxy groups are optionally substituted by halogen or hydroxy; or $Q^1$ and $Q^2$ may be linked by a bond or a heteroatom selected from N, O and S to form a ring of 4 to 7 atoms, where said ring is optionally substituted by halogen, hydroxy, $C_{1-4}$ alkyl or $C_{1-4}$ alkoxy;

A is $C_{3-6}$ alkyl or $C_{2-6}$ alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$ alkyl or $C_{1-4}$ alkoxy;

D is N or $CR^8$; $R^8$ is hydrogen, fluorine, chlorine, $C_{1-4}$ alkyl, $C_{2-4}$ alkenyl or $C_{1-4}$ alkoxy, where said $C_{1-4}$ alkyl, $C_{2-4}$ alkenyl and $C_{1-4}$ alkoxy groups are optionally substituted by hydroxy or fluorine;

W is a bond, C=O, O, $S(O)_{0-2}$ or $—(CR^{10}R^{11})—(CR^{12}R^{13})_{0-1}—$;

Y is a bond, C=O, O, $—CR^{14}R^{15}—$ or $NR^{14}$;

Z is a bond, C=O, O, $S(O)_{0-2}$, $—(CR^{10}R^{11})—(CR^{12}R^{13})_{0-1}—$ or $NR^{10}$;

and none, one or two of W, Y and Z are a bond;

X is $—C(R^9)—$ or N;

$R^9$, $R^{10}$, $R^{11}$, $R^{12}$, $R^{13}$, $R^{14}$ and $R^{15}$ are each independently selected from hydrogen, fluoro, hydroxy, $C_{1-6}$ alkyl, $C_{2-6}$ alkenyl, $C_{1-6}$ alkoxy, $C(O)C_{1-6}$ alkyl, a heteroaliphatic ring of 4 to 7 ring atoms, which ring may contain 1, 2 or 3 heteroatoms selected from N, O or S or a group S(O), $S(O)_2$, NH or $NC_{1-4}$alkyl $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{1-3}NR^{16}R^{17}$, $S(O)_{0-2}(CH_2)_{0-3}NR^{16}R^{17}$ and $C(O)(CH_2)_{0-3}OR^{16}$; or one of $R^{10}$, $R^{14}$ and $R^9$ is linked to $R^{20}$ or $R^{21}$ to form a ring of 4 to 10 atoms, where said ring is optionally substituted by halogen, hydroxy, $C_{1-4}$ alkyl or $C_{1-4}$ alkoxy; or, when X is $—CR^9—$ and Z is $—CR^{10}R^{11}—$ or $NR^{10}$, $R^{10}$ is joined to $R^9$ to form a $—(CH_2)—_{1-4}$ group, optionally substituted by $C_{1-4}$ alkyl; or when X is $—CR^9—$, $R^9$ is joined with an atom of the linker M to form an aliphatic ring of 4-7 ring atoms, said aliphatic ring optionally containing one or two heteroatoms selected from O, N or S or a group S(O), $S(O)_2$, NH or $NC_{1-4}$alkyl;

$R^{16}$ and $R^{17}$ are independently selected from hydrogen, $C_{1-6}$ alkyl and $(CH_2)_{0-4}NR^{18}R^{19}$; or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$ alkyl, and which ring is optionally substituted by halogen, hydroxy, $C_{1-4}$ alkyl or $C_{1-4}$ alkoxy;

$R^{18}$ and $R^{19}$ are independently selected from hydrogen and $C_{1-6}$alkyl; or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$ alkyl, and which ring is optionally substituted by halogen, hydroxy, $C_{1-4}$ alkyl or $C_{1-4}$ alkoxy;

$R^7$ is hydrogen or $C_{1-6}$ alkyl;

B is $N(R^{20})—$ and M is $C_{3-7}$ alkylene or $C_{3-7}$ alkenylene, optionally substituted by $R^{21}$, where 1 or 2 of the carbon atoms in the $C_{3-7}$ alkylene or $C_{3-7}$ alkenylene groups is optionally replaced by O, $NR^{22}$, S, SO, $SO_2$, piperidinyl, piperazinyl, homopiperazinyl or pyrrolidinyl, where $R^{20}$ and $R^{22}$ are each independently hydrogen, $C_{1-6}$ alkyl, $C_{2-6}$ alkenyl, $(CH_2)_{0-3}C_{3-6}$ cycloalkyl, $(CH_2)_{1-3}$OH, $C_{1-6}$ alkoxy, $C(O)C_{1-6}$ alkyl, $(CH_2)_{0-3}$aryl, $(CH_2)_{0-3}$heteroaryl, $(CH_2)_{1-3}NR^{16}R^{17}$, $C(O)(CH_2)_{1-3}NR^{16}R^{17}$, $S(O)_{0-2}(CH_2)_{1-3}NR^{16}R^{17}$, $C(O)(CH_2)_{1-3}OR^{16}$, $(CH_2)_{1-3}O(CH_2)_{0-3}$aryl, or $R^{20}$ is linked to one of $R^{10}$, $R^{14}$ and $R^9$ to form a ring of 4 to 10 atoms as hereinbefore described; or where 1 or 2 of the carbon atoms in the $C_{3-7}$ alkylene or $C_{3-7}$ alkenylene group are replaced by $NR^{22}$, then the $R^{20}$ and $R^{22}$ groups can be joined to form a $—(CH_2)—_{1-3}$ group, optionally substituted by $C_{1-2}$alkyl, where $R^{21}$ is halo, $C_{1-4}$alkyl, $—(CH_2)—_{0-3}$ $C_{3-8}$cycloalkyl, $(CH_2)_{0-3}$aryl, $(CH_2)_{0-3}$heteroaryl, $(CH_2)_{0-3}$Het, oxo or $(CH_2)_{0-3}NR^{16}R^{17}$ or $R^{21}$ is linked to one of $R^{10}$, $R^{14}$ and $R^9$ to form a ring of 4 to 10 atoms as hereinbefore described;

wherein each of said heteroaryl is independently a 5-10-membered heteroaromatic ring system containing 1 to 4 heteroatoms selected from N, O and S;

or a pharmaceutically acceptable salt thereof.

2. A compound according to claim 1 in which Ar is phenyl optionally substituted by groups $Q^1$ and $Q^2$ as hereinbefore defined, A is cyclohexyl, cyclopentyl or fluorocyclohexyl and D is $CR^8$ where $R^8$ is hydrogen.

3. A compound of the formula (II):

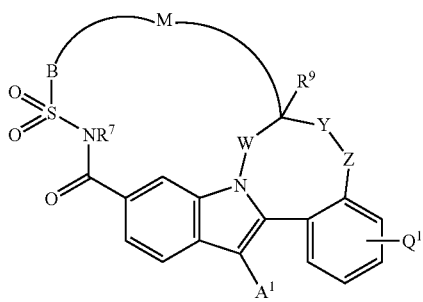

wherein $Q^1$ is hydrogen, halogen, hydroxy, a group $(O)_{0-1}(CR^gR^h)_{0-4}R^i$ wherein $R^g$ is hydrogen or $C_{1-6}$ alkyl; $R^h$ is hydrogen or $C_{1-6}$ alkyl; and $R^i$ is hydrogen, $C_{1-5}$alkyl optionally substituted by $C_{3-6}$ cycloalkyl, or $R^i$ is aryl, $C_{1-6}$ alkoxy, heteroaryl or a 4-, 5-, 6- or 7-membered heteroaliphatic ring optionally substituted by halogen, hydroxy, $C_{1-4}$ alkyl or $C_{1-4}$ alkoxy, or a group $NR^jR^k$, or $CONR^jR^k$, wherein $R^j$ and $R^k$ are each independently selected from hydrogen, $C_{1-4}$ alkyl and $C(O)C_{1-4}$ alkyl; or $R^j$, $R^k$ and the nitrogen atom to which they are attached form a heteroaliphatic ring of 4 to 7 ring atoms optionally substituted by halogen, hydroxy, $C_{1-4}$ alkyl or $C_{1-4}$ alkoxy; and wherein said alkyl, alkoxy, heteroaryl and aryl groups are optionally substituted by halogen or hydroxy;

$A^1$ is cyclohexyl, cyclopentyl or fluorocyclohexyl;

W is a bond, C=O, O, $S(O)_{0-2}$ or $—(CR^{10}R^{11})—(CR^{12}R^{13})_{0-1}—$;

Y is a bond, C=O, O, $—CR^{14}R^{15}—$ or $NR^{14}$;

Z is a bond, C=O, O, $S(O)_{0-2}$, $—(CR^{10}R^{11})—(CR^{12}R^{13})_{0-1}—$ or $NR^{10}$;

and none, one or two of W, Y and Z are a bond;

$R^9$ is a bond, hydrogen, fluoro or hydroxyl;

$R^{10}$, $R^{11}$, $R^{12}$, $R^{13}$, $R^{14}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, a heteroaliphatic ring of 4 to 7 ring atoms containing 1, 2 or 3 heteroatoms selected from N, O or S or a group $S(O)$, $S(O)_2$, NH or $NC_{1-4}$alkyl, $(CH_2)_{0-3}NR^{16}R^{17}$, or $R^{10}$, $R^{11}$, $R^{12}$, $R^{13}$, $R^{14}$ and $R^{15}$ are each independently selected from $(CH_2)_{0-3}NR^{16}R^{17}$, $C(O)(CH_2)_{0-3}NR^{16}R^{17}$, $NR^1C(O)(CH_2)_{0-3}NR^{16}R^{17}$ where $R^1$ is hydrogen or $C_{1-4}$ alkyl, $O(CH_2)_{1-3}NR^{16}R^{17}$, $S(O)_{0-2}(CH_2)_{0-3}NR^{16}R^{17}$ and $C(O)(CH_2)_{0-3}OR^{16}$; or one of $R^{10}$, $R^{14}$ and $R^9$ is linked to $R^{20}$ or $R^{21}$ to form a 4-10 membered carbocyclic ring, where said ring is optionally substituted by halogen, hydroxy, $C_{1-4}$alkyl or $C_{1-4}$alkoxy; or, when Z is $—CR^{10}R^{11}—$ or $NR^{10}$, $R^{10}$ is joined to $R^9$ to form a $—(CH_2)—_{1-4}$ group, optionally substituted by $C_{1-4}$alkyl; or $R^9$ is joined with an atom of the linker M to form an aliphatic ring of 4-7 ring atoms, said aliphatic ring optionally containing one or two heteroatoms selected from O, N or S or a group $S(O)$, $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$; or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl; or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group $S(O)$, $S(O)_2$, NH or $NC_{1-4}$alkyl, and which ring is optionally substituted by halogen, hydroxy, $C_{1-4}$alkyl or $C_{1-4}$alkoxy;

$R^7$ is hydrogen or $C_{1-6}$alkyl;

B is $N(R^{20})—$ and $R^{20}$ is hydrogen, $C_{1-6}$alkyl optionally substituted by 1-3 fluoro, $C_{2-6}$alkenyl, $(CH_2)_{0-3}C_{3-6}$cycloalkyl, $(CH_2)_{1-3}OH$, $C_{1-6}$alkoxy, $C(O)C_{1-6}$alkyl, $(CH_2)_{0-3}$aryl, $(CH_2)_{0-3}$Het, $(CH_2)_{0-3}$heteroaryl, $(CH_2)_{1-3}NR^{16}R^{17}$, $C(O)(CH_2)_{1-3}NR^{16}R^{17}$, $S(O)_{0-2}(CH_2)_{1-3}NR^{16}R^{17}$, $C(O)(CH_2)_{1-3}OR^{16}$, $(CH_2)_{1-3}O(CH_2)_{0-3}$aryl, or $R^{20}$ is linked to one of $R^{10}$, $R^{14}$ and $R^9$ to form a ring of 4 to 10 atoms as hereinbefore described, or $R^{20}$ and one of the $R^{21}$ groups can be joined to form a $—(CH_2)—_{1-3}$ group, optionally substituted by $C_{1-2}$alkyl;

and M is $C_{3-7}$alkylene or $C_{3-7}$alkenylene, optionally substituted by one or two groups $R^{21}$, which can be substituents on the same carbon atom, where $R^{21}$ is halo, $C_{1-4}$ alkyl optionally substituted by 1-3 fluoro, $(CH_2)_{0-3}C_{3-5}$cycloalkyl, $(CH_2)_{0-3}$aryl, $(CH_2)_{0-3}$heteroaryl, $(CH_2)_{0-3}$Het, oxo or $(CH_2)_{0-3}NR^{16}R^{17}$, or $R^{21}$ is linked to one of $R^{10}$, $R^{14}$ and $R^9$ to form a ring of 4 to 10 atoms as hereinbefore described or $R^{20}$ and one of the $R^{21}$ groups can be joined to form a $—(CH_2)—_{1-3}$ group, optionally substituted by $C_{1-2}$alkyl as herebefore described; and 1, 2 or 3 of the carbon atoms in the $C_{3-7}$alkylene or $C_{3-7}$alkenylene groups is optionally replaced by O, $NR^{22}$, S, SO, $SO_2$, piperidinyl, piperazinyl, homopiperazinyl or pyrrolidinyl;

and each group $R^{22}$ is independently hydrogen, $C_{1-6}$ alkyl optionally substituted with 1-3 fluoro, $C_{2-6}$ alkenyl, $(CH_2)_{0-3}C_{3-6}$cycloalkyl, $(CH_2)_{1-3}OH$, $C_{1-6}$ alkoxy, $C(O)C_{1-6}$ alkyl, $(CH_2)_{0-3}$aryl, $(CH_2)_{0-3}$Het, $(CH_2)_{0-3}$heteroaryl, $(CH_2)_{1-3}NR^{16}R^{17}$, $C(O)(CH_2)_{1-3}NR^{16}R^{17}$, $(CH_2)_{1-3}C(O)NR^{16}R^{17}$, $S(O)_{0-2}(CH_2)_{1-3}NR^{16}R^{17}$, $C(O)(CH_2)_{1-3}OR^{16}$, $(CH_2)_{1-3}O(CH_2)_{0-3}$aryl, or where 1, 2 or 3 of the carbon atoms in the $C_{3-7}$ alkylene or $C_{3-7}$ alkenylene group are replaced by $NR^{22}$, then the $R^{20}$ and $R^{22}$ groups can be joined to form a $—(CH_2)—_{1-3}$ group, optionally substituted by $C_{1-2}$alkyl;

wherein each of said heteroaryl is a 5-10-membered heteroaromatic ring system containing 1 to 4 heteroatoms selected from N, O and S;

or a pharmaceutically acceptable salt thereof.

4. A compound according to claim 3 in which $Q^1$ is hydrogen, $O—CH_2$-(2-pyridyl), $O—CH_2CH_2$-(1-pyrrolidine), fluorine, chlorine, methyl or methoxy.

5. A compound according to claim 4 in which $R^7$ is hydrogen and $R^9$ is hydrogen.

6. A compound according to claim 5 in which $A^1$ is cyclohexyl.

7. A compound according to claim 6 in which W is $—CH_2—$, Y is $CH_2$ or a bond and Z is O, $NCH_3$ or $CH_2$.

8. A compound according to claim 7 in which W is $—CH_2—$, Y is $CH_2$ and Z is O.

9. A compound according to claim 2 of formula (Ia):

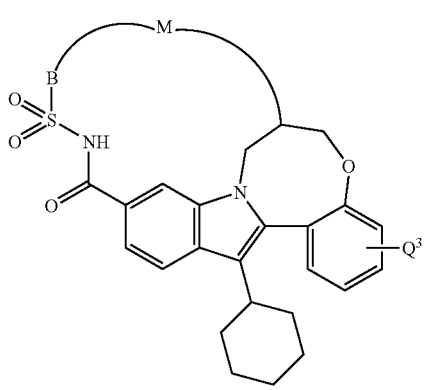

(Ia)

or a pharmaceutically acceptable salt thereof, wherein M and B are as defined in relation to formula (I) and $Q^3$ is hydrogen, O—CH$_2$-(2-pyridyl), O—CH$_2$CH$_2$-(1-pyrrolidine), halogen, hydroxy, $C_{1-4}$ alkyl or $C_{1-4}$ alkoxy.

10. A compound according to claim 9 in which $R^{20}$ is hydrogen, methyl or $R^{20}$ and one of the $R^{21}$ groups or $R^{20}$ and $R^{22}$ can be joined to form a —(CH$_2$)$_2$— group.

11. A compound according to claim 10 in which M is $C_{3-7}$ alkylene, optionally substituted by methyl or gem dimethyl or gem difluoro, and where one or two of the carbon atoms in the $C_{3-7}$alkylene group is replaced by O or NR$^{22}$, where $R^{22}$ is hydrogen, $C_{1-4}$ alkyl, (CH$_2$)C$_{3-6}$ cycloalkyl, (CH$_2$)$_2$OH, CH$_2$phenyl, CH$_2$pyridyl, (CH$_2$)$_2$NR$^{16}$R$^{17}$, C(O)CH$_2$NR$^{16}$R$^{17}$ or (CH$_2$)$_2$OCH$_2$phenyl, where $R^{16}$ and $R^{17}$ are each hydrogen or $C_{1-4}$ alkyl or $R^{16}$ and $R^{17}$ are linked to form a nitrogen containing heteroaliphatic ring containing 4 to 7 ring members.

12. A compound according to claim 11 in which M is a chain of six or seven atoms chosen from carbon, nitrogen and oxygen optionally substituted as hereinbefore described, at least one of the atoms being nitrogen and optionally one of the atoms being nitrogen or oxygen, the rest being carbon.

13. A compound according to claim 8 in which B-M-X is selected from the group consisting of:

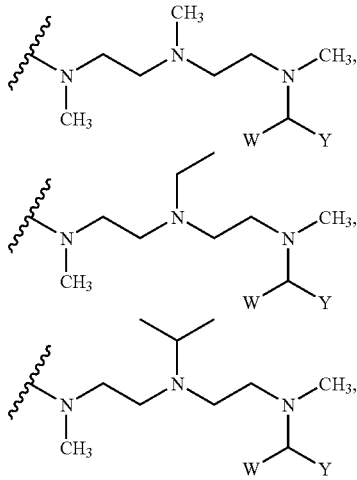

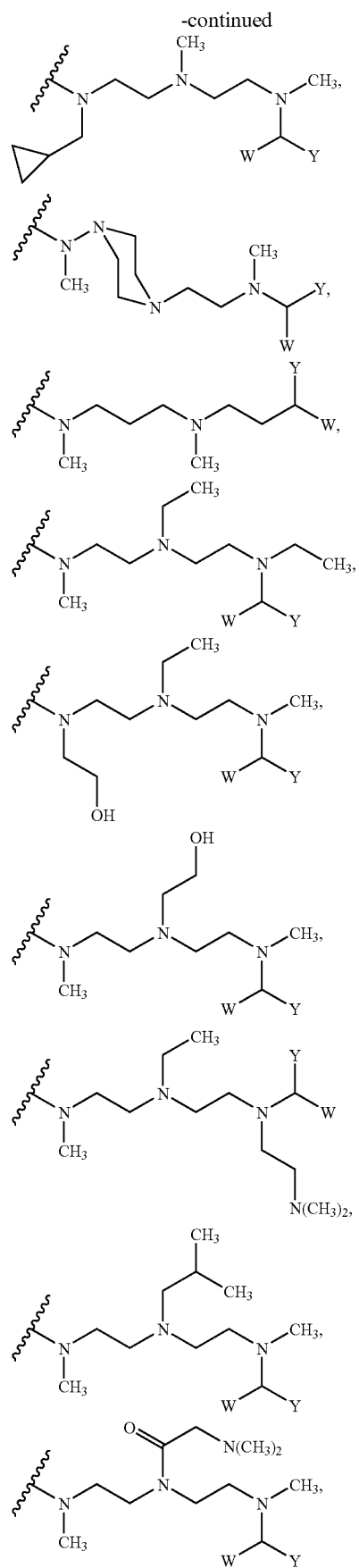

-continued

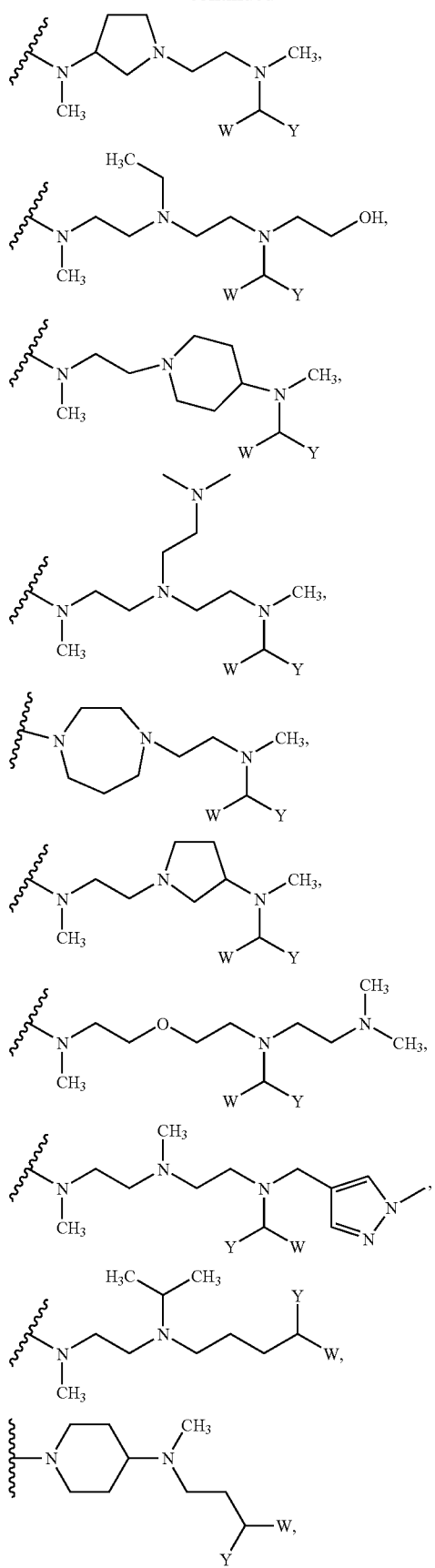

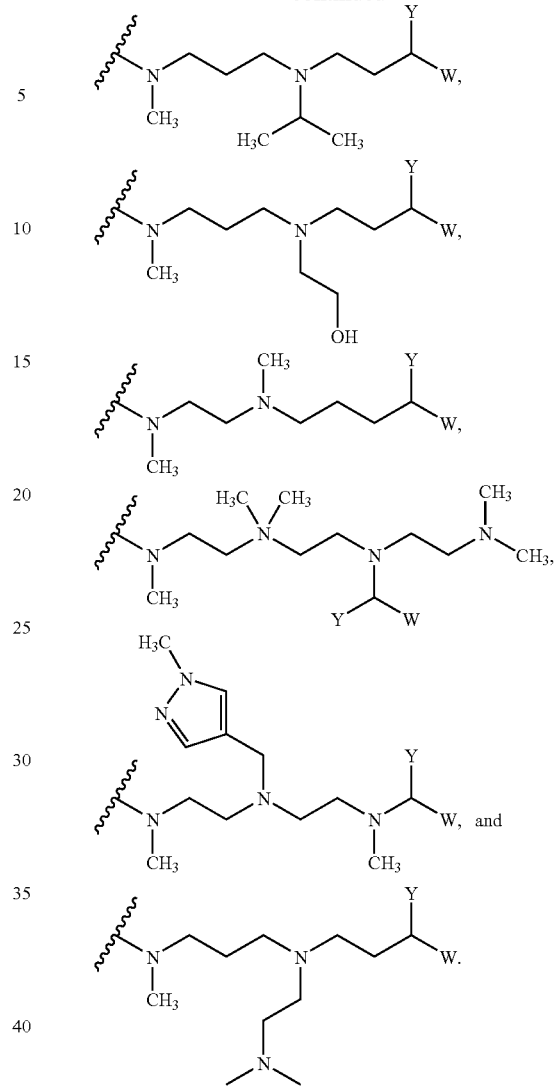

14. A compound according to claim 11 in which W is —CH$_2$—, Y is CH$_2$ or a bond and Z is O, NCH$_3$ or CH$_2$.

15. A compound according to claim 14 in which W is —CH$_2$—, Y is CH$_2$ and Z is O.

16. A compound according to claim 3 selected from the group consisting of:
- (7R)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;
- (7R)-14-cyclohexyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;
- (7R)-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide;
- (7R)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;
- (7R)-14-cyclohexyl-18-(cyclopropylmethyl)-21,24-dimethyl-7,8-dihydro-6H-7,11-(epiminoethanoiminoethanoiminothioiminomethano)indolo[1,2-e][1,5]benzoxazocin-15-one 17,17-dioxide;

(20R)-30-cyclohexyl-21-methyl-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(7S)-14-cyclohexyl-18,21-dimethyl-7,8-dihydro-6H-7,11-(epoxyethanoiminoethanoiminothioiminomethano)indolo[1,2-e][1,5]benzoxazocin-15-one 17,17-dioxide;

(7R)-14-cyclohexyl-18,21,24-trimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide;

13-cyclohexyl-5,17,20,23-tetramethyl-6,7-dihydro-5H-10,6-(methanoiminothioiminoethanoiminoethanoiminomethano)indolo[1,2-d][1,4]benzodiazepin-14-one 16,16-dioxide;

13-cyclohexyl-3-methoxy-17,20-dimethyl-6,7-dihydro-5H-6,10-(ethanoiminoethanoiminothioiminomethano)indolo[2,1-a][2]benzazepin-14-one 16,16-dioxide;

(7R)-14-cyclohexyl-3-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-3-fluoro-18-methyl-7,8-dihydro-6H-7,11-(epiminoethanoiminoethanoiminothioiminomethano)-indolo[1,2-e][1,5]benzoxazocin-15-one 17,17-dioxide;

(+)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(−)-14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(7S)-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R,S)-14-[(1R,2S) or (1S,2R)-2-fluorocyclohexyl]-18,23-dimethyl-7,8-dihydro-6H-11,7-(methanoiminothioiminobutanoiminomethano)indolo[1,2-e][1,5]benzoxazocin-15-one 17,17-dioxide;

(20S)-31-cyclohexyl-10-methyl-19,22-dioxa-9-thia-1,8,10,13-tetraazahexacyclo[18.9.1.1$^{2,6}$.1$^{3,29}$.0$^{13,17}$.0$^{23,28}$]dotriaconta-2(32),3,5,23,25,27,29(31)-heptaen-7-one 9,9-dioxide;

(18R)-29-cyclohexyl-10,17-dimethyl-20-oxa-9-thia-1,8,10,14,17-pentaazahexacyclo[16.9.1.1$^{2,6}$.1$^{3,27}$.1$^{11,14}$.0$^{21,26}$]hentriaconta-2(31),3,5,21,23,25,27(29)-heptaen-7-one 9,9-dioxide;

(7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,24-dimethyl-7,8-dihydro-6H-7,11-(epiminoethanooxyethanoiminothioiminomethano)indolo[1,2-e][1,5]benzoxazocin-15-one 17,17-dioxide;

(16S,18R)-29-cyclohexyl-10,17-dimethyl-20-oxa-9-thia-1,8,10,13,17-pentaazahexacyclo[16.9.1.1$^{2,6}$.1$^{3,27}$.1$^{13,16}$.0$^{21,26}$]hentriaconta-2(31),3,5,21,23,25,27(29)-heptaen-7-one 9,9-dioxide;

(7R)-14-cyclohexyl-21-ethyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide;

31-cyclohexyl-8-oxa-24-thia-1,4,16,23,25-pentaazaheptacyclo[23.2.2.1$^{4,6}$.1$^{6,16}$.1$^{15,18}$.1$^{17,21}$.0$^{9,14}$]tritriaconta-9,11,13,15(31),17(30), 18,20-heptaen-22-one 24,24-dioxide;

(7R)-14-cyclohexyl-18,19,19,21,24-pentamethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-21-ethyl-18,24-dimethyl-4-(piperidin-1-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-4-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]-N-methylacetamide;

(7R)-14-cyclohexyl-24-[2-(dimethylamino)ethyl]-18,21,21-trimethyl-7,8-dihydro-6H-7,11-(epiminopentanoiminothioiminomethano)indolo[1,2-e][1,5]benzoxazocin-15-one 17,17-dioxide;

(7R)-14-cyclohexyl-18,21,24-trimethyl-4-(2-pyrrolidin-1-ylethoxy)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,22-dimethyl-7,8-dihydro-6H-7,11-(ethanoiminopropanoiminothioiminomethano)indolo[1,2-e][1,5]benzoxazocin-15-one 17,17-dioxide;

30-cyclohexyl-18-oxa-2-thia-1,3,10,24-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(−)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(+)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide;

(−)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide;

14-[(1R,2S) or (1S,2R)-2-fluorocyclohexyl]-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R or 7S)-14-cyclohexyl-18,21-dimethyl-7,8-dihydro-6H-7,11-(methanooxyethanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-18,21-dimethyl-7,8-dihydro-6H-7,11-(propanoiminoethanoiminothioiminomethano)indolo[1,2-e][1,5]benzoxazocin-15-one 17,17-dioxide;

14-cyclohexyl-18,22-dimethyl-7,8-dihydro-6H-7,11-(ethanoiminopropanoiminothioiminomethano)indolo[1,2-e][1,5]benzoxazocin-15-one 17,17-dioxide;

(7R)-21-[2-(benzyloxy)ethyl]-14-cyclohexyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-(2-hydroxyethyl)-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isobutyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-(N,N-dimethylglycyl)-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18-(2-hydroxyethyl)-24-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21,24-diethyl-18-methyl-7,8-dihydro-6H-7,11-(epiminoethanoiminoethanoiminothioiminomethano)indolo[1,2-e][1,5]benzoxazocin-15-one 17,17-dioxide;

20-benzyl-13-cyclohexyl-17,23-dimethyl-6,7-dihydro-5H-6,10-(epiminoethanoiminoethanoiminothioiminomethano)indolo[2,1-a][2]benzazepin-14-one 16,16-dioxide;

(7R)-14-cyclohexyl-2-fluoro-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-2-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-2-fluoro-18-methyl-24-(pyridin-3-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-3-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-fluoro-18-methyl-24-[2-(methylamino)ethyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-2-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3-methoxy-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18,24-dimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,21,24-trimethyl-4-propyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isopropyl-18,24-dimethyl-4-propyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-24-(2-hydroxyethyl)-3,18-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-3,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-3,18,21,24-tetramethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-18-methyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-isopropyl-3,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-21-ethyl-4,18-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-[2-(dimethylamino)ethyl]-18,24-dimethyl-7,8-dihydro-6H-7,11-(epiminoethanoiminoethanoiminothioiminomethano)indolo[1,2-e][1,5]benzoxazocin-15-one 17,17-dioxide;

(18R)-29-cyclohexyl-10,17-dimethyl-20-oxa-9-thia-1,8,10,13,17-pentaazahexacyclo[16.9.1.1$^{2,6}$.1$^{3,27}$.1$^{13,16}$.0$^{21,26}$]hentriaconta-2(31),3,5,21,23,25,27(29)-heptaen-7-one 9,9-dioxide;

(3R)-31-cyclohexyl-2,22-dimethyl-5-oxa-21-thia-2,13,20,22,25-pentaazahexacyclo[23.2.2.1$^{3,13}$.1$^{12,15}$.1$^{14,18}$.0$^{6,11}$]dotriaconta-6,8,10,12(31),14(30),15,17-heptaen-19-one 21,21-dioxide;

(5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31),16(30),17,19-heptaen-21-one 23,23-dioxide;

(20R)-31-cyclohexyl-21-methyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

(5R)-31-cyclohexyl-4,24-dimethyl-7-oxa-23-thia-1,4,15,22,24-pentaazahexacyclo[23.2.2.1$^{5,15}$.1$^{14,17}$.1$^{16,20}$.0$^{8,13}$]dotriaconta-8,10,12,14(31),16(30),17,19-heptaen-21-one 23,23-dioxide;

(20R)-31-cyclohexyl-21-methyl-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide;

(20R)-31-cyclohexyl-21-[2-(dimethylamino)ethyl]-18,24-dioxa-2-thia-1,3,10,21-tetraazahexacyclo[23.2.2.1$^{5,9}$.1$^{8,11}$.1$^{10,20}$.0$^{12,17}$]dotriaconta-5(32),6,8,11(31),12,14,16-heptaen-4-one 2,2-dioxide;

(20R)-30-cyclohexyl-21-(2-fluoroethyl)-18-oxa-2-thia-1,3,10,21,24-pentaazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(20R)-21-benzyl-31-cyclohexyl-18-oxa-2-thia-1,3,10,21,24-pentaazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

(7S)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-24-[2-(dimethylamino)ethyl]-18-methyl-7,8-dihydro-6H-7,11-(epiminoethanooxyethanoiminothioiminomethano)indolo[1,2-e][1,5]benzoxazocin-15-one 17,17-dioxide;

(7R)-4-allyl-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-4-fluoro-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-fluoro-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-18,24-dimethyl-4-(trifluoromethyl)-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-(cyclopropylmethyl)-18,21,24-trimethyl-7,8-dihydro-6H-7,11-(epiminoethanoiminoethanoiminothioiminomethano)indolo[1,2-e][1,5]benzoxazocin-15-one 17,17-dioxide;

2-[(7R)-14-cyclohexyl-18,21-dimethyl-17,17-dioxido-15-oxo-7,8-dihydro-6H-7,11-(epiminoethanoiminoethanoiminothioiminomethano)indolo[1,2-e][1,5]benzoxazocin-24-yl]acetamide;

(7R)-14-cyclohexyl-18,21-dimethyl-24-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-18,24-dimethyl-4-(morpholin-4-ylmethyl)-7,8-dihydro-6H-7,11-(epiminoethanoiminoethanoiminothioiminomethano)indolo[1,2-e][1,5]benzoxazocin-15-one 17,17-dioxide;

(7R)-4-(benzyloxy)-14-cyclohexyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-18,21,24-trimethyl-7,8-dihydro-6H-7,11-(epiminoethanoiminoethanoiminothioiminomethano)indolo[1,2-e][1,5]benzoxazocin-15-one 17,17-dioxide;

14-[(1R,2S) or (1S,2R)-2-fluorocyclohexyl]-18,22-dimethyl-7,8-dihydro-6H-7,11-(ethanoiminopropanoiminothioiminomethano)indolo[1,2-e][1,5]benzoxazocin-15-one 17,17-dioxide;

30-[(1R,2S) or (1S,2R)-2-fluorocyclohexyl]-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-[(1R,2S) or (1S,2R)-2-fluorocyclohexyl]-22-methyl-18-oxa-2-thia-1,3,10,22-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-cyclohexyl-23-methyl-6-oxa-22-thia-1,14,21,23-tetraazahexacyclo[22.2.2.1$^{4,14}$.1$^{13,16}$.1$^{15,19}$.0$^{7,12}$]hentriaconta-7,9,11,13(30),15(29),16,18-heptaen-20-one 22,22-dioxide;

(7R) or (7S)-14-cyclohexyl-22-methyl-18-(2-pyrrolidin-1-ylethyl)-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-isopropyl-18-methyl-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-(2-hydroxyethyl)-18-methyl-7,8-dihydro-6H-7,11-(ethanoiminopropanoiminothioiminomethano)indolo[1,2-e][1,5]benzoxazocin-15-one 17,17-dioxide;

31-cyclohexyl-18-oxa-2-thia-1,3,10,24-tetraazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

14-cyclohexyl-21-isopropyl-18-methyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4-methoxy-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21,21,24-tetramethyl-7,8-dihydro-6H-7,11-(epiminopentanoiminothioiminomethano)indolo[1,2-e][1,5]benzoxazocin-15-one 17,17-dioxide;

14-[(1R,2S) or (S2R)-2-fluorocyclohexyl]-18,22-dimethyl-7,8-dihydro-6H-7,11-(ethanoiminopropanoiminothioiminomethano)indolo[1,2-e][1,5]benzoxazocin-15-one 17,17-dioxide;

30-[(1R,2S)-2-fluorocyclohexyl]-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-[(1R,2S)-2-fluorocyclohexyl]-22-methyl-18-oxa-2-thia-1,3,10,22-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

30-cyclohexyl-23-methyl-6-oxa-22-thia-1,14,21,23-tetraazahexacyclo[22.2.2.1$^{4,14}$.1$^{13,16}$.1$^{15,19}$.0$^{7,12}$]hentriaconta-7,9,11,13(30),15(29),16,18-heptaen-20-one 22,22-dioxide;

(7R) or (7S)-14-cyclohexyl-22-methyl-18-(2-pyrrolidin-1-ylethyl)-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-isopropyl-18-methyl-7,8-dihydro-6H-7,11-(ethanoiminopropanoiminothioiminomethano)indolo[1,2-e][1,5]benzoxazocin-15-one 17,17-dioxide;

(7R) or (7S)-14-cyclohexyl-22-(2-hydroxyethyl)-18-methyl-7,8-dihydro-6H-7,11-(ethanoiminopropanoiminothioiminomethano)indolo[1,2-e][1,5]benzoxazocin-15-one 17,17-dioxide;

31-cyclohexyl-18-oxa-2-thia-1,3,10,24-tetraazahexacyclo[22.3.2.1$^{5,9}$.1$^{8,11}$.1$^{10,20}$.0$^{12,17}$]dotriaconta-5(32),6,8,11(31),12,14,16-heptaen-4-one 2,2-dioxide;

14-cyclohexyl-21-isopropyl-18-methyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4-methoxy-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21,21,24-tetramethyl-7,8-dihydro-6H-7,11-(epiminopentanoiminothioiminomethano)indolo[1,2-e][1,5]benzoxazocin-15-one 17,17-dioxide;

(7R)-14-[(1R,2S)-2-fluorocyclohexyl]-4,18,21-trimethyl-7,8-dihydro-6H-7,11-(propanoiminoethanoiminothioiminomethano)indolo[1,2-e][1,5]benzoxazocin-15-one 17,17-dioxide;

2-[(7R)-14-cyclohexyl-4,18,24-trimethyl-17,17-dioxido-15-oxo-7,8-dihydro-6H-7,11-(epiminoethanoiminoethanoiminothioiminomethano)indolo[1,2-e][1,5]benzoxazocin-21-yl]-N,N-dimethylacetamide;

(7R)-14-cyclohexyl-4,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,21,24-tetramethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,24-trimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;

(7R)-14-cyclopentyl-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4-methoxy-18,24-dimethyl-7,8-dihydro-6H-7,11-(epiminoethanooxyethanoiminothioiminomethano)indolo[1,2-e][1,5]benzoxazocin-15-one 17,17-dioxide;

(7R)-14-cyclohexyl-4,18,21-trimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-4,18,22-trimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-22-[2-(dimethylamino)ethyl]-4,18-dimethyl-7,8-dihydro-6H-7,11-(ethanoiminopropanoiminothioiminomethano)indolo[1,2-e][1,5]benzoxazocin-15-one 17,17-dioxide;

(20R)-30-cyclohexyl-15-methoxy-23-methyl-18-oxa-2-thia-1,3,10,23-tetraazahexacyclo[22.2.2.1$^{5,9}$.1$^{8,11}$.1$^{10,20}$.0$^{12,17}$]hentriaconta-5(31),6,8,11(30),12,14,16-heptaen-4-one 2,2-dioxide;

(7R)-14-cyclohexyl-20,20-difluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-20-fluoro-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

or a pharmaceutically acceptable salt thereof.

17. The compound of claim 16, wherein said compound is selected from the group consisting of:

(7R)-14-cyclohexyl-21-isopropyl-18,24-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,21,24-tetramethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-18,21,24-trimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-21-ethyl-24-(2-hydroxyethyl)-3,18-dimethyl-7,8-dihydro-6H-7,11-(epiminoethanoiminoethanoiminothioiminomethano)indolo[1,2-e][1,5]benzoxazocin-15-one 17,17-dioxide;

(7R)-14-cyclohexyl-4,18,22-trimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-3-methoxy-18,21-dimethyl-7,8-dihydro-6H-7,11-(propanoiminoethanoiminothioiminomethano)indolo[1,2-e][1,5]benzoxazocin-15-one 17,17-dioxide;

(7R)-14-[(1R,2S) or (1S,2R)-2-fluorocyclohexyl]-4,18,21-trimethyl-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21-dimethyl-4-(2-pyrrolidin-1-ylethoxy)-7,8-dihydro-6H-7,11-(propanoiminoethanoiminothioiminomethano)indolo[1,2-e][1,5]benzoxazocin-15-one 17,17-dioxide;

(7R)-14-cyclohexyl-18,21,24-trimethyl-4-(2-pyrrolidin-1-ylethoxy)-7,8-dihydro-6H-7,11-(epiminoethanoiminoethanoiminothioiminomethano)indolo[1,2-e][1,5]benzoxazocin-15-one 17,17-dioxide;

(7R)-14-[(1R,2S)-2-fluorocyclohexyl]-3-methoxy-18,22-dimethyl-7,8-dihydro-6H-7,11-(ethanoiminopropanoiminothioiminomethano)indolo[1,2-e][1,5]benzoxazocin-15-one 17,17-dioxide;

(7R)-14-cyclohexyl-24-[2-(dimethylamino)ethyl]-21-ethyl-4,18-dimethyl-7,8-dihydro-6H-7,11-(epiminoethanoiminoethanoiminothioiminomethano)indolo[1,2-e][1,5]benzoxazocin-15-one 17,17-dioxide;
(7R)-14-cyclohexyl-18,21,24-trimethyl-3-(pyridin-2-ylmethoxy)-7,8-dihydro-6H-7,11-(epiminoethanoiminoethanoiminothioiminomethano)indolo[1,2-e][1,5]benzoxazocin-15-one 17,17-dioxide;
(7R)-14-cyclohexyl-4-methoxy-18,22-dimethyl-7,8-dihydro-6H-7,11-(ethanoiminopropanoiminothioiminomethano)indolo[1,2-e][1,5]benzoxazocin-15-one 17,17-dioxide;
(7R)-14-[(1R,2S)-2-fluorocyclohexyl]-18,21-dimethyl-7,8-dihydro-6H-7,11-(propanoiminoethanoiminothioiminomethano)indolo[1,2-e][1,5]benzoxazocin-15-one 17,17-dioxide;
(7R)-14-cyclohexyl-21-ethyl-18,24-dimethyl-7,8-dihydro-6H-7,11-(epiminoethanoiminoethanoiminothioiminomethano)indolo[1,2-e][1,5]benzoxazocin-15-one 17,17-dioxide;
(7R)-14-cyclohexyl-22-[2-(dimethylamino)ethyl]-4,18-dimethyl-7,8-dihydro-6H-7,11-(ethanoiminopropanoiminothioiminomethano)indolo[1,2-e][1,5]benzoxazocin-15-one 17,17-dioxide;
(7R)-14-cyclohexyl-4-methoxy-18,24-dimethyl-21-[(1-methyl-1H-pyrazol-4-yl)methyl]-7,8-dihydro-6H-7,11-(epiminoethanoiminoethanoiminothioiminomethano)indolo[1,2-e][1,5]benzoxazocin-15-one 17,17-dioxide;
(7R)-14-cyclohexyl-24-[2-(dimethylamino)ethyl]-18,21,21-trimethyl-7,8-dihydro-6H-7,11-(epiminopentanoiminothioiminomethano)indolo[1,2-e][1,5]benzoxazocin-15-one 17,17-dioxide;
(7R)-14-cyclohexyl-21-ethyl-18-(2-hydroxyethyl)-24-methyl-7,8-dihydro-6H-7,11-(epiminoethanoiminoethanoiminothioiminomethano)indolo[1,2-e][1,5]benzoxazocin-15-one 17,17-dioxide; or a pharmaceutically salt thereof.

18. The compound of claim 17, wherein said compound is (7R)-14-cyclohexyl-21-ethyl-4,18,24-trimethyl-7,8-dihydro-6H-7,11-(epiminoethanoiminoethanoiminothioiminomethano)indolo[1,2-e][1,5]benzoxazocin-15-one 17,17-dioxide or a pharmaceutically salt thereof.

19. The compound of claim 17, wherein said compound is (7R)-14-cyclohexyl-4,18,21,24-tetramethyl-7,8-dihydro-6H-7,11-(epiminoethanoiminoethanoiminothioiminomethano)indolo[1,2-e][1,5]benzoxazocin-15-one 17,17-dioxide or a pharmaceutically salt thereof.

20. The compound of claim 17, wherein the compound is (7R)-14-cyclohexyl-3-methoxy-18,22-dimethyl-7,8-dihydro-6H-7,11-(ethanoiminopropanoiminothioiminomethano)indolo[1,2-e][1,5]benzoxazocin-15-one 17,17-dioxide or a pharmaceutically salt thereof.

21. A pharmaceutical composition comprising a therapeutically effective amount of the compound according to claim 3 with a pharmaceutically acceptable carrier.

22. A method of inhibiting hepatitis C virus polymerase in a human or animal patient infected with HCV comprising the step of administering to the patient a therapeutically effective amount of the compound of claim 3.

23. A method of treating a patient infected with HCV comprising the step of administering to said patient a therapeutically effective amount of the compound of claim 3.

24. The method of claim 23, wherein said patient is a human.

* * * * *